(12) United States Patent
Jin et al.

(10) Patent No.: US 9,174,968 B2
(45) Date of Patent: *Nov. 3, 2015

(54) PYRIMIDINONE COMPOUNDS FOR USE IN THE TREATMENT OF DISEASES OR CONDITIONS MEDIATED BY LP-PLA2

(71) Applicant: GLAXO GROUP LIMITED, Brentford, Middlesex (GB)

(72) Inventors: Yun Jin, Shanghai (CN); Zehong Wan, Shanghai (CN); Qing Zhang, Shanghai (CN)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,970

(22) Filed: Dec. 15, 2014

(65) Prior Publication Data

US 2015/0099756 A1 Apr. 9, 2015

Related U.S. Application Data

(63) Continuation of application No. 13/991,955, filed as application No. PCT/EP2011/071690 on Dec. 5, 2011, now abandoned.

(30) Foreign Application Priority Data

Dec. 6, 2010 (WO) ................ PCT/CN2010/079465

(51) Int. Cl.

| | | |
|---|---|---|
| *C07D 403/14* | (2006.01) | |
| *C07D 239/36* | (2006.01) | |
| *C07D 239/52* | (2006.01) | |
| *C07D 239/56* | (2006.01) | |
| *C07D 401/06* | (2006.01) | |
| *C07D 401/12* | (2006.01) | |
| *C07D 401/14* | (2006.01) | |
| *C07D 403/06* | (2006.01) | |
| *C07D 403/12* | (2006.01) | |
| *C07D 413/06* | (2006.01) | |
| *C07D 417/06* | (2006.01) | |
| *C07D 239/22* | (2006.01) | |
| *C07D 239/47* | (2006.01) | |
| *A61K 31/505* | (2006.01) | |
| *A61K 31/506* | (2006.01) | |

(52) U.S. Cl.
CPC ............ *C07D 403/14* (2013.01); *C07D 239/22* (2013.01); *C07D 239/36* (2013.01); *C07D 239/47* (2013.01); *C07D 239/52* (2013.01); *C07D 239/56* (2013.01); *C07D 401/06* (2013.01); *C07D 401/12* (2013.01); *C07D 401/14* (2013.01); *C07D 403/06* (2013.01); *C07D 403/12* (2013.01); *C07D 413/06* (2013.01); *C07D 417/06* (2013.01); *A61K 31/505* (2013.01); *A61K 31/506* (2013.01)

(58) Field of Classification Search
CPC .. C07D 239/36; C07D 239/47; C07D 239/52; C07D 239/56; C07D 401/06; C07D 401/12; C07D 401/14; C07D 403/06; C07D 403/12; C07D 403/14; C07D 413/06; C07D 417/06; C07D 239/22; A61K 31/506; A61K 31/505; A61K 31/513
See application file for complete search history.

(56) References Cited

U.S. PATENT DOCUMENTS

| | | | | |
|---|---|---|---|---|
| 8,637,536 B2 * | 1/2014 | Jin et al. | ......................... | 514/274 |
| 8,859,573 B2 * | 10/2014 | Wan et al. | ..................... | 514/274 |
| 2014/0113922 A1 * | 4/2014 | JIN et al. | ...................... | 514/274 |

FOREIGN PATENT DOCUMENTS

| | | |
|---|---|---|
| WO | WO 00/10980 | 3/2000 |
| WO | WO 00/68208 | 11/2000 |
| WO | WO 02085860 A1 * | 10/2002 |

OTHER PUBLICATIONS

CAS Registry No. 1012211-02-7 (2008).*
CAS Registry No. 1011690-92-8 (2008).*
CAS Registry No. 879857-09-7 (2006).*
CAS Registry No. 786660-84-2 (2004).*
CAS Registry No. 1004442-41-4 (Entered STN: Feb. 19, 2008).*
CAS Registry No. 900725-64-6 (Entered STN: Aug. 11, 2006).*
CAS Registry No. 304661-90-3 (Entered STN: Nov. 28, 2000).*
A.I. Rakhimov et al., 43 Russian Journal of Organic Chemistry, 96-102 (2007).*

* cited by examiner

*Primary Examiner* — Alexander R Pagano
(74) *Attorney, Agent, or Firm* — Fang Qian; William R. Majarian

(57) ABSTRACT

The present invention relates to novel compounds that inhibit Lp-PLA$_2$ activity, processes for their preparation, to compositions containing them and to their use in the treatment of diseases associated with the activity of Lp-PLA$_2$, for example atherosclerosis, Alzheimer's disease, and/or diabetic macular edema.

14 Claims, No Drawings

PYRIMIDINONE COMPOUNDS FOR USE IN THE TREATMENT OF DISEASES OR CONDITIONS MEDIATED BY LP-PLA2

RELATED APPLICATION

The present application claims priority from PCT International Application No. PCT/CN2010/079465, filed on Dec. 6, 2010 at the State Intellectual Property Office of the People's Republic of China, the entire contents of which is incorporated herein by reference.

FIELD OF THE INVENTION

The present invention relates to novel pyrimidinone compounds, processes for their preparation, intermediates useful in their preparation, pharmaceutical compositions containing them, and their use in therapy for the treatment of diseases or conditions mediated by Lp-PLA$_2$.

BACKGROUND OF THE INVENTION

Lipoprotein-associated phospholipase A$_2$ (Lp-PLA$_2$) previously known as platelet-activating factor acetylhydrolase (PAF-AH), is a phospholipase A2 enzyme involved in hydrolysis of lipoprotein lipids or phospholipids. Lp-PLA$_2$ travels with low-density lipoprotein (LDL) and rapidly cleaves oxidized phosphatidylcholine molecules derived from the oxidation of LDL. (See e.g., Zalewski A, et al., *Arterioscler. Thromb. Vasc. Biol.*, 25, 5, 923-31(2005)). Lp-PLA$_2$ hydrolyzes the sn-2 ester of the oxidized phosphatidylcholines to give lipid mediators, lysophosphatidylcholine (lysoPC) and oxidized nonesterified fatty acids (NEFAs). It has been observed that lysoPC and NEFAs elicit inflammatory responses. (See e.g., Zalewski A, et al. (2005)).

A number of Lp-PLA$_2$ inhibitors and/or uses thereof have been previously described. (See. for example, published patent application nos. WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, and WO08/048866.) Disclosed uses include treating disease that involves or is associated with endothelial dysfunction, disease that involves lipid oxidation in conjunction with Lp-PLA$_2$ activity (e.g., associated with the formation of lysophosphatidylcholine and oxidized free fatty acids), and disease that involves activated monocytes, macrophages or lymphocytes or which is associated with increased involvement of monocytes, macrophages or lymphocytes. Examples of particular diseases or conditions include atherosclerosis (e.g. peripheral vascular atherosclerosis and cerebrovascular atherosclerosis), diabetes, hypertension, angina pectoris, after ischaemia and reperfusion, rheumatoid arthritis, stroke, inflammatory conditions of the brain such as Alzheimer's Disease, various neuropsychiatric disorders such as schizophrenia, myocardial infarction, ischaemia, reperfusion injury, sepsis, acute and chronic inflammation, and psoriasis.

Lp-PLA$_2$ inhibitors and/or uses thereof are also reported, for example, in PCT Publication Nos. WO05/003118 (and its Canadian family member CA 2530816A1); WO06/063811; WO06/063813 and WO 2008/141176; JP 200188847; and US Published Patent Application Nos. US 2008/0279846 A1, US 2010/0239565 A1, and US 2008/0280829 A1.

Other researchers have studied the effects related to Lp-PLA$_2$ and inhibitors thereof. For example, research data has also indicated that LysoPC promotes atherosclerotic plaque development, which can ultimately lead to the formation of a necrotic core. (See e.g., Wilensky et al., *Current Opinion in Lipidology*, 20, 415-420 (2009)). In addition, the effect of Lp-PLA$_2$ inhibitors on atherosclerotic plaque composition was demonstrated in a diabetic and hypercholesterolemic porcine model of accelerated coronary atherosclerosis. (See e.g., Wilensky et al., *Nature Medicine*, 10, 1015-1016 (2008)). These research results provided further evidence that Lp-PLA$_2$ inhibitors may be used to treat atherosclerosis.

Additional researches have found that high Lp-PLA$_2$ activity is associated with high risk of dementia, including Alzheimer's disease (AD) (See e.g., Van Oijen, et al. Annals of Neurology, 59, 139 (2006)). Higher level of oxidized LDL has also been observed in AD patients (See e.g., Kassner et al. *Current Alzheimer Research*, 5, 358-366 (2008); Dildar, et al., *Alzheimer Dis Assoc Disord*, 24, April-June (2010); Sinem, et al. *Current Alzheimer Research*, 7, 463-469 (2010)). Further, research data has shown that neuroinflammation are present in AD patients and multiple cytotoxic inflammatory cytokines are up-regulated in AD patients. (See e.g., Colangelo, et al., *Journal of Neuroscience Research*, 70, 462-473 (2002); Wyss-Coray, *Nature Medicine*, 12, Sep. (2006)). Research has shown that LysoPC function as a pro-inflammatory factor inducing multiple cytotoxic inflammatory cytokine release (See Shi, et al. *Atherosclerosis*, 191, 54-62 (2007)). Therefore, these rescent researches have provided additional evidence that that the inhibitors of Lp-PLA$_2$ can be used to treat AD by inhibiting activity of Lp-PLA$_2$ and reducing lysoPC production.

In addition, the treatment of an Lp-PLA$_2$ inhibitor on a diabetic and hypercholesterolemia swine model demonstrated that the blood-brain-barrier leakage and the brain amyloid beta protein (Aβ) burden, the pathological hallmarks of Alzheimer's disease, were reduced. (See U.S. Patent Application Publication No. 2008/0279846). This publication describes several uses of Lp-PLA$_2$ inhibitors for treating diseases associated with blood-brain-barrier leakage, including, e.g., Alzheimer's disease and vascular dementia.

Further, neuroinflammation, including multiple cytotoxic cytokine release, is a common feature of all neurodegenerative diseases including multiple sclerosis, amyotrophic lateral sclerosis, Parkinson's disease, Alzheimer's disease, etc. (See e.g., Perry, *Acta Neuropathol*, 120, 277-286 (2010)). As discussed above, Lp-PLA$_2$ inhibitors can reduce inflammation, for example, reducing multiple cytokine release by suppressing lysoPC production. (See e.g., Shi, et al. *Atherosclerosis* 191, 54-62 (2007)). Thus, inhibiting Lp-PLA$_2$ is a potential therapeutic treatment for neurodegenerative diseases including multiple sclerosis, amyotrophic lateral sclerosis, Parkinson's disease, etc.

In addition to the inflammatory effect, LysoPC has been implicated in leukocyte activation, induction of apoptosis and mediation of endothelial dysfunction (See, e.g., Wilensky et al., *Current Opinion in Lipidology*, 20, 415-420 (2009)). Therefore, it is believed that Lp-PLA$_2$ inhibitors can be used to treat tissue damage associated with diabetes by reducing the production of lysoPC, which can cause a continuous cycle of vascular inflammation and increased reactive oxygen species (ROS) production. In light of the inflammatory roles of Lp-PLA$_2$ and the association between localized inflammatory processes and diabetic retinopathy, it is postulated that Lp-PLA$_2$ can be used to treat diabetic eye disease.

Glaucoma and age-related macular degeneration (AMD) are retina neurodegenerative diseases. Studies suggested that inflammation, including TNF-alpha signaling, may play an important role in the pathogenesis of glaucoma and AMD (See e.g., Buschini et al., *Progress in Neurobiology*, 95, 14-25 (2011); Tezel, *Progress in Brain Research*, vol. 173, ISSN0079-6123, Chapter 28). Thus, considering Lp-PLA$_2$ inhibitors' function of blocking inflammatory cytokine release (See e.g., Shi, et al. *Atherosclerosis*, 191, 54-62 (2007)), it is believed that Lp-PLA$_2$ inhibitors can provide a potential therapeutic application for both glaucoma and AMD.

In view of the number of pathological responses that are mediated by Lp-PLA$_2$, attempts have been made to prepare compounds that inhibit its activity. Though a number of such compounds have been disclosed in the art, there remains a continuing need for inhibitors of Lp-PLA$_2$ which can be used in the treatment of a variety of conditions.

SUMMARY OF THE INVENTION

In a first aspect, this invention relates to a compound of Formula (I)

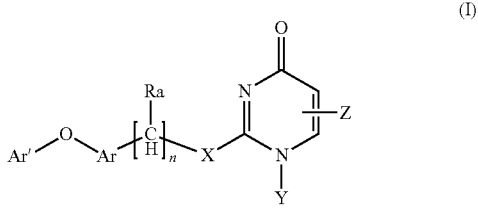

(I)

wherein:
n is 0, 1, 2 or 3;
X is $CH_2$, O, S, NH, or $N(C_1-C_6alkyl)$;
Y is H, $C_1-C_6$alkyl or $C_3-C_6$ cycloalkyl;
Z is H, $C_1-C_6$alkyl, $C_1-C_6$haloalkyl, —$CH_2$-phenyl, —$CH_2$-heteroaryl, —$(CH_2)_2C(=O)$—$OCH_3$, —$CH_2$-heterocycloalkyl, —$CH_2COOH$, —$CH_2C(=O)$-heterocycloalkyl, wherein phenyl, heteroaryl or heterocycloalkyl is optionally substituted with one or more substituents independently selected from the group consisting of $C_1-C_6$alkyl, $C_1-C_6$alkoxyl, $C_1-C_3$haloalkyl, CN, halo and —OH;
Ra is hydrogen or $C_1-C_3$alkyl;
Ar is phenyl or heteroaryl, either of which is optionally substituted with one or more substituents independently selected from the group consisting of CN, halo, $C_1-C_6$alkyl, $C_1-C_6$alkoxy, and $C_1-C_6$haloalkyl; and
Ar' is phenyl or heteroaryl, either of which is optionally substituted with one or more substituents independently selected from the group consisting of CN, halo, $C_1-C_6$alkyl, $C_1-C_6$alkoxy, $C_1-C_6$haloalkyl, and —O—$C_1-C_6$haloalkyl; and
with the proviso that when X is S and Z is $C_1-C_6$alkyl, Ar' is not unsubstituted phenyl.

This invention also provides pharmaceutical compositions comprising a compound of present invention and pharmaceutically acceptable carriers.

The invention also provides methods of treating a disease associated with the activity of Lp-PLA$_2$, which comprises treating a subject in need thereof with a therapeutically effective amount of an inhibitor of Lp-PLA$_2$. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

This invention also provides methods of treating a disease by inhibiting Lp-PLA$_2$ activity. Exemplary disease includes, but is not limited to, neurodegeneration disease (e.g., Alzheimer's disease, vascular dementia), atherosclerosis, stroke, metabolic bone disorder (e.g., bone marrow abnormalities), dyslipidemia, Paget's diseases, type II diseases, metabolic syndrome, insulin resistance, and hyperparathyroidism, diabetic ocular disorder (e.g., macular edema, diabetic retinopathy, and posterior uveitis), macular edema, wound healing, rheumatoid arthritis, chronic obstructive pulmonary disease (COPD) and multiple sclerosis. The methods comprise administering a safe and effective amount of a compound of this invention to a subject in need thereof. It is not intended that the present invention to be limited to any particular stage of the disease (e.g. early or advanced).

This invention also provides methods of treating Alzheimer's disease. The methods comprise administering to a subject in need thereof a safe and effective amount of a compound of this invention.

This invention also provides methods of decreasing beta amyloid (also referred to as "Aβ") accumulation in the brain of a subject. The methods comprise administering to a subject in need thereof a safe and effective amount of a compound of the present invention. In certain embodiment, the beta amyloid is Abeta-42.

This invention also provides methods for treating eye diseases and disorders by administering a compound of this invention. In certain embodiment, this invention provides methods of treating macular edema, which comprises administering to the subject a safe and effective amount of a compound of this invention. In certain embodiment, the macular edema is associated with diabetic eye disease, for example, diabetic retinopathy. In one embodiment, the macular edema is associated with posterior uveitis.

This invention also provides the use of a compound of this invention for manufacturing a medicament for treating diseases described herein.

This invention also provides a compound described herein for use in carrying out methods of treatment described herein.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology and virology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. DEFINITIONS

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

The term "neurodegeneration disease" or "neurodegenerative disease" as used herein refers to a varied assortment of central nervous system disorders characterized by gradual and progressive loss of neural tissue and/or neural tissue function. A neurodegeneration disease is a class of neurological disorder or disease where the neurological disease is characterized by a gradual and progressive loss of neural tissue, and/or altered neurological function, typically reduced neurological function as a result of a gradual and progressive loss of neural tissue. In one embodiment, the neurodegeneration diseases described herein are neurodegeneration diseases or disorders where there is an abnormal blood brain barrier, for example a permeable blood brain barrier. Examples of neurodegeneration diseases where there is a defective blood brain barrier include, but are not limited to, Alzheimer's disease, Huntington's disease, Parkinson's disease, vascular dementia and the like.

The term "vascular dementia" is also referred to as "multi-infarct dementia", which refers to a group of syndromes caused by different mechanisms, which all result in vascular lesions in the brain. The main subtypes of vascular dementia are, for example, vascular mild cognitive impairment, multi-infarct dementia, vascular dementia due to a strategic single infarct, (affecting the thalamus, the anterior cerebral artery, the parietal lobes or the cingulated gyms), vascular dementia due to hemorrhagic lesions, small vessel disease (including, e.g. vascular dementia due to lacunar lesions and Binswanger disease), and mixed Alzheimer's Disease with vascular dementia.

The phrase "blood-brain barrier" or "BBB" are used interchangeably herein, and are used to refer to the permeability barrier that exists in blood vessels as they travel through the brain tissue that severely restricts and closely regulates what is exchanged between the blood and the brain tissue. The blood brain barrier components include the endothelial cells that form the innermost lining of all blood vessels, the tight junctions between adjacent endothelial cells that are structural correlate of the BBB, the basement membrane of endothelial cells and the expanded foot process of nearby astrocytes which cover nearly all of the exposed outer surface of the blood vessel.

The phrase "metabolic bone disease" as used herein refers to a varied assortment of bone diseases and disorders characterized by gradual and progressive loss of bone tissue. Metabolic bone diseases described herein are metabolic bone diseases whereby there is a condition of diffusely decreased bone density and/or diminished bone strength. Such diseases are characterized by histological appearance. Exemplary metabolic bone diseases include, but are not limited to, osteoporosis which is characterized by decreased mineral and bone matrix, and osteomalacia which is characterized by decreased mineral but intact bone matrix.

The term "osteopenic diseases" or "osteopenia" are used interchangeably herein, and refer to conditions with decreased calcification and/or bone density, and is a descriptive term used to refer to all skeletal systems in which decreased calcification and/or bone density is observed. Osteopenia also refers to a reduced bone mass due to inadequate osteoid synthesis.

The term "osteoporosis" refers to conditions which mineral and/or bone matrix are decreased and/or bone mass is reduced.

"Alkyl" refers to a monovalent, saturated hydrocarbon chain having a specified number of carbon atoms. For example, $C_1$-$C_6$ alkyl refers to an alkyl group having from 1 to 6 carbon atoms. In still other embodiments, alkyl groups contain 1 to 2, 3, 4, or 5 carbon atoms. Alkyl groups may be optionally substituted with one or more substituent as defined herein. Alkyl groups may be straight or branched. In one embodiment, branched alkyl groups may have one, two, or three branches. Exemplary alkyl includes, but is not limited to, methyl, methylethyl, ethyl, propyl (n-propyl and isopropyl), methylpropyl, butyl (n-butyl, isobutyl, and t-butyl), pentyl (n-pentyl, isopentyl, and neopentyl), and hexyl.

"Alkoxy" refers to the group —O-alkyl. In one embodiment, alkoxyl groups contain 1 to 2, 3, 4, 5 or 6 carbon atoms. Exemplary alkoxy groups include, but are not limited to, methoxy, ethoxy and propoxy. "Cycloalkyl" refers to a saturated monocyclic hydrocarbon ring of 3 to 10 carbon atoms. In some embodiments, the cycloalkyl has 3 to 6 carbon atoms. Examples of cycloalkyl include cyclopropyl, cyclobutyl, cyclopentyl and cyclohexyl.

"Halogen" refers to fluorine (F), chlorine (Cl), bromine (Br), or iodine (I). "Halo" refers to the halogen radicals: fluoro (—F), chloro (—Cl), bromo (—Br), and iodo (—I).

"Haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms. Exemplary haloalkyl groups include, but are not limited to, chloromethyl, bromoethyl, trifluoromethyl, dichloromethyl, —$CH_2CF_3$.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Heterocycloalkyl groups are monocyclic ring systems or are fused, spiro, or bridged bicyclic ring systems. Monocyclic heterocycloalkyl rings have from 4 to 8 member atoms. Bicyclic heterocycloalkyl rings have from 7 to 11 member atoms. In some embodiments, heterocycloalkyl is monocyclic. In one embodiment, heterocycloalkyl contains one or two nitrogen atoms as member atoms. In certain embodiments, heterocycloalkyl is saturated. In other embodiments, heterocycloalkyl is unsaturated but not aromatic. Examples of heterocycloalkyl include piperidinyl, piperazinyl, pyrrolidinyl, azetidinyl, tetrahydrofuranyl, dihydrofuranyl, pyranyl, tetrahydropyranyl, dihydropyranyl, tetrahydrothienyl, pyrazolidinyl, oxazolidinyl, and thiazolidinyl.

"Heteroaryl" refers to a monocyclic or bicyclic aromatic ring containing from 1 to 4 heteroatoms member atoms in the ring. Heteroaryl groups containing more than one heteroatom may contain different heteroatoms. Heteroaryl groups may be optionally substituted with one or more substituent as defined herein. Heteroaryl groups are monocyclic ring systems having 5, 6 or 7 member atoms or bicyclic ring systems having 7, 8, 9, 10, or 11 member atoms. In one embodiment, heteroaryl groups are monocyclic ring system having 6 member atoms. In other embodiments, heteroaryl group have one or two nitrogen atom as member atoms. Examples of heteroaryl include, but are not limited to, pyrrolyl, pyrazolyl, pyridinyl, pyrimidinyl, indolyl, pyrimidinonyl, oxadiazolyl, thiazolyl, pyrimidin-2(1H)-onyl, pyridazinyl, 2-pyridonyl.

"Optionally substituted" indicates that a group, such as alkyl, alkenyl, alkynyl, aryl (for example phenyl), cycloalkyl, cycloalkenyl, heterocycloalkyl, or heteroaryl, may be unsubstituted, or the group may be substituted with one or more substituent as defined.

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, halo, hydroxyl, amino, substituted amine, amide, —SH, cyano, nitro, thioalkyl, carboxylic acid, —NH—C(=NH)—NH$_2$, alkyl, alkenyl, alkynyl, alkoxyl, aryl, heteroaryl, cycloalkyl, heterocycloalkyl, in which alkyl, alkenyl, alkynyl, alkoxyl, aryl, heteroaryl, cycloalkyl, thioalkyl and heterocycloalkyl may be further substituted. Suitable substituents are defined herein for each substituted or optionally substituted group.

As used herein, "treat", "treating" or "treatment" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, and/or (4) to slow the progression of the condition or one or more of the biological manifestations of the condition.

As used herein, "solvate" refers to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. In one embodiment, the solvent used is a pharmaceutically acceptable solvent. Examples of suitable pharmaceutically acceptable solvents include, without limitation, water, ethanol and acetic acid. In certain embodiment, the solvent used is water. As used herein, "subject" means a mammalian subject (e.g., dog, cat, horse, cow, sheep, goat, monkey, etc.), and human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

B. COMPOUNDS

This invention provides, in a first aspect, compounds of Formula (I) and pharmaceutically acceptable salts thereof:

$$Ar'—O—Ar—[\underset{H}{\overset{Ra}{C}}]_n—X—\text{(pyrimidinone ring with N-Y and Z substituents)} \quad (I)$$

wherein:
n is 0, 1, 2 or 3;
X is $CH_2$, O, S, NH, or $N(C_1\text{-}C_6\text{alkyl})$;
Y is H $C_1$-$C_6$alkyl, or $C_3$-$C_6$ cycloalkyl;
Z is H, $C_1$-$C_6$alkyl, $C_1$-$C_6$haloalkyl, —$CH_2$-phenyl, —$CH_2$-heteroaryl, —$(CH_2)_2C(=O)$—$OCH_3$, —$CH_2$-heterocycloalkyl, —$CH_2COOH$, —$CH_2C(=O)$-heterocycloalkyl, wherein phenyl, heteroaryl or heterocycloalkyl is optionally substituted with one or more substituents independently selected from the group consisting of $C_1$-$C_6$alkyl, $C_1$-$C_6$alkoxyl, $C_1$-$C_3$haloalkyl, CN, halo and —OH;
Ra is hydrogen or $C_1$-$C_3$alkyl;
Ar is phenyl or heteroaryl, either of which is optionally substituted with one or more substituents independently selected from the group consisting of CN, halo, $C_1$-$C_6$alkyl, $C_1$-$C_6$alkoxy, and $C_1$-$C_6$haloalkyl; and
Ar' is phenyl or heteroaryl, either of which is optionally substituted with one or more substituents independently selected from the group consisting of CN, halo, $C_1$-$C_6$alkyl, $C_1$-$C_6$alkoxy, $C_1$-$C_6$haloalkyl, —O—$C_1$-$C_6$haloalkyl; and with the proviso that when X is S and Z is $C_1$-$C_6$-alkyl, Ar' is not unsubstituted phenyl.

In one embodiment, this invention provides compounds of Formula (I), wherein n is 1 or 2;
X is $CH_2$, O, S, NH, or $NCH_3$;
Y is H or $C_1$-$C_3$alkyl;
Z is H, $C_1$-$C_3$alkyl, $C_1$-$C_3$haloalkyl, —$CH_2$-phenyl, —$CH_2$-heteroaryl, $(CH_2)_2C$(=O)—$OCH_3$, —$CH_2$-heterocycloalkyl, —$CH_2COOH$, —$CH_2C$(=O)-heterocycloalkyl, wherein phenyl, heteroaryl or heterocycloalkyl is optionally substituted with one or more substituents independently selected from the group consisting of $C_1$-$C_6$alkyl, $C_1$-$C_6$alkoxyl, $C_1$-$C_3$haloalkyl, CN, halo and —OH;
Ra is hydrogen or $CH_3$;
Ar is phenyl optionally substituted with one or more substituents independently selected from the group consisting of CN, halo, $C_1$-$C_6$alkyl, $C_1$-$C_6$alkoxy and $CF_3$; and
Ar' is phenyl or heteroaryl, either of which is optionally substituted with one or more substituents independently selected from the group consisting of CN, halo, $C_1$-$C_6$alkyl, $C_1$-$C_6$alkoxy, $C_1$-$C_6$haloalkyl, and —O—$C_1$-$C_6$haloalkyl.

In one embodiment, this invention provides compounds of Formula (I), wherein n is 1, 2 or 3;
X is absent, O, S, NH, or N($C_1$-$C_6$ alkyl);
Y is H, or $C_1$-$C_6$alkyl;
Z is H, $C_1$-$C_6$-alkyl, —$CH_2$-heteroaryl, —$(CH_2)_2C$(=O)—$OCH_3$, —$CH_2COOH$, wherein heteroaryl may be optionally substituted with one or more substituents independently selected from the group consisting of $C_1$-$C_6$alkyl, $C_1$-$C_6$alkoxyl, $C_1$-$C_3$haloalkyl, CN, halo and —OH;
$R_a$ is hydrogen or $C_1$-$C_3$ alkyl;
Ar is phenyl which is optionally substituted with one or more substituents selected from the group consisting of CN, halo, $C_1$-$C_6$alkyl, $C_1$-$C_6$alkoxy, and $C_1$-$C_6$haloalkyl; and
Ar' is phenyl or heteroaryl, either of which is optionally substituted with one or more substituents selected from the group consisting of CN, halo, $C_1$-$C_6$alkyl, $C_1$-$C_6$alkoxy, and $C_1$-$C_6$haloalkyl.

In one embodiment, this invention also relates to compounds of any of the above embodiments, wherein n is 1. In one embodiment, this invention also relates to compounds of any of the above embodiments, wherein n is 2.

In one embodiment, this invention also relates to compounds of any of the above embodiments, wherein X is O. In one embodiment, this invention also relates to compounds of any of the above embodiments, wherein X is $CH_2$. In one embodiment, this invention also relates to compounds of any of the above embodiments, wherein X is NH or $NCH_3$. In one embodiment, this invention also relates to compounds of any of the above embodiments, wherein X is S.

In one embodiment, this invention also relates to compounds of any of the above embodiments, wherein Y is H or $CH_3$. In one embodiment, this invention also relates to compounds of any of the above embodiments, wherein Y is H. In one embodiment, this invention also relates to compounds of any of the above embodiments, wherein Y is $CH_3$. In one embodiment, this invention also relates to compounds of any of the above embodiments, wherein Y is $C_3$-$C_6$ cycloalkyl.

In one embodiment, this invention also relates to compounds of any of the above embodiments, wherein Z is —$CH_2$-heteroaryl, —$CH_2$-heterocycloalkyl or —$CH_2C$(=O)-heterocycloalky, wherein heteroaryl is selected from the group consisting of pyrimidinyl, pyrazolyl, indolyl, pyrimidinonyl, oxadiazolyl, thiazolyl, pyridinyl, pyridazinyl, pyrrolidinyl, and 2-pyridonyl and heterocycloalkyl is selected from the group consisting of piperidinyl, piperazinyl, and pyrrolidinyl.

In one embodiment, this invention also relates to compounds of any of the above embodiments, wherein Z is —$CH_2$-phenyl wherein phenyl is optionally substituted with one or more substituents independently selected from the group consisting of CN, halo and —OH. In one embodiment, this invention also relates to compounds of any of the above embodiments, wherein Z is —$CH_2$-pyrimidinyl, wherein pyrimidinyl is optionally substituted with one or more substituent independently selected from the group consisting of $CH_3$, $CF_3$ and $OCH_3$. In one embodiment, this invention also relates to compounds of any of the above embodiments, wherein Z is —$CH_2$-pyrimidinyl, wherein pyrimidinyl is unsubstituted. In one embodiment, this invention also relates to compounds of any of the above embodiments, wherein Z is —$CH_2$-pyrimidinyl substituted with one substituent selected from $CH_3$ or $OCH_3$. In one embodiment, this invention also relates to compounds of any of the above embodiments, wherein Z is —$CH_2$-phenyl, wherein phenyl is unsubstituted. In one embodiment, this invention also relates to compounds of any of the above embodiments, wherein Z is —$CH_2$-phenyl substituted with one or more substituents independently selected from the group consisting of CN, halo and —OH. In one embodiment, this invention also relates to compounds of any of the above embodiments, wherein Z is —$CH_2$-pyrazolyl optionally substituted with $CH_3$.

In one embodiment, the invention also relates to compounds of any of the above embodiments, wherein Z is —$CH_2$-heterocycloalkyl, —$CH_2C$(=O)-heterocycloalkyl, wherein heterocycloalkyl is selected from the group consisting of piperidinyl, piperazinyl, and pyrrolidinyl and the heterocycloalkyl is optionally substituted with one or more substituents independently selected from the group consisting of halo and $CH_3$.

In one embodiment, this invention also relates to compounds of any of the above embodiments, wherein Z is $C_1$-$C_3$alkyl. In one embodiment, this invention also relates to compounds of any of the above embodiments, wherein Z is ethyl. In one embodiment, this invention also relates to compounds of any of the above embodiments, wherein Z is —$CH_2$-thioazolyl. In one embodiment, this invention also relates to compounds of any of the above embodiments, wherein Z is —$CH_2$-pyrimidin-2(1H)-only. In one embodiment, this invention also relates to compounds of any of the above embodiments, wherein Z is —$CH_2$-2-pyridonyl. In one embodiment, this invention also relates to compounds of any of the above embodiments, wherein Z is —$CH_2$-indolyl optionally substituted with $CH_3$.

In one embodiment, this invention also relates to compounds of any of the above embodiments, wherein Z is —$(CH_2)_2C$(=O)—$OCH_3$. In one embodiment, this invention also relates to compounds of any of the above embodiments, wherein Z is —$CH_2COOH$. In one embodiment, this invention also relates to compounds of any of the above embodiments, wherein Z is —$CH_2CF_3$.

In one embodiment, this invention also relates to compounds of any of the above embodiments, wherein Ra is hydrogen. In one embodiment, this invention also relates to compounds of any of the above embodiments, wherein Ra is $CH_3$.

In one embodiment, this invention also relates to compounds of any of the above embodiments, wherein Ar is phenyl optionally substituted with one or more substituents independently selected from the group consisting of CN, halo, $C_1$-$C_6$alkyl, $C_1$-$C_6$alkoxy and $CF_3$. In one embodiment, this invention also relates to compounds of any of the above embodiments, wherein Ar is unsubstituted phenyl. In one embodiment, this invention also relates to compounds of any of the above embodiments, wherein Ar is phenyl substituted with one or more substituents independently selected from the group consisting of CN, F, $CF_3$ and $OCH_3$. In one embodiment, this invention also relates to compounds of any of the above embodiments, wherein Ar is phenyl substituted with one CN. In one embodiment, this invention also relates to compounds of any of the above embodiments, wherein Ar is phenyl substituted one or more F. In one embodiment, this invention also relates to compounds of any of the above embodiments, wherein Ar is phenyl substituted with one $OCH_3$. In one embodiment, this invention also relates to compounds of any of the above embodiments, wherein Ar is phenyl substituted with one $CF_3$. In one embodiment, this invention also relates to compounds of any of the above embodiments, wherein Ar is phenyl substituted with one halo and one $CH_3$. In one embodiment, this invention also relates to compounds of any of the above embodiments, wherein Ar is phenyl substituted with one —$OCF_3$ and one Cl. In one embodiment, this invention also relates to compounds of any of the above embodiments, wherein Ar is phenyl substituted with one or more halo and each substituent may be the same or different.

In one embodiment, this invention also relates to compounds of any of the above embodiments, wherein Ar' is phenyl substituted with Cl and $CF_3$. In one embodiment, this invention also relates to compounds of any of the above embodiments, wherein Ar' is phenyl substituted with one $CF_3$. In one embodiment, this invention also relates to compounds of any of the above embodiments, wherein Ar' is phenyl substituted with one or more F. In one embodiment, this invention also relates to compounds of any of the above embodiments, wherein Ar' is phenyl substituted with one F and one $CF_3$. In one embodiment, this invention also relates to compounds of any of the above embodiments, wherein Ar' is phenyl substituted with one halo and one $CH_3$. In one embodiment, this invention also relates to compounds of any of the above embodiments, wherein Ar' is phenyl substituted with one Cl and one —$OCF_3$. In one embodiment, this invention also relates to compounds of any of the above embodiments, wherein Ar' is phenyl substituted with one or more halo, and each substituent may be the same or different. In one embodiment, this invention also relates to compounds of any of the above embodiments, wherein Ar' is heteroaryl optionally substituted with one or more substituents independently selected from the group consisting of CN, halo, $C_1$-$C_6$alkyl, $C_1$-$C_6$alkoxy, and $C_1$-$C_6$haloalkyl and wherein the heteroaryl is selected from the group consisting of pyridinyl, pyridazinyl or pyrimidinyl. In one embodiment, this invention also relates to compounds of any of the above embodiments, wherein Ar' is pyridinyl substituted with $CF_3$. In one embodiment, this invention also relates to compounds of any of the above embodiments, wherein Ar' is pyridinyl substituted with Cl. In one embodiment, this invention also relates to compounds of any of the above embodiments, wherein Ar' is pyridinyl substituted with one Cl and one $CF_3$. In one embodiment, this invention also relates to compounds of any of the above embodiments, wherein Ar' is pyridinyl substituted with one $CH_3$. In one embodiment, this invention also relates to compounds of any of the above embodiments, wherein Ar' is pyridazinyl substituted with one $CF_3$. In one embodiment, this invention also relates to compounds of any of the above embodiments, wherein Ar' is pyridazinyl substituted with one Cl. In one embodiment, this invention also relates to compounds of any of the above embodiments, wherein Ar' is pyrimidinyl substituted with one $CF_3$ and one Cl. In one embodiment, this invention also relates to compounds of any of the above embodiments, wherein Ar' is pyrimidinyl substituted with one Cl. In one embodiment, this invention also relates to compounds of any of the above embodiments, wherein Ar' is unsubstituted pyrimidinyl.

In one embodiment, the compounds of Formula (I) has the structure of Formula (IA)

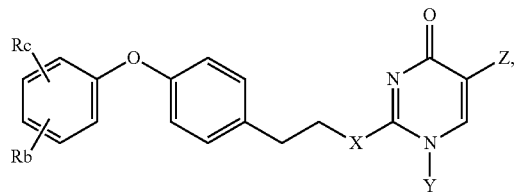

or a pharmaceutically acceptable salt thereof,
wherein Z, X, and Y are defined as in Formula (I),
Rc and Rb are independently selected from the group consisting of H, halo and $CF_3$.

In one embodiment, the compound of Formula (IA) wherein

Z is —$CH_2$-phenyl or —$CH_2$-heteroaryl, wherein phenyl or heteroaryl may be optionally substituted with one or more substituents selected from the group consisting of H, $C_1$-$C_6$alkyl, $C_1$-$C_6$alkoxyl, $C_1$-$C_3$haloalkyl, CN, halo and —OH;

X is O, S, NH, or N—$CH_3$;
Y is H or $CH_3$, and
Rc and Rb are independently selected from the group consisting of H, halo and $CF_3$.

In one embodiment, the compound of Formula (IA), wherein Z is —$CH_2$-phenyl, wherein phenyl is optionally substituted with one or more substituents independently selected from the group consisting of CN, halo and —OH. In one embodiment, the compound of Formula (IA), wherein Z is —$CH_2$-pyrimidinyl, wherein pyrimidinyl is optionally substituted with one substituent selected from $CH_3$ or $OCH_3$. In one embodiment, the compound of Formula (IA), wherein Z is —$CH_2$-unsubstituted pyrimidinyl. In one embodiment, the compound of Formula (IA), wherein Z is —$CH_2$-pyrimidinyl substituted with one substituent selected from $CH_3$ or $OCH_3$. In one embodiment, the compound of Formula (IA), wherein Z is —$CH_2$-pyrimidinyl optionally substituted with one $OCH_3$. In one embodiment, the compound of Formula (IA), wherein Z is —$CH_2$-unsubstituted phenyl. In one embodiment, the compound of Formula (IA), wherein Z is —$CH_2$-phenyl optionally substituted with one or more substituents independently selected from the group consisting of CN, halo and —OH.

In one embodiment, this invention also relates to compounds of any of the above embodiments related to Formula (IA), wherein X is O. In one embodiment, this invention also relates to compounds of any of the above embodiments related to Formula (IA), wherein X is absent. In one embodiment, this invention also relates to compounds of any of the above embodiments related to Formula (IA), wherein X is NH or $NCH_3$.

In one embodiment, this invention also relates to compounds of any of the above embodiments related to Formula (IA), wherein Y is H. In one embodiment, this invention also relates to compounds of any of the above embodiments related to Formula (IA), wherein Y is $CH_3$.

In one embodiment, this invention also relates to compounds of any of the above embodiments related to Formula (IA), Rc and Rb are independently halo or CF$_3$. In one embodiment, this invention also relates to compounds of any of the above embodiments related to Formula (IA), Rc and Rb are independently Cl or CF$_3$.

In one embodiment, the compound of Formula (I) has the structure of Formula (IA), or pharmaceutically acceptable salts thereof, wherein Z is —CH$_2$-pyrimidinyl, wherein pyrimidinyl is optionally substituted with one OCH$_3$; X is O; Y is H; Rc and Rb are independently halo or CF$_3$.

In one embodiment, a compound according to Formula (I) or Formula (IA) has the structure of

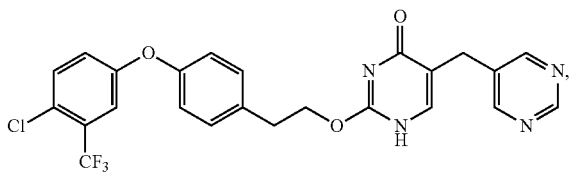 [SMILES: O=c1nc(OCCc2ccc(Oc3ccc(Cl)c(C(F)(F)F)c3)cc2)[nH]cc1Cc1cncnc1]

or a pharmaceutically acceptable salt thereof.

In one embodiment, a compound according to Formula (I) or Formula (IA) has the structure of,

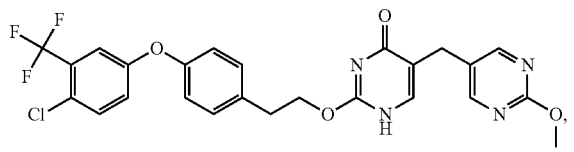 [SMILES: COc1ncc(Cc2c[nH]c(OCCc3ccc(Oc4ccc(Cl)c(C(F)(F)F)c4)cc3)nc2=O)cn1]

or a pharmaceutically acceptable salt thereof.

The compounds of Formula (I), Formula (IA), or pharmaceutically acceptable salts thereof, or pharmaceutically acceptable solvates thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I) or Formula (IA) or pharmaceutically acceptable salts, or pharmaceutically acceptable solvates thereof as mixtures with isomers thereof in which one or more chiral centers are inverted. Likewise, it is understood that the compounds of Formula (I) or Formula (IA), or pharmaceutically acceptable salts thereof, or pharmaceutically acceptable solvates thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of Formula (I) or Formula (IA) or pharmaceutically acceptable salts thereof, or pharmaceutically acceptable solvates thereof as well as any wholly or partially equilibrated mixtures thereof. The present invention also includes the individual isomers of the compounds of Formula (I) or Formula (IA) or pharmaceutically acceptable salts thereof, or pharmaceutically acceptable solvates thereof as well as mixtures with isomers thereof in which one or more chiral centers are inverted. It is to be understood that the present invention includes all combinations and subsets of the particular groups defined hereinabove.

Certain compounds described herein may contain one or more chiral atoms, or may otherwise be capable of existing as enantiomers. The compounds of the present invention include mixtures of enantiomers as well as purified enantiomers or enantiomerically enriched mixtures. Also included within the scope of the invention are the individual isomers of the compounds of the present invention as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the compounds described herein are included within the scope of the compounds of the present invention. The different isomeric forms may be separated or resolved one from the other by conventional methods, or any given isomer may be obtained by conventional synthetic methods or by stereospecific or asymmetric syntheses.

The invention also includes various deuterated forms of compounds of Formula (I) or Formula (IA), or pharmaceutically acceptable salts thereof, or pharmaceutically acceptable solvates thereof. Each available hydrogen atom attached to a carbon atom may be independently replaced with a deuterium atom. A person of ordinary skill in the art will know how to synthesize deuterated forms of compounds of Formula (I) or Formula (IA) or pharmaceutically acceptable salts thereof, or pharmaceutically acceptable solvates thereof. Commercially available deuterated starting materials may be employed in the preparation of deuterated forms of compounds of Formula (I) or Formula (IA) or pharmaceutically acceptable salts thereof, or pharmaceutically acceptable solvates thereof or they may be synthesized using conventional techniques employing deuterated reagents (e.g. lithium aluminum deuteride).

In addition to the free base form of the compounds described herein, the salt form of the compounds is also within the scope of the present invention. The pharmaceutically-acceptable salts may be prepared in situ during the final isolation and purification of the compound, or by separately reacting the purified compound in its free acid or free base form with a suitable base or acid, respectively.

In one embodiment, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amophorus. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

As used herein, the term "compounds of the invention" means both the compounds according to Formula I, Formula (IA), the pharmaceutically-acceptable salts thereof, and the pharmaceutically-acceptable solvates thereof. The term "a compound of the invention" also appears herein and refers to both a compound according to Formula I, Formula (IA), the pharmaceutically-acceptable salts thereof, and the pharmaceutically-acceptable solvates thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing vaiable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The invention includes all such polymorphs.

C. SYNTHESIS OF COMPOUNDS

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Schemes A-C provide an exemplary process of synthesis for preparing some compounds of the present invention.

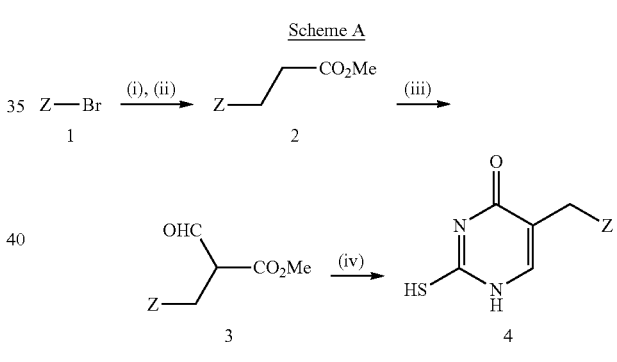

General Experimental Scheme A provides an exemplary synthesis for preparing intermediate 3 and 4. When Z comprises an aromatic ring, step (i) is a Heck reaction by reacting 1 with methyl acrylate using an appropriate palladium catalyst system such Pd(OAc)/tri-o-tolylphosphine, Pd(dppf)Cl$_2$ in a suitable solvent such as dimethylformamide (DMF) at a suitable temperature such as about 130° C. to provide the intermediate which is then reduced by H$_2$ (step (ii)) using catalyst such as palladium/carbon, Raney-Nickel in an alcohol solvent to provide 2.

When Z is H, alkyl chain, —(CH$_2$)$_2$C(=O)—OCH$_3$, —CH$_2$COOH, 2 is generally commercial available.

Step (iii) is carried out by reacting 2 with methyl formate using an appropriate base such as sodium hydride, potassium tert-butoxide in a suitable solvent such as tetrahydrofuran (THF) to provide 3. Further reacting 3 with thiourea using a suitable base such as potassium tert-butoxide, sodium hydroxide in an appropriate alcohol solvent such as isopropanol, ethanol to provide 4.

Scheme B

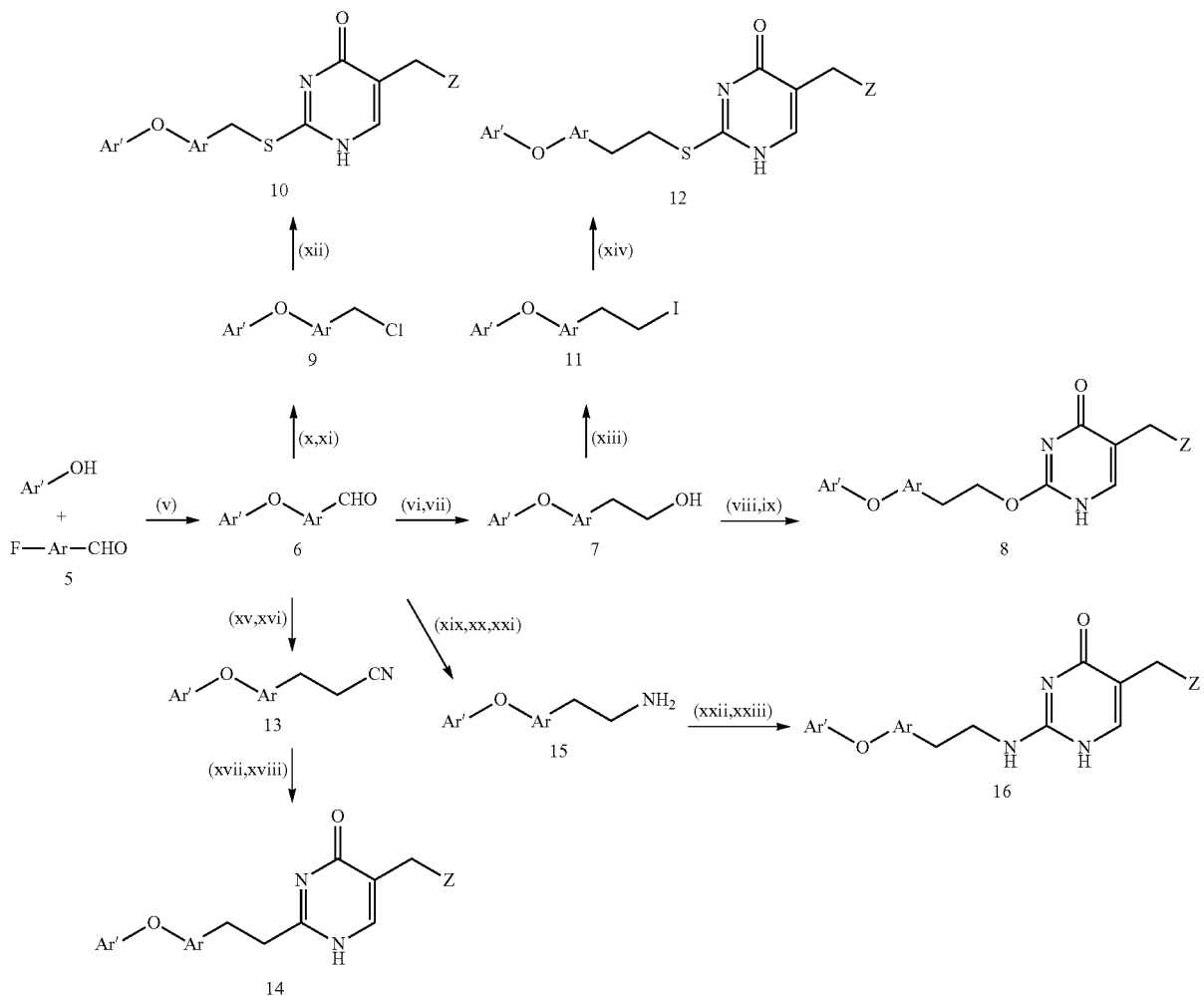

Scheme B provides an exemplary synthesis for preparing compound 8, 10, 12, 14, and 16 where X is defined in Formula (I). Step (v) is carried out by reacting Ar'OH and 5 with a suitable inorganic base such as potassium carbonate in a polar solvent such as DMF at an suitable temperature such as a temperature in a range of 80-140° C. to provide intermediate 6.

Intermediate 6 is reduced in step (x) by a suitable reductive reagent such as NaBH$_4$ in a suitable alcohol solvent such as ethanol to provide an intermediate alcohol which is then chlorinated in step (xi) by a suitable chlorination reagent such as sulfurous dichloride in an appropriate solvent such as dichloromethane to provide 9. Step (xii) is taken place by reacting 9 with 4 by a suitable base such as diisopropylethylamine (DIPEA), triethylamine (TEA), K$_2$CO$_3$ in a suitable solvent such as chloroform, dichloromethane under a suitable temperature such as a temperature in a range of room temperature to 60° C. to provide 10 where Ar', Ar, Z are defined in Formula (I)

Step (xv) is a Wittig reaction by reacting 2-(triphenylphosphanylidene) acetonitrile with 6 using an appropriate base such as NaOH, potassium tert-butoxide, n-BuLi in a suitable solvent such as dichloromethane, THF at a suitable temperature such as a temperature in a range of 0° C. to room temperature to provide alkene which may be reduced by H$_2$ as step (ii) described above to give 13. Step (xvii) can be taken place by reacting 13 with methanol in an acidic condition such as acetate chloride/methanol then followed by reacting with ammonia in methanol to give imidamide intermediate which can be cyclized with 3 in step (xviii) with a suitable base such as potassium acetate in a suitable solvent such as toluene refluxed overnight to provide 14 where Ar', Ar, Z are defined in Formula (I).

Step (vi) is Wittig reaction by reacting 6 with methyltriphenylphosphonium bromide to provide alkene which can be reacted with an appropriate base such as 9-borabicyclo[3,3,1]nonane (9-BBN) then H$_2$O$_2$ in a suitable solvent such as THF to provide alcohol 7. Step (viii) is taken place by reacting 7 with cyanamide by a suitable strong acidic reagent such as trifluoromethanesulfonic acid, HCl in a suitable solvent such as THF, 1,4-dioxane at an appropriate temperature such as 0° C. to provide carbamimidate intermediate. Step (ix) is carried out by reacting the carbamimidate intermediate with 3 with an appropriate base such as K$_2$CO$_3$ in suitable solvent such as N-Methyl-2-pyrrolidone (NMP), 1,4-dioxane under an appropriate temperature range such as 120-160° C. to provide 8 where Ar', Ar, Z are defined in Formula (I).

Step (xiii) is carried out by reacting 7 with an appropriate reagent such as Ph$_3$P/iodine in a suitable solvent such as dichloromethane to provide 11. Step (xiv) is taken place by reacting 11 with 4 under a suitable basic reagent such as $K_2CO_3$ in a suitable polar solvent such as DMF to provide 12 where Ar', Ar, Z are defined in Formula (I).

Step (xix) is carried out by reacting 6 with nitromethane in the presence of ammonium acetate in a suitable solvent such as acetic acid to provide nitrovinyl intermediate which is reduced by $H_2$ in step (xx) as step (ii). The resulted nitroethyl is then reacted with a suitable reductive reagent such as $NaBH_4$ in step (xxi) in an appropriate solvent such as methanol in the presence of a suitable reagent such as nickel(II) chloride hexahydrate to provide amine 15. Step (xxii) is carried out by reacting 15 with 1H-pyrazole-1-carboximidamide in presence of a suitable base such as diisopropylethylamine (DIPEA) in a suitable solvent such as DMF to give a guanidine intermediate which is then cyclized in step (xxiii) by reacting with 3 in a suitable solvent such as ethanol at an appropriate temperature such as 100° C. to provide 16 where Ar', Ar, Z are defined in Formula (I).

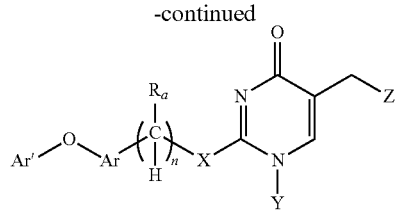

21

X = absent, S, O, NH, $N(C_1-C_6 alkyl)$

Alternatively, the compounds of Formula (I) can be prepared using procedures described in Scheme D. 3 can be prepared as described in Scheme A. Step (xxv) can be carried out by reacting 19 with 3 and a suitable base such as $K_2CO_3$, DIPEA, KOAc, $^tBuOK$, EtONa at an appropriate temperature such as 80-160° C. in a suitable solvent such as DMF, ethanol, toluene, NMP to provide 20. Step (xxvi) can be taken place similar to step (xxiv) as described in Scheme C to give 21 where Ar', Ar, X, Y, $R_a$, Z are defined in Formula (I).

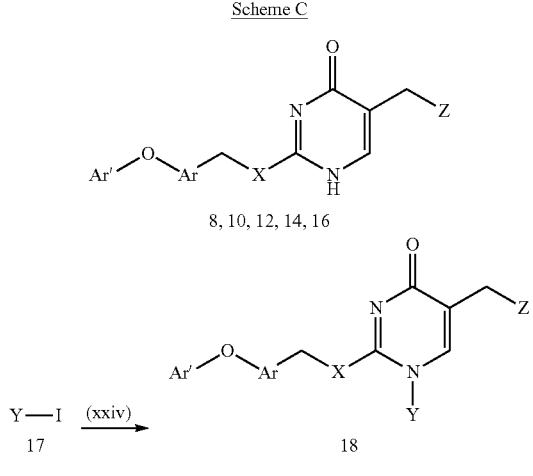

Scheme C provides an exemplary synthesis for preparing compound 18. Step (xxiv) is carried out by reacting starting material 8, 10, 12, 14 or 16 with 17 in the presence of a suitable base such as DIPEA, $K_2CO_3$ in a suitable solvent such as dichloromethane to provide 18 where Ar', Ar, X, Y, Z are defined in Formula (I).

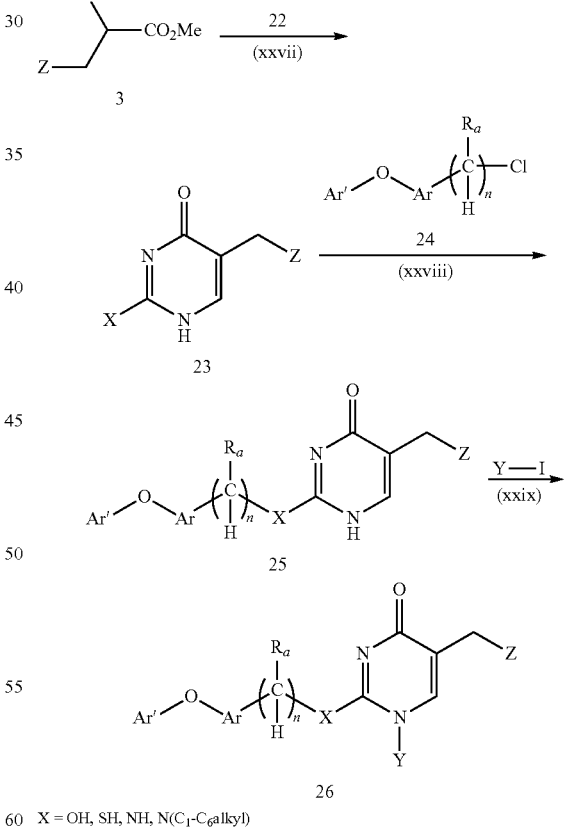

X = OH, SH, NH, $N(C_1-C_6 alkyl)$

Alternatively, the compounds of Formula (I) can also be made using process described in Scheme E. Step (xxvii) can be taken place by reacting 3 with 22 and a suitable base such as $K_2CO_3$, DIPEA, KOAc, $^tBuOK$, EtONa at an appropriate temperature in a temperature range such as 80-160° C. in a

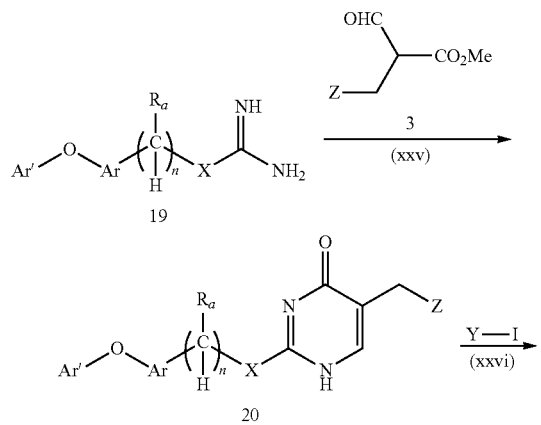

suitable solvent such as DMF, ethanol, toluene, NMP to provide 23. Step (xxviii) is alkylation reaction by reacting 23 with 24 in presence of suitable base such as $K_2CO_3$ in a suitable solvent such as DMF, NMP at an appropriate temperature such as 25-80° C. to provide 25. Step (xxix) can be carried out as step (xxiv) to provide 26, where Ar', Ar, X, Y, $R_a$, Z are defined in Formula (I).

General Experimental Procedures

Heating of reaction mixtures with microwave irradiations was carried out on a Smith Creator (purchased from Personal Chemistry, Forboro/MA, now owned by Biotage), an Emrys Optimizer (purchased from Personal Chemistry) or an Explorer (provided by CEM Discover, Matthews/NC) microwave.

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or recrystallization using suitable solvents. Chromatographic methods are known to the skilled person and include e.g. column chromatography, flash chromatography, HPLC (high performance liquid chromatography), and MDAP (mass directed autopreparation, also referred to as mass directed LCMS purification). MDAP is described in e.g. W. Goetzinger et al, *Int. J. Mass Spectrom.*, 2004, 238, 153-162.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5u C18(2) 100 A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a prepacked $SiO_2$ column, a detector with UV wavelength at 254 nm and mixed solvents.

The terms "CombiFlash", "Biotage®", "Biotage 75" and "Biotage SP4®" when used herein refer to commercially available automated purification systems using pre-packed silica gel cartridges.

Final compounds were characterized with LCMS (conditions listed below) or NMR. $^1$H-NMR spectra were recorded using a Bruker Avance 400 MHz spectrometer. $CDCl_3$ is deuteriochloroform, DMSO-$d_6$ is hexadeuteriodimethylsulfoxide, and $CD_3OD$ (or MeOD) is tetradeuteriomethanol. Chemical shifts are reported in parts per million (δ) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on instruments, using electrospray (ES) ionization techniques. All temperatures are reported in degrees Celsius. All other abbreviations are as described in the ACS Style Guide (American Chemical Society, Washington, D.C., 1986).

LCMS Conditions:
1) Acidic conditions:
Mobile phase: water containing 0.05% TFA/0.05% acetonitrile
Column: Agilent SB-C18 4.6×30 mm-1.8 microns
Detection: MS and photodiode array detector (PDA)
2) Basic conditions:
Mobile phase: water containing 10 mmol $NH_4HCO_3$/acetonitrile
Column: XBridge™ C18 4.6×50 mm-3.5 microns
Detection: MS and photodiode array detector (PDA)
MDAP Conditions:
1) Acidic conditions:
Instrument: Waters instrument
Column: Sunfire Prep C18 column (5 um, 19×50 mm)
Mobile phase: water containing 0.05% TFA/acetonitrile.
2) Basic conditions:
Instrumnet: Waters instrument
Column: Xbridge Prep C18 column (5 um, 19×50 mm)
Mobile phase: water containing 0.04% ammonia/acetonitrile.

Abbreviations and Resource Sources

The following abbreviations and resources are used herein below:
ISCO system—Teledyne ISCO (http://www.isco.com/html/seFlashChromatography.html)
r.t/rt/RT—Room Temperature;
ACN—Acetonitrile;
AcCl—Acetic chloride
Aq.—aqueous
CV—Column volumesDABCO-1,4-diazabicyclo[2.2.2]octane
DAST—Diethylaminosulfur trifluoride
DABCO—1,4-diazabicyclo[2.2.2]octane
DBU—1,8-Diazabicyclo[5.4.0]undec-7-ene
DCE—Dichloroethene
DCM—Dichloromethane;
DIAD—Diisopropyl azodiformate
DIPEA—N,N-Diisopropylethylamine
DMA—N,N-Dimethylacetamide;
DMAP—4-Dimethylaminopyridine
DME—1,2-Dimethoxyethane;
DMF—Dimethylformamide;
EA—Ethyl acetate;
EDC—1-ethyl-3-(3-dimethylaminopropyl)carbodiimide hydrochloride
HATU—2-(1H-7-Azabenzotriazol-1-yl)-1,1,3,3-tetramethyl uronium hexafluorophosphate Methanaminium
HOBT—Hydroxybenzotriazole
NBS—N-bromosuccinamide;
NIS—N-iodosuccinimide
NMP—N-methyl-2-pyrrolidone;
TBAF—Tetra-n-butylammonium fluoride
TEA—Triethylamine;
TFA—Trifluoro acetic acid
TfOH—Trifluoromethanesulfonic acid
THF—Tetrahydrofuran;
PE—Petroleum ether;
DIBAL-H—Diisobutylaluminum hydride;
9-BBN—9-Borabicyclo[3,3,1]nonane;
Nomenclature
ChemBioDraw Ultra, or MDL ISIS/Draw 2.5 SPI

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

Intermediates D1: Methyl (2E)-3-(5-pyrimidinyl)-2-propenoate

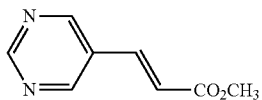

A solution of 5-bromopyrimidine (22.82 g, 144 mmol), methyl 2-propenoate (14.83 g, 172 mmol), palladium(II) acetate (0.322 g, 1.435 mmol), tri-o-tolylphosphine (0.874 g, 2.87 mmol), and TEA (32.0 g, 316 mmol) in DMF (100 mL) was heated at 130° C. under $N_2$ for 7 h. After cooling, the reaction mixture was partitioned between water (200 mL) and DCM (200 mL). The organic phase was collected, washed with water (200 mL×4), brine, dried over sodium sulphate, and concentrated in vacuo to give the crude title compound as a pale yellow solid (18.4 g, 95 mmol, 66.4%). LCMS: rt=1.01 min, [M+H$^+$]=165

D2: Methyl 3-(5-pyrimidinyl)propanoate

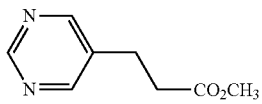

A solution of methyl (2E)-3-(5-pyrimidinyl)-2-propenoate (19.2 g, 117 mmol) and Pd/C (2 g, 1.879 mmol) in methanol (100 mL) was stirred under $H_2$ at 50° C. overnight. The mixture was filtered through a pad of celite and concentrated to give the crude title compound as yellow oil (18 g, 55.6% yield). LCMS: rt=1.11 min, [M+H$^+$]=167

D3: Methyl 2-formyl-3-(5-pyrimidinyl)propanoate

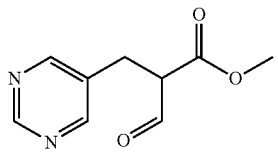

To an ice-cooled solution of KO$^t$Bu (43.0 g, 384 mmol) in anhydrous THF (300 ml) stirred under nitrogen was added methyl formate (18.43 g, 307 mmol) and methyl 3-(pyrimidin-5-yl)propanoate (25.5 g, 153 mmol) in anhydrous THF (10 mL) dropwise for 1 h. The mixture was stirred for 3 hr. The solvent was removed, and the residue was dissolved in water (150 mL). The aqueous phase was washed with ether (200 mL×3), and then to the aqueous solution was added AcOH to adjust the pH=5. The solid was collected and dried to give the target compound. The filtrate was extracted with DCM (200 mL×2), and the combined organic phase was dried over sodium sulfate, filtered and concentrated. The two crops were combined to give the title product as a yellow solid (18 g, 57.4% yield). LCMS: rt=0.96 min, [M+H$^+$]=195

D4: Methyl (2E)-3-[2-(methyloxy)-5-pyrimidinyl]-2-propenoate

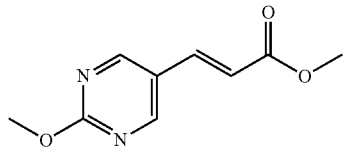

A mixture of 5-bromo-2-(methyloxy)pyrimidine (25.0 g, 132 mmol), methyl 2-propen-oate (13.7 g, 159 mmol), palladium(II) acetate (0.297 g, 1.32 mmol), tri-o-tolylphosphine (0.805 g, 2.65 mmol) and triethylamine (29.4 g, 291 mmol) in DMF (75 mL) was heated at 130° C. under $N_2$ for 3 h, then diluted with water (200 mL) and DCM (200 mL). The organic layer was collected, washed with water (200 mL×4) and brine, dried over sodium sulphate and concentrated to give the title compound as a pale yellow solid (24 g, 81%), which was used without further purification D5: Methyl 3-[2-(methyloxy)-5-pyrimidinyl]propanoate

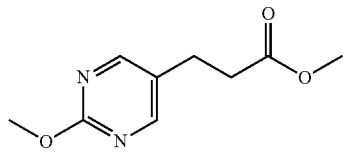

A mixture of methyl (2E)-3-[2-(methyloxy)-5-pyrimidinyl]-2-propenoate (24.0 g, 124 mmol) and Pd/C (300 mg) in methanol (250 mL) was stirred at 50° C. under $H_2$ for two days, filtered through a pad of Celite and concentrated to give the title compound as a yellow oil (20 g, 68%), which was used without further purification. LCMS: rt=1.17 min, [M+H$^+$]=196

D6: (2E) methyl-3-Hydroxy-2-{[2-(methyloxy)-5-pyrimidinyl]methyl}-2-propenoate

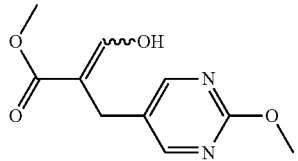 [SMILES: COC(=O)C(=CO)Cc1cnc(OC)nc1]

To a suspension of NaH (14.7 g, 367 mmol) in DME (216 mL) was added dropwise a mixture of methyl 3-[2-(methyloxy)-5-pyrimidinyl]propanoate (18 g, 92 mmol) and methyl formate (33.1 g, 550 mmol) in DME (216 mL) under $N_2$ at 0° C. The reaction mixture was stirred at 25° C. overnight, then filtered through a pad of Celite. The filtrate was diluted with ether (500 mL), kept standing for about 2 h and re-filtered. The filtrated cake was washed with diethyl ether and dried to give the title compound (14 g, 51.7%), which was used into next step without further purification.

D7: 1-Methyl-1H-pyrazole-4-carbaldehyde

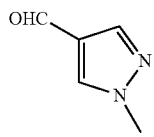

A solution of 1-methyl-1H-pyrazole (20 g, 244 mmol) in dry DMF (50 ml) was heated to 90° C., then POCl$_3$ (23.84 ml, 256 mmol) was added dropwise over 1 h, while the internal temperature was maintained between 95-100° C. After heating for a further 2 h, the mixture was cooled and poured onto ice (500 g). It was extracted with DCM (300 ml×2), the collected organic parts were washed with brine (50 ml), dried over MgSO$_4$, and concentrated to give title compound as brown oil (18 g). LCMS: rt=0.90 min, [M+H$^+$]=111

D8: (E)-3-(1-Methyl-1H-pyrazol-4-yl)acrylic acid

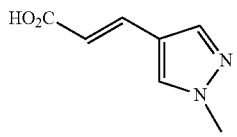

A mixture of 1-methyl-1H-pyrazole-4-carbaldehyde (13 g, 118 mmol), malonic acid (12.29 g, 118 mmol), pyridine (65 ml) and piperidine (0.234 ml, 2.361 mmol) was heated to 110° C. under argon for 4 h. After cooling, water (100 ml) was added, followed by aqueous ammonia (12 ml) to obtain a clear solution, which was acidified to pH~1 with hydrochloric acid. The precipitate was collected by filtration, washed with water and dried to obtain the title compound (7.5 g, 40.5% yield). LCMS: rt=0.92 min, [M+H$^+$]=153

D9: (E)-Methyl 3-(1-methyl-1H-pyrazol-4-yl)acrylate

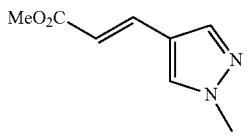

(2E)-3-(1-Methyl-1H-pyrazol-4-yl)-2-propenoic acid (7.5 g, 49.3 mmol) was added to a solution of H$_2$SO$_4$ (1.760 ml, 33.0 mmol) in methanol (40 ml), and the resultant mixture was refluxed for 4 h. It was cooled to room temperature, then poured into ice. The acid was neutralized with aqueous sodium hydroxide and extracted with DCM (80 ml×2). The organic phases were collected and combined, dried over MgSO$_4$, and concentrated. The residue was washed with petroleum ether and concentrated to give the title compound (7 g, 71.8% yield). LCMS: rt=1.13 min, [M+H$^+$]=167

D10: Methyl 3-(1-methyl-1H-pyrazol-4-yl)propanoate

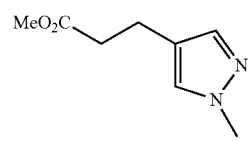

To a solution of methyl ((E)-Methyl 3-(1-methyl-1H-pyrazol-4-yl)acrylate (18 g, 108 mmol) in ethanol (300 ml) was added Pd/C (4 g, 37.6 mmol) at room temperature. The reaction mixture was stirred at 40° C. for 12 h under hydrogen. The reaction mixture was cooled to room temperature, then the solid was removed by filtration. The filtrate was concentrated in vacuo to give the title compound as colorless oil (17.8 g, 80% yield). LCMS: rt=1.27 min, [M+H$^+$]=169

D11: Methyl 2-formyl-3-(1-methyl-1H-pyrazol-4-yl)propanoate

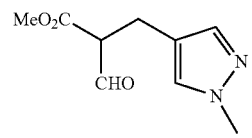

A solution of methyl 3-(1-methyl-1H-pyrazol-4-yl)propanoate (18.7 g, 111 mmol) and methyl formate (14.02 g, 233 mmol) in dry THF (20 ml) was added dropwise over 2 h to a stirred, ice-cooled suspension of t-BuOK (31.2 g, 278 mmol) in dry THF (160 ml) under argon. The mixture was then allowed to warm to room temperature and stirred for 16 h. The solvents were removed in vacuo, and the residue was dissolved in water (50 ml). The solution was extracted with ethyl acetate (30 ml×2), and the aqueous phase was neutralized with 1M HCl to pH~5. The solid was collected. The filtrate was extracted with ethyl acetate (40 ml×2), dried over Na$_2$SO$_4$, filtered and concentrated in vacuo. The solids were combined to give the title compound as a white solid (9.1 g, 39.8% yield). LCMS: rt=1.05 min, [M+H$^+$]=197

D12: 2-(Triphenylphosphanylidene)acetonitrile

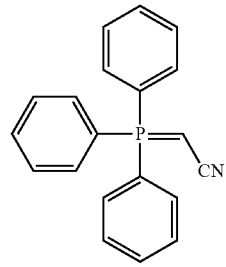 [SMILES: N#CC=P(c1ccccc1)(c1ccccc1)c1ccccc1]

A solution of bromoacetonitrile (26.2 g, 218 mmol) and triphenylphosphine (52.0 g, 198 mmol) in ethyl acetate (240 mL) was stirred at 85° C. overnight, filtered and washed with petroleum ether. The filtrated cake was dried in air to give the title compound as a white solid (75 g), which was used without further purification. LCMS: rt=0.95 min, [M+H$^+$]=302

D13: (E)-3-(3-Bromo-4-fluorophenyl)acrylonitrile

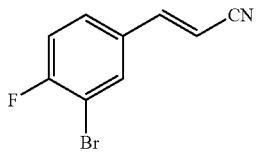 [SMILES: N#C/C=C/c1ccc(F)c(Br)c1]

To a mixture of (cyanomethyl)triphenylphosphonium bromide (70.6 g, 185 mmol) and sodium hydroxide (7.39 g, 185 mmol) in DCM (100 mL) and water (300.00 mL) at 0° C. was added 3-bromo-4-fluorobenzaldehyde (25.0 g, 123 mmol). It was allowed to warm to room temperature and stirred for 2 h. The organic layer was separated, and the water layer was extracted with DCM twice. The combined organic phases were dried over Na$_2$SO$_4$ and concentrated to give a crude product, which was washed with diethyl ether. The residue was purified to give the title compound as a white solid (35 g, 88% yield). LCMS: rt=1.50 min, [M+H$^+$]=226

D14: 3-(3-Bromo-4-fluorophenyl)propanenitrile

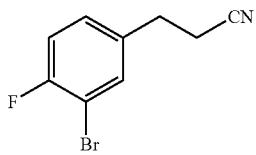 [SMILES: N#CCCc1ccc(F)c(Br)c1]

To a solution of (E)-3-(3-bromo-4-fluorophenyl)acrylonitrile (35.0 g, 108 mmol) in ethanol (20 mL) at 0° C. was added sodium tetrahydroborate (16.40 g, 434 mmol). The reaction mixture was allowed to warm to 70° C. and stirred for 4 h. Water was added to quench the reaction, and the organic layer was separated. The water layer was extracted with DCM twice, and the combined organic phase was dried and concentrated. The residue was purified by chromatography to afford the title compound as an oil (20 g, 64.7% yield). LCMS: rt=1.45 min, [M+H$^+$]=228

D15: 3-(3-Bromo-4-fluorophenyl)propanimidamide hydrochloride

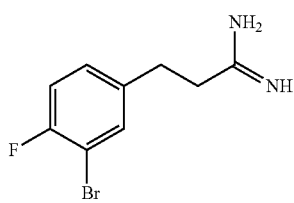 [SMILES: N=C(N)CCc1ccc(F)c(Br)c1]

To a solution of 3-(3-bromo-4-fluorophenyl)propanenitrile (5.0 g, 21.05 mmol) in toluene (20 mL) and methanol (6.32 mL, 156 mmol) at 0° C. was added acetyl chloride (7.51 mL, 105 mmol) dropwise over 5 min. The reaction mixture was allowed to warm to room temperature and stirred for 2 h. The mixture was cooled to 0° C. by an ice bath, to which ammonia (30.1 mL, 210 mmol) was added dropwise. The reaction mixture was stirred at room temperature overnight. The mixture was filtered, and the filtrate was concentrated to give a crude product. Recrystallization from toluene/methanol (1:1) then afforded the title compound as a white solid (5.2 g, 93% yield). LCMS: rt=1.18 min, [M+H$^+$]=245

D16: 2-(3-Bromo-4-fluorophenethyl)-5-(pyrimidin-5-ylmethyl)pyrimidin-4(1H)-one

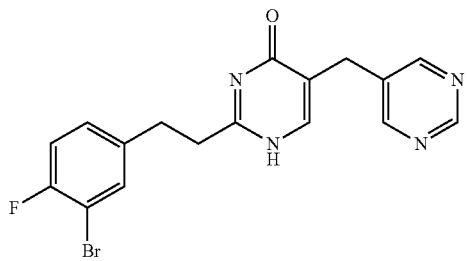 [SMILES: O=c1nc(CCc2ccc(F)c(Br)c2)[nH]cc1Cc1cncnc1]

The mixture of 3-(3-bromo-4-fluorophenyl)propanimidamide hydrochloride (5.0 g, 19.38 mmol), potassium carbonate (9.37 g, 67.8 mmol) and ethyl 2-formyl-3-(5-pyrimidinyl)propanoate (4.03 g, 20.35 mmol) in toluene (100 mL) was stirred at 115° C. for 2.5 h. After cooling, the mixture was diluted with water, then extracted with DCM (50 mL×2). The combined organic phase was concentrated to give the crude title compound as a light yellow solid (6.0 g, 77% yield). The crude was used without further purification. LCMS: rt=1.20 min, [M+H$^+$]=389

D17: 2-Fluoro-5-(2-(4-oxo-5-(pyrimidin-5-ylmethyl)-1,4-dihydropyrimidin-2-yl)ethyl)benzonitrile

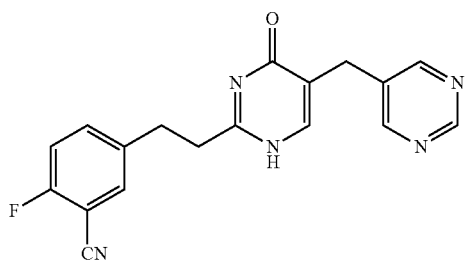 [SMILES: N#Cc1cc(CCc2nc(=O)c(Cc3cncnc3)c[nH]2)ccc1F]

A mixture of 2-(3-bromo-4-fluorophenethyl)-5-(pyrimidin-5-ylmethyl)pyrimidin-4(1H)-one (1.5 g, 3.7 mmol), copper(I) cyanide (399 mg, 4.4 mmol) in NMP (5 mL) was heated with a microwave reactor at 200° C. for 1.5 h. After cooling to room temperature, the mixture was filtered. The filtrate was partitioned between ethyl acetate (20 mL) and water (30 mL). The organic phase was collected, washed with water (30 mL×2), brine (20 mL), dried over Na$_2$SO$_4$, filtered, and concentrated to give the title compound as a gray solid (1.0 g, 55% yield), which was used without further purification. LCMS: rt=1.31 min, [M+H$^+$]=336

D18: 2-(3-Bromo-4-fluorophenethyl)-5-((2-methoxypyrimidin-5-yl)methyl)pyrimidin-4(1H)-one

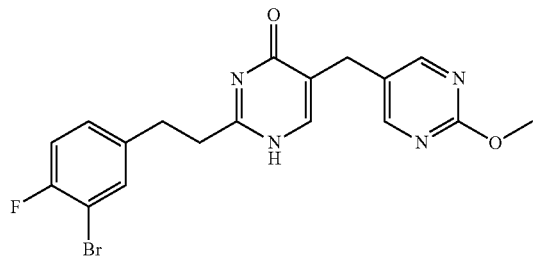 [SMILES: COc1ncc(Cc2c[nH]c(CCc3ccc(F)c(Br)c3)nc2=O)cn1]

The mixture of 3-(3-bromo-4-fluorophenyl)propanimidamide (3.28 g, 13.38 mmol), methyl (2Z)-3-hydroxy-2-{[2-(methyloxy)-5-pyrimidinyl]methyl})-2-propenoate (1.5 g, 6.69 mmol) and K$_2$CO$_3$ (2.77 g, 20.07 mmol) in NMP (20 mL) was heated with a microwave reactor at 130° C. for 2 h. The mixture was purified with a reverse phase Biotage to provide the title compound (1.2 g, 40.6% yield). LCMS: rt=2.52 min, [M+H$^+$]=419

D19: 2-Fluoro-5-(2-(5-((2-methoxypyrimidin-5-yl)methyl)-4-oxo-1,4-dihydropyrimidin-2-yl)ethyl)benzonitrile

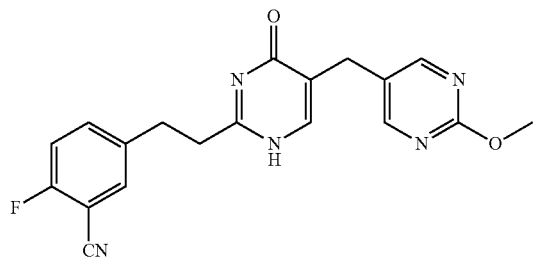 [SMILES: COc1ncc(Cc2c[nH]c(CCc3ccc(F)c(C#N)c3)nc2=O)cn1]

The mixture of 2-[2-(3-bromo-4-fluorophenyl)ethyl]-5-{[2-(methyloxy)-5-pyrimidinyl]methyl})-4(1H)-pyrimidinone (300 mg, 0.716 mmol) and copper(I) cyanide (77 mg, 0.859 mmol) in NMP (2 mL) was heated with a microwave reactor at 200° C. for 2 h. Purification via Biotage then afforded the title compound (80 mg, 30.6% yield). LCMS: rt=2.21 min, [M+H$^+$]=366

D20: 4-{[4-Chloro-3-(trifluoromethyl)phenyl]oxy}benzaldehyde

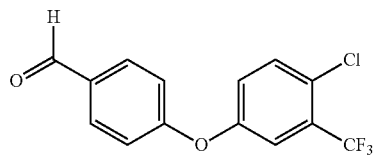 [SMILES: O=Cc1ccc(Oc2ccc(Cl)c(C(F)(F)F)c2)cc1]

The mixture of 4-chloro-3-(trifluoromethyl)phenol (3.2 g, 16.28 mmol), 4-fluorobenz aldehyde (2.425 g, 19.54 mmol) and K$_2$CO$_3$ (3.38 g, 24.42 mmol) in DMF (25 mL) was heated with a microwave reactor at 120° C. for 20 min. Purification via an ISCO system then afforded the title compound as a yellow solid (4.9 g, 100% yield). LCMS: rt=3.78 min, [M+H$^+$]=300.9

D21: 1-Chloro-2-(trifluoromethyl)-4-(4-vinylphenoxyl)benzene

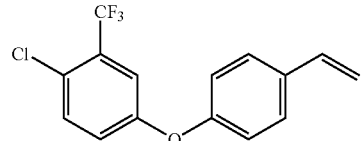

(a) NaH (16.76 g, 419 mmol) was added to a solution of 4-{[4-chloro-3-trifluoromethyl)phenyl]oxy}benzaldehyde (20 g, 66.5 mmol) and ethyltriphenylphosphonium iodide (25.7 g, 71.9 mmol) in THF (140 mL) at 0° C. The resultant mixture was stirred at room temperature overnight. Brine (80 mL) was added slowly to quench the reaction. The organic phase was collected, and washed with brine (80 mL×2), dried over anhydrous sodium sulfate, and concentrated. Purification via a column chromatography then afforded the title compound as a colorless oil (15.75 g, 78% yield).

(b) An alternative synthesis was provided to prepare the compound of D21: To a suspension of methyltriphenylphosphonium bromide (64.7 g, 181 mmol) in anhydrous tetrahydrofuran (THF) (20 mL) was added dropwise n-butyllithium (113 mL, 181 mmol) under −78° C. over 30 mins. The reaction mixture was stirred for 1 h, and then was added a solution of 4-{[4-chloro-3-(trifluoromethyl)phenyl]oxy}benzaldehyde (36.3 g, 121 mmol) in anhydrous tetrahydrofuran (15 ml). The reaction mixture was warmed slowly to room temperature and stirred overnight at room temperature. The mixture was quenched with water and extracted with ethyl acetate. The organic phase was dried with anhydrous Na$_2$SO$_4$ and concentrated under reduced pressure. The crude sample was purified by silica gel column (220 g) using hexane/ethyl acetate (20:1) as eluent to afford the title compound (28 g, 94 mmol, 78% yield) LCMS: rt=4.29 min.

D22: 2-(4-(4-Chloro-3-(trifluoromethyl)phenoxy)phenyl)ethanol

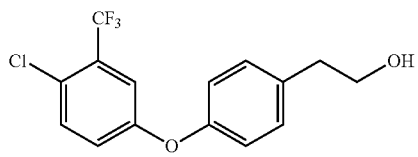 [SMILES: OCCc1ccc(Oc2ccc(Cl)c(C(F)(F)F)c2)cc1]

9-BBN (158 mL, 79 mmol) was added to a solution of 1-chloro-2-(trifluoromethyl)-4-(4-vinylphenoxyl)benzene (15.75 g, 52.7 mmol) in THF (160 mL) at 0° C. The resultant reaction mixture was stirred at room temperature overnight. To the mixture was added water (16 mL), 3M NaOH solution (80 mL) and 30% hydrogen peroxide (80 mL). It was stirred at 50° C. for 2 h, concentrated in vacuo, and diluted with ethyl acetate (200 mL). The organic phase was collected, washed with water (100 mL×2) & brine (100 mL), dried over sulfate, and concentrated. Purification via a column chromatography then provided the title compound as a colorless oil (12.13 g, 71.7% yield). LCMS: rt=2.08 min, [M+H$^+$]=299

D23: (2E)-3-(4-{[4-Chloro-3-(trifluoromethyl)phenyl]oxy}phenyl)-2-propenenitrile

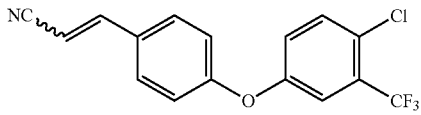 [SMILES: N#CC=Cc1ccc(Oc2ccc(Cl)c(C(F)(F)F)c2)cc1]

To the mixture of (triphenylphosphanylidene)acetonitrile (19.8 g, 51.9 mmol) and NaOH (2.59 g, 64.9 mmol) in DCM (30 mL) and water (60 mL) was added 4-{[4-chloro-3-(trifluoromethyl)phenyl]oxy}benzaldehyde (13.0 g, 43.2 mmol)) at 0° C. It was stirred at rt for 4 h. Purification via a flash chromatography afforded the title compound as a white solid (12 g).

D24: 3-(4-(4-chloro-3-(trifluoromethyl)phenoxy)phenyl)propanenitrile

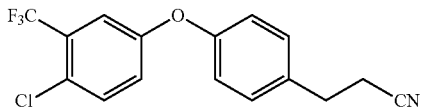 [SMILES: N#CCCc1ccc(Oc2ccc(Cl)c(C(F)(F)F)c2)cc1]

The mixture of (2E)-3-(4-{[4-chloro-3-(trifluoromethyl)phenyl]oxy}phenyl)-2-propenenitrile (18.0 g, 55.6 mmol) and Pd/C (2.00 g, 1.88 mmol) in THF (150 mL) was stirred at 25° C. under H$_2$ overnight, filtered through a pad of Celite, and concentrated. Purification via a column chromatography afforded the title compound as a white solid (15 g).

D25: 3-(4-{[4-Chloro-3-(trifluoromethyl)phenyl]oxy}phenyl)propanimidamide hydrochloride

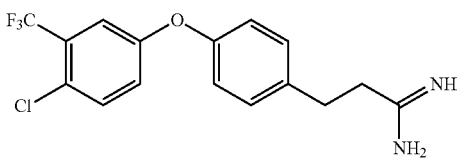 [SMILES: N=C(N)CCc1ccc(Oc2ccc(Cl)c(C(F)(F)F)c2)cc1]

To a solution of 3-(4-{[4-chloro-3-(trifluoromethyl)phenyl]oxy}phenyl)propanenitrile (20.0 g, 61.4 mmol) in toluene (30 mL) and methanol (30 mL) was added dropwise acetyl chloride (18.8 g, 239 mmol) over 5 min at 0° C. under N$_2$. The reaction mixture was stirred at 25° C. for 8 h, then concentrated. It was dissolved with toluene (5 mL), cooled to 0° C. in an ice-bath, slowly mixed with ammonia (30.0 mL, 210 mmol), stirred at 25° C. overnight, filtered, washed with toluene/methanol (1/1) and concentrated. Purification via recrystallization with diethyl ether (50 mL) then afforded the title compound as a white solid (5.4 g, 25.7%).

D26: [(4-{[4-Chloro-3-(trifluoromethyl)phenyl]oxy}phenyl)methyl]methylamine

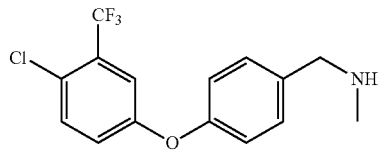 [SMILES: CNCc1ccc(Oc2ccc(Cl)c(C(F)(F)F)c2)cc1]

4-{[4-Chloro-3-(trifluoromethyl)phenyl]oxy}benzaldehyde (3 g, 9.98 mmol) was mixed with a methylamine (1.549 g, 49.9 mmol) alcohol solution. The reaction mixture was stirred at 23° C. overnight. NaBH$_4$ (1.132 g, 29.9 mmol) was added and stirred for additional 2 h. Purification via an ISCO system then provided the title compound as a yellow solid. LCMS: rt=2.53 min, [M+H$^+$]=316.1

D27: (E)-1-Chloro-4-(4-(2-nitrovinyl)phenoxy)-2-(trifluoromethyl)benzene

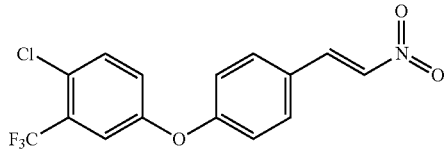 [SMILES: O=[N+]([O-])/C=C/c1ccc(Oc2ccc(Cl)c(C(F)(F)F)c2)cc1]

To the mixture of 4-(4-chloro-3-(trifluoromethyl)phenoxy)benzaldehyde (600 mg, 1.996 mmol), ammonium acetate (77 mg, 0.998 mmol) in AcOH (5 mL) was added nitromethane (0.323 mL, 5.99 mmol). It was heated at 120° C. for 3 h, then concentrated in vacuo. The residue was dissolved in DCM (30 ml), washed with saturated NaHCO$_3$ aqueous solution (20 ml×2), and brine. The organic phase was collected, dried over Na$_2$SO$_4$, filtered, concentrated to provide the title compound as a brown solid (680 mg, 66.4% yield), which was used without further purification. LCMS: rt=4.17 min, [M+H$^+$]=344.1

D28: Chloro-4-(4-(2-nitroethyl)phenoxy)-2-(trifluoromethyl)benzene

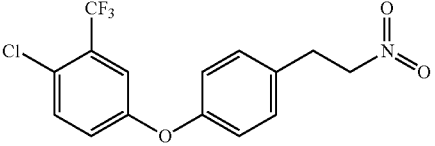 [SMILES: O=[N+]([O-])CCc1ccc(Oc2ccc(Cl)c(C(F)(F)F)c2)cc1]

To the solution of (E)-1-chloro-4-(4-(2-nitrovinyl)phenoxy)-2-(trifluoromethyl)benzene (640 mg, 1.862 mmol) in 2-pentanol (5 mL) and chloroform (15.00 mL) was added silica-gel (2 g), and then NaBH$_4$ (282 mg, 7.45 mmol). The reaction mixture was stirred at rt for 3 h. The mixture was purified via a flash column affording the title compound (330 mg, 49.2% yield). LCMS: rt=4.62 min, [M+H$^+$]=NA

D29: 2-(4-(4-Chloro-3-(trifluoromethyl)phenoxy)phenyl)ethanamine

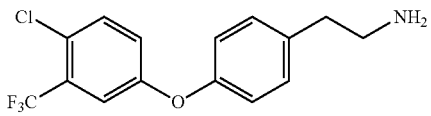 [SMILES: NCCc1ccc(Oc2ccc(Cl)c(C(F)(F)F)c2)cc1]

To the mixture of 1-chloro-4-(4-(2-nitroethyl)phenoxy)-2-(trifluoromethyl)benzene (17 g, 49.2 mmol) and nickel(II) chloride hexahydrate (46.6 g, 197 mmol) in methanol (300 mL) at 0° C. was added NaBH$_4$ (3.72 g, 98 mmol) portion wise. The reaction mixture was stirred at rt overnight. Purification via a column chromatography afforded the title compound as a yellow oil (8.86 g, 51.4% yield). LCMS: rt=2.51 min, [M+H$^+$]=316.1

D30: N-Nitroguanidine

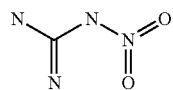

To a pre-cooled H$_2$SO$_4$ (20 mL, 375 mmol was added guanidine nitrate (20 g, 164 mmol) portion wise. The internal temperature was not allowed to rise above 20° C. during the addition. When all had been added, the milky mixture was allowed to stand at room temperature with occasional stirring until it was homogeneous and free from crystal. (overnight). It was then poured with stirring into 500 ml of cracked ice and water. The precipitated nitroguanidine was filtered. Recrystallization from 400 mL boiling water then afforded the title compound as a needle alike crystal (17 g, 100% yield).

D31: 5-[(1-Methyl-1H-pyrazol-4-yl)methyl]-2-(nitroamino)-4(1H)-pyrimidinone

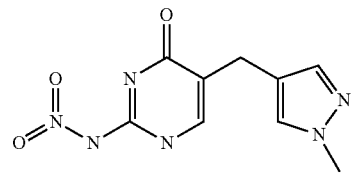 [SMILES: Cn1cc(Cc2c[nH]c(N[N+](=O)[O-])nc2=O)cn1]

To the solution of N-nitroguanidine (912 mg, 8.76 mmol) in ethanol (50.0 mL) was added methyl 2-formyl-3-(1-methyl-1H-pyrazol-4-yl)propanoate (858 mg, 4.38 mmol). It was stirred at 70° C. overnight. After removing the solvent, 10 mL water was added. Then HCl (conc) was added to adjust pH~3, and the solution was stirred at 0° C. for 1 h. The solid was collected after filtration. It was dried overnight at 50° C. to get the title compound as an off-white solid (674 mg, 61.5% yield). LCMS: rt=1.17 min, [M+H$^+$]=251.1

D32: 5-{[2-(Methyloxy)-5-pyrimidinyl]methyl}-2-(nitroamino)-4(1H)-pyrimidinone

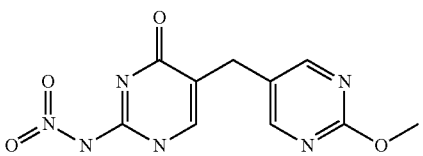 [SMILES: COc1ncc(Cc2c[nH]c(N[N+](=O)[O-])nc2=O)cn1]

To the solution of methyl 2-formyl-3-[2-(methyloxy)-5-pyrimidinyl]propanoate (2 g, 8.92 mmol) and potassium tert-butoxide (3.00 g, 26.8 mmol) in ethanol (15 mL) was added neat N-nitroguanidine (1.857 g, 17.84 mmol). The reaction mixture was stirred at 120° C. for 1 h. After removing the solvent, 5 mL water was added to dissolve the solid, and HCl (conc.) was used to adjust pH~3. The precipitate was collected to provide the title compound (1.8 g, 72.5% yield). LCMS: rt=0.96 min, [M+H$^+$]=279.1

D33: 1-Methyl-5-{[2-(methyloxy)-5-pyrimidinyl]methyl}-2-(nitroamino)-4(1H)-pyrimidinone

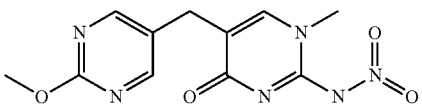 [SMILES: COc1ncc(Cc2cn(C)c(N[N+](=O)[O-])nc2=O)cn1]

A solution of 5-{[2-(methyloxy)-5-pyrimidinyl]methyl}-2-(nitroamino)-4(1H)-pyrimidinone (200 mg, 0.719 mmol) in chloroform (5 mL) was mixed with methyl iodide (0.054 mL, 0.863 mmol). The reaction mixture was stirred at 23° C. overnight. Purification via a reverse phase Biotage then provided the title compound (35 mg, 16.66% yield). LCMS: rt=1.62 min, [M+H$^+$]=293.1

D34: 1-Methyl-5-[(1-methyl-1H-pyrazol-4-yl)methyl]-2-(nitroamino)-4(1H)-pyrimidinone

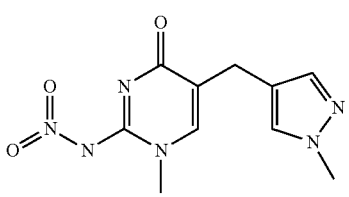 [SMILES: Cn1cc(Cc2cn(C)c(N[N+](=O)[O-])nc2=O)cn1]

A solution of 5-[(1-methyl-1H-pyrazol-4-yl)methyl]-2-(nitroamino)-4(1H)-pyrimidinone (500 mg, 1.998 mmol) and DIPEA (1.745 mL, 9.99 mmol) in chloroform (5 mL) was mixed with methyl iodide (0.150 mL, 2.398 mmol). The reaction mixture was stirred at 23° C. overnight. Purification via HPLC then afforded the title compound (103 mg, 19.51% yield). LCMS: rt=1.46 min, [M+H$^+$]=265.1

D35: N-[2-(4-{[4-Chloro-3-(trifluoromethyl)phenyl]oxy}phenyl)ethyl]-N-methylguanidine

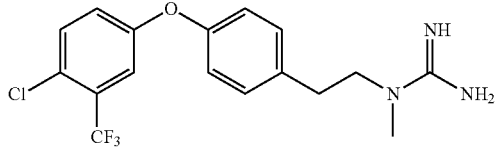 [SMILES: CN(CCc1ccc(Oc2ccc(Cl)c(C(F)(F)F)c2)cc1)C(=N)N]

To a solution of 2-(4-{[4-chloro-3-(trifluoromethyl)phenyl]oxy}phenyl)-N-methylethanamine (300 mg, 0.910 mmol) and DIPEA (0.477 mL, 2.73 mmol) in DMF (5 mL) was added 1H-pyrazole-1-carboximidamide (150 mg, 1.365 mmol). The reaction mixture was stirred at room temperature overnight. Purification via a reverse phase Biotage then afforded the title compound (315 mg, 93% yield) as a white powder. LCMS: rt=2.88 min, [M+H$^+$]=371.9

D36: Ethyl (2E)-3-(4-cyanophenyl)-2-propenoate

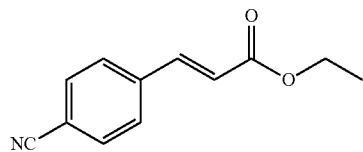

To the mixture of 4-bromobenzonitrile (2.6 g, 14.28 mmol), Pd(OAc)$_2$ (0.064 g, 0.286 mmol) and tri-o-tolylphosphine (0.261 g, 0.857 mmol) in dry DMF (20 mL) was added ethyl 2-propenoate (2.282 mL, 21.43 mmol) and TEA (3.98 mL, 28.6 mmol). It was heated at 110° C. for 1 h. Purification via a flash column chromatography then provided the title compound as a white solid (2.7 g, 92% yield). LCMS: rt=3.03 Min, [M+H$^+$]=202.0

D37: Ethyl 3-(4-cyanophenyl)propanoate

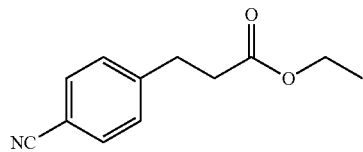

Pd/C (0.6 g, 10%, 50% water wet) was added to a solution of ethyl (2E)-3-(4-cyanophenyl)-2-propenoate (2.7 g, 13.42 mmol) in ethyl acetate (40 mL) under an argon atmosphere. It was mixed with TEA (3.74 mL, 26.8 mmol) and formic acid (2.57 mL, 67.1 mmol). The reaction mixture was refluxed at 90° C. under argon for 1 h. It was filtered through a Celite pad. The filtrate was then washed with water, 5% NaHCO$_3$ solution and brine, dried over Na$_2$SO$_4$, and concentrated to provide the title compound as a pale yellow oil (2.65 g, 97% yield). LCMS: rt=2.94 min, [M+H$^+$]=204.0

D38: Ethyl (2E)-3-(2,4,6-trifluorophenyl)-2-propenoate

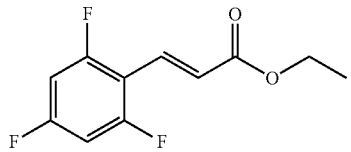 [SMILES: CCOC(=O)/C=C/c1c(F)cc(F)cc1F]

To the solution of ethyl[bis(methyloxy)phosphoryl]acetate (1.980 mL, 11.99 mmol) in THF-DMF (60 mL, v/v=5:1) at 0° C. was added t-BuOK (1.458 g, 12.99 mmol) portion wise. The resultant mixture was stirred at room temperature for 30 minutes, then mixed with a solution of 2,4,6-trifluorobenzaldehyde (1.6 g, 9.99 mmol) in THF (10 mL) at 0° C. It was allowed to warm to room temperature and the mixture was stirred for 45 min. It was mixed with aqueous ammonium chloride and then extracted with ethyl acetate. The organic layer was washed with brine, dried over Na$_2$SO$_4$, filtered, and concentrated. The residue was purified by a flash column chromatography to give the title compound as a pale yellow oil (2.0 g, 87% yield). LCMS: rt=3.52 min, [M+H$^+$]=231.1

D39: Ethyl 3-(2,4,6-trifluorophenyl)propanoate

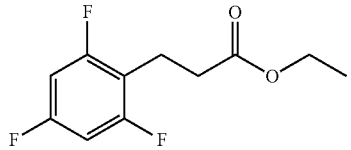 [SMILES: CCOC(=O)CCc1c(F)cc(F)cc1F]

Pd/C (0.5 g, 10%, 50% water wet) was added to a solution of ethyl (2E)-3-(2,4,6-trifluorophenyl)-2-propenoate (2.0 g, 8.69 mmol) in ethyl acetate (40 mL) under an argon atmosphere, followed by TEA (2.409 mL, 17.38 mmol) and formic acid (1.666 mL, 43.4 mmol). The reaction mixture was refluxed at 90° C. under argon for 1 h. The reaction mixture was filtered through a celite pad and the filtrate was then washed with water, 5% NaHCO$_3$ solution and brine, before being dried over Na$_2$SO$_4$. Solvent evaporation under reduced pressure yielded the title compound as a pale yellow oil (1.8 g, 89% yield). LCMS: 3.41 min, [M+H$^+$]=232.9

D40: Ethyl 3-(4-cyanophenyl)-2-formylpropanoate

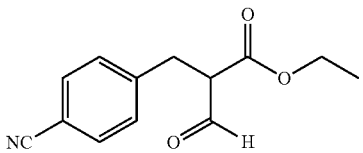 [SMILES: CCOC(=O)C(C=O)Cc1ccc(C#N)cc1]

To a suspension of NaH (1.102 g, 27.6 mmol) in DME (15 mL) was added dropwise a solution of ethyl 3-(4-cyanophenyl)propanoate (1.4 g, 6.89 mmol) and ethyl formate (2.77 mL, 34.4 mmol) in DME (15 mL). The reaction mixture was then stirred at room temperature overnight. It was neutralized with acetic acid (1.7 mL), then extracted with EtOAc. The organic phases were collected, washed with brine, dried over Na$_2$SO$_4$, filtered, and concentrated. The residue was purified by a flash column chromatography, eluting with PE:EA=2: 1, to give the title compound as a pale yellow oil (1.3 g, 82% yield). LCMS: rt=2.47 and 3.13 min (a mixture of ketone and enol isomer), [M+H$^+$]=232.2

D41: Ethyl 2-formyl-3-phenylpropanoate

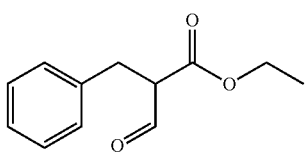

To a suspension of NaH (2.338 g, 58.5 mmol) in DME (20 mL) was added dropwise a solution of ethyl 3-phenylpropanoate (3.2 g, 19.49 mmol) and ethyl formate (6.28 mL, 78 mmol) in DME (20 mL) at room temperature. The reaction mixture was then stirred overnight. It was neutralized with acetic acid (4 mL), then extracted with EtOAc. The organic phase was collected, washed with brine, dried over Na$_2$SO$_4$, filtered, and concentrated affording the crude title compound (4.02 g, 100% yield). LCMS: rt=2.82 and 3.51 min (a mixture of ketone and enol isomer), [M+H$^+$]=207.1

D42: Ethyl 2-formyl-3-(2,4,6-trifluorophenyl)propanoate

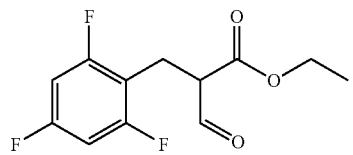 [SMILES: CCOC(=O)C(C=O)Cc1c(F)cc(F)cc1F]

To a suspension of NaH (1.240 g, 31.0 mmol) in DME (15 mL) was added dropwise a solution of ethyl 3-(2,4,6-trifluorophenyl)propanoate (1.8 g, 7.75 mmol) and ethyl formate (3.12 mL, 38.8 mmol) in DME (15 mL) at room temperature. The reaction mixture was then stirred overnight. It was neutralized with acetic acid (1.8 mL), then extracted with EA. The organic layer was collected, washed with brine, dried over Na$_2$SO$_4$, filtered, and concentrated to afford the title compound (2.017 g, 100% yield). LCMS: rt=2.98 and 3.67 min, [M+H$^+$]=261.0, as a mixture of ketone (RT=2.98 min) and enol (RT=3.67 min) isomer.

D43: 2-(4-{[4-Chloro-3-(trifluoromethyl)phenyl]oxy}phenyl)ethyl imidocarbamate triflate

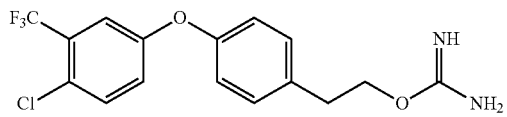 [SMILES: N=C(N)OCCc1ccc(Oc2ccc(Cl)c(C(F)(F)F)c2)cc1]

To a solution of 2-(4-{[4-chloro-3-(trifluoromethyl)phenyl]oxy}phenyl)ethanol (2.63 g, 8.30 mmol) and cyanamide (0.419 g, 9.97 mmol) in dry THF (25 mL) under argon was added trifluoromethanesulfonic acid (0.885 mL, 9.97 mmol). The mixture was heated to 55° C. for 3 hrs. Purification via a reverse phase biotage with TFA then afforded the title compound (2.65 g, 62.8% yield). LCMS: rt=2.906 min, [M+H$^+$]=359

D44: 4-(3-(Trifluoromethyl)phenoxy)benzaldehyde

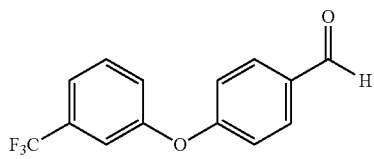 [SMILES: O=Cc1ccc(Oc2cccc(C(F)(F)F)c2)cc1]

K$_2$CO$_3$ (23.45 g, 170 mmol) was added to a solution of 3-(trifluoromethyl)phenol (25 g, 154 mmol) and 4-fluorobenzaldehyde (19.14 g, 154 mmol) in DMF (300 mL), and the reaction mixture was stirred at 140° C. for 4 h. After cooling down to room temperature, the reaction mixture was poured into ice water (2500 ml), extracted with ethyl acetate (500 ml×2), and washed with brine (200 mL×2). The organic phase was dried with sodium sulfate, filtered, and concentrated to give the title compound as a brown solid (35 g, 66.9% yield). LCMS: rt=1.62 min, [M+H$^+$]=267

D45: 1-(Trifluoromethyl)-3-(4-vinylphenoxyl)benzene

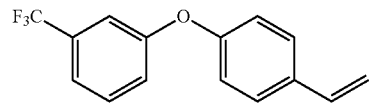 [SMILES: C=Cc1ccc(Oc2cccc(C(F)(F)F)c2)cc1]

NaH (23.66 g, 592 mmol) was added to the solution of 4-(3-(trifluoromethyl)phenoxy)-benzaldehyde (25 g, 94 mmol) and methyltriphenylphosphonium iodide (36.2 g, 101 mmol) in THF (180 mL) at 0° C. The reaction mixture was stirred at room temperature overnight. Purification via a flash column chromatography then afforded the title compound as a colorless oil (24.4 g, 98% yield).

D46: 2-(4-(3-(Trifluoromethyl)phenoxy)phenyl)ethanol

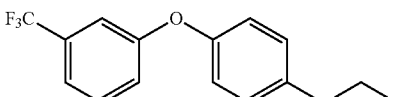

9-BBN (277 mL, 139 mmol) was added to a solution of 1-(trifluoromethyl)-3-(4-vinylphenoxyl)benzene (24.4 g, 92 mmol) in THF (200 mL) at 0° C., and the resulting reaction mixture was stirred at room temperature overnight. To the mixture was added 3M NaOH solution (140 mL) and 30% hydrogen peroxide (123 mL) slowly at 0° C., and the reaction mixture was stirred at 50° C. for 2 h. Purification via column chromatography then afforded the title compound as a colorless oil (17 g, 63.8% yield). LCMS: rt=1.79 min, [M-OH]+=265

D47: 2-(4-{[3-(Trifluoromethyl)phenyl]oxy}phenyl)ethyl imidocarbamate triflate

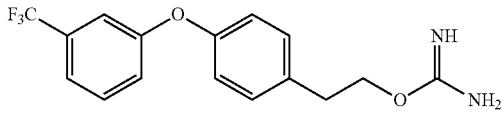

To a solution of 2-(4-(3-(trifluoromethyl)phenoxy)phenyl) ethanol (1.395 g, 4.94 mmol) and cyanamide (0.249 g, 5.93 mmol) in THF (15 mL) was added triflic acid (0.527 mL, 5.93 mmol) under argon. The mixture was heated at 55° C. for 3 h. The mixture was purified by a reverse phase biotage with TFA affording the title compound (1.4 g, 59.8% yield). LCMS: rt=1.23 min, [M+H+]=325

D48: (E)-Ethyl 2-(hydroxymethylene)butanoate

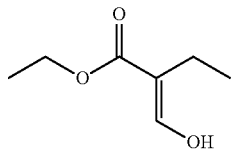

To a suspension of potassium tert-butoxide (3.86 g, 34.4 mmol) in THF (20 mL) under nitrogen at room temperature was added a solution of ethyl butanoate (2.275 mL, 17.22 mmol) in diethyl ether (20.0 mL). The reaction mixture was stirred at rt for 3 hrs. The mixture was quenched and concentrated to give the title compound. LCMS: rt=2.34 min, [M+H+]=143

D49: 4-{[4-Chloro-3-(trifluoromethyl)phenyl]oxy}-3,5-difluorobenzaldehyde

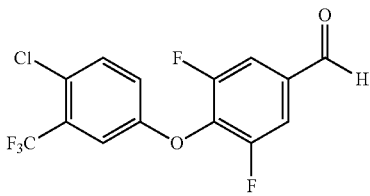 [SMILES: O=Cc1cc(F)c(Oc2ccc(Cl)c(C(F)(F)F)c2)c(F)c1]

The mixture of 4-chloro-3-(trifluoromethyl)phenol (3.4 g, 17.30 mmol), 3,4,5-trifluorobenzaldehyde (2.7 g, 16.87 mmol) and K2CO3 (2.80 g, 20.24 mmol) in DMF was heated with a microwave reactor at 60° C. for 1 h. Purification via a flash column chromatography then afforded the title compound (4.5 g, 79% yield). LCMS: rt=3.88 min, [M+H+]=337

D50: 4-Chloro-3-(trifluoromethyl)phenyl-4-ethenyl-2,6-difluorophenyl ether

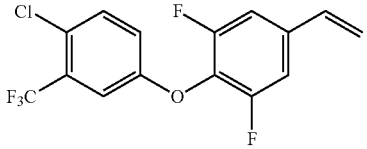 [SMILES: C=Cc1cc(F)c(Oc2ccc(Cl)c(C(F)(F)F)c2)c(F)c1]

To suspension of methyltriphenylphosphonium bromide (5.73 g, 16.04 mmol) in anhydrous THF (20 mL) was added dropwise n-butyllithium (10.03 mL, 16.04 mmol) under −78° C. over 30 min. It was stirred for 1 h, then was added by 4-{[4-chloro-3-(trifluoromethyl)phenyl]oxy}-3,5-difluorobenzaldehyde (4.5 g, 13.37 mmol). It was warmed slowly to room temperature, and stirred for overnight at room temperature. Purification via a flash column chromatography then afforded the title (3.2 g, 71.5% yield). LCMS: rt=5.73 min, [M+H+]=334

D51: 2-(4-{[4-Chloro-3-(trifluoromethyl)phenyl]oxy}-3,5-difluorophenyl)ethanol

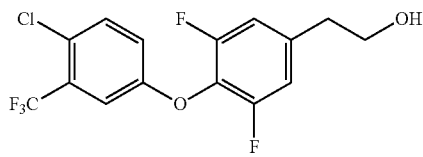 [SMILES: OCCc1cc(F)c(Oc2ccc(Cl)c(C(F)(F)F)c2)c(F)c1]

To a solution of 4-chloro-3-(trifluoromethyl)phenyl 4-ethenyl-2,6-difluorophenyl ether (3.2 g, 9.56 mmol) in THF (10 mL) was added dropwise 9-BBN (38.2 mL, 19.12 mmol) at 0° C. The reaction mixture was stirred at room temperature for overnight. It was mixed with NaOH (19.12 mL, 57.4 mmol) and H2O2 (5.86 mL, 57.4 mmol), the mixture was stirred at 55° C. for 4 h. It was quenched by Na2SO3 and extracted with EA (100 ml×3). Organic phases were collected, combined, dried with anhydrous Na2SO4, and concentrated to afford the title compound (3.10 g, 92% yield). LCMS: rt=4.72 min, [M+H+]=352

D52: 2-(4-{[4-Chloro-3-(trifluoromethyl)phenyl]oxy}-3,5-difluorophenyl)ethyl

To a solution of 2-(4-{[4-chloro-3-(trifluoromethyl)phenyl]oxy}-3,5-difluorophenyl)ethanol (3.1 g, 8.79 mmol) and cyanamide (0.443 g, 10.55 mmol) in anhydrous THF (20 mL) was added trifluoromethanesulfonic acid (1.873 mL, 21.10 mmol) at 0° C. The reaction mixture was stirred at 60° C. for 4 h. Purification via reverse phase Biotage then afforded the title compound as a white solid (1.5 g, 31.3% yield). LCMS: rt=3.64 min, [M+H+]=395

D53: 4-{[4-Chloro-3-(trifluoromethyl)phenyl]oxy}-3-fluorobenzaldehyde

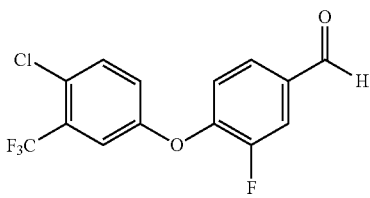 [SMILES: O=Cc1ccc(Oc2ccc(Cl)c(C(F)(F)F)c2)c(F)c1]

The mixture of 4-chloro-3-(trifluoromethyl)phenol (7.61 g, 38.7 mmol), 3,4-difluorobenzaldehyde (5.0 g, 35.2 mmol) and $Cs_2CO_3$ (11.46 g, 35.2 mmol) was heated with a microwave reactor at 80° C. for 1 h. Purification via a flash column chromatography then afforded the title compound (9.0 g, 80% yield). LCMS: rt=3.80 min, $[M+H^+]$=319

D54: 4-Chloro-3-(trifluoromethyl)phenyl 4-ethenyl-2-fluorophenyl ether

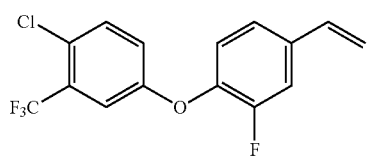 [SMILES: C=Cc1ccc(Oc2ccc(Cl)c(C(F)(F)F)c2)c(F)c1]

To a suspension of methyltriphenylphosphonium bromide (6.73 g, 18.83 mmol) in anhydrous THF (20 mL) was added dropwise n-butyllithium (11.77 mL, 18.83 mmol) under −78° C. over 30 min. It was stirred for 1 h, then was added by 4-{[4-chloro-3-(trifluoromethyl)phenyl]oxy}-3-fluorobenzaldehyde (5.0 g, 15.69 mmol). It was warmed slowly to room temperature and stirred for overnight at room temperature. Purification via a flash column chromatography then afforded the title compound (4.0 g, 80% yield). LCMS: rt=5.7 min, $[M+H^+]$=316

D55: 2-(4-{[4-Chloro-3-(trifluoromethyl)phenyl]oxy}-3-fluorophenyl)ethanol

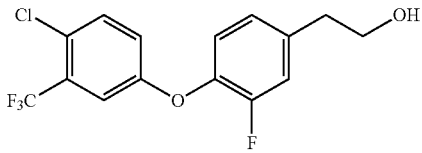 [SMILES: OCCc1ccc(Oc2ccc(Cl)c(C(F)(F)F)c2)c(F)c1]

To a solution of 4-chloro-3-(trifluoromethyl)phenyl 4-ethenyl-2-fluorophenyl ether (4.0 g, 12.63 mmol) in THF (13 mL) was added dropwise 9-BBN (50.5 mL, 25.3 mmol) at 0° C. The reaction mixture was stirred at room temperature for overnight, then mixed with NaOH (25.3 mL, 76 mmol) and $H_2O_2$ (7.74 mL, 76 mmol). The mixture was stirred at 55° C. for 4 h, quenched by $Na_2SO_3$, and extracted with EA (100 mL×3). Organic phases were collected, combined, dried with anhydrous $Na_2SO_4$, and concentrated to provide the title compound (4.02 g, 95% yield). LCMS: rt=4.6 min, $[M+H^+]$=334

D56: 2-(4-{[4-Chloro-3-(trifluoromethyl)phenyl]oxy}-3-fluorophenyl)ethyl imidocarbamate

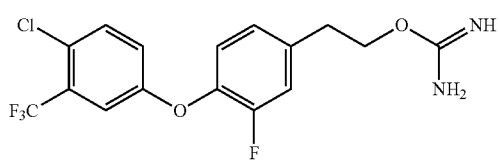 [SMILES: N=C(N)OCCc1ccc(Oc2ccc(Cl)c(C(F)(F)F)c2)c(F)c1]

To the solution of 2-(4-{[4-chloro-3-(trifluoromethyl)phenyl]oxy}-3-fluorophenyl)ethanol (4.0 g, 11.95 mmol) and cyanamide (0.603 g, 14.34 mmol) in anhydrous THF (25 mL) was added trifluoromethanesulfonic acid (2.55 mL, 28.7 mmol) at 0° C. The reaction mixture was stirred at 60° C. for 4 h. Purification via a reverse phase Biotage then afforded the title compound as a white solid (1.5 g, 23.82% yield). LCMS: rt=3.68 min, $[M+H^+]$=377

D57: 4-{[4-Chloro-3-(trifluoromethyl)phenyl]oxy}benzonitrile

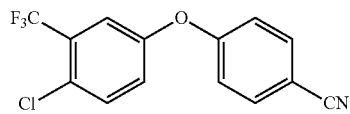 [SMILES: N#Cc1ccc(Oc2ccc(Cl)c(C(F)(F)F)c2)cc1]

The mixture of 4-chloro-3-(trifluoromethyl)phenol (2 g, 10.18 mmol), $K_2CO_3$ (2.109 g, 15.26 mmol) and 4-fluorobenzonitrile (1.232 g, 10.18 mmol) in DMF (20 ml), was heated at 120° C. overnight. It was diluted with water and extracted with EtOAc. The organic phases were collected, washed with water and brine, dried over $Na_2SO_4$ and concentrated to afford the title compound as a brown oil. LCMS: rt=3.81 min, $[M+H^+]$=298

D58: [(4-{[4-Chloro-3-(trifluoromethyl)phenyl]oxy}phenyl)methyl]amine trifluoroacetate

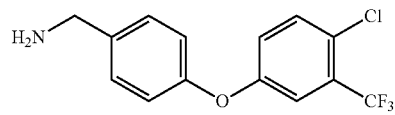 [SMILES: NCc1ccc(Oc2ccc(Cl)c(C(F)(F)F)c2)cc1]

To the suspension of $LiAlH_4$ (280 mg, 7.38 mmol) in dry THF (15 ml) at 0° C. under $N_2$ was added 4-{[4-chloro-3-(trifluoromethyl)phenyl]oxy}benzonitrile (1.5 g, 5.04 mmol) in THF (10 ml) dropwise. The solution was stirred at r.t. for 2.5 h. Purification via a reverse phase Biotage then afforded the title compound as a brown oil. LCMS: rt=2.55 min, $[M+H^+]$=285

D59: N-[(4-{[4-Chloro-3-(trifluoromethyl)phenyl]oxy}phenyl)methyl]guanidine trifluoroacetate

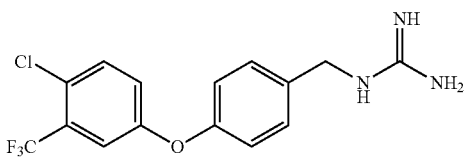 [SMILES: N=C(N)NCc1ccc(Oc2ccc(Cl)c(C(F)(F)F)c2)cc1]

To the solution of [(4-{[4-chloro-3-(trifluoromethyl)phenyl]oxy}phenyl)methyl]amine (800 mg, 1.929 mmol) and DIPEA (0.337 ml, 1.929 mmol) in dry DMF (8 ml) was added 1H-pyrazole-1-carboximidamide (285 mg, 1.929 mmol). The reaction mixture was sealed and stirred at rt overnight. Purification via a reverse phase Biotage then afforded the title compound as a yellow solid. LCMS: rt=2.78 min, [M+H$^+$]= 344

D60: 1-(4-(4-Chloro-3-(trifluoromethyl)phenoxy)benzyl)-1-methylguanidine trifluoroacetate

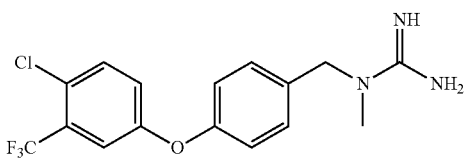 [SMILES: CN(Cc1ccc(Oc2ccc(Cl)c(C(F)(F)F)c2)cc1)C(=N)N]

To the solution of [(4-{[4-chloro-3-(trifluoromethyl)phenyl]oxy}phenyl)methyl]methylamine (374 mg, 1.185 mmol) and DIPEA (0.207 ml, 1.185 mmol) in DMF (3.5 ml), was added 1H-pyrazole-1-carboximidamide (175 mg, 1.185 mmol). The reaction flask was sealed and stirred at rt overnight. Purification via a reverse phase Biotage then afforded the title compound as a white solid. LCMS: rt=2.88 min, [M+H$^+$]=358

D61: 4-(4-fluorophenoxyl)benzaldehyde

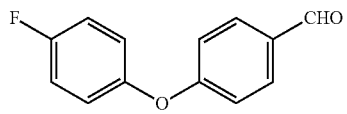 [SMILES: O=Cc1ccc(Oc2ccc(F)cc2)cc1]

To a solution of 4-fluorophenol (10 g, 89 mmol) and 4-fluorobenzaldehyde (11.07 g, 89 mmol) in DMF (200 mL) was added K$_2$CO$_3$ (13.33 g, 96 mmol). The mixture was heated at 140° C. for 4 h. After cooling to room temperature, the mixture was poured into of ice water (300 mL), and left stand overnight. The solid was collected by filtration, washed with water, re-dissolved in EA (200 mL) and washed with brine (100 mL). The organic phase was dried with sodium sulfate, filtered and concentrated to afford the title compound (17 g, 75 mmol, 84% yield) as yellow solid. LCMS: rt=1.52 min, [M+H$^+$]=217

D62: 3-(4-(4-fluorophenoxyl)phenyl)acrylonitrile

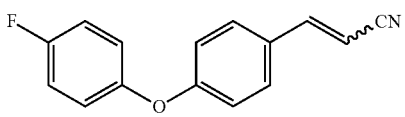 [SMILES: N#CC=Cc1ccc(Oc2ccc(F)cc2)cc1]

To a solution of (cyanomethyl)triphenylphosphonium bromide (10.61 g, 27.8 mmol) and NaOH (1.387 g, 34.7 mmol) in water (30 mL) and DCM (15 mL) was added 4-(4-fluorophenoxyl)benzaldehyde (5 g, 23.13 mmol) at 0° C. The mixture was stirred at room temperature for 4 h. DCM (50 mL) and water (50 mL) was added to the mixture, the organic phase was washed with water (50 mL), brine (50 mL), dried over anhydrous sodium sulfate and concentrated. Purification via flash chromatography afforded the title compound (5.1 g, 21.09 mmol, 91% yield) as white solid. LCMS: rt=1.60 min, [M+H$^+$]=240

D63: 3-(4-(4-fluorophenoxyl)phenyl)propanenitrile

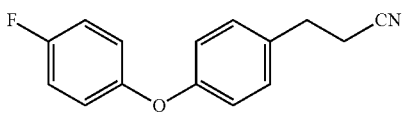 [SMILES: N#CCCc1ccc(Oc2ccc(F)cc2)cc1]

To a solution of 3-(4-(4-fluorophenoxyl)phenyl)acrylonitrile (5 g, 20.90 mmol) in ethanol (80 mL) was added NaBH$_4$ (5.44 g, 144 mmol). The mixture was heated at 70° C. overnight. After cooling to room temperature, the reaction mixture was quenched with water (50 mL), and ethanol was removed under reduced pressure. The residue was partitioned between EA (100 mL) and water (50 mL). The organic phase was washed with saturated NaHCO$_3$ solution (80 mL), brine (50 mL), dried over sodium sulfate, concentrated, and purified via flash chromatography to afford the title compound (4.7 g, 16.48 mmol, 79% yield) as a white solid. LCMS: rt=1.55 min, [M+H$^+$]=242

D64: 3-(4-(4-fluorophenoxyl)phenyl)propanimidamide

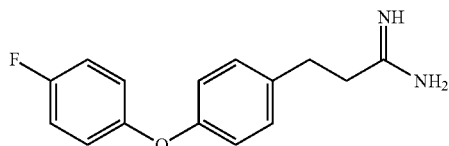

To a solution of 3-(4-(4-fluorophenoxyl)phenyl)propanenitrile (4.4 g, 18.24 mmol) in toluene (25 mL) and methanol (5.94 mL) was added dropwise AcCl (6.48 mL, 91 mmol) at 0° C. in 5 min. The mixture was stirred at room temperature for 2 h. The mixture was cooled to 0° C. in an ice bath, and ammonia (26.1 mL, 182 mmol) in methanol was added dropwise in 5 min. The mixture was stirred at room temperature overnight. The mixture was filtered to remove the solid, and the solid was washed with toluene (40 mL) and methanol (40 mL). The combined filtrate was concentrated in vacuo, the residue was triturated with diethyl ether, the resulting white solid was collected by filtration, washed with

D65: 3-(4-(4-chloro-3-(trifluoromethyl)phenoxy)phenyl)propanimidamide

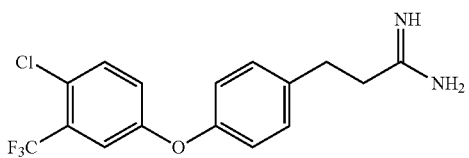 [SMILES: N=C(N)CCc1ccc(Oc2ccc(Cl)c(C(F)(F)F)c2)cc1]

To a solution of 3-(4-(4-chloro-3-(trifluoromethyl)phenoxy)phenyl)propanenitrile (1 g, 3.07 mmol) in toluene (4 mL) and methanol (1 mL) was added dropwise AcCl (1.091 mL, 15.35 mmol) at 0° C. in 5 min. The mixture was stirred at room temperature for 2 h. The mixture was cooled to 0° C. in an ice bath, and ammonia (4.39 mL, 30.7 mmol) in methanol was added dropwise in 5 min. The mixture was stirred at room temperature overnight. The mixture was filtered to remove the solid, and the solid was washed with toluene (20 mL) and methanol (20 mL). The combined filtrate was concentrated in vacuo, the residue was triturated with diethyl ether, the resulting white solid was collected by filtration, washed with diethyl ether and dried in vacuo to afford the title compound (0.85 g, 2.242 mmol, 73.0% yield) as white solid. LCMS: rt=1.17 min, [M+H$^+$]=343

D66: 3-(4-(3-(trifluoromethyl)phenoxy)phenyl)acrylonitrile

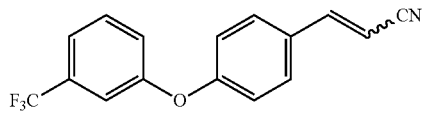 [SMILES: N#CC=Cc1ccc(Oc2cccc(C(F)(F)F)c2)cc1]

To a solution of (cyanomethyl)triphenylphosphonium bromide (8.61 g, 22.54 mmol) and NaOH (1.127 g, 28.2 mmol) in water (24 mL) and DCM (12 mL) was added 4-(3-(trifluoromethyl)phenoxy)benzaldehyde (5 g, 18.78 mmol) at 0° C. The mixture was stirred at room temperature for 4 h. DCM (50 mL) and water (50 mL) was added to the mixture, the organic phase was washed with water (50 mL), brine (50 mL), dried over anhydrous sodium sulfate and concentrated. Purification via flash chromatography afforded the title compound (5.07 g, 17.26 mmol, 92% yield) as pale yellow oil (slowly solidify to white solid). LCMS: rt=1.67 min, [M+H$^+$]=290

D67: 3-(4-(3-(trifluoromethyl)phenoxy)phenyl)propanenitrile

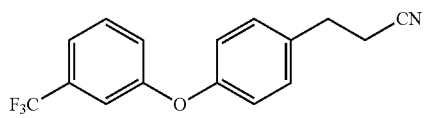 [SMILES: N#CCCc1ccc(Oc2cccc(C(F)(F)F)c2)cc1]

To a solution of 3-(4-(3-(trifluoromethyl)phenoxy)phenyl)acrylonitrile (5 g, 17.29 mmol) in Ethanol (80 mL) was added NaBH$_4$ (4.5 g, 119 mmol). The reaction mixture was stirred at 70° C. overnight. After cooling to room temperature, the reaction mixture was quenched with water (50 mL), and ethanol was removed under reduced pressure. The residue was partitioned between EA (100 mL) and water (50 mL). The organic phase was washed with saturated NaHCO$_3$ solution (80 mL), brine (50 mL), dried over sodium sulfate, concentrated, and purified via flash chromatography to afford the title compound (4.3 g, 13.89 mmol, 80% yield) as colorless oil. LCMS: rt=1.64 min, no MS signal

D68: 3-(4-(3-(trifluoromethyl)phenoxy)phenyl)propanimidamide

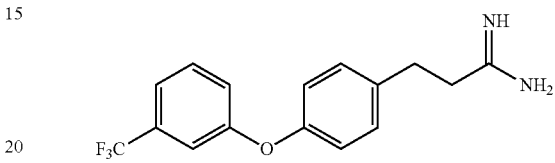

To a solution of 3-(4-(3-(trifluoromethyl)phenoxy)phenyl)propanenitrile (4 g, 13.73 mmol) in toluene (18 mL) and methanol (4.47 mL) was added dropwise AcCl (4.88 mL, 68.7 mmol) at 0° C. in 5 min. The mixture was stirred at room temperature for 2 h. The mixture was cooled to 0° C. in an ice bath, and ammonia (19.62 mL, 137 mmol) in methanol was added dropwise in 5 min. The mixture was stirred at room temperature overnight. The mixture was filtered to remove the solid, and the solid was washed with toluene (40 mL) and methanol (40 mL). The filtrate was concentrated in vacuo. The residue was triturated with diethyl ether to give only trace white solid (0.3 g). The filtrate was concentrated in vacuo to afford the title compound (3.13 g, 8.03 mmol, 58.5% yield) as pale yellow solid. LCMS: rt=1.07 min, [M+H$^+$]=309

D69: (4-(4-fluorophenoxyl)phenyl)methanol

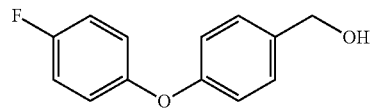 [SMILES: OCc1ccc(Oc2ccc(F)cc2)cc1]

To a solution of 4-(4-fluorophenoxyl)benzaldehyde (10 g, 46.3 mmol) in methanol (50 mL) was added NaBH$_4$ (1.750 g, 46.3 mmol) portionwise, after addition the mixture was stirred at room temperature overnight. After removing the solvent, the residue was diluted with DCM (50 mL), the suspension was filtered though a pad of Celite, the filtrate was concentrated to afford the title compound (7 g, 30.5 mmol, 65.9% yield) as a gray solid. LCMS: rt=1.49 min, [M+H$^+$]=219

D70: 1-(chloromethyl)-4-(4-fluorophenoxyl)benzene

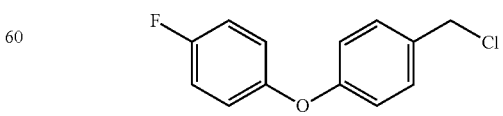

To the solution of (4-(4-fluorophenoxyl)phenyl)methanol (7 g, 32.1 mmol) and pyridine (5.19 mL, 64.2 mmol) in dichloromethane (DCM) (100 mL) was added sulfurous dichloride (7.63 g, 64.2 mmol) dropwise at 0° C. After addition the mixture was stirred at room temperature overnight. The mixture was washed with saturated NaHCO₃ solution (40 mL×2) and brine (40 mL), the organic phase was dried over Na₂SO₄, filtered and concentrated to leave the crude product, which was purified by column chromatography (silica-gel, elution with PE: EtOAc=6:1) to afford the pure 1-(chloromethyl)-4-(4-fluorophenoxyl)benzene (2.2 g, 8.83 mmol, 27.5% yield) as light yellow oil. LCMS: rt=1.56 min, [M+H⁺]=237

D71: (4-(4-chloro-3-(trifluoromethyl)phenoxy)phenyl)methanol

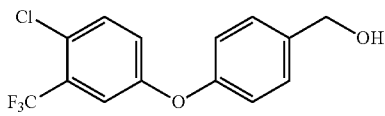

To a solution of 4-{[4-chloro-3-(trifluoromethyl)phenyl]oxy}benzaldehyde (21 g, 69.8 mmol) in methanol (200 mL) was added slowly NaBH₄ (2.64 g, 69.8 mmol) portionwise. The mixture was stirred at room temperature overnight. After removing the solvent, the residue diluted with DCM. The resulting suspension was filtered, the filtrate was concentrated in vacuo to afford the title compound (17.6 g, 55.2 mmol, 79% yield) as yellow solid. LCMS: rt=1.71 min, [M+H⁺]=303, 305

D72: 4-(4-(bromomethyl)phenoxy)-1-chloro-2-(trifluoromethyl)benzene

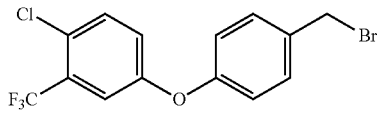 [SMILES: FC(F)(F)c1cc(Oc2ccc(CBr)cc2)ccc1Cl]

To the solution of (4-(4-chloro-3-(trifluoromethyl)phenoxy)phenyl)methanol (4.5 g, 14.87 mmol) in Diethyl ether (100 mL) was added PBr₃ (1.402 mL, 14.87 mmol) dropwise at 0° C. The mixture was stirred at room temperature for 5 h. The mixture was poured into ice water and neutralized with sat. NaHCO₃ solution to pH-7, then extracted with Et₂O. The organic was dried over Na₂SO₄, filtered and concentrated in vacuo to afford the title compound (3.2 g, 7.88 mmol, 53.0% yield) as a light yellow solid. LCMS: rt=2.01 min, [M+H⁺]= 365, 367.

D73: 1-chloro-4-{[4-(chloromethyl)phenyl]oxy}-2-(trifluoromethyl)benzene

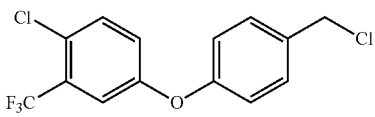 [SMILES: FC(F)(F)c1cc(Oc2ccc(CCl)cc2)ccc1Cl]

To the solution of (4-{[4-chloro-3-(trifluoromethyl)phenyl]oxy}phenyl)methanol (3 g, 9.91 mmol) in DCM (90 mL), was added thionyl chloride (7.5 mL, 103 mmol) dropwise. The mixture was stirred at room temperature for 1.5 h. After removing the solvent, the residue was dissolved in DCM, then washed with water twice, dried over Na₂SO₄. Concentration in vacuo afforded the title compound (2.8 g, 88% yield) as light brown oil. LCMS: rt=4.14 min D74: 5-(5-pyrimidinylmethyl)-2-thioxo-2,3-dihydro-4(1H)-pyrimidinone

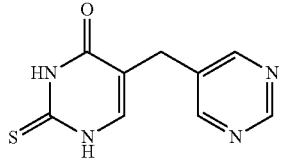 [SMILES: O=c1[nH]c(=S)[nH]cc1Cc1cncnc1]

To a solution of ethyl (2Z)-3-hydroxy-2-(5-pyrimidinylmethyl)-2-propenoate (3 g, 7.20 mmol) in isopropanol (30 ml) was added thiourea (1.1 g, 14.45 mmol) and potassium tert-butoxide (1 g, 8.91 mmol). The mixture was heated at 80° C. for 4 h. The solvent was evaporated and residue was dissolved in water, extracted with ether twice to remove impurity. The aqueous phase was acidified to PH 4 with AcOH, and white participate formed. The mixture was filtered to afford the title compound as a white solid.

D75: 5-ethyl-2-thioxo-2,3-dihydro-4(1H)-pyrimidinone

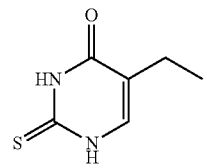

To a suspension of potassium tert-butoxide (12.08 g, 108 mmol) in THF (40 mL) was added a solution of ethyl butyrate (5.69 mL, 43.0 mmol) and ethyl formate (6.93 mL, 86 mmol) in diethyl ether (40.0 mL) dropwise under nitrogen. The mixture was stirred at room temperature for 3 h. After removing the solvent, the residue oil was dissolved in isopropanol (350 mL), and thiourea (6.55 g, 86 mmol) was added. The mixture was stirred at reflux overnight, and then concentrated in vacuo to get a solid. The solid was dissolved in water, adjusted pH to 4 with AcOH, and extracted by DCM. The organic layer was dried over Na₂SO₄, filtered and concentrated to afford the title compound (5.5 g, 82% yield) as a pink solid.

D76: methyl 3-(4-oxo-2-thioxo-1,2,3,4-tetrahydro-5-pyrimidinyl)propanoate

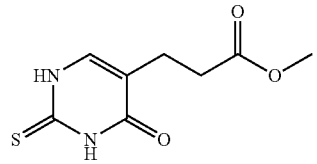

To a suspension of potassium tert-butoxide (7.29 g, 64.9 mmol) in t-butylmethyl ether (100 mL) was added a solution of dimethyl pentanedioate (5.2 g, 32.5 mmol) and methyl formate (1.950 g, 32.5 mmol) in t-butylmethyl ether (50 mL). The mixture was stirred overnight and concentrated to dryness afford the yellow oil. The oil was dissolved in methanol (80 mL), to which thiourea (2.72 g, 35.7 mmol) was added. The mixture was heated to reflux overnight. The result mixture was concentrated and dissolved in water, adjust pH to 3 with AcOH. The solution was extracted with DCM three times. The combined organic layers were dried over $Na_2SO_4$, filtered and concentrated to afford the title compound (2.1 g, 9.80 mmol, 30.2% yield).

D77: ethyl 2-{[(4-{[4-chloro-3-(trifluoromethyl) phenyl]oxy}phenyl)methyl]thio}-4-oxo-1,4-dihydro-5-pyrimidinecarboxylate

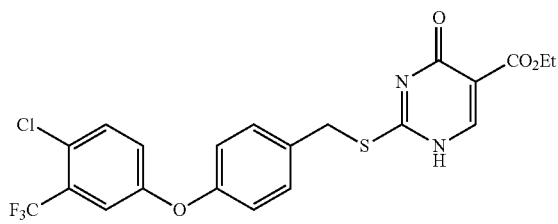 [SMILES: CCOC(=O)c1c[nH]c(SCc2ccc(Oc3ccc(Cl)c(C(F)(F)F)c3)cc2)nc1=O]

A mixture of ethyl 4-oxo-2-thioxo-1,2,3,4-tetrahydro-5-pyrimidinecarboxylate (1.016 g, 5.07 mmol), 1-chloro-4-{[4-(chloromethyl)phenyl]oxy}-2-(trifluoromethyl)benzene (1.793 g, 5.58 mmol) and $K_2CO_3$ (0.771 g, 5.58 mmol) in DMF (15 mL) was heated with a microwave reactor at 80° C. for 0.5 h. The mixture was poured into 100 mL water and extracted with EA. The organic phase was dried over sodium sulfate, filtered, and concentrated to afford the title compound (2.461 g, 5.07 mmol, 100% yield). LCMS: rt=3.64 min, [M+H]=485

D78: 2-{[(4-{[4-chloro-3-(trifluoromethyl)phenyl] oxy}phenyl)methyl]thio}-5-(hydroxymethyl)-4(1H)-pyrimidinone

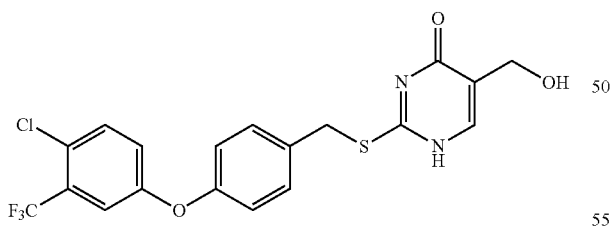

To a solution of ethyl 2-{[(4-{[4-chloro-3-(trifluoromethyl)phenyl]oxy}phenyl)methyl]thio}-4-oxo-1,4-dihydro-5-pyrimidinecarboxylate (2.36 g, 4.87 mmol) in dry THF (20 mL) was added borane-methyl sulfide complex (2.0M in toluene) (7.30 mL, 14.60 mmol) dropwise under argon at 0° C. The mixture was stirred at 0° C. for 0.5 h, and warmed to room temperature for 1 h, then quenched with acetone. Purification via reverse phase flash chromatography then afforded the title compound (921 mg, 2.080 mmol, 42.7% yield). LCMS: rt=3.28 min, [M+H]=443

D79: 1-(4-{[4-chloro-3-(trifluoromethyl)phenyl] oxy}phenyl)ethanone

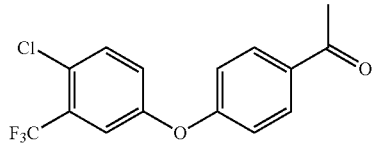 [SMILES: CC(=O)c1ccc(Oc2ccc(Cl)c(C(F)(F)F)c2)cc1]

A mixture of 4-chloro-3-(trifluoromethyl)phenol (2 g, 10.18 mmol), 1-(4-fluorophenyl) ethanone (1.406 g) and $K_2CO_3$ (2.3 g, 16.64 mmol) in DMF (18 mL) was heated with a microwave condition at 145° C. for 4 h. The solution was diluted with EA and washed with water twice, dried over $Na_2SO_4$ and concentrated in vacuo to afford the title compound (3.12 g, 97% yield) as a brown oil. LCMS: rt=3.83 min, [M+H]=315

D80: 1-(4-{[4-chloro-3-(trifluoromethyl)phenyl] oxy}phenyl)ethanol

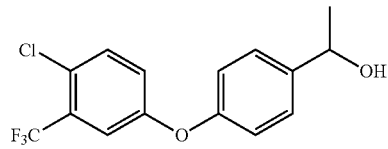

To the solution of 1-(4-{[4-chloro-3-(trifluoromethyl)phenyl]oxy}phenyl)ethanone (3.12 g, 9.91 mmol) in Ethanol (60 ml), was added $NaBH_4$ (0.450 g, 11.90 mmol). The solution was stirred at room temperature under nitrogen for 1 h. After removing the solvent, the residue was dissolved in DCM, then washed with water twice. The solvent was dried over $Na_2SO_4$, concentrated to afford the title compound (2.3 g, 73.2% yield) as light yellow oil. LCMS: rt=3.63 min, [M+H$^+$]=299

D81: 1-chloro-4-{[4-(1-chloroethyl)phenyl]oxy}-2-(trifluoromethyl)benzene

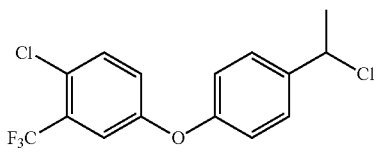 [SMILES: CC(Cl)c1ccc(Oc2ccc(Cl)c(C(F)(F)F)c2)cc1]

To the solution of 1-(4-{[4-chloro-3-(trifluoromethyl)phenyl]oxy}phenyl)ethanol (50 mg, 0.158 mmol) in DCM (1.5 mL), was added thionyl chloride (0.1 mL, 1.378 mmol) dropwise. The mixture was stirred at room temperature for 1 h. After removing the solvent, the residue was dissolved in DCM, then washed with water twice, dried over $Na_2SO_4$, and concentrated in vacuo to afford the title compound (50 mg, 95% yield). LCMS: rt=3.63 min, [M+H$^+$]=299

D82: 2-{[4-chloro-3-(trifluoromethyl)phenyl]oxy}-5-formylbenzonitrile

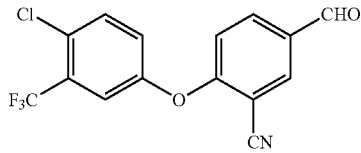

A mixture of 4-chloro-3-(trifluoromethyl)phenol (1 g, 5.09 mmol), 2-fluoro-5-formylbenzonitrile (0.759 g, 5.09 mmol) and K$_2$CO$_3$ (0.844 g, 6.11 mmol) in DMF (10 mL) was heated with a microwave condition at 130° C. for 4 h. The solution was diluted with EA and washed with water twice, dried over Na$_2$SO$_4$ and concentrated in vacuo to afford the title compound (1.59 g, 96% yield) as a yellow solid. LCMS: rt=3.54 min, [M+H$^+$]=326

D83: 2-{[4-chloro-3-(trifluoromethyl)phenyl]oxy}-5-(hydroxymethyl)benzonitrile

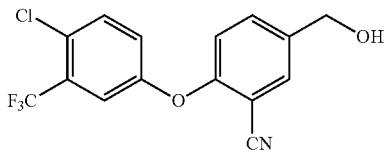

To the solution of 2-{[4-chloro-3-(trifluoromethyl)phenyl]oxy}-5-formylbenzonitrile (1.59 g, 4.88 mmol) in ethanol (45 ml), was added NaBH$_4$ (0.203 g, 5.37 mmol). The solution was stirred at room temperature under nitrogen for 1.5 h. After removing the solvent, the residue was dissolved in DCM, then washed with water twice. The solvent was dried over Na$_2$SO$_4$, concentrated to afford the title compound (1.43 g, 89% yield) as a white solid. LCMS: rt=3.31 min, [M+H$^+$]=328

D84: 2-(4-chloro-3-(trifluoromethyl)phenoxy)-5-(chloromethyl)benzonitrile

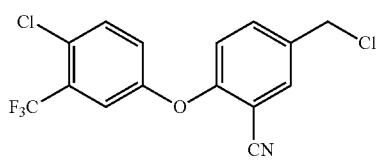 [SMILES: N#Cc1cc(CCl)ccc1Oc1ccc(Cl)c(C(F)(F)F)c1]

To the solution of 2-{[4-chloro-3-(trifluoromethyl)phenyl]oxy}-5-(hydroxymethyl)benzonitrile (500 mg, 1.526 mmol) in DCM (30 mL), was added thionyl chloride (1.671 mL, 22.89 mmol) dropwise. The mixture was stirred at room temperature for 2 h. After removing the solvent, the residue was dissolved in DCM, then washed with water twice, dried over Na$_2$SO$_4$, concentrated and purified via flash chromatography to afford the title compound (479 mg, 89% yield) as a white solid. LCMS: rt=3.45 min

D85: 2-{[4-fluoro-3-(trifluoromethyl)phenyl]oxy}-5-formylbenzonitrile

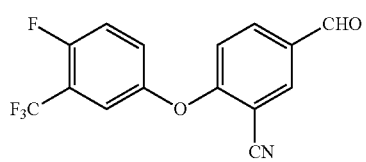 [SMILES: N#Cc1cc(C=O)ccc1Oc1ccc(F)c(C(F)(F)F)c1]

A mixture of 4-fluoro-3-(trifluoromethyl)phenol (1 g, 5.55 mmol), 2-fluoro-5-formylbenzonitrile (0.828 g, 5.55 mmol) and K$_2$CO$_3$ (0.921 g, 6.66 mmol) in DMF (10 mL) was heated with a microwave condition at 130° C. for 2 h. The solution was diluted with EA and washed with water twice, dried over Na$_2$SO$_4$ and concentrated in vacuo to afford the title compound (1.74 g, 101% yield) as a brown oil. LCMS: rt=3.38 min, [M+H$^+$]=310

D86: 2-{[4-fluoro-3-(trifluoromethyl)phenyl]oxy}-5-(hydroxymethyl)benzonitrile

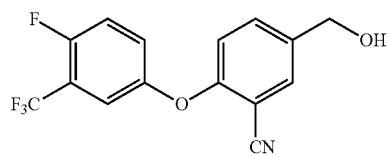 [SMILES: N#Cc1cc(CO)ccc1Oc1ccc(F)c(C(F)(F)F)c1]

To the solution of 2-{[4-fluoro-3-(trifluoromethyl)phenyl]oxy}-5-formylbenzonitrile (1.74 g, 5.63 mmol) in ethanol (40 ml), was added NaBH$_4$ (0.255 g, 6.75 mmol). The solution was stirred at room temperature under nitrogen for 1.5 h. After removing the solvent, the residue was dissolved in DCM, then washed with water twice. The solvent was dried over Na$_2$SO$_4$, concentrated to afford the title compound (1.23 g, 70% yield) as a green solid. LCMS: rt=3.06 min

D87: 5-(chloromethyl)-2-{[4-fluoro-3-(trifluoromethyl)phenyl]oxy}benzonitrile

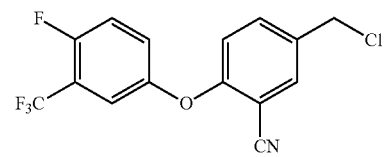 [SMILES: N#Cc1cc(CCl)ccc1Oc1ccc(F)c(C(F)(F)F)c1]

To the solution of 2-{[4-fluoro-3-(trifluoromethyl)phenyl]oxy}-5-(hydroxymethyl)benzonitrile (700 mg, 2.249 mmol) in DCM (40 mL), was added thionyl chloride (2.462 mL, 33.7 mmol) dropwise. The mixture was stirred at room temperature for 1.5 h. After removing the solvent, the residue was dissolved in DCM, then washed with water twice, dried over Na$_2$SO$_4$, and concentrated in vacuo to afford the title compound (665 mg, 90% yield) as a light yellow solid. LCMS: rt=3.71 min

D88: 5-formyl-2-(3-(trifluoromethyl)phenoxy)benzonitrile

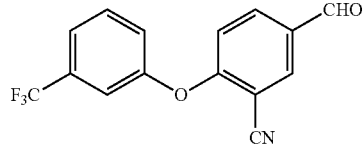 [SMILES: N#Cc1cc(C=O)ccc1Oc1cccc(C(F)(F)F)c1]

A mixture of 2-fluoro-5-formylbenzonitrile (1.0 g, 6.71 mmol), 3-(trifluoromethyl) phenol (1.087 g, 6.71 mmol), $K_2CO_3$ (2.78 g, 20.12 mmol) in DMSO (20 mL) was heated at 100° C. overnight. After cooling to room temperature, the mixture was partitioned between EA (100 mL) and water (100 mL), the aqueous layer was extracted with EA (50 mL) twice. The combine the organic layers were washed with water, brine and dried over sodium sulfate, filtered, concentrated and purified via flash chromatography to afford the title compound (820 mg, 2.79 mmol, 41.6% yield). LCMS: rt=3.33 min, [M+H$^+$]=292

D89: 5-(hydroxymethyl)-2-(3-(trifluoromethyl)phenoxy)benzonitrile

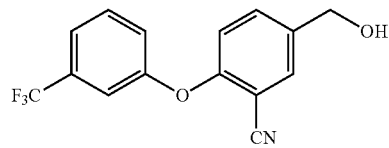 [SMILES: N#Cc1cc(CO)ccc1Oc1cccc(C(F)(F)F)c1]

A mixture of 5-formyl-2-{[3-(trifluoromethyl)phenyl]oxy}benzonitrile (1 g, 3.43 mmol) and NaBH$_4$ (0.156 g, 4.12 mmol) in ethanol (20 mL) was stirred at room temperature for 3 h. The reaction was quenched with NH$_4$Cl saturated solution and extracted with EA. The organic layer was separated and concentrated to afford the title compound (0.9 g, 89% yield) as a white solid. LCMS: rt=3.71 min

D90: 5-(chloromethyl)-2-{[3-(trifluoromethyl)phenyl]oxy}benzonitrile

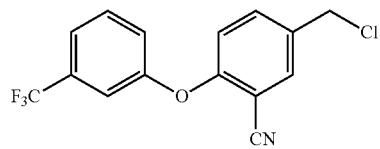 [SMILES: N#Cc1cc(CCl)ccc1Oc1cccc(C(F)(F)F)c1]

To a suspension of 5-(hydroxymethyl)-2-{[3-(trifluoromethyl)phenyl]oxy})benzonitrile (250 mg, 0.853 mmol) in DCM (4 mL) was added thionyl chloride (0.124 mL, 1.705 mmol) dropwise under nitrogen. The mixture was stirred at room temperature for 2 h. The reaction was quenched with water, adjusted pH about 7 and extracted with DCM. The organic layer was separated and concentrated to afford the title compound (250 mg, 0.802 mmol, 94% yield).

D91: 3-methoxy-4-(3-(trifluoromethyl)phenoxy)benzaldehyde

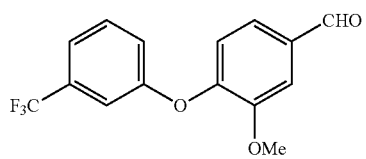 [SMILES: COc1cc(C=O)ccc1Oc1cccc(C(F)(F)F)c1]

To a solution of 4-fluoro-3-(methyloxy)benzaldehyde (1.07 g, 6.94 mmol) and 3-(trifluoromethyl)phenol (1.238 g, 7.64 mmol) in DMF (25 mL) was added K$_2$CO$_3$ (2.88 g, 20.83 mmol) under argon. The mixture was heated at 90° C. for 0.5 h. After removing the solvent, the residue was diluted with water, extracted with DCM. The organic phase was dried over sodium sulfate, filtered, and concentrated to afford the title compound (1.735 g, 5.86 mmol, 84% yield). LCMS: rt=3.53 min, [M+H$^+$]=297

D92: (3-methoxy-4-(3-(trifluoromethyl)phenoxy)phenyl)methanol

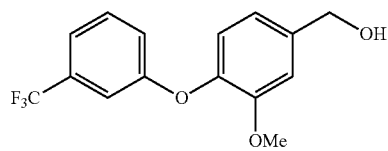 [SMILES: COc1cc(CO)ccc1Oc1cccc(C(F)(F)F)c1]

To a solution of 3-(methyloxy)-4-{[3-(trifluoromethyl)phenyl]oxy}benzaldehyde (720 mg, 2.430 mmol) in ethanol (20 mL) was added slowly NaBH$_4$ (110 mg, 2.92 mmol) at 0° C. The mixture was then allowed to warm to room temperature and stirring continued for 2 h. The reaction was quenched with NH$_4$Cl sat. solution and extracted with EA. The organic layer was separated and concentrated to afford the title compound (715 mg, 2.397 mmol, 99% yield). LCMS: rt=3.12 min, [M+H$^+$–H$_2$O]=281

D93: 3-(trifluoromethyl)-4-(3-(trifluoromethyl)phenoxy)benzaldehyde

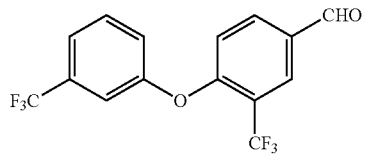 [SMILES: O=Cc1ccc(Oc2cccc(C(F)(F)F)c2)c(C(F)(F)F)c1]

A mixture of 4-fluoro-3-(trifluoromethyl)benzaldehyde (0.355 mL, 2.60 mmol), 3-(trifluoromethyl)phenol (0.289 mL, 2.60 mmol) and K$_2$CO$_3$ (1079 mg, 7.81 mmol) were in DMSO (10 mL) was heated at 100° C. overnight. Purification via reverse phase flash chromatography afforded the title compound (989 mg, 2.368 mmol, 91.0% yield). LCMS: rt=3.84 min, [M+H$^+$]=335

D94: (3-(trifluoromethyl)-4-(3-(trifluoromethyl)phenoxy)phenyl)methanol

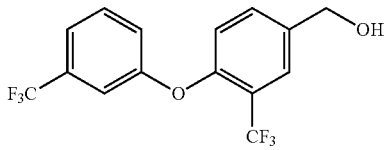 [SMILES: OCc1ccc(Oc2cccc(C(F)(F)F)c2)c(C(F)(F)F)c1]

To a solution of 3-(trifluoromethyl)-4-{[3-(trifluoromethyl)phenyl]oxy}benzaldehyde (400 mg, 1.197 mmol) in methanol (10 mL) was added sodium borohydride (47.5 mg, 1.257 mmol) at 0° C. The mixture was stirred at room temperature for 15 min. The result mixture was quenched by acetone, concentrated, and purified via flash chromatography to afford the title compound (350 mg, 0.989 mmol, 83% yield).

D95: 4-(chloromethyl)-2-(trifluoromethyl)-1-{[3-(trifluoromethyl)phenyl]oxy}benzene

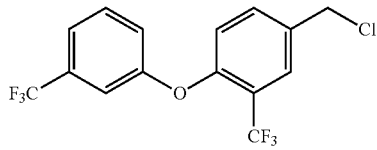 [SMILES: FC(F)(F)c1cccc(Oc2ccc(CCl)cc2C(F)(F)F)c1]

To a suspension of (3-(trifluoromethyl)-4-{[3-(trifluoromethyl)phenyl]oxy})phenyl) methanol (300 mg, 0.892 mmol) in DCM (4 mL) was added thionyl chloride (0.130 mL, 1.784 mmol) dropwise under nitrogen. The mixture was stirred at room temperature for 2 h. The mixture was stirred at room temperature for 2 h. The reaction was quenched with water, adjusted pH about 7 and extracted with DCM. The organic layer was separated and concentrated to afford the crude title compound (430 mg, 0.970 mmol, 109% yield) which can be used in next step directly.

D96: Methyl 3-cyano-4-((5-(trifluoromethyl)pyridin-2-yl)oxy)benzoate

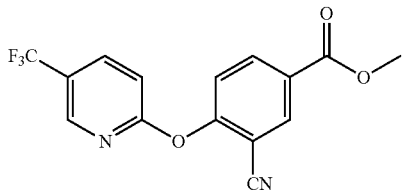 [SMILES: COC(=O)c1ccc(Oc2ccc(C(F)(F)F)cn2)c(C#N)c1]

To a solution of 5-iodo-2-(5-trifluoromethyl-pyridin-2-yloxy)-benzonitrile (110 g, 0.29 mol) in MeOH (1500 mL) and DMF (400 mL) was added Pd(dppf)Cl$_2$ (20 g). The mixture was stirred in autoclave (10 L) at 100° C. under CO (1 MPa) for 72 hours. MeOH and DMF was removed in vacuo, the crude product was purified by column chromatography on silica gel (PE: EA=20:1 to 10:1) to afford 3-cyano-4-(5-trifluoromethyl-pyridin-2-yloxy)-benzoic acid methyl ester as a yellow oil (45 g, 48.2%). $^1$H NMR (400 MHz, CDCl3) δ: 8.39 (s, 1H), 8.29 (d, J=8.8 Hz, 1H), 8.01 (d, J=8.8 Hz, 1H), 7.40 (d, J=8.8 Hz, 1H), 7.27 (d, J=8.4 Hz, 1H), 3.94 (s, 3H).

D97: 5-(hydroxymethyl)-2-((5-(trifluoromethyl)pyridin-2-yl)oxy)benzonitrile

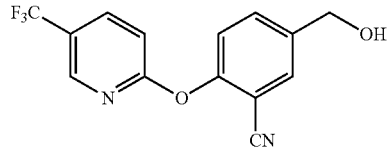 [SMILES: N#Cc1cc(CO)ccc1Oc1ccc(C(F)(F)F)cn1]

To a solution of 3-cyano-4-(5-trifluoromethyl-pyridin-2-yloxy)-benzoic acid methyl ester (23 g, 0.070 mol) in anhydrous THF (200 mL) was added portionwise LiAlH$_4$ (4.07 g, 0.11 mmol) at −78° C. The reaction mixture was warmed to −55° C. slowly and stirred for 20 mins, diluted with water (3 mL 0.16 mmol, slow addition), filtered and concentrated. Purification via column chromatography on silica gel (petroleum ether/ethyl acetate=10/1 to 5/1) afforded the title product (12.5 g) as a colorless oil. LCMS: rt=2.81 min, [M+H$^+$]= 295.

D98: 5-(chloromethyl)-2-((5-(trifluoromethyl)pyridin-2-yl)oxy)benzonitrile

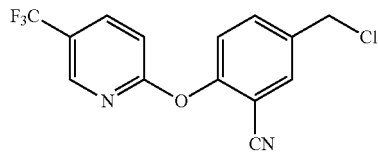 [SMILES: N#Cc1cc(CCl)ccc1Oc1ccc(C(F)(F)F)cn1]

To the solution of 5-(hydroxymethyl)-2-((5-(trifluoromethyl)pyridin-2-yl)oxy)benzonitrile (269 mg, 0.999 mmol) in DCM (20 mL), was added thionyl chloride (0.7 mL, 9.59 mmol) dropwise. The mixture was stirred at room temperature for 2 h. After removing the solvent, the residue was dissolved in DCM, then washed with water twice, dried over Na$_2$SO$_4$, and concentrated in vacuo to afford the title compound (275 mg, 96% yield) as a light green solid. LCMS: rt=3.54 min, [M+H$^+$]=313

D99: 5-formyl-2-{[3-(trifluoromethyl)phenyl]oxy}benzonitrile

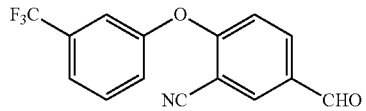 [SMILES: N#Cc1cc(C=O)ccc1Oc1cccc(C(F)(F)F)c1]

To a solution of 3-(trifluoromethyl)phenol (1.435 g, 8.85 mmol) and 2-fluoro-5-formylbenzonitrile (1.2 g, 8.05 mmol) in DMF (25 mL) was added K$_2$CO$_3$ (3.34 g, 24.14 mmol) under argon. The mixture was heated at 90° C. for 0.5 h. After removing the solvent, the residue was diluted with water, extracted with DCM. The organic phase was dried over sodium sulfate, filtered, and concentrated. Recrystallization in EA then afforded the title compound (2.5 g, 8.58 mmol, 107% yield). LCMS: rt=3.34 min, [M+H$^+$]=292

D100: 5-ethenyl-2-{[3-(trifluoromethyl)phenyl]oxy}benzonitrile

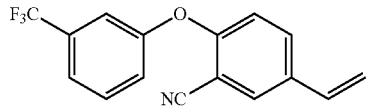 [SMILES: C=Cc1ccc(Oc2cccc(C(F)(F)F)c2)c(C#N)c1]

To a solution of methyltriphenylphosphonium bromide (11.78 g, 33.0 mmol) in dry THF (100 mL) was added dropwise a solution of NaH (4.79 g, 110 mmol) in THF (100 mL) under nitrogen for 0.5 h. Then a solution of 5-formyl-2-{[3-(trifluoromethyl)phenyl]oxy}benzonitrile (8 g, 27.5 mmol) in THF (1 mL) was added slowly into the reaction mixture. The mixture was then allowed to warm to room temperature and stirring continued for 2 h. Purification via flash chromatography then afforded the title compound (4 g, 13.83 mmol, 50.3% yield).

D101: 5-(2-hydroxyethyl)-2-{[3-(trifluoromethyl)phenyl]oxy}benzonitrile

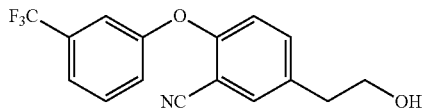 [SMILES: N#Cc1cc(CCO)ccc1Oc1cccc(C(F)(F)F)c1]

To a stirred a solution of 9-BBN (10.37 mL, 5.19 mmol) in dry THF (30 mL) was added dropwise a solution of 5-ethenyl-2-{[3-(trifluoromethyl)phenyl]oxy}benzonitrile (1 g, 3.46 mmol) in THF (30 mL) under nitrogen at 0° C. for 0.5 h. The mixture was then allowed to warm to room temperature and stirring continued for 2 h. Na$_2$SO$_3$ was added to quench the reaction. Purification via flash chromatography then afforded the title compound (546 mg, 1.777 mmol, 51.4% yield).

D102: 5-(2-iodoethyl)-2-{[3-(trifluoromethyl)phenyl]oxy}benzonitrile

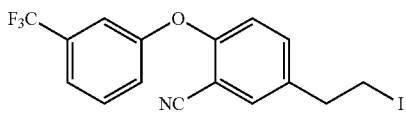 [SMILES: N#Cc1cc(CCI)ccc1Oc1cccc(C(F)(F)F)c1]

To a solution of 5-(2-hydroxyethyl)-2-{[3-(trifluoromethyl)phenyl]oxy}benzonitrile (1.3 g, 4.23 mmol) in DCM (2 mL) stirred at 0° C. was added triphenylphosphine (2.219 g, 8.46 mmol), iodine (2.148 g, 8.46 mmol) and imidazole (0.576 g, 8.46 mmol). The mixture was stirred at 0° C. for 1.5 h, and then quenched with Na$_2$SO$_3$. The mixture was extracted with ether and dried over magnesium sulfate, filtered, and concentrated. Purification via flash chromatography then afforded the title compound (1.3 g, 3.12 mmol, 73.7% yield).

D103: 1-chloro-2-(trifluoromethyl)-4-(4-vinylphenoxyl)benzene

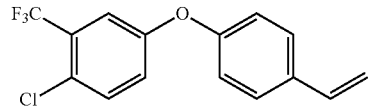 [SMILES: C=Cc1ccc(Oc2ccc(Cl)c(C(F)(F)F)c2)cc1]

To a solution of methyltriphenylphosphonium bromide (5.99 g, 16.76 mmol) and NaH (1.397 g, 34.9 mmol) in THF (50 mL) was added a solution of 4-{[4-chloro-3-(trifluoromethyl)phenyl]oxy}benzaldehyde (4.2 g, 13.97 mmol) in THF (50 mL) under nitrogen at 0° C. The reaction mixture was stirred at 0° C. for 0.5 h, then at room temperature overnight. Purification via flash chromatography then afforded the title compound (3.6 g, 12.05 mmol, 86% yield).

D104: 2-(4-{[4-chloro-3-(trifluoromethyl)phenyl]oxy}phenyl)ethanol

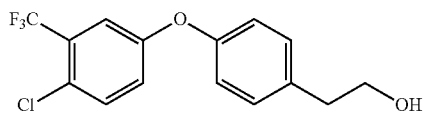 [SMILES: OCCc1ccc(Oc2ccc(Cl)c(C(F)(F)F)c2)cc1]

To a solution of 1-chloro-2-(trifluoromethyl)-4-(4-vinylphenoxyl)benzene (3 g, 10.04 mmol) in THF (50 mL) was added 9-BBN (24.11 mL, 12.05 mmol) under nitrogen. The reaction mixture was stirred at 0° C. for 0.5 h, then the temperature was allowed to warm up to room temperature. NaOH (13.39 mL, 40.2 mmol) and H$_2$O$_2$ (14.36 mL, 141 mmol) was added. The mixture was then heated at 60° C. for 2 h. Na$_2$SO$_3$ was added to quench the reaction after cooling. Purification via flash chromatography then afforded the title compound (2.2 g, 6.95 mmol, 69.2% yield). LCMS: rt=3.55 min, [M+H$^+$-H$_2$O]=299

D105: 1-chloro-4-{[4-(2-iodoethyl)phenyl]oxy}-2-(trifluoromethyl)benzene

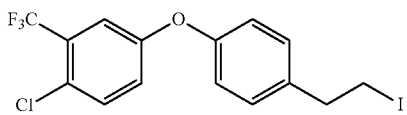 [SMILES: FC(F)(F)c1cc(Oc2ccc(CCI)cc2)ccc1Cl]

To the solution of 2-(4-{[4-chloro-3-(trifluoromethyl)phenyl]oxy}phenyl)ethanol (80 mg, 0.253 mmol) in DCM (2.5 ml), was added Ph$_3$P (133 mg, 0.505 mmol), imidazole (34.4 mg, 0.505 mmol) and iodide (128 mg, 0.505 mmol) at 0° C., The mixture was stirred at 0° C. for 10 min, then at room temperature for 1 h. The reaction was quenched with sat. Na$_2$SO$_3$ solution. The aqueous phase was extracted with DCM. The combined organic phase was washed with brine, dried over Na$_2$SO$_4$, concentrated and purified via flash chromatography to afford the title compound (50 mg, 46.4% yield) as colorless oil. LCMS: rt=4.47 min

D106: 2-{[4-chloro-3-(trifluoromethyl)phenyl]oxy}-5-ethenylbenzonitrile

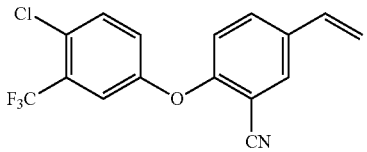 [SMILES: C=Cc1ccc(Oc2ccc(Cl)c(C(F)(F)F)c2)c(C#N)c1]

To a solution of NaH (0.798 g, 19.96 mmol) in dry THF (15 mL) was added methyltriphenylphosphonium bromide (7.13 g, 19.96 mmol). The mixture was stirred at room temperature for 0.5 h. Then 2-{[4-chloro-3-(trifluoromethyl)phenyl]oxy}-5-formylbenzonitrile (5.0 g, 15.35 mmol) was added. Stirring continued for 1.5 h, and the mixture was quenched by ice water. THF was removed by evaporation; the aqueous layer was extracted with DCM. The combined organic layers were washed with brine, dried over $Na_2SO_4$, filtered and concentrated to afford the title compound (1.8 g, 5.56 mmol, 36.2% yield).

D107: 2-{[4-chloro-3-(trifluoromethyl)phenyl]oxy}-5-(2-hydroxyethyl)benzonitrile

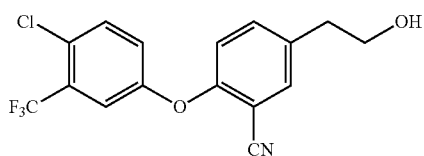 [SMILES: N#Cc1cc(CCO)ccc1Oc1ccc(Cl)c(C(F)(F)F)c1]

To the solution of 2-{[4-chloro-3-(trifluoromethyl)phenyl]oxy}-5-ethenylbenzonitrile (2.0 g, 6.18 mmol) in dry THF (14 mL), was added 9-BBN (18 mL, 9.00 mmol) at 0° C. The mixture was stirred at room temperature overnight. Water (1.113 mL, 61.8 mmol), aq. NaOH (12.36 mL, 37.1 mmol), and 30% $H_2O_2$ (3.16 mL, 30.9 mmol) were added then. The reaction mixture was heated at 55° C. for 4 h. Then THF was removed under reduced pressure, and the residue was diluted with EA. The organic layer was washed with water and brine, dried over anhydrous $Na_2SO_4$ and concentrated and purified by flash chromatography to afford the title compound (1.0 g, 2.93 mmol, 47.4% yield).

D108: 2-{[4-chloro-3-(trifluoromethyl)phenyl]oxy}-5-(2-iodoethyl)benzonitrile

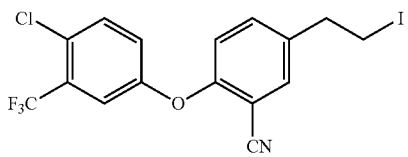 [SMILES: N#Cc1cc(CCI)ccc1Oc1ccc(Cl)c(C(F)(F)F)c1]

To a solution of Ph$_3$P (1036 mg, 3.95 mmol) and iodine (1003 mg, 3.95 mmol) in DCM (5 mL), which was stirred at room temperature for 10 min, was added imidazole (448 mg, 6.58 mmol). After stirring for another 10 min, 2-{[4-chloro-3-(trifluoromethyl)phenyl]oxy}-5-(2-hydroxyethyl)benzonitrile (900 mg, 2.63 mmol) was added. The mixture was stirred at room temperature for 1 h, and quenched by water, extracted with DCM. Purification via flash chromatography then afforded the title compound (1.0 g, 2.214 mmol, 84% yield).

D109: 4-(4-fluorophenoxyl)phenethyl carbamimidate

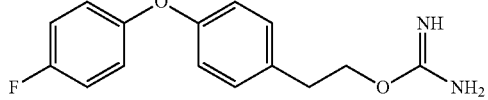

To a solution of 2-{4-[(4-fluorophenyl)oxy]phenyl}ethanol (750 mg, 3.23 mmol) and cyanamide (149 mg, 3.55 mmol) in THF (15 mL) was added trifluoromethanesulfonic acid (0.344 mL, 3.88 mmol) at 0° C. The reaction mixture was stirred at room temperature overnight. After removing the solvent, the residue was diluted with water, extracted with DCM. The organic phase was dried over sodium sulfate, filtered, and concentrated. Purification via reverse phase flash chromatography then afforded the title compound (290 mg, 1.057 mmol, 32.7% yield).

D110: 4-{[4-(trifluoromethyl)phenyl]oxy}benzaldehyde

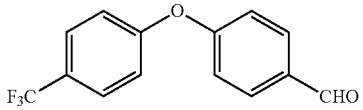 [SMILES: O=Cc1ccc(Oc2ccc(C(F)(F)F)cc2)cc1]

To a solution of 4-(trifluoromethyl)phenol (3 g, 18.51 mmol) and 4-fluorobenzaldehyde (2.3 g, 18.53 mmol) in DMF (20 mL), was added $Cs_2CO_3$ (7.24 g, 22.21 mmol). The mixture was heated with a microwave condition at 120° C. for 4 h. After cooling, the reaction mixture was diluted in water, extracted with EA. The organic phase was washed with water and brine, dried over $Na_2SO_4$ and evaporated in vacuo to afford the title compound (4.68 g, 95% yield) as a brown oil. LCMS: rt=3.58 min, [M+H$^+$]=267

D111: 1-ethenyl-4-{[4-(trifluoromethyl)phenyl]oxy}benzene

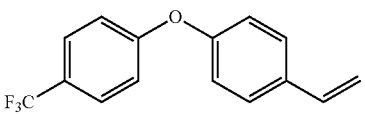

To a stirred suspension of 4-{[4-(trifluoromethyl)phenyl]oxy}benzaldehyde (4.68 g, 17.58 mmol) and methyl(triphenyl)phosphonium bromide (6.28 g, 17.58 mmol) in dry THF (50 mL) was added NaH (3 g, 75 mmol) under nitrogen at 0° C. The mixture was stirred at room temperature for 3 h. The organic layer was washed three times with brine, dried over $Na_2SO_4$, filtered, and concentrated. Purification via flash

D112: 2-(4-{[4-(trifluoromethyl)phenyl]oxy}phenyl) ethanol

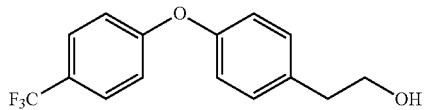 [SMILES: OCCc1ccc(Oc2ccc(C(F)(F)F)cc2)cc1]

To the solution of 1-ethenyl-4-{[4-(trifluoromethyl)phenyl]oxy}benzene (890 mg, 3.37 mmol) in dry THF (10 mL), was added 9-BBN (10 mL, 5.00 mmol) at 0° C. and stirred at room temperature overnight. Then the reaction mixture was quenched by addition of water (3 mL), followed by aq. NaOH (3M, 4.5 mL), and 30% $H_2O_2$ (5 mL). The reaction mixture was heated at 50° C. for 3 h. Then the THF and some water were removed under reduced pressure, and the residue was diluted with EA. The organic layer was washed with water and brine, dried over $Na_2SO_4$ and concentrated. Purification via flash chromatography afforded the title compound (914 mg, 96% yield). LCMS: rt=3.38 min, [M+H$^+$]=265

D113: 2-(4-{[4-(trifluoromethyl)phenyl]oxy}phenyl) ethyl imidocarbamate

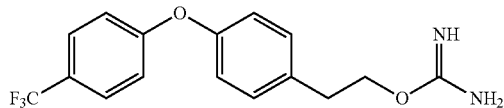

To a solution of 2-(4-{[4-(trifluoromethyl)phenyl]oxy}phenyl)ethanol (500 mg, 1.771 mmol) and cyanmide (89 mg, 2.126 mmol) in dry THF (5 mL) under nitrogen was added triflic acid (0.189 mL, 2.126 mmol). The mixture was heated at 55° C. for 2 h. Purification via reverse phase flash chromatography afforded the title compound (240 mg, 31.0% yield). LCMS: rt=2.63 min, [M+H$^+$]=265

D114: methyl (2-{[2-(4-{[4-chloro-3-(trifluoromethyl)phenyl]oxy}phenyl)ethyl]oxy}-4-oxo-1,4-dihydro-5-pyrimidinyl)acetate

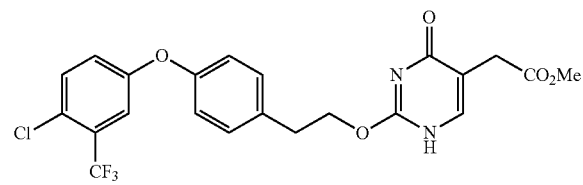 [SMILES: COC(=O)Cc1c[nH]c(OCCc2ccc(Oc3ccc(Cl)c(C(F)(F)F)c3)cc2)nc1=O]

To a solution of 2-(4-{[4-chloro-3-(trifluoromethyl)phenyl]oxy}phenyl)ethyl imidocarbamate (437 mg, 0.861 mmol) and dimethyl 2-formylbutanedioate (450 mg, 2.58 mmol) in NMP (5 mL) was added $K_2CO_3$ (357 mg, 2.58 mmol). The mixture was heated at 130° C. for 1.5 h. Purification via reverse phase flash chromatography then afforded the title compound, together with ethyl ester (102 mg, 0.211 mmol, 24.55% yield).

D115: N'-acetyl-2-(2-{[2-(4-{[4-chloro-3-(trifluoromethyl)phenyl]oxy}phenyl)ethyl]oxy}-4-oxo-1,4-dihydro-5-pyrimidinyl)acetohydrazide

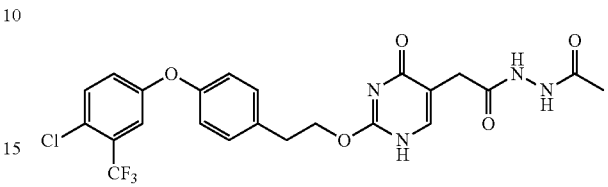

To a solution of (2-{[2-(4-{[4-chloro-3-(trifluoromethyl)phenyl]oxy}phenyl)ethyl]oxy}-4-oxo-1,4-dihydro-5-pyrimidinyl)acetic acid (91 mg, 0.194 mmol) in THF (2 mL) was added EDC (149 mg, 0.776 mmol) and HOBT (89 mg, 0.582 mmol). The mixture was stirred at room temperature for 15 min and acetohydrazide (21.57 mg, 0.291 mmol) was added. The mixture was stirred at room temperature overnight. Purification via reverse phase flash chromatography then afforded the title compound (28 mg, 0.053 mmol, 27.5% yield). LCMS: rt=3.04 min, [M+H$^+$]=525

D116: 4-((6-(trifluoromethyl)pyridin-2-yl)oxy)benzaldehyde

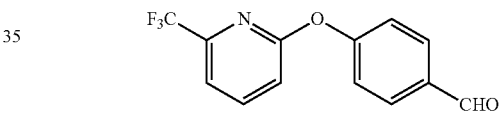

To a solution of 2-chloro-6-(trifluoromethyl)pyridine (1.5 g, 8.26 mmol) and 4-hydroxybenzaldehyde (1.009 g, 8.26 mmol) in DMF (18 mL), was added $K_2CO_3$ (1.713 g, 12.39 mmol). The mixture was heated at 130° C. for 5 h, and then transferred to a sealed tube and heated with a microwave condition at 135° C. for 3 h. After cooling, the reaction mixture was diluted in water, extracted with EA. The organic phase was washed with water and brine, dried over $Na_2SO_4$, concentrated to afford the title compound (2.10 g) as a brown oil. LCMS: rt=3.25 min, [M+H$^+$]=268

D117: 2-(trifluoromethyl)-6-(4-vinylphenoxyl)pyridine

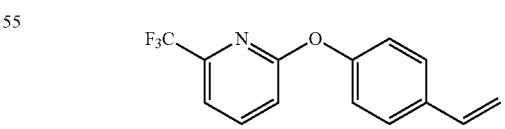

To a stirred suspension of 4-((6-(trifluoromethyl)pyridin-2-yl)oxy)benzaldehyde (4 g, 14.97 mmol) and methyl(triphenyl)phosphonium bromide (5.35 g, 14.97 mmol) in dry THF (40 mL) was added NaH (2.096 g, 52.4 mmol) under nitrogen at 0° C. The mixture was stirred at room temperature for 2 h. The organic layer was washed three times with brine, dried over $Na_2SO_4$, filtered, and concentrated. Purification via flash chromatography afforded the title compound (2.4 g, 9.05 mmol, 60.4% yield) as a light green oil. LCMS: rt=3.80 min, [M+H⁺]=266

D118: 2-(4-((6-(trifluoromethyl)pyridin-2-yl)oxy)phenyl)ethanol

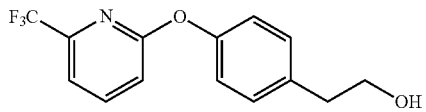 [SMILES: OCCc1ccc(Oc2cccc(C(F)(F)F)n2)cc1]

To the solution of 2-(trifluoromethyl)-6-(4-vinylphenoxyl)pyridine (2.4 g, 9.05 mmol) in dry THF (25 mL), was added 9-BBN (30 ml, 15.00 mmol) at 0° C. The mixture was stirred at room temperature overnight, and quenched with water (2 mL), followed by aq. NaOH (12 mL, 36.0 mmol), and 30% $H_2O_2$ (12 mL). The reaction mixture was heated at 50° C. for 1 h. Then THF was removed under reduced pressure, and the residue was diluted with EA. The organic layer was washed with water and brine, dried over anhydrous $Na_2SO_4$ and concentrated and purified by flash chromatography to afford the title compound (3.68 g, 8.44 mmol, 93% yield) as a white oil. LCMS: rt=3.00 min, [M+H⁺]=284

D119: 4-((6-(trifluoromethyl)pyridin-2-yl)oxy)phenethyl carbamimidate, Trifluoroacetate

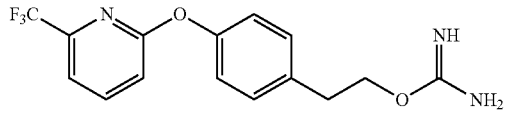

To a solution of 2-(4-((6-(trifluoromethyl)pyridin-2-yl)oxy)phenyl)ethanol (1.6 g, 3.67 mmol) and cyanamide (0.35 g, 8.33 mmol) in dry THF (15 mL) under nitrogen was added triflic acid (0.710 mL, 8.00 mmol). The mixture was heated at 55° C. for 2 h. Purification via reverse phase flash chromatography afforded the title compound (830 mg, 1.894 mmol, 51.6% yield) as a white solid. LCMS: rt=2.55 min, [M+H⁺]=326

D120: 2-(4-(5-(trifluoromethyl)pyridin-2-yl)oxy)phenyl)ethanol

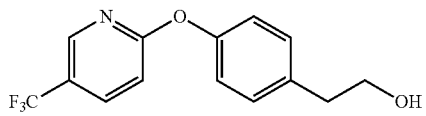 [SMILES: OCCc1ccc(Oc2ccc(C(F)(F)F)cn2)cc1]

To a solution of 2-bromo-5-(trifluoromethyl)pyridine (500 mg, 2.212 mmol) and 4-(2-hydroxyethyl)phenol (306 mg, 2.212 mmol) in DMF (10 mL) was added $K_2CO_3$ (459 mg, 3.32 mmol). The mixture was heated at 110° C. for 1 h. The reaction mixture was diluted with water and extracted with EA twice. The organic phase was washed with brine, dried over $Na_2SO_4$ and evaporated in vacuo to afford the title compound (720 mg, 2.54 mmol, 115% yield). LCMS: rt=2.93 min, [M+H⁺]=284

D121: 4-((5-(trifluoromethyl)pyridin-2-yl)oxy)phenethyl carbamimidate, trifluoroacetate

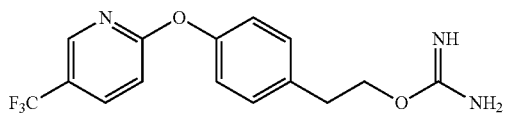 [SMILES: N=C(N)OCCc1ccc(Oc2ccc(C(F)(F)F)cn2)cc1]

To a solution of 2-(4-((5-(trifluoromethyl)pyridin-2-yl)oxy)phenyl)ethanol (720 mg, 2.54 mmol) and cyanamide (427 mg, 10.17 mmol) in dry THF (10 mL) under nitrogen was added triflic acid (0.903 mL, 10.17 mmol). The mixture was heated at 55° C. overnight. Purification via reverse phase flash chromatography afforded the title compound (800 mg, 1.825 mmol, 71.8% yield). LCMS: rt=2.51 min, [M+H⁺]=326

D122: 4-{[6-(trifluoromethyl)-3-pyridinyl]oxy}benzaldehyde

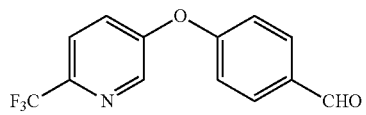 [SMILES: O=Cc1ccc(Oc2ccc(C(F)(F)F)nc2)cc1]

To a solution of 6-(trifluoromethyl)-3-pyridinol (2 g, 12.26 mmol) and 4-fluorobenzaldehyde (1.315 ml, 12.26 mmol) in DMF (50 mL), was added $K_2CO_3$ (2.54 g, 18.39 mmol). The mixture was heated at 130° C. overnight. After cooling, the reaction mixture was diluted in water, extracted with EA. The organic phase was washed with water and brine, dried over $Na_2SO_4$, concentrated to afford the title compound (3.28 g, 12.26 mmol, 100% yield) as a brown oil. LCMS: rt=3.16 min, [M+H⁺]=268

D123: 5-[(4-ethenylphenyl)oxy]-2-(trifluoromethyl)pyridine

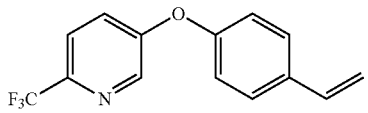 [SMILES: C=Cc1ccc(Oc2ccc(C(F)(F)F)nc2)cc1]

To a stirred suspension of 4-{[6-(trifluoromethyl)-3-pyridinyl]oxy})benzaldehyde (3.28 g, 12.28 mmol) and methyl(triphenyl)phosphonium bromide (4.39 g, 12.28 mmol) in dry THF (60 mL) was added NaH (1.718 g, 43.0 mmol) under nitrogen at 0° C. The mixture was stirred at room temperature for 2 h. The organic layer was washed three times with brine, dried over $Na_2SO_4$, filtered, and concentrated. Purification via flash chromatography afforded the title compound (1.83 g, 6.90 mmol, 56.2% yield) as light green oil. LCMS: rt=3.77 min, [M+H⁺]=266

D124: 2-(4-{[6-(trifluoromethyl)-3-pyridinyl]oxy}phenyl)ethanol

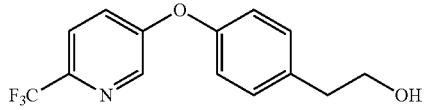

To the solution of 5-[(4-ethenylphenyl)oxy]-2-(trifluoromethyl)pyridine (1.83 g, 6.90 mmol) in dry THF (20 mL), was added 9-BBN (20.70 mL, 10.35 mmol) at 0° C. The mixture was stirred at room temperature overnight, and quenched with water (2 mL), followed by aq. NaOH (3M, 9 mL), and 30% H₂O₂ (8 mL). The reaction mixture was heated at 50° C. for 3 h. Then THF was removed under reduced pressure, and the residue was diluted with EA. The organic layer was washed with water and brine, dried over anhydrous Na₂SO₄ and concentrated and purified by flash chromatography to afford the title compound (2.67 g, 9.43 mmol, 137% yield) as a colorless oil. LCMS: rt=2.97 min, [M+H⁺]=284

D125: 2-(4-{[6-(trifluoromethyl)-3-pyridinyl]oxy}phenyl)ethyl imidocarbamate

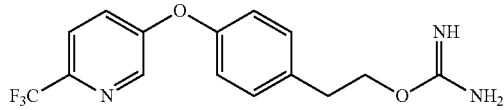 [SMILES: N=C(N)OCCc1ccc(Oc2ccc(C(F)(F)F)nc2)cc1]

To a solution of 2-(4-{[6-(trifluoromethyl)-3-pyridinyl]oxy}phenyl)ethanol (1.95 g, 6.88 mmol) and cyanamide (0.5 g, 11.89 mmol) in dry THF (20 mL) under nitrogen was added triflic acid (1 mL, 11.26 mmol). The mixture was heated at 55° C. for 4 h. Purification via reverse phase flash chromatography afforded the title compound (1.72 g, 3.92 mmol, 57.0% yield) as a white solid. LCMS: rt=2.42 min, [M+H⁺]=326

D126: 2-(trifluoromethyl)-1,4,5,6-tetrahydro-5-pyrimidinol

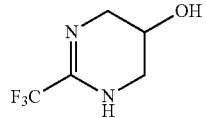

To a solution of ethyl trifluoroacetate (5.80 g, 40.8 mmol) in p-Xylene (30 mL) was added 1,3-diamino-2-propanol (3.60 g, 40 mmol). The mixture was stirred at 160° C. for 4 h. Concentration in vacuo then afforded the title compound (6.55 g, 39.0 mmol, 97% yield).

D127: 2-(trifluoromethyl)-5-pyrimidinol

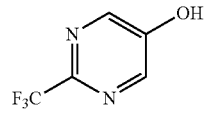

A mixture of 2-(trifluoromethyl)-1,4,5,6-tetrahydro-5-pyrimidinol (6.50 g, 38.7 mmol) and nitrobenzene (30 mL) was heated to 90° C. to form a homogeneous solution. At this temperature, a solution of sodium methoxide (8.5 g, 157 mmol) in methanol (30 mL) was added portionwise, allowing the methanol to distill off before next addition (the whole process took about 3 h). Then the reaction mixture was heated to 120° C. for 1 h. The reaction mixture was cooled to room temperature, and then partitioned between ethyl acetate and water. The organic phase was separated off. The aqueous phase adjusted to pH 4.0 with 6M aqueous HCl and then extracted with EA. The organic phase was dried over sodium sulfate, and filtered. Concentrated in vacuo then afforded the title compound (533 mg, 3.25 mmol, 8.4% yield). LCMS: rt=1.78 min, [M+H⁺]=165

D128: 4-{[2-(trifluoromethyl)-5-pyrimidinyl]oxy}benzaldehyde

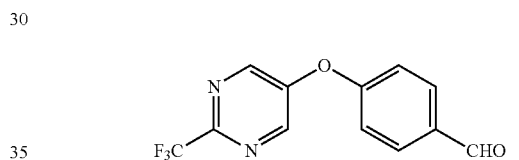

A mixture of 4-fluorobenzaldehyde (0.196 mL, 1.828 mmol), 2-(trifluoromethyl)-5-pyrimidinol (300 mg, 1.828 mmol), and K₂CO₃ (505 mg, 3.66 mmol) in DMF (2 mL) was heated with a microwave reactor at 130° C. for 1 h. After removing the solvent, the residue was diluted with water, extracted with DCM. The organic phase was dried over sodium sulfate, filtered, and concentrated. Purification via flash chromatography then afforded the title compound (351 mg, 1.309 mmol, 71.6% yield). LCMS: rt=2.97 min, [M+H⁺]=269

D129: 5-[(4-ethenylphenyl)oxy]-2-(trifluoromethyl)pyrimidine

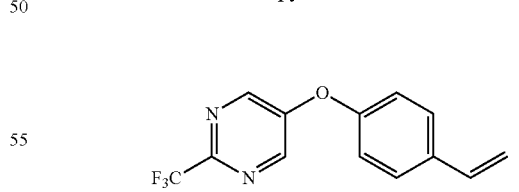

To a suspension of NaH (373 mg, 9.32 mmol) and methyltriphenylphosphonium bromide (799 mg, 2.237 mmol) in THF (5 mL), which was stirred at 0° C. for 1 h was added 4-{[2-(trifluoromethyl)-5-pyrimidinyl]oxy}benzaldehyde (500 mg, 1.864 mmol). The mixture was stirred at room temperature for 2 h, and then quenched with NH₄Cl sat. solution. The organic layer was separated and the aqueous phase was extracted with DCM. The organic phase was dried over sodium sulfate, filtered, and concentrated. Purification via flash chromatography then afforded the title compound (300 mg, 1.127 mmol, 60.4% yield).

D130: 2-(4-{[2-(trifluoromethyl)-5-pyrimidinyl]oxy}phenyl)ethanol

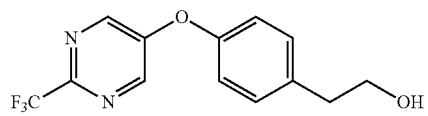 [SMILES: OCCc1ccc(Oc2cnc(C(F)(F)F)nc2)cc1]

To a solution of 5-[(4-ethenylphenyl)oxy]-2-(trifluoromethyl)pyrimidine (100 mg, 0.376 mmol) and 9-BBN (1.503 mL, 0.751 mmol) in THF (5 mL) under nitrogen, which was stirred overnight was added NaOH (0.501 mL, 1.503 mmol) and H$_2$O$_2$ (0.460 mL, 4.51 mmol). The mixture was heated at 60° C. for 1 h, and then quenched with NH$_4$Cl sat. solution after cooling. The organic layer was separated and washed with Na$_2$SO$_3$ solution and brine. The organic layer was dried by Na$_2$SO$_4$. Concentration then afforded the title compound (80 mg, 0.281 mmol, 74.9% yield). LCMS: rt=2.82 min, [M+H]=285

D131: 2-(4-{[2-(trifluoromethyl)-5-pyrimidinyl]oxy}phenyl)ethyl imidocarbamate

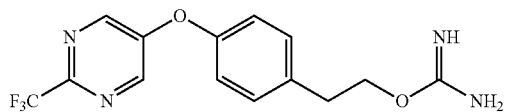 [SMILES: N=C(N)OCCc1ccc(Oc2cnc(C(F)(F)F)nc2)cc1]

To a solution of 2-(4-{[2-(trifluoromethyl)-5-pyrimidinyl]oxy}phenyl)ethyl imidocarbamate (143 mg, 0.503 mmol) and cyanamide (25.4 mg, 0.604 mmol) in THF (1 mL) was added trifluoromethanesulfonic acid (0.134 mL, 1.509 mmol) at 0° C. The reaction mixture was stirred at room temperature overnight. After removing the solvent, the residue was diluted with water, extracted with DCM. The organic phase was dried over sodium sulfate, filtered, and concentrated. Purification via reverse phase flash chromatography then afforded the title compound (60 mg, 0.184 mmol, 36.6% yield). LCMS: rt=2.33 min, [M+H]=327

D132: 5-ethyl-2-(4-((2-(trifluoromethyl)pyrimidin-5-yl)oxy)phenethoxy)pyrimidin-4(1H)-one, trifluoroacetic acid salt

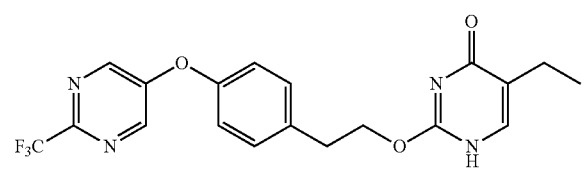 [SMILES: CCc1c[nH]c(OCCc2ccc(Oc3cnc(C(F)(F)F)nc3)cc2)nc1=O]

A mixture of 2-(4-{[2-(trifluoromethyl)-5-pyrimidinyl]oxy}phenyl)ethyl imidocarbamate (100 mg, 0.306 mmol), methyl 2-formylbutanoate (47.9 mg, 0.368 mmol) and K$_2$CO$_3$ (169 mg, 1.226 mmol) in NMP (1 mL) was heated with a microwave reactor at 130° C. for 1 h. Purification via MDAP then afforded the title compound (24 mg, 0.059 mmol, 19.27% yield). LCMS: rt=3.16 min, [M+H]=407

D133: 2-(4-((5-(trifluoromethyl)pyrimidin-2-yl)oxy)phenyl)ethanol(crude)

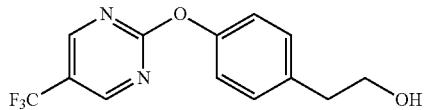

To a solution of 4-(2-hydroxyethyl)phenol (0.795 g, 5.75 mmol) in DMF (15 mL) was added 2-chloro-5-(trifluoromethyl)pyrimidine (1 g, 5.48 mmol) and K$_2$CO$_3$ (0.909 g, 6.57 mmol). The mixture was heated at 110° C. for 3 h. The mixture was poured into 100 mL water and extracted with EA three times. The organic layer was dried over Na$_2$SO$_4$ and concentrated to afford the title compound (1.557 g, 5.48 mmol, 100% yield). LCMS: rt=2.66 min, [M+H$^+$]=285

D134: 4-((5-(trifluoromethyl)pyrimidin-2-yl)oxy)phenethyl carbamimidate, Trifluoromethanesulphonate

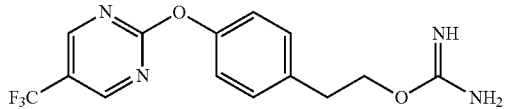

To a solution of 2-(4-((5-(trifluoromethyl)pyrimidin-2-yl)oxy)phenyl)ethanol(crude) (1.56 g, 5.49 mmol) and cyanamide (0.277 g, 6.59 mmol) in THF (10 mL) was added TfOH (1.218 mL, 13.72 mmol). The mixture was heated at 40° C. for 2 h. Purification via reverse phase flash chromatography then afforded the title compound (777 mg, 1.635 mmol, 29.8% yield). LCMS: rt=2.17 min, [M+H$^+$]=327

D135: 2-(4-((5-chloropyrimidin-2-yl)oxy)phenyl)ethanol

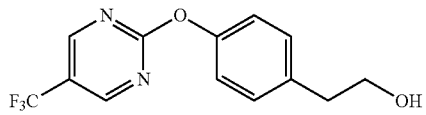 [SMILES: OCCc1ccc(Oc2ncc(C(F)(F)F)cn2)cc1]

To a solution of 4-(2-hydroxyethyl)phenol (555 mg, 4.02 mmol) in DMF (15 mL) was added 2,5-dichloropyrimidine (570 mg, 3.83 mmol) and K$_2$CO$_3$ (635 mg, 4.59 mmol). The mixture was heated at 110° C. overnight. Purification via reverse phase flash chromatography then afforded the title compound (861 mg, 3.43 mmol, 90% yield). LCMS: rt=2.38 min, [M+H$^+$]=251

D136: 4-((5-chloropyrimidin-2-yl)oxy)phenethyl carbamimidate, trifluoromethanesulphonate

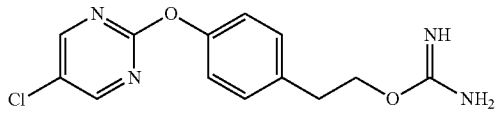 [SMILES: N=C(N)OCCc1ccc(Oc2ncc(Cl)cn2)cc1]

To a solution of 2-(4-((5-chloropyrimidin-2-yl)oxy)phenyl)ethanol (861 mg, 3.43 mmol) and cyanamide (173 mg, 4.12 mmol) in THF (10 mL) at 0° C. was added TfOH (0.458 mL, 5.15 mmol). The mixture was heated at 40° C. for 2 h. Purification via reverse phase flash chromatography then afforded the title compound (700 mg, 1.584 mmol, 46.1% yield). LCMS: rt=1.98 min, [M+H$^+$]=293

D137: 2-(4-(pyrimidin-2-yloxy)phenyl)ethanol

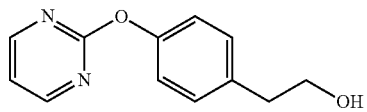 [SMILES: OCCc1ccc(Oc2ncccn2)cc1]

To a solution of 4-(2-hydroxyethyl)phenol (950 mg, 6.88 mmol) in DMF (15 mL) was added 2-chloropyrimidine (750 mg, 6.55 mmol) and K$_2$CO$_3$ (1086 mg, 7.86 mmol). The mixture was heated at 110° C. overnight. Purification via reverse phase flash chromatography then afforded the title compound (1.3 g, 6.01 mmol, 92% yield). LCMS: rt=1.85 min, [M+H$^+$]=218

D138: 4-(pyrimidin-2-yloxy)phenethyl carbamimidate, trifluoromethanesulphonate

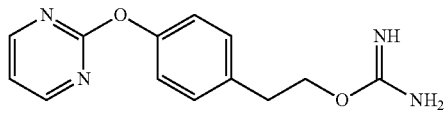 [SMILES: N=C(N)OCCc1ccc(Oc2ncccn2)cc1]

To a solution of 2-(4-(pyrimidin-2-yloxy)phenyl)ethanol (1.2 g, 5.55 mmol) and cyanamide (0.350 g, 8.32 mmol) in THF (15 mL) was added TfOH (1.478 mL, 16.65 mmol). The mixture was stirred at room temperature for 2 h. Purification via reverse phase flash chromatography then afforded the title compound (1.5 g, 3.68 mmol, 66.4% yield). LCMS: rt=1.55 min, [M+H$^+$]=259

D139: 2-(4-((6-chloropyridazin-3-yl)oxy)phenyl) ethanol

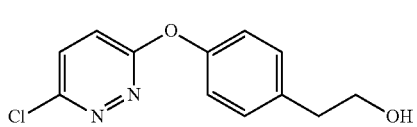 [SMILES: OCCc1ccc(Oc2ccc(Cl)nn2)cc1]

To a solution of 4-(2-hydroxyethyl)phenol (1.533 g, 11.09 mmol) in DMF (15 mL) was added 3,6-dichloropyridazine (1.574 g, 10.57 mmol) and K$_2$CO$_3$ (1.752 g, 12.68 mmol). The mixture was heated at 110° C. overnight. Purification via reverse phase flash chromatography then afforded the title compound (1.5 g, 5.98 mmol, 56.6% yield). LCMS: rt=2.23 min, [M+H$^+$]=251

D140: 4-((6-chloropyridazin-3-yl)oxy)phenethyl carbamimidate, trifluoromethanesulphonate

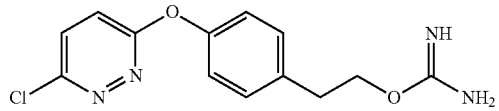 [SMILES: N=C(N)OCCc1ccc(Oc2ccc(Cl)nn2)cc1]

To a solution of 2-(4-((6-chloropyridazin-3-yl)oxy)phenyl)ethanol (1.14 g, 4.55 mmol) and cyanamide (0.229 g, 5.46 mmol) in THF (20 mL) was added TfOH (1.212 mL, 13.64 mmol). The mixture was stirred at 40° C. for 15 min, and quenched with NH$_4$OH. After removing the solvent, the residue was diluted with water, extracted with EA. The organic phase was dried over sodium sulfate, filtered, and concentrated to afford the title compound (1 g, 2.264 mmol, 49.8% yield). LCMS: rt=1.90 min, [M+H$^+$]=293

D141: 4-[(3-chloro-4-methylphenyl)oxy]benzaldehyde

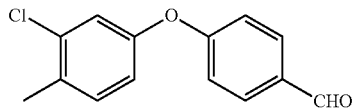 [SMILES: Cc1ccc(Oc2ccc(C=O)cc2)cc1Cl]

To a solution of 3-chloro-4-methylphenol (2.5 g, 17.53 mmol) and 4-fluorobenzaldehyde (2.2 g, 17.73 mmol) in DMF (40 ml), was added K$_2$CO$_3$ (2.91 g, 21.04 mmol). The solution was heated at 120° C. overnight: The reaction mixture was diluted in water, extracted with EA. The organic phase was washed with water and brine, dried over Na$_2$SO$_4$ and evaporated in vacuo to afford the title compound (5.5 g, 15.61 mmol, 89% yield). LCMS: rt=3.80 min, [M+H$^+$]=247

D142: 2-chloro-4-[(4-ethenylphenyl)oxy]-1-methylbenzene

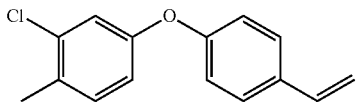 [SMILES: C=Cc1ccc(Oc2ccc(C)c(Cl)c2)cc1]

To a stirred suspension of 4-[(3-chloro-4-methylphenyl)oxy]benzaldehyde (5.5 g, 22.30 mmol) and methyl(triphenyl)phosphonium bromide (7.96 g, 22.30 mmol) in THF (50 mL) was added NaH (3.12 g, 78 mmol) under nitrogen at 0° C. After the mixture was stirred at room temperature for 3 h, the organic layer was washed three times with brine, dried over Na$_2$SO$_4$, filtered, and concentrated. Purification via flash chromatography afforded the title compound (2.8 g, 51.3% yield). LCMS: rt=4.37 min, [M+H$^+$]=323

D143: 2-{4-[(3-chloro-4-methylphenyl)oxy]phenyl}ethanol

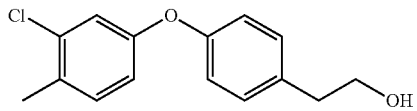 [SMILES: Cc1ccc(Oc2ccc(CCO)cc2)cc1Cl]

To the solution of 2-chloro-4-[(4-ethenylphenyl)oxy]-1-methylbenzene (2.8 g, 11.44 mmol) in dry THF (20 mL), was added 9-BBN (30 mL, 15.00 mmol) at 0° C. and stirred at room temperature overnight. Then the reaction mixture was quenched by addition of water (3 mL), followed by aq. NaOH (3M, 15 mL), and 30% $H_2O_2$ (15 mL). The reaction mixture was heated at 50° C. for 4 h. Then the THF and some water were removed under reduced pressure, and the residue was diluted with EA (30 mL). The organic layer was washed with water and brine, dried over $Na_2SO_4$ and concentrated. Purification via flash chromatography afforded the title compound (2 g, 66.5% yield). LCMS: rt=3.51 min, [M+H$^+$]=245

D144: 2-{4-[(3-chloro-4-methylphenyl)oxy]phenyl}ethyl imidocarbamate

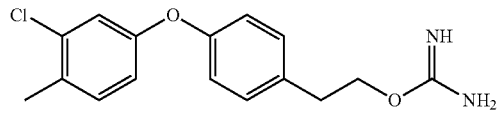 [SMILES: Cc1ccc(Oc2ccc(CCOC(=N)N)cc2)cc1Cl]

To a solution of 2-{4-[(3-chloro-4-methylphenyl)oxy]phenyl}ethanol (1.7 g, 6.47 mmol) and cyanmide (0.326 g, 7.76 mmol) in dry THF (20 mL) under nitrogen was added triflic acid (0.690 mL, 7.76 mmol) The mixture was heated at 55° C. for 2 h. Purification via reverse phase flash chromatography then afforded the title compound (680 mg, 1.628 mmol, 25.2% yield). LCMS: rt=2.76 min, [M+H$^+$]=245

D145: 4-[(4-chloro-3-methylphenyl)oxy]benzaldehyde

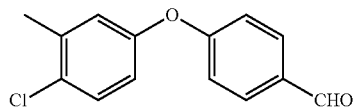 [SMILES: Cc1cc(Oc2ccc(C=O)cc2)ccc1Cl]

To solution of 4-chloro-3-methylphenol (2.5 g, 17.53 mmol) and 4-fluorobenzaldehyde (2.2 g, 17.73 mmol) in DMF (20 ml), was added $K_2CO_3$ (2.91 g, 21.04 mmol). The mixture was heated with a microwave condition at 130° C. for 4 h. After cooling, the mixture was diluted in water, extracted with EA. The combined organic phase was washed with water and brine, dried over $Na_2SO_4$ and evaporated in vacuo to afford the title compound (4.2 g, 97% yield). LCMS: rt=3.79 min, [M+H$^+$]=247

D146: 1-chloro-4-[(4-ethenylphenyl)oxy]-2-methylbenzene

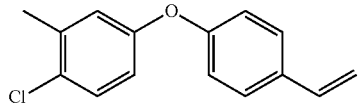 [SMILES: C=Cc1ccc(Oc2ccc(Cl)c(C)c2)cc1]

To a stirred suspension of 4-[(4-chloro-3-methylphenyl)oxy]benzaldehyde (4.2 g, 17.03 mmol) and methyl(triphenyl)phosphonium bromide (6 g, 16.80 mmol) in dry THF (50 mL) was added NaH (3.4 g, 85 mmol) under nitrogen at 0° C. The mixture was stirred at room temperature for 3 h. The organic layer was washed three times with brine, dried over $Na_2SO_4$, filtered, and concentrated. Purification via flash chromatography afforded the title compound (2.46 g, 59% yield) as a light green oil. LCMS: rt=4.34 min, [M+H$^+$]=280

D147: 2-{4-[(4-chloro-3-methylphenyl)oxy]phenyl}ethanol

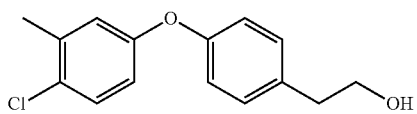 [SMILES: Cc1cc(Oc2ccc(CCO)cc2)ccc1Cl]

To the solution of 1-chloro-4-[(4-ethenylphenyl)oxy]-2-methylbenzene (2.46 g, 10.05 mmol) in dry THF (30 mL), was added 9-BBN (30.2 mL, 15.08 mmol) at 0° C. The mixture was stirred at room temperature overnight, and quenched with water (3 mL), followed by aq. NaOH (13.00 mL, 39.0 mmol), and 30% $H_2O_2$ (13.00 mL, 126 mmol). The reaction mixture was heated at 50° C. for 3 h. Then THF was removed under reduced pressure, and the residue was diluted with EA. The organic layer was washed with water and brine, dried over anhydrous $Na_2SO_4$ and concentrated and purified by flash chromatography to afford the title compound (1.13 g, 42.8% yield) as colorless oil. LCMS: rt=3.49 min, [M+H$^+$]=245

D148: 2-{4-[(4-chloro-3-methylphenyl)oxy]phenyl}ethyl imidocarbamate

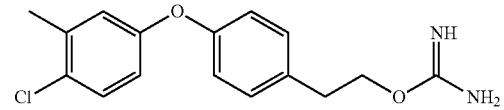

To a solution of 2-{4-[(4-chloro-3-methylphenyl)oxy]phenyl}ethanol (500 mg, 1.903 mmol) and cyanmide (96 mg, 2.284 mmol) in dry THF (6 mL) under nitrogen was added triflic acid (0.203 mL, 2.285 mmol). The mixture was heated at 55° C. for 2 h. Purification via reverse phase flash chromatography afforded the title compound (270 mg, 0.646 mmol, 34.0% yield) as white solid. LCMS: rt=2.76 min, [M+H$^+$]=245

D149: 4-[(3-fluoro-4-methylphenyl)oxy]benzaldehyde

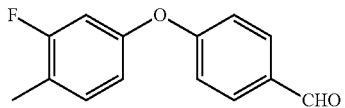 [SMILES: Cc1ccc(Oc2ccc(C=O)cc2)cc1F]

To a solution of 3-fluoro-p-cresol (2.5 g, 19.82 mmol) and 4-fluorobenzaldehyde (2.460 g, 19.82 mmol) in DMF (15 mL), was added $K_2CO_3$ (4.11 g, 29.7 mmol). The mixture was heated with a microwave condition at 130° C. for 1 h. After cooling, the reaction mixture was diluted in water, extracted with EA. The organic phase was washed with water and brine, dried over $Na_2SO_4$, concentrated and purified via flash chromatography to afford the title compound (2.741 g, 11.91 mmol, 60.1% yield) as a yellow oil. LCMS: rt=3.57 min, [M+H$^+$]=231

D150: 4-[(4-ethenylphenyl)oxy]-2-fluoro-1-methylbenzene 4-ethenylphenyl 3-fluoro-4-methylphenyl ether

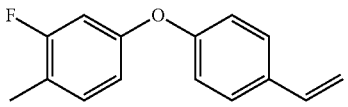 [SMILES: C=Cc1ccc(Oc2ccc(C)c(F)c2)cc1]

To a solution of methyltriphenylphosphonium bromide (3.72 g, 10.42 mmol) and NaH (1.737 g, 43.4 mmol) in dry THF (50 mL) was added a solution of 4-[(3-fluoro-4-methylphenyl)oxy]benzaldehyde (2 g, 8.69 mmol) in THF under nitrogen at 0° C. The mixture was stirred at 0° C. for 0.5 h, and then at room temperature for 2 h. The organic layer was washed three times with brine, dried over $Na_2SO_4$, filtered, and concentrated. Purification via flash chromatography afforded the title compound (982 mg, 4.30 mmol, 49.5% yield) as a light green oil. LCMS: rt=4.17 min, [M+H]=229

D151: 2-{4-[(3-fluoro-4-methylphenyl)oxy]phenyl}ethanol

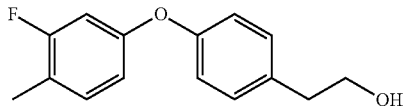 [SMILES: Cc1ccc(Oc2ccc(CCO)cc2)cc1F]

To the solution of 4-ethenylphenyl 3-fluoro-4-methylphenyl ether (900 mg, 3.94 mmol) in dry THF (30 mL), was added 9-BBN (9.46 mL, 4.73 mmol) at 0° C. The mixture was stirred at room temperature overnight, and quenched with water (1.2 mL), followed by aq. NaOH (5.26 mL, 15.77 mmol), and 30% $H_2O_2$ (4.03 mL, 39.4 mmol). The reaction mixture was heated at 50° C. for 2 h. Then THF was removed under reduced pressure, and the residue was diluted with DCM. The organic layer was washed with water and brine, dried over anhydrous $Na_2SO_4$ and concentrated and purified by flash chromatography to afford the title compound (1.02 g, 4.14 mmol, 105% yield) as a yellow oil. LCMS: rt=3.29 min, [M+H]=229

D152: 2-{4-[(3-fluoro-4-methylphenyl)oxy]phenyl}ethyl imidocarbamate

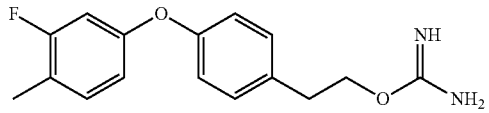 [SMILES: Cc1ccc(Oc2ccc(CCOC(=N)N)cc2)cc1F]

To a solution of 2-{4-[(3-fluoro-4-methylphenyl)oxy]phenyl}ethanol (1 g, 4.06 mmol) and cyanamide (0.205 g, 4.87 mmol) in dry THF (15 mL) under nitrogen was added triflic acid (0.433 mL, 4.87 mmol). The mixture was heated at 55° C. for 2 h. Purification via reverse phase flash chromatography afforded the title compound (420 mg, 1.047 mmol, 25.8% yield) as white solid. LCMS: rt=2.61 min, [M+H$^+$]=229

D153: 4-[(6-methyl-2-pyridinyl)oxy]benzaldehyde

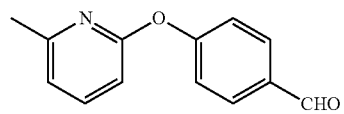 [SMILES: Cc1cccc(Oc2ccc(C=O)cc2)n1]

To a solution of 6-methyl-2(1H)-pyridinone (2 g, 18.33 mmol) and 4-fluorobenzaldehyde (2 ml, 18.64 mmol) in DMF (60 mL), was added $K_2CO_3$ (3.80 g, 27.5 mmol). The mixture was heated at 130° C. overnight. After cooling, the reaction mixture was diluted in water, extracted with EA. The organic phase was washed with water and brine, dried over $Na_2SO_4$, concentrated to afford the title compound (3.24 g, 15.19 mmol, 83% yield) as a brown oil. LCMS: rt=2.77 min, [M+H$^+$]=214

D154: 2-[(4-ethenylphenyl)oxy]-6-methylpyridine

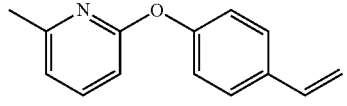 [SMILES: C=Cc1ccc(Oc2cccc(C)n2)cc1]

To a stirred suspension of 4-[(6-methyl-2-pyridinyl)oxy]benzaldehyde (2.43 g, 11.40 mmol) and methyl(triphenyl)phosphonium bromide (4.07 g, 11.40 mmol) in dry THF (30 mL) was added NaH (1.595 g, 39.9 mmol) under nitrogen at 0° C. The mixture was stirred at room temperature for 2 h. The organic layer was washed three times with brine, dried over $Na_2SO_4$, filtered, and concentrated. Purification via flash chromatography afforded the title compound (1.23 g, 5.82 mmol, 51.1% yield) as a light green oil. LCMS: rt=3.27 min, [M+H$^+$]=212

D155: 2-{4-[(6-methyl-2-pyridinyl)oxy]phenyl}ethanol

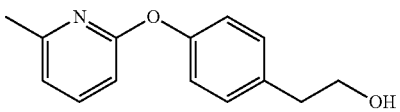 [SMILES: Cc1cccc(Oc2ccc(CCO)cc2)n1]

To the solution of 2-[(4-ethenylphenyl)oxy]-6-methylpyridine (1.23 g, 5.82 mmol) in dry THF (20 mL), was added 9-BBN (17 mL, 8.50 mmol) at 0° C. The mixture was stirred at room temperature overnight, and quenched with water (2 mL), followed by aq. NaOH (3M, 7 mL), and 30% $H_2O_2$ (7.2 mL). The reaction mixture was heated at 50° C. for 3 h. Then THF was removed under reduced pressure, and the residue was diluted with DCM. The organic layer was washed with water and brine, dried over anhydrous $Na_2SO_4$ and concentrated and purified by flash chromatography to afford the title compound (1.71 g, 7.46 mmol, 128% yield) as a colorless oil. LCMS: rt=2.07 min, [M+H$^+$]=230

D156: 2-{4-[(6-methyl-2-pyridinyl)oxy]phenyl}ethyl imidocarbamate

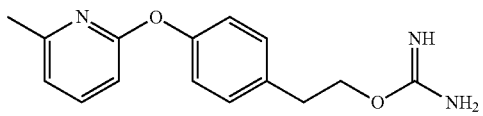 [SMILES: Cc1cccc(Oc2ccc(CCOC(=N)N)cc2)n1]

To a solution of 2-{4-[(6-methyl-2-pyridinyl)oxy]phenyl}ethanol (1.7 g, 7.41 mmol) and cyanamide (0.405 g, 9.64 mmol) in dry THF (20 mL) under nitrogen was added triflic acid (0.856 mL, 9.64 mmol). The mixture was heated at 55° C. for 4 h. Purification via reverse phase flash chromatography afforded the title compound (1.4 g, 3.64 mmol, 49.1% yield) as a colorless oil. LCMS: rt=1.87 min, [M+H]=272

D157: 2-(4-((5-chloro-6-(trifluoromethyl)pyridin-2-yl)oxy)phenyl)ethanol

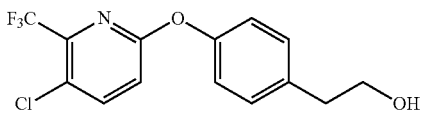 [SMILES: OCCc1ccc(Oc2ccc(Cl)c(C(F)(F)F)n2)cc1]

To the solution of 6-bromo-3-chloro-2-(trifluoromethyl)pyridine (2 g, 7.68 mmol) and 4-(2-hydroxyethyl)phenol (1.061 g, 7.68 mmol) in DMF (30 mL) was added $K_2CO_3$ (1.592 g, 11.52 mmol). The mixture was heated at 110° C. for 2 h. Purification via reverse phase flash chromatography afforded the title compound (200 mg, 8.2% yield) as brown solid. LCMS: rt=3.14 min, [M+H$^+$]=318

D158: 4-((5-chloro-6-(trifluoromethyl)pyridin-2-yl)oxy)phenethyl carbamimidate, trifluoroacetate

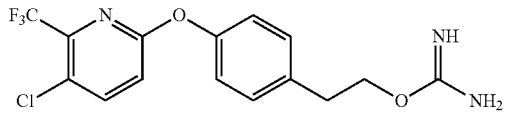 [SMILES: N=C(N)OCCc1ccc(Oc2ccc(Cl)c(C(F)(F)F)n2)cc1]

To a solution of 2-(4-((5-chloro-6-(trifluoromethyl)pyridin-2-yl)oxy)phenyl)ethanol (0.2 g, 0.630 mmol) and cyanamide (0.053 g, 1.259 mmol) in dry THF (3 mL) under nitrogen was added triflic acid (0.112 mL, 1.259 mmol). The mixture was heated at 55° C. for 1 h. Purification via reverse phase flash chromatography afforded the title compound (250 mg, 0.529 mmol, 84% yield) as a white solid. LCMS: rt=2.77 min, [M+H$^+$]=360

D159: 4-{[3-chloro-5-(trifluoromethyl)phenyl]oxy}benzaldehyde

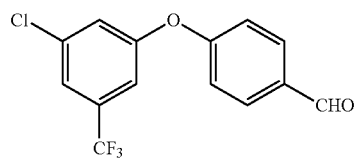 [SMILES: O=Cc1ccc(Oc2cc(Cl)cc(C(F)(F)F)c2)cc1]

To a solution of 3-chloro-5-(trifluoromethyl)phenol (2 g, 10.18 mmol) and 4-fluorobenzaldehyde (1.201 ml, 11.19 mmol) in DMF (30 mL), was added $K_2CO_3$ (2.109 g, 15.26 mmol). The mixture was heated at 130° C. overnight. After cooling, the reaction mixture was diluted in water, extracted with EA. The organic phase was washed with water and brine, dried over $Na_2SO_4$, concentrated to afford the title compound (3.3 g, 10.98 mmol, 108% yield) as a brown oil. LCMS: rt=3.89 min, [M+H$^+$]=301

D160: 1-chloro-3-[(4-ethenylphenyl)oxy]-5-(trifluoromethyl)benzene

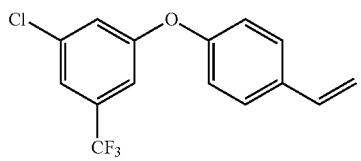 [SMILES: C=Cc1ccc(Oc2cc(Cl)cc(C(F)(F)F)c2)cc1]

To a stirred suspension of 4-{[3-chloro-5-(trifluoromethyl)phenyl]oxy})benzaldehyde (3.3 g, 10.98 mmol) and methyl (triphenyl)phosphonium bromide (3.92 g, 10.98 mmol) in dry THF (30 mL) was added NaH (1.536 g, 38.4 mmol) under nitrogen at 0° C. The mixture was stirred at room temperature for 2 h. The organic layer was washed three times with brine, dried over $Na_2SO_4$, filtered, and concentrated. Purification via flash chromatography afforded the title compound (2.63 g, 8.81 mmol, 80% yield) as a light green oil. LCMS: rt=4.45 min, [M+H$^+$]=324

D161: 2-(4-{[3-chloro-5-(trifluoromethyl)phenyl]oxy}phenyl)ethanol

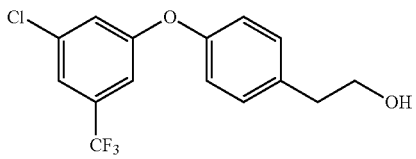 [SMILES: OCCc1ccc(Oc2cc(Cl)cc(C(F)(F)F)c2)cc1]

To the solution of 1-chloro-3-[(4-ethenylphenyl)oxy]-5-(trifluoromethyl)benzene (2.63 g, 8.81 mmol) in dry THF (25 mL), was added 9-BBN (30 mL, 15.00 mmol) at 0° C. The mixture was stirred at room temperature overnight, and quenched with water (2 mL), followed by aq. NaOH (11 mL, 33.0 mmol), and 30% $H_2O_2$ (10 mL). The reaction mixture was heated at 50° C. for 3 h. Then THF was removed under reduced pressure, and the residue was diluted with EA. The organic layer was washed with water and brine, dried over anhydrous $Na_2SO_4$, concentrated and purified by flash chromatography to afford the title compound (2.8 g, 8.84 mmol, 100% yield) as a colorless oil. LCMS: rt=3.70 min, [M+H$^+$]=299

D162: 2-(4-{[3-chloro-5-(trifluoromethyl)phenyl]oxy}phenyl)ethyl imidocarbamate

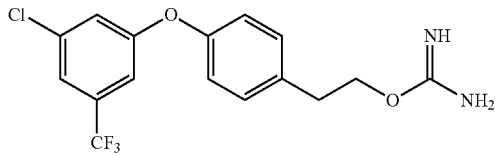 [SMILES: N=C(N)OCCc1ccc(Oc2cc(Cl)cc(C(F)(F)F)c2)cc1]

To a solution of 2-(4-{[3-chloro-5-(trifluoromethyl)phenyl]oxy}phenyl)ethanol (2 g, 6.32 mmol) and cyanamide (0.4 g, 9.51 mmol) in dry THF (20 mL) under nitrogen was added triflic acid (0.8 mL, 9.01 mmol). The mixture was heated at 55° C. for 4 h. Purification via reverse phase flash chromatography afforded the title compound (2.1 g, 4.45 mmol, 70.5% yield) as a brown oil. LCMS: rt=2.95 min, [M+H$^+$]=359

D163: 3-fluoro-4-((6-(trifluoromethyl)pyridin-2-yl)oxy)benzaldehyde

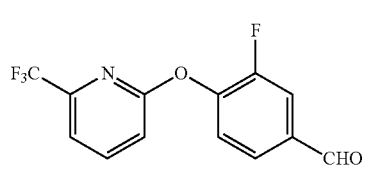 [SMILES: O=Cc1ccc(Oc2cccc(C(F)(F)F)n2)c(F)c1]

To a solution of 6-(trifluoromethyl)pyridin-2-ol (1.205 g, 7.39 mmol) in DMF (7 mL), was added 3,4-difluorobenzaldehyde (0.776 mL, 7.04 mmol) and $K_2CO_3$ (1.167 g, 8.44 mmol). The mixture was heated with a microwave condition at 150° C. for 1 h. After cooling, the mixture was diluted with EA, washed with water, brine, and concentrated. The residue was purified via flash chromatography to afford the title compound (890 mg, 44.3% yield) as a white solid. LCMS: rt=2.62 min, [M+H$^+$]=286

D164: 2-(2-fluoro-4-vinylphenoxy)-6-(trifluoromethyl)pyridine

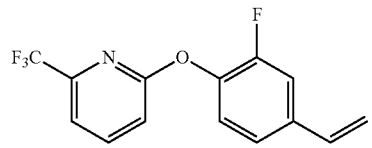 [SMILES: C=Cc1ccc(Oc2cccc(C(F)(F)F)n2)c(F)c1]

To a solution of methyltriphenylphosphonium bromide (1226 mg, 3.43 mmol) in THF (15 mL) was added n-BuLi (2.145 mL, 3.43 mmol), stirred for 10 min. then 3-fluoro-4-((6-(trifluoromethyl)pyridin-2-yl)oxy)benzaldehyde (0.691 mL, 3.12 mmol) was added. The mixture was stirred at 0° C. for 1 h, then at room temperature for another 2 h. The reaction mixture was diluted with EA, washed with water, brine (50 mL), and concentrated. The residue was purified via flash chromatography to afford the title compound (449 mg, 49.8% yield) as colorless oil. LCMS: rt=3.13 min

D165: 2-(3-fluoro-4-((6-(trifluoromethyl)pyridin-2-yl)oxy)phenyl)ethanol

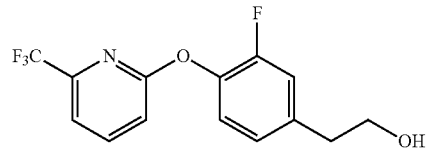 [SMILES: OCCc1ccc(Oc2cccc(C(F)(F)F)n2)c(F)c1]

To a solution of 2-(2-fluoro-4-vinylphenoxy)-6-(trifluoromethyl)pyridine (0.342 mL, 1.554 mmol) in THF (10 mL) was added 9-BBN (4.66 mL, 2.330 mmol) at 0° C. The mixture was stirred at room temperature overnight, and quenched with water (2 mL), followed by aq. NaOH (3 M, 4 mL), and 30% $H_2O_2$ (5 mL). The reaction mixture was stirred at 50° C. for 2 h. Then the THF and some water was removed under reduced pressure, and the residue was diluted with EA. The organic layer was washed with water and brine, dried over anhydrous $Na_2SO_4$, concentrated and purified by flash chromatography to afford the title compound (183 mg, 39.1% yield) as a colorless oil. LCMS: rt=2.45 min

D166: 2-(3-fluoro-4-{[6-(trifluoromethyl)-2-pyridinyl]oxy}phenyl)ethyl imidocarbamate

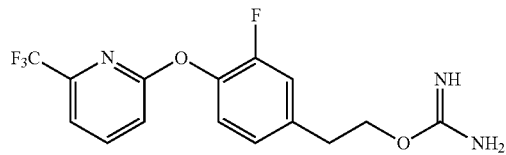 [SMILES: N=C(N)OCCc1ccc(Oc2cccc(C(F)(F)F)n2)c(F)c1]

To a solution of 2-(3-fluoro-4-{[6-(trifluoromethyl)-2-pyridinyl]oxy}phenyl)ethanol (70 mg, 0.232 mmol) and cyanamide (11.72 mg, 0.279 mmol) in THF (5 mL) was added triflic acid (0.025 mL, 0.279 mmol) under argon. The mixture was heated at 55° C. for 3 h. Purification via reverse phase flash chromatography then afforded the title compound (50 mg, 0.102 mmol, 43.7% yield). LCMS: rt=2.53 min, [M+H⁺]= 344

D167: 3-fluoro-4-((2-(trifluoromethyl)pyrimidin-5-yl)oxy)benzaldehyde

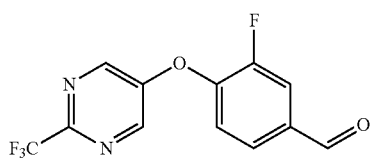

To a solution of 2-(trifluoromethyl)pyrimidin-5-ol (1.5 g, 9.14 mmol) and 3,4-difluorobenzaldehyde (1.299 g, 9.14 mmol) in DMF (18 mL), was added $K_2CO_3$ (1.642 g, 11.88 mmol). The mixture was heated with a microwave condition at 130° C. for 1 h. After cooling, the reaction mixture was diluted in water, extracted with EA. The organic phase was washed with water and brine, dried over $Na_2SO_4$, concentrated to afford the title compound (2.18 g, 7.62 mmol, 83% yield) as a brown oil. LCMS: rt=3.08 min, [M+H⁺]=287

D168: 5-(2-fluoro-4-vinylphenoxy)-2-(trifluoromethyl)pyrimidine

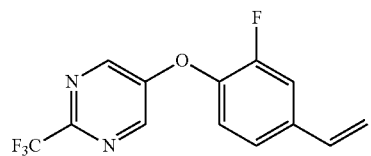 [SMILES: C=Cc1ccc(Oc2cnc(C(F)(F)F)nc2)c(F)c1]

To a stirred suspension of 3-fluoro-4-((2-(trifluoromethyl)pyrimidin-5-yl)oxy)benzaldehyde (2 g, 6.99 mmol) and methyltriphenylphosphonium bromide (2.496 g, 6.99 mmol) in dry THF (40 mL) was added NaH (0.978 g, 24.46 mmol) under nitrogen at 0° C. The mixture was stirred at room temperature for 4 h. The organic layer was washed three times with brine, dried over $Na_2SO_4$, filtered, and concentrated. Purification via flash chromatography afforded the title compound (540 mg, 1.900 mmol, 27.2% yield). LCMS: rt=3.65 min, [M+H⁺]=285

D169: 2-(3-fluoro-4-((2-(trifluoromethyl)pyrimidin-5-yl)oxy)phenyl)ethanol

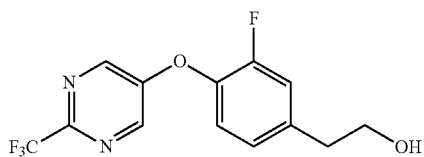 [SMILES: OCCc1ccc(Oc2cnc(C(F)(F)F)nc2)c(F)c1]

To the solution of 5-(2-fluoro-4-vinylphenoxy)-2-(trifluoromethyl)pyrimidine (540 mg, 1.900 mmol) in dry THF (8 mL), was added 9-BBN (5.70 mL, 2.85 mmol) at 0° C. The mixture was stirred at room temperature overnight, and quenched with water (1 mL), followed by aq. NaOH (2.5 mL, 7.50 mmol), and 30% $H_2O_2$ (2.585 g, 22.80 mmol). The reaction mixture was heated at 50° C. for 3 h. Then THF was removed under reduced pressure, and the residue was diluted with EA. The organic layer was washed with water and brine, dried over anhydrous $Na_2SO_4$ and concentrated and purified by flash chromatography to afford the title compound (756 mg, 2.501 mmol, 132% yield) as a white oil. LCMS: rt=3.63 min, [M+H⁺]=285

D 170: 3-fluoro-4-((2-(trifluoromethyl)pyrimidin-5-yl)oxy)phenethyl carbamimidate, trifluoroacetate

To a solution of 2-(3-fluoro-4-((2-(trifluoromethyl)pyrimidin-5-yl)oxy)phenyl)ethanol (756 mg, 1.251 mmol) and cyanamide (105 mg, 2.501 mmol) in dry THF (6 mL) under nitrogen was added triflic acid (0.222 mL, 2.501 mmol). The mixture was heated at 55° C. for 3 h. Purification via reverse phase flash chromatography afforded the title compound (1 g, 2.104 mmol, 24.95% yield). LCMS: rt=2.41 min, [M+H⁺]= 345

D171: 3,5-difluoro-4-((2-(trifluoromethyl)pyrimidin-5-yl)oxy)benzaldehyde

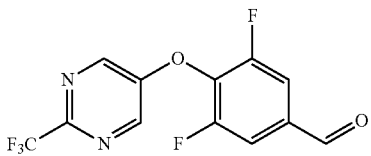

To a solution of 2-(trifluoromethyl)pyrimidin-5-ol (1.5 g, 9.14 mmol) and 3,4,5-trifluorobenzaldehyde (1.464 g, 9.14 mmol) in DMF (18 mL), was added $K_2CO_3$ (1.642 g, 11.88 mmol). The mixture was heated with a microwave condition at 130° C. for 1 h. After cooling, the reaction mixture was diluted in water, extracted with EA. The organic phase was washed with water and brine, dried over $Na_2SO_4$, concentrated to afford the title compound (2.73 g, 8.98 mmol, 98% yield) as brown oil. LCMS: rt=3.16 min, [M+H⁺]=305

D172: 5-(2,6-difluoro-4-vinylphenoxy)-2-(trifluoromethyl)pyrimidine

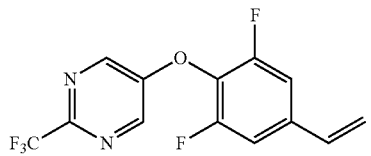

To a stirred suspension of methyltriphenylphosphonium bromide (3.85 g, 10.77 mmol) and KO$^t$Bu (1.309 g, 11.67 mmol) in dry THF (50 mL), which was stirred at room temperature for 1 h under nitrogen, was added 3,5-difluoro-4-((2-

(trifluoromethyl) pyrimidin-5-yl)oxy)benzaldehyde (2.73 g, 8.98 mmol). The mixture was stirred at room temperature for 3 h. The reaction mixture was neutrilized with sat. NH₄Cl. The aqueous phase was extracted with EA. The combined organic layers were washed with brine, dried over Na₂SO₄, filtered, and concentrated. Purification via flash chromatography afforded the title compound (1.47 g, 4.86 mmol, 54.2% yield) as a yellow oil. LCMS: rt=3.72 min, [M+H⁺]=303

D173: 2-(3,5-difluoro-4-((2-(trifluoromethyl)pyrimidin-5-yl)oxy)phenyl)ethanol

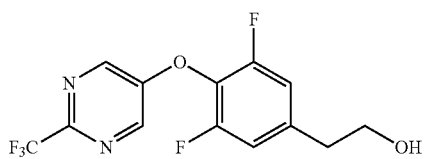 [SMILES: OCCc1cc(F)c(Oc2cnc(C(F)(F)F)nc2)c(F)c1]

To the solution of 5-(2,6-difluoro-4-vinylphenoxy)-2-(trifluoromethyl)pyrimidine (1.67 g, 5.53 mmol) in dry THF (25 mL), was added 9-BBN (20 ml, 10.00 mmol) at 0° C. The mixture was stirred at room temperature overnight, and quenched with water (2 mL), followed by aq. NaOH (7 mL, 21.0 mmol), and 30% H₂O₂ (7 mL, 5.53 mmol). The reaction mixture was heated at 50° C. for 3 h. Then THF was removed under reduced pressure, and the residue was diluted with EA. The organic layer was washed with water and brine, dried over anhydrous Na₂SO₄ and concentrated and purified by flash chromatography to afford the title compound (2.7 g, 8.43 mmol, 153% yield) as a white oil. LCMS: rt=2.97 min, [M+H⁺]=321

D174: 3,5-difluoro-4-((2-(trifluoromethyl)pyrimidin-5-yl)oxy)phenethyl carbamimidate, Trifluoroacetate

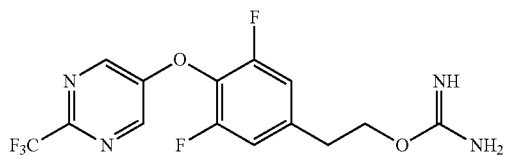 [SMILES: N=C(N)OCCc1cc(F)c(Oc2cnc(C(F)(F)F)nc2)c(F)c1]

To a solution of 2-(3,5-difluoro-4-((2-(trifluoromethyl)pyrimidin-5-yl)oxy)phenyl) ethanol (2.7 g, 8.43 mmol) and cyanamide (0.709 g, 16.86 mmol) in dry THF (20 mL) under nitrogen was added triflic acid (1.4 mL, 15.77 mmol). The mixture was heated at 55° C. overnight. Purification via reverse phase flash chromatography afforded the title compound (1 g, 2.104 mmol, 24.95% yield). LCMS: rt=2.47 min, [M+H]=363

D175: 4-(4-chloro-3-(trifluoromethoxy)phenoxy) benzaldehyde

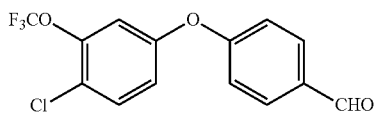 [SMILES: O=Cc1ccc(Oc2ccc(Cl)c(OC(F)(F)F)c2)cc1]

To a solution of 4-chloro-3-(trifluoromethoxy)phenol (1.5 g, 7.06 mmol) and 4-fluorobenzaldehyde (0.76 mL, 7.08 mmol) in DMF (3 mL), was added K₂CO₃ (1.2 g, 8.68 mmol). The mixture was heated with a microwave condition at 100° C. for 1 h. After cooling, the reaction mixture was diluted in water, extracted with EA. The organic phase was washed with water and brine, dried over Na₂SO₄, concentrated to afford the title compound (2.10 g, 94% yield) as a yellow oil. LCMS: rt=3.90 min, [M+H]=317

D176: 1-chloro-2-(trifluoromethoxy)-4-(4-vinylphenoxyl)benzene

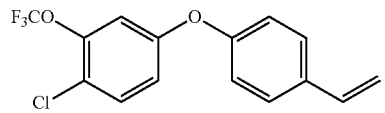 [SMILES: C=Cc1ccc(Oc2ccc(Cl)c(OC(F)(F)F)c2)cc1]

To a suspension of methyltriphenylphosphonium bromide (3.9 g, 10.92 mmol) in dry THF (20 mL) was added n-butyllithium (6.8 mL, 10.88 mmol) dropwise at −78° C. for 0.5 h, the mixture was stirred for 1 h, and then was added a solution of 4-(4-chloro-3-(trifluoromethoxy)phenoxy)benzaldehyde (2.8 g, 8.84 mmol) in THF (5 mL). The reaction was warmed slowly to room temperature, stirred for overnight, and quenched with water. The aqueous layer was extracted with DCM. The organic phase was dried with anhydrous Na₂SO₄, concentrated and purified via flash chromatography to afford the title compound (1.2 g, 3.81 mmol, 43.1% yield). LCMS: rt=4.42 min, [M+H⁺]=315

D177: 2-(4-(4-chloro-3-(trifluoromethoxy)phenoxy) phenyl)ethanol

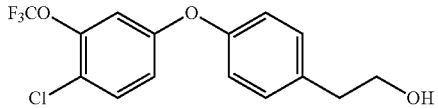 [SMILES: OCCc1ccc(Oc2ccc(Cl)c(OC(F)(F)F)c2)cc1]

To the solution of 1-chloro-2-(trifluoromethoxy)-4-(4-vinylphenoxyl)benzene (1.2 g, 3.81 mmol) in dry THF (10 mL), was added 9-BBN (15.25 mL, 7.63 mmol) at 0° C. The mixture was stirred at room temperature overnight. aq. NaOH (6.5 mL, 19.50 mmol), and 30% H₂O₂ (2.0 mL, 19.58 mmol) were added. The reaction mixture was heated at 55° C. for 4 h. Then THF was removed under reduced pressure, and the residue was diluted with EA. The organic layer was washed with water and brine, dried over anhydrous Na₂SO₄ and concentrated and purified by flash chromatography to afford the title compound (450 mg, 1.353 mmol, 35.5% yield) as a white oil.

D178: 4-(4-chloro-3-(trifluoromethoxy)phenoxy)phenethyl carbamimidate, trifluoroacetic acid salt

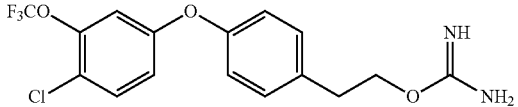 [SMILES: N=C(N)OCCc1ccc(Oc2ccc(Cl)c(OC(F)(F)F)c2)cc1]

To a solution of 2-(4-(4-chloro-3-(trifluoromethoxy)phenoxy)phenyl)ethanol (450 mg, 1.353 mmol) and cyanamide (140 mg, 3.33 mmol) in dry THF (10 mL) under nitrogen was added triflic acid (0.3 mL, 3.38 mmol) at 0° C. The mixture was stirred at room temperature for 2 h. Purification via reverse phase flash chromatography afforded the title compound (380 mg, 0.777 mmol, 57.5% yield). LCMS: rt=3.00 min, [M+H⁺]=381

D179: 4-(4-chloro-2,6-difluorophenoxy)benzaldehyde

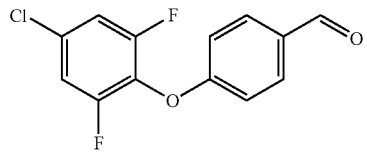 [SMILES: O=Cc1ccc(Oc2c(F)cc(Cl)cc2F)cc1]

To a solution of 4-chloro-2,6-difluorophenol (5.0 g, 30.4 mmol), 4-fluorobenzaldehyde (3.1 mL, 28.9 mmol) in DMF (30 mL), was added $K_2CO_3$ (5.0 g, 36.2 mmol). The mixture was heated at 100° C. overnight. After cooling, the reaction mixture was diluted in water, extracted with EA. The organic phase was washed with water and brine, dried over $Na_2SO_4$, concentrated, purified by flash chromatography to afford the title compound (5.4 g, 20.10 mmol, 66.1% yield) as a colorless oil. LCMS: rt=3.52 min, [M+H⁺]=269

D180: 5-chloro-1,3-difluoro-2-(4-vinylphenoxyl)benzene

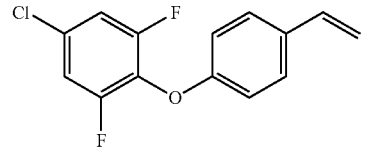 [SMILES: C=Cc1ccc(Oc2c(F)cc(Cl)cc2F)cc1]

To a stirred suspension of methyltriphenylphosphonium bromide (8.7 g, 24.35 mmol) and KO$^t$Bu (3.4 g, 30.3 mmol) in dry THF (20 mL), which was stirred at room temperature for 1 h under nitrogen, was added a solution of 4-(4-chloro-2,6-difluorophenoxy)benzaldehyde (5.4 g, 20.10 mmol) in THF (8 mL). The mixture was stirred at room temperature overnight, and quenched with water. The aqueous phase was extracted with DCM. The combined organic layers were washed with brine, dried over $Na_2SO_4$, filtered, and concentrated. Purification via flash chromatography afforded the title compound (2.6 g, 9.75 mmol, 48.5% yield). LCMS: rt=4.06 min, [M+H⁺]=267

D181: 2-(4-(4-chloro-2,6-difluorophenoxy)phenyl)ethanol

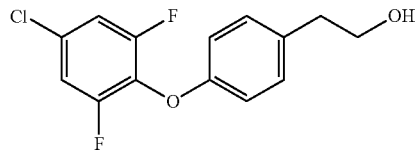 [SMILES: OCCc1ccc(Oc2c(F)cc(Cl)cc2F)cc1]

To the solution of 5-chloro-1,3-difluoro-2-(4-vinylphenoxyl)benzene (2.6 g, 9.75 mmol) in dry THF (10 mL), was added 9-BBN (39.0 mL, 19.50 mmol) at 0° C. The was stirred at room temperature overnight. aq. NaOH (7.0 mL, 21.00 mmol), and 30% $H_2O_2$ (2.0 mL, 19.58 mmol) were added then. The reaction mixture was heated at 50° C. for 4 h. Then THF was removed under reduced pressure, and the residue was diluted with EA. The organic layer was washed with water and brine, dried over anhydrous $Na_2SO_4$ and concentrated and purified by flash chromatography to afford the title compound (1.6 g, 5.62 mmol, 57.6% yield) as a white oil.

D182: 4-(4-chloro-2,6-difluorophenoxy)phenethyl carbamimidate

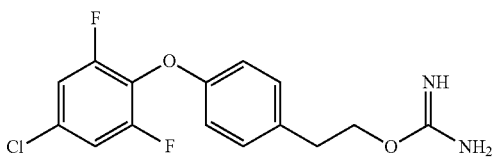 [SMILES: N=C(N)OCCc1ccc(Oc2c(F)cc(Cl)cc2F)cc1]

To a solution of 2-(4-(4-chloro-2,6-difluorophenoxy)phenyl)ethanol (1.6 g, 5.62 mmol) and cyanamide (0.600 g, 14.27 mmol) in dry THF (10 mL) under nitrogen was added triflic acid (1.3 mL, 14.64 mmol) at 0° C. The mixture was stirred at room temperature for 2 h. Purification via reverse phase flash chromatography afforded the title compound (1.74 g, 3.65 mmol, 64.9% yield). LCMS: rt=2.66 min, [M+H⁺]=327

D183: (Z)-methyl 3-amino-2-((1-methyl-1H-pyrazol-4-yl)methyl)acrylate

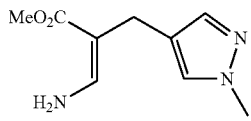

To a stirred ice-cooled suspension of KO$^t$Bu (31.2 g, 278 mmol) in dry THF (160 mL) was added dropwise a solution of methyl 3-(1-methyl-1H-pyrazol-4-yl)propanoate (18.7 g, 111 mmol) and methyl formate (14.02 g, 233 mmol) in dry THF (20 mL) over 2 h under argon. The mixture was then allowed to warm to room temperature and stirring continued for 16 h. The solvents were evaporated in vacuo and the residue dissolved in water (50 mL), after washed with EA twice, the aqueous phase was neutralized with 1M HCl to adjust the pH to 5, the participate was collected. The filtrate was further extracted with EA twice, dried over $Na_2SO_4$, filtered and concentrated in vacuo to afford another batch of product as solid, the solids were combined to afford the title compound (9.1 g, 44.3 mmol, 39.8% yield) as a white solid. LCMS: rt=1.05 min, [M+H⁺]=197

D184: 5-[(1-methyl-1H-pyrazol-4-yl)methyl]-2-thioxo-2,3-dihydro-4(1H)-pyrimidinone

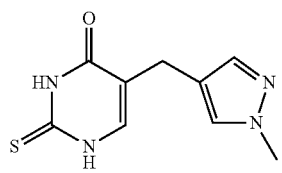

To a stirred ice-cooled solution of potassium tert-butoxide (8.41 g, 74.9 mmol) in dry THF (150 mL) under argon was added dropwise a solution of methyl 3-(1-methyl-1H-pyrazol-4-yl)propanoate (4.2 g, 24.97 mmol) and methyl formate (4.50 g, 74.9 mmol) in THF (150 mL). The mixture was then allowed to warm to room temperature and stirring continued overnight. After removing the solvent, thiourea (1.901 g, 24.97 mmol) and methanol (100 mL) was added. The mixture was heated at 50° C. overnight. After removing the solvent, water (10 mL) was added. and acidified to pH 3 with HCl. The mixture was stirred in ice bath for 1 h. Filtration then drying in vacuo at 50° C. overnight then afforded the title compound (2.8 g, 12.60 mmol, 50.4% yield). LCMS: rt=0.99 min, [M+H]=223

D185: 4-[(4-oxo-2-thioxo-1,2,3,4-tetrahydro-5-pyrimidinyl)methyl]benzonitrile

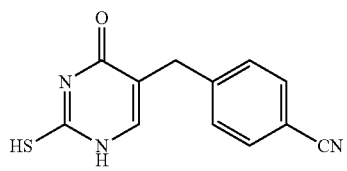 [SMILES: N#Cc1ccc(Cc2c[nH]c(S)nc2=O)cc1]

To a solution of ethyl 3-(4-cyanophenyl)-2-formylpropanoate (1.3 g, 5.62 mmol) in Ethanol (60 mL) was added thiourea (1.712 g, 22.49 mmol) under argon. The mixture was heated at 90° C. for 3 h. After removing the solvent, the residue was dissolved in water (80 mL), washed with ether twice. The aqueous solution was acidified to pH 4-5 with acetic acid, and the resulting precipitate was collected by filtration, washed with water until the wash waters were neutral to afford the title compound (0.95 g, 3.90 mmol, 69.5% yield). LCMS: rt=1.86 min, [M+H$^+$]=224

D186: (Z)-methyl 4,4,4-trifluoro-2-(hydroxymethylene)butanoate

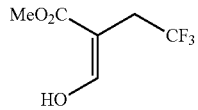

To a suspension of NaH (0.512 g, 12.81 mmol) in DME (15 mL) was added a solution of methyl 4,4,4-trifluorobutanoate (1 g, 6.41 mmol) and methyl formate (0.594 mL, 9.61 mmol) in DME (10 mL) dropwise at 0° C. The mixture was stirred at room temperature overnight. After removing the solvent, the residue was diluted with water (50 mL), extracted with ether once, and neutralized to pH<7 by AcOH. The aqueous layer was separated and extracted with EA twice. The combined organic phase was dried over sodium sulfate, filtered, and concentrated to afford the title compound (0.875 g, 4.75 mmol, 74.2% yield). LCMS: rt=2.23 min, [M+H$^+$]=185

D187: (Z)-methyl 2-(hydroxymethylene)butanoate

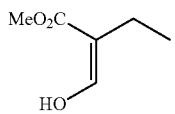

To a suspension of NaH (7.99 g, 200 mmol) in DME (100 mL) was added a mixture of methyl butyrate (5.1 g, 49.9 mmol) and methyl formate (17.99 g, 300 mmol) in DME (100 mL) dropwise at 0° C. under nitrogen. The mixture was stirred at room temperature overnight, and then filtered through a pad of celite. To the filtrate was added ether (200 mL), and let the suspension stand for 4 h. The solid was collected by filtration, washed with diethyl ether and dried in vacuo to afford the title compound (3 g, 23.05 mmol). LCMS: rt=1.108 min, [M+H$^+$]=130

D188: 1-Indole-3-propionic acid methyl ester

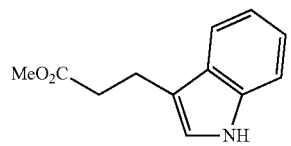 [SMILES: COC(=O)CCc1c[nH]c2ccccc12]

A mixture of indole-3-propionic acid (6.0 g, 31.7 mmol), potassium carbonate (1.5 g, 10.85 mmol), and dimethyl carbonate (8.0 mL, 95 mmol) in DMF (60 mL) was heated at 130° C. for 5 h. After cooling to room temperature, the mixture was diluted with water, extracted with tert-butyl methyl ether. The organic phase was dried over sodium sulfate, filtered, and concentrated. Purification via flash chromatography then afforded the title compound (5.77 g, 25.6 mmol, 81% yield). LCMS: rt=2.80 min, [M+H$^+$]=204

D189: 1-Methylindole-3-propionic acid methyl ester

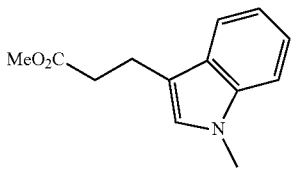 [SMILES: COC(=O)CCc1cn(C)c2ccccc12]

To the solution of 1-indole-3-propionic acid methyl ester (500 mg, 2.460 mmol) in dry DMF (10 mL) was added NaH (200 mg, 5.00 mmol) at 0° C. After 15 min, iodomethane (0.30 mL, 4.80 mmol) was added dropwise. The mixture was stirred at room temperature for 1 h. After quenched with water (50 mL), the mixture was extracted with EA (50 mL×3). The organic phase was dried over sodium sulfate, filtered, and concentrated. Purification via flash chromatography then afforded the title compound (480 mg, 1.988 mmol, 81% yield). LCMS: rt=3.29 min, [M+H$^+$]=218

D190: Methyl (2Z)-3-hydroxy-2-[(1-methyl-1H-indol-3-yl)methyl]-2-propenoate

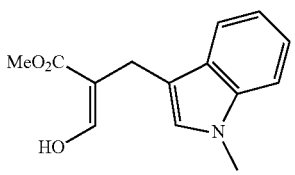 [SMILES: COC(=O)/C(=C\O)Cc1cn(C)c2ccccc12]

To the solution of 1-methylindole-3-propionic acid methyl ester (700 mg, 3.22 mmol) and methyl formate (0.397 mL, 6.44 mmol) in THF (20 mL) was added potassium tert-butoxide (723 mg, 6.44 mmol). The mixture was stirred at room temperature for 1 h. concentration in vacuo then afforded the title compound. LCMS: rt=2.81 min, [M+H$^+$]=246

D191: 5-[(1-Methyl-1H-indol-3-yl)methyl]-2-thioxo-2,3-dihydro-4(1H)-pyrimidinone

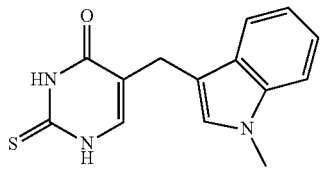 [SMILES: Cn1cc(Cc2c[nH]c(=S)[nH]c2=O)c2ccccc21]

To the solution of methyl (2Z)-3-hydroxy-2-[(1-methyl-1H-indol-3-yl)methyl]-2-propenoate (0.790 g, 3.22 mmol) in methanol (10 mL) was added thiourea (0.25 g, 3.28 mmol). The mixture was heated at 50° C. for 6 h. After cooling to room temperature, purification via reverse phase flash chromatography then afforded the title compound (200 mg, 0.590 mmol, 18.31% yield). LCMS: rt=2.36 min, [M+H$^+$]=272

D192: Methyl 3-(1H-indol-1-yl)propanoate

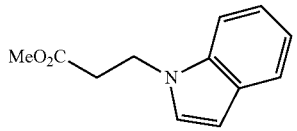 [SMILES: COC(=O)CCn1ccc2ccccc21]

To the solution of indole (1.20 g, 10.24 mmol) and methyl acrylate (1.384 mL, 15.37 mmol) in MeCN (20 mL) was added DBU (0.772 mL, 5.12 mmol). The mixture was heated at 50° C. overnight. Purification via flash chromatography then afforded the title compound (1.0 g, 4.43 mmol, 90% purity, 43.2% yield). LCMS: rt=3.04 min, [M+H$^+$]=204

D193: Methyl (2Z)-3-hydroxy-2-(1H-indol-1-ylmethyl)-2-propenoate

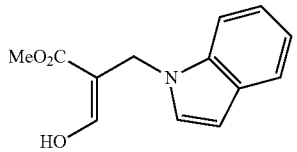 [SMILES: COC(=O)/C(=C\O)Cn1ccc2ccccc21]

To the suspension of potassium tert-butoxide (1.0 g, 8.91 mmol) in dry THF (10 mL) was added dropwise solution of methyl formate (1.0 ml, 16.22 mmol) and methyl 3-(1H-indol-1-yl)propanoate (1.0 g, 4.92 mmol) in dry THF over 30 min. The mixture was stirred at room temperature for 1 h. Concentration in vacuo then afforded the crude title compound (1.3 g). LCMS: rt=2.59 min, [M+H]=232

D194: 5-(1H-Indol-1-ylmethyl)-2-thioxo-2,3-dihydro-4(1H)-pyrimidinone

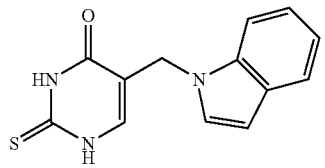 [SMILES: O=c1[nH]c(=S)[nH]cc1Cn1ccc2ccccc21]

To a solution of methyl (2Z)-3-hydroxy-2-(1H-indol-1-ylmethyl)-2-propenoate (1.138 g, 4.92 mmol) in MeOH (20 mL) was added thiourea (1.0 g, 13.14 mmol) in one portion. The mixture was heated at 50° C. overnight. Purification via reverse phase flash chromatography then afforded the title compound (0.93 g, 3.47 mmol, 70.5% yield). LCMS: rt=2.28 min, [M+H$^+$]=258

D195: 1-(1,1-Dimethylethyl) 6-methyl 2-(2-nitrophenyl)-3-oxohexanedioate

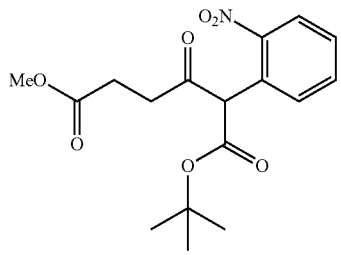 [SMILES: COC(=O)CCC(=O)C(C(=O)OC(C)(C)C)c1ccccc1[N+](=O)[O-]]

To the suspension of NaH (2.3 g, 57.5 mmol) in DMF (50 mL) was added 2-fluoro-1-nitrobenzene (4.04 g, 28.7 mmol) and 1-(1,1-dimethylethyl) 6-methyl 3-oxohexanedioate (6.6 g, 28.7 mmol). The mixture was heated at 60° C. for 12 h. After cooling to room temperature, the mixture was quenched with NH$_4$Cl aqueous solution, and extracted with ethyl acetate. The combined organic phase was dried over sodium sulfate, filtered, and concentrated. Purification via flash chromatography then afforded the title compound (6.0 g, 45.3% yield). LCMS: rt=4.15 min, [M+H$^+$]=350

D196: Methyl 5-(2-nitrophenyl)-4-oxopentanoate

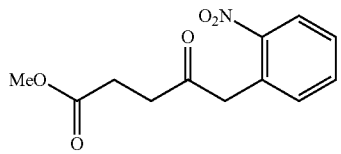 [SMILES: COC(=O)CCC(=O)Cc1ccccc1[N+](=O)[O-]]

To a solution of 1-(1,1-dimethylethyl) 6-methyl 2-(2-nitrophenyl)-3-oxohexanedioate (6.0 g, 17.08 mmol) in DCM (60 mL) were added trifluoroacetic acid (22 ml, 286 mmol) and triethylsilane (8 ml, 50.1 mmol). The mixture was stirred at room temperature for 2 h. Concentration in vacuo then afforded the title compound (8.7 g, 17.08 mmol, 99% yield). LCMS: rt=2.55 min, [M+H$^+$]=252.

D197: Methyl 3-(1H-indol-2-yl)propanoate

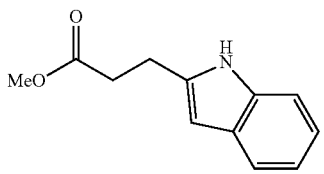 [SMILES: COC(=O)CCc1cc2ccccc2[nH]1]

The mixture of Methyl 5-(2-nitrophenyl)-4-oxopentanoate (4.29 g, 17.08 mmol) and Iron powder (6.0 g, 107 mmol) in AcOH (75 mL) was heated at reflux for 3 h. The crude mixture was concentrated under reduced pressure and diluted with ethyl acetate. The organic solution was washed with NaOH solution, brine, sodium sulfate, filtered, and concentrated. Purification via flash chromatography then afforded the title compound (3.1 g, 14.49 mmol, 85% yield). LCMS: rt=2.86 min, [M+H$^+$]=204.

D198: Methyl 3-(1-methyl-1H-indol-2-yl)propanoate

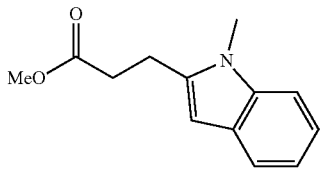 [SMILES: COC(=O)CCc1cc2ccccc2n1C]

To a solution of methyl 3-(1H-indol-2-yl)propanoate (800 mg, 3.94 mmol) in dry DMF (10 mL) was added NaH (300 mg, 7.50 mmol) at 0° C. After 15 min, MeI (0.40 mL, 6.40 mmol) was added dropwise. The mixture was stirred at room temperature for 1 h. The reaction was quenched with water (50 mL) and extracted with EA (50 mL×3). The combined organic phase was dried over sodium sulfate, filtered, and concentrated. Purification via flash chromatography then afforded the title compound (332 mg, 1.299 mmol, 85% purity, 33% yield). LCMS: rt=3.17 min, [M+H$^+$]=218.

D199: Methyl 3-hydroxy-2-[(1-methyl-1H-indol-2-yl)methyl]-2-propenoate

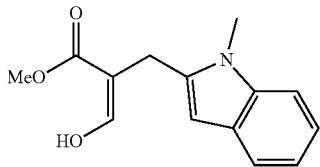 [SMILES: COC(=O)/C(=C\O)Cc1cc2ccccc2n1C]

To a suspension of potassium tert-butoxide (300 mg, 2.67 mmol) in dry THF (5 mL) were added dropwise a solution of methyl 3-(1-methyl-1H-indol-2-yl)propanoate (322 mg, 1.482 mmol) and methyl formate (0.30 mL, 4.87 mmol) in dry THF (5 mL) over 15 min. The mixture was stirred at room temperature for 1 h. Concentration in vacuo then afforded the title compound (400 mg, 0.522 mmol, 35.2% yield). LCMS: rt=2.82 min, [M+H$^+$]=246

D200: 5-[(1-methyl-1H-indol-2-yl)methyl]-2-thioxo-2,3-dihydro-4(1H)-pyrimidinone

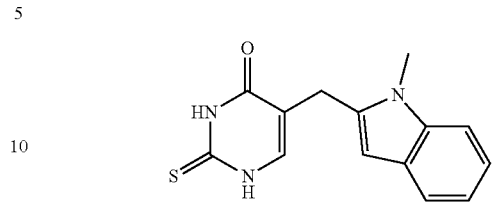

To a solution of methyl 3-hydroxy-2-[(1-methyl-1H-indol-2-yl)methyl]-2-propenoate (0.363 g, 1.482 mmol) in MeOH (5 mL) was added thiourea (0.30 g, 3.94 mmol). The mixture was heated at 50° C. for 6 h. Purification via MDAP then afforded the title compound (240 mg, 0.840 mmol, 56.7% yield). LCMS: rt=2.40 min, [M+H$^+$]=272

D201: 2-(4-hydroxyphenethoxy)-5-((2-methoxypyrimidin-5-yl)methyl)pyrimidin-4(1H)-one

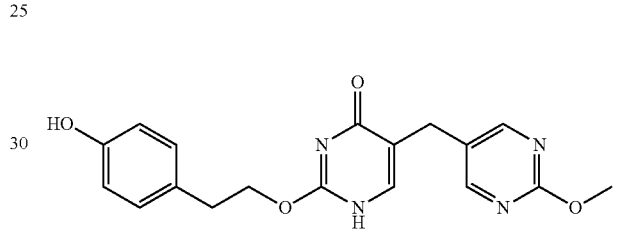

To a solution of 4-hydroxyphenethyl carbamimidate, trifluoroacetic acid salt (255 mg, 0.867 mmol), (Z)-methyl 3-hydroxy-2-((2-methoxypyrimidin-5-yl)methyl)acrylate (214 mg, 0.953 mmol) and in 1,4-dioxane (5 mL), K$_2$CO$_3$ (264 mg, 1.907 mmol) was added. The mixture was heated with a microwave condition at 100° C. for 1.5 h. Purification via reverse phase flash chromatography afforded the title compound (233 mg, 0.658 mmol, 76% yield).

D202: 5-((2-methoxypyrimidin-5-yl)methyl)-2-thioxo-2,3-dihydropyrimidin-4(1H)-one

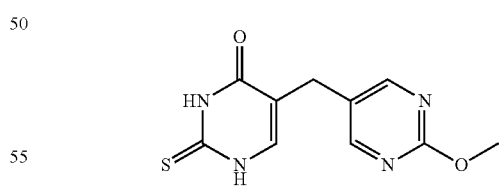

A mixture of (Z)-methyl 3-hydroxy-2-((2-methoxypyrimidin-5-yl)methyl)acrylate (10 g, 42.0 mmol) and thiourea (6.39 g, 84 mmol) in isopropanol (200 mL) was heated at 83° C. overnight. After removing the solvent, the residue was dissolved in water, washed with diethyl ether twice and acidified with AcOH to pH=4.5. The resulting solid was filtered and concentrated in vacuo to afford the title compound (4.4 g, 16.70 mmol, 39.8% yield) as yellow solid. LCMS: rt=1.31 min, [M+H$^+$]=251

D203: methyl (2E)-3-[2-(trifluoromethyl)-5-pyrimidinyl]-2-propenoate

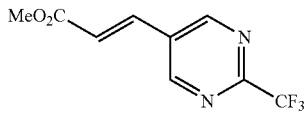

A mixture of 5-bromo-2-(trifluoromethyl)pyrimidine (900 mg, 3.97 mmol), methyl 2-propenoate (0.533 mL, 5.95 mmol), Pd(OAc)$_2$ (44.5 mg, 0.198 mmol), tri-o-tolylphosphine (241 mg, 0.793 mmol) and TEA (1.105 mL, 7.93 mmol) in DMF (6 mL) under argon was heated at 130° C. for 1 h. After cooling to room temperature, water (40 mL) was added to the reaction mixture and then extracted by EA (3×50 mL). The organic phase was washed with brine, dried over MgSO$_4$ and evaporated in vacuo to afford the title compound (900 mg, 3.88 mmol, 98% yield) as a yellow solid. LCMS: rt=2.67 min, [M+H$^+$]=233

D204: methyl 3-[2-(trifluoromethyl)-5-pyrimidinyl]propanoate

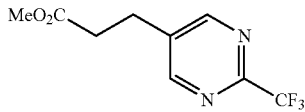

A mixture of methyl (2E)-3-[2-(trifluoromethyl)-5-pyrimidinyl]-2-propenoate (870 mg, 3.75 mmol) and Pd/C (39.9 mg, 0.375 mmol) in methanol (4 mL) was stirred at room temperature for 1 h under hydrogen. After cooling, the mixture was filtered through silica gel. The filtrate was concentrated to afford the title compound (577 mg, 2.47 mmol, 65.8% yield). LCMS: rt=2.47 min, [M+H$^+$]=235

D205: methyl (2Z)-3-hydroxy-2-{[2-(trifluoromethyl)-5-pyrimidinyl]methyl}-2-propenoate

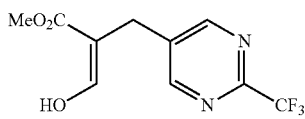

To a solution of NaH (360 mg, 9.00 mmol) in DME (20 mL) was added a solution of methyl formate (0.254 mL, 4.10 mmol) and methyl 3-[2-(trifluoromethyl)-5-pyrimidinyl]propanoate (800 mg, 3.42 mmol) in DME (20 mL) at 0° C. The mixture was stirred at room temperature overnight, and quenched with MeOH. Purification via reverse phase flash chromatography afforded the title compound (730 mg, 2.78 mmol, 82% yield) as yellow solid. LCMS: rt=2.03 min, [M+H$^+$]=263.

D206: 2-Methylsulfanyl-5-pyrimidin-5-ylmethyl-1H-pyrimidin-4-one

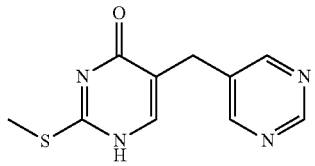 [SMILES: CSc1nc(=O)c(Cc2cncnc2)c[nH]1]

Into a stirred solution of sodium ethoxide (157.7 mg, 2.32 mmol, 2 eq) in EtOH (5.2 ml) was added 5-pyrimidin-5-ylmethyl-2-thioxo-2,3-dihydro-1H-pyrimidin-4-one (270 mg, 1.22 mmol, 1 eq) at rt. After 30 min, the reaction mixture was treated with methyl iodide (190.7 µl, 3.05 mmol, 2.5 eq) and was stirred at rt overnight. Solvent was evaporated and water (1 ml) was added. pH was adjusted ~4 with 1N HCl and precipitate was formed to give 2-methylsulfanyl-5-pyrimidin-5-ylmethyl-1H-pyrimidin-4-one (196 mg, yield=62.4%, purity=91%). [M+H]$^+$=235.28. $^1$H NMR (300 MHz; CDCl$_3$) δ/ppm 2.45 (s, 3H), 3.62 (s, 2H), 3.50 (s, 2H), 7.89 (s, 1H), 8.69 (s, 2H), 9.00 (s, 1H)

D207: {2-[4-(3-Trifluoromethyl-phenoxy)-phenyl]-ethyl}-carbamic acid tert-butyl ester

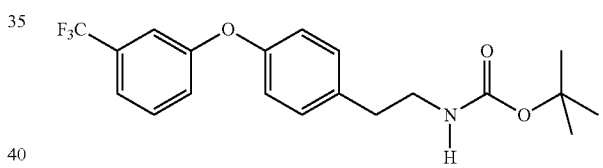

4 Å molecular sieves were added to a stirred solution of 3-(trifluoromethyl)phenylboronic acid (2.4 g, 12.643 mmol, 2 eq) and [2-(4-Hydroxy-phenyl)-ethyl]-carbamic acid tert-butyl ester (1.5 g, 6.321 mmol, 1 eq) in dry DCM (68.7 ml) at ambient temperature in a dark flask flushed with dry air. The reaction mixture was stirred for 10 min with a drying tube attached. Copper (II) acetate (1.16 g, 6.385 mmol, 1.01 eq), TEA (4.4 ml, 31.609 mmol, 5 eq) and pyridine (2.55 ml, 31.609 mmol, 5 eq) were added and the reaction mixture was stirred at ambient temperature overnight. The reaction mixture was diluted with 50 ml of Et$_2$O, filtered through celite and washed with 0.5 M HCl. Organic layer was dried over anhydrous Na$_2$SO$_4$, filtered and evaporated to give a crude product. Crude product was purified via Biotage SP-1 Snap Si 50 g; 40 mil/min; in the gradient of EtOAc in Cy: 3% for 1.5 CV, 3-25% for 12 CV; 25-40% for 8 CV. The appropriate fractions were combined and evaporated in vacuo to give the required product {2-[4-(3-trifluoromethyl-phenoxy)-phenyl]-ethyl}-carbamic acid tert-butyl ester (710 mg, yield=22.4%, purity=76%). [M+H]$^+$=382.40 $^1$H NMR (300 MHz; CDCl$_3$) δ/ppm 1.43 (s, 9H), 2.77 (t, J=7.0 Hz, 2H), 3.37 (q, J=6.5 Hz, 2H), 4.58 (br. s., 1H), 6.92-6.97 (m, 1H), 7.06-7.22 (m, 5H), 7.28-7.33 (m, 1H), 7.34-7.45 (m, 1H)

D208: 2-[4-(3-Trifluoromethyl-phenoxy)-phenyl]-ethylamine

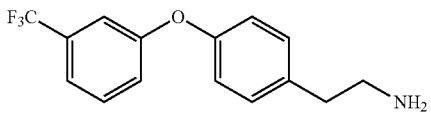 [SMILES: NCCc1ccc(Oc2cccc(C(F)(F)F)c2)cc1]

{2-[4-(3-Trifluoromethyl-phenoxy)-phenyl]-ethyl}-carbamic acid tert-butyl ester (354 mg, 0.928 mmol, 1 eq) was dissolved in dry DCM (3 ml) under argon atmosphere and TFA (355 μl, 5 eq) was added. Reaction mixture was stirred for 5 h. In the reaction mixture was added more DCM (15 ml) and was extracted with saturated NaHCO$_3$ (3×15 ml) and brine. Organic layer was dried over anhydrous Na$_2$SO$_4$, filtered and evaporated to give a product 2-[4-(3-trifluoromethyl-phenoxy)-phenyl]-ethylamine (206 mg, yield=64.7%, purity=65%). [M+H]$^+$=282.28 $^1$H NMR (300 MHz; CDCl$_3$) δ/ppm 2.76-2.80 (m, 2H), 2.93-3.04 (m, 2H), 6.92-6.98 (m, 2H), 7.02-7.35 (m, 5H), 7.37-7.45 (m, 1H)

D209: Methyl-{2-[4-(3-trifluoromethyl-phenoxy)-phenyl]-ethyl}-carbamic acid tert-butyl ester

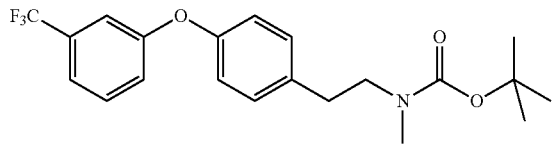 [SMILES: CN(CCc1ccc(Oc2cccc(C(F)(F)F)c2)cc1)C(=O)OC(C)(C)C]

{2-[4-(3-Trifluoromethyl-phenoxy)-phenyl]-ethyl)}-carbamic acid tert-butyl ester (333 mg, 0.873 mmol, 1 eq) was dissolved in dry THF (4.5 ml) and NaH, 60% (101 mg, 2.53 mmol, 2.9 eq) was added. After 30 min, the reaction mixture was treated with methyl iodide (545 μl, 8.73 mmol, 10 eq) and was stirred overnight. After overnight the excess NaH was quenched by a slow addition of water, diluted with brine (30 ml) and extracted with Et$_2$O (3×20 ml). Combined organic layers were dried over anhydrous Na$_2$SO$_4$, filtered and evaporated to give a product methyl-{2-[4-(3-trifluoromethyl-phenoxy)-phenyl]-ethyl)}-carbamic acid tert-butyl ester (306 mg, yield=78%, purity=88%). [M+H]$^+$=396.43 $^1$H NMR (300 MHz; CDCl$_3$) δ/ppm 1.43 (s, 9H), 2.74-2.93 (m, 5H), 3.44 (t, J=8.53 Hz, 2H), 6.92-6.99 (m, 2H), 7.09-7.24 (m, 4H), 7.29-7.35 (m, 1H), 7.37-7.45 (m, 1H)

D210: Methyl-{2-[4-(3-trifluoromethyl-phenoxy)-phenyl]-ethyl}-amine

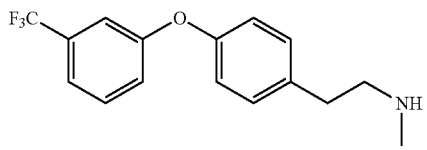 [SMILES: CNCCc1ccc(Oc2cccc(C(F)(F)F)c2)cc1]

Methyl-{2-[4-(3-trifluoromethyl-phenoxy)-phenyl]-ethyl}-carbamic acid tert-butyl ester (300 mg, 0.759 mmol, 1 eq) was dissolved in dry DCM (3 ml) under argon atmosphere and TFA (290.6 μl, 5 eq) was added. Reaction mixture was stirred for overnight. In the reaction mixture was added more DCM (15 ml) and was extracted with saturated NaHCO$_3$ (3×15 ml) and brine. Organic layer was dried over anhydrous Na$_2$SO$_4$, filtered and evaporated to give a product methyl-{2-[4-(3-trifluoromethyl-phenoxy)-phenyl]-ethyl}-amine (211.5 mg, yield=82.1%, purity=87%). [M+H]$^+$=296.31 $^1$H NMR (300 MHz; CDCl$_3$) δ/ppm 2.44 (s, 3H), 2.74-2.89 (m, 4H), 6.90-6.98 (m, 2H), 7.09-7.22 (m, 4H), 7.27-7.33 (m, 1H), 7.35-7.45 (m, 1H)

D211: {2-[4-(4-fluoro-phenoxy)-phenyl]-ethyl}-carbamic acid tert-butyl ester

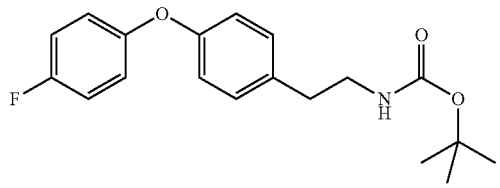 [SMILES: CC(C)(C)OC(=O)NCCc1ccc(Oc2ccc(F)cc2)cc1]

Entire reaction was performed under dry air using syringe septa technique. 4 Å molecular sievies were added to a stirred solution of para-4-fluorbenzene boronic acid (0.025 mmol. 1 eq) and [2-(4-hydroxy-phenyl)-ethyl]-carbamic acid tert butyl ester (0.051 mol, 2 eq) in dry DCM (275 ml) at ambient temperature in a flame dried flask flushed with dry air. The reaction was stirred for 15 min. After that, copper (II) acetate (0.033 mol, 1.3 eq), triethylamine (0.126 mol, 5 eq) and pyridine (0.126 mol, 5 eq) were added in succession and the reaction was stirred for 50 hours. The reaction mixture was sequential washed with 0.5 M HCl (4×250 ml), water (3×150 ml) and brine (1×150 ml). Organic layers were combined, dried over Na$_2$SO$_4$/MgSO$_4$, filtered and evaporated. Crude product was purified on Biotage SP1 Snap Si 100; 40 ml/min in the gradient of EtOAc in Cyclohexane: 0-30% in 25 CV. The appropriate fractions were combined and evaporated in vacuo to give the required product {2-[4-(4-fluoro-phenoxy)-phenyl]-sthyl}-carbamic acid tert-butyl ester (0.014 mol, yield=54%, purity=89%). [M+H]$^+$=276.26 $^1$H NMR (300 MHz, CDCl$_3$) δ/ppm 1.42 (s, 9H), 2.69-2.80 (m, 2H), 3.27-3.40 (m, 2H), 4.37-4.64 (m, 1H), 6.84-7.04 (m, 5H), 7.09-7.15 (m, 2H), 7.22-7.26 (m, 1H)

D212: 2-[4-(4-fluoro-phenoxy)-phenyl]ethylamine

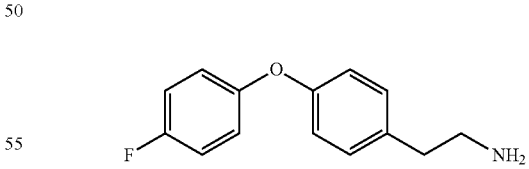

Entire reaction was performed under argon atmosphere using syringe septa technique. ({2-[4-(4-fluoro-phenoxy)-phenyl]-ethyl}-carbamic acid tert-butyl ester (3.018 mmol, 1 eq) was dissolved in dichloromethane (10 ml) and stirred at 0° C. for 5 min. TFA (15.088 mmol, 5 eq) was added and stirring was continued for overnight. Reaction mixture was diluted with 50 ml NaHCO$_3$ (sat.) and extraction with DCM (3×20 ml) followed. Organic layers were combined and evaporated in vacuo to give 2-[4-(4-fluoro-phenoxy)-phenyl]ethylamine (3.027 mmol, yield=94%, purity=94%). [M+H]$^+$=265.25 $^1$H NMR (300 MHz, CDCl₃) δ/ppm 2.86 (s, 2H), 3.09 (s, 2H), 7.01 (d, J=8.7 Hz, 5H), 7.24 (s, 2H), 7.37 (s, 1H)

D213: 1-Methyl-2-methylsulfanyl-5-pyrimidin-5-ylmethyl-1H-pyrimidin-4-one

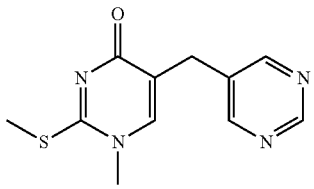 [SMILES: CSc1nc(=O)c(Cc2cncnc2)cn1C]

2-Methylsulfanyl-5-pyrimidin-5-ylmethyl-1H-pyrimidin-4-one (50 mg, 0.213 mmol, 1 eq) was dissolved in dry THF (0.7 ml) and NaH, 60% (24.7 mg, 0.618 mmol, 2.9 eq) was added. After 30 min, the reaction mixture was treated with methyl iodide (133 μl, 2.13 mmol, 10 eq) and was stirred overnight. After overnight the excess NaH was quenched by a slow addition of water, diluted with brine (30 ml) and extracted with Et₂O (3×20 ml). Combined organic layers were dried over anhydrous Na₂SO₄, filtered and evaporated to give a crude residue. Crude residue was purified via Biotage SP-1 Snap Si 10 g; 15 ml/min in the gradient of MeoH in DCM: 1% for 1 CV then from 1-5% for 20 CV. The appropriate fractions were combined and evaporated in vacuo to give the required product 1-methyl-2-methylsulfanyl-5-pyrimidin-5-ylmethyl-1H-pyrimidin-4-one (25.5 mg, yield=47.4%, purity=98%). [M+H]⁺=249.31 ¹H NMR (300 MHz; DMSO-d6) δ/ppm 2.49 (s, 3H), 3.53 (s, 3H), 3.58 (s, 2H), 7.80 (s, 1H), 8.72 (s, 2H), 9.03 (s, 1H)

D214: {2-[4-(4-Chloro-phenoxy)-phenyl]-ethyl}-carbamic acid tert-butyl ester

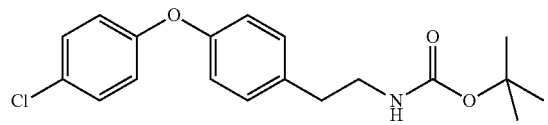 [SMILES: CC(C)(C)OC(=O)NCCc1ccc(Oc2ccc(Cl)cc2)cc1]

4-chlorobenzeneboronic acid (2.05 eq, 2.05 g), N-boc tyramine (1 eq, 6.55 mmol, 1.60 g), cooper(II)-acetate (1.01 eq, 1.20 g) and pyridine (5 eq, 2.64 ml) were dissolved in 70 ml of dry DCM. In the solution were added 4 Å molecular sieves (3 g) and the resulting mixture was stirred at room temperature for 24 hours. The reaction mixture was then filtered over a celite pad, it was diluted with 150 ml of diethyl ether and was subsequently washed with 150 ml of 0.5 N HCl water solution, 150 ml of water and 150 ml of brine. The organic phase was dried, the solvent was evaporated and the resulting crude was purified by chromatography on BIOTAGE SP1 purification device using 50 g normal phase silica SNAP column and cyclohexane/EtOAc solvent system (gradient 5-30% of EtOAc in 20 column volumes). Solvent from the gathered fractions of appropriate composition was evaporated and obtained was {2-[4-(4-chloro-phenoxy)-phenyl]-ethyl}-carbamic acid tert-butyl ester (1.7 g, yield=68.14%, purity=94%). MS: [M−H]⁻=346.13 ¹H NMR (300 MHz; CDCl₃) δ/ppm 1.42 (s, 9H), 2.75 (t, J=7.0 Hz, 2H), 3.35 (m, 2H), 6.87-6.95 (m, 4H), 7.14 (d, J=8.45 Hz, 2H), 7.22-7.28 (m, 2H)

D215: 2-[4-(4-Chloro-phenoxy)-phenyl]-ethylamine

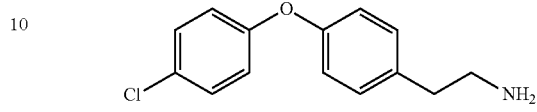

{2-[4-(4-Chloro-phenoxy)-phenyl]-ethyl}-carbamic acid tert-butyl ester (600 mg, 1.72 mmol, 1 eq) and TFA (658 μl) were dissolved in 50 ml of dry DCM under argon atmosphere. The mixture was stirred at room temperature for 60 hours. The solvent was evaporated, the resulting crude was dissolved in 10 ml of MeOH and was purified using 20 g SCX column. The free base was rinsed from the column using 1 N NH₃/ethanol solution. The solvent was evaporated and obtained was 2-[4-(4-chloro-phenoxy)-phenyl]-ethylamine (404 mg, yield=90.8%, purity=96%) in form of yellowish oil. MS: [M+H]⁺=248.21 ¹H NMR (300 MHz; CDCl₃) δ/ppm 1.22 (s, 2H), 2.71 (t, J=6.62 Hz, 2H), 2.95 (t, J=6.62 Hz, 2H), 6.85-6.96 (m, 4H), 7.16 (d, J=7.60 Hz, 2H), 7.25 (d, J=7.60 Hz, 2H)

D216: {2-[4-(4-Chloro-3-trifluoromethyl-phenoxy)-phenyl]-ethyl}-carbamic acid tert-butyl ester

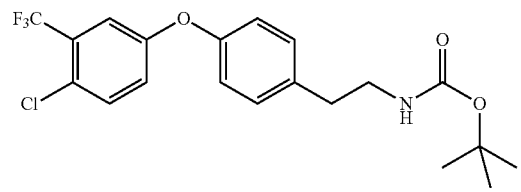 [SMILES: CC(C)(C)OC(=O)NCCc1ccc(Oc2ccc(Cl)c(C(F)(F)F)c2)cc1]

Entire reaction was performed under dry air using syringe septa technique. 4 Å molecular sievies were added to a stirred solution of 4-chloro-3-(trifluoromethyl)phenylboronic acid (5.00 g, 0.022 mmol) and [2-(4-hydroxy-phenyl)-ethyl]-carbamic acid tert butyl ester (2.64 g, 0.051 mol, 2 eq) in dry DCM (120 ml) at ambient temperature in a flame dried flask flushed with dry air. The reaction was stirred for 15 min. After that, copper (II) acetate (5.33 g, 0.010 mol, 1.3 eq), triethylamine (7.34 ml, 0.052 mol, 5 eq) and pyridine (4.25 ml, 0.052 mol, 5 eq) were added in succession and the reaction was stirred for 50 hours. The reaction mixture was sequential washed with 0.5 M HCl (4×250 ml), water (3×150 ml) and brine (1×150 ml). Organic layers were combined, dried over Na₂SO₄/MgSO₄, filtered and evaporated. Crude product was purified on Biotage SP1 Snap Si 100; 40 ml/min in the gradient of EtOAc in Cyclohexan: 0-30% in 25 CV. The appropriate fractions were combined and evaporated in vacuo to give the required product {2-[4-(4-chloro-3-trifluoromethyl-phenoxy)-phenyl]-ethyl}-carbamic acid tert-butyl ester (2.21 g, yield=24%, purity=82%). [M+H]⁺=416.84 [M+H-56]⁺=360.27 ¹H NMR (300 MHz; CDCl₃) δ/ppm 1.50 (s, 9H), 2.85 (t, J=6.97 Hz, 2H), 3.38-3.48 (m, 2H), 4.63 (br. S., 1H), 7.01

(d, J=8.57 Hz, 2H), 7.11 (dd, J=8.77, J=2.79 Hz, 1H), 7.25 (d, J=8.57 Hz, 2H), 7.36 (d, J=2.79 Hz, 1H), 7.47 (d, J=8.77 Hz, 1H)

D217: {2-[4-(4-Chloro-3-trifluoromethyl-phenoxy)-phenyl]-ethyl}-methyl-carbamic acid tert-butyl ester

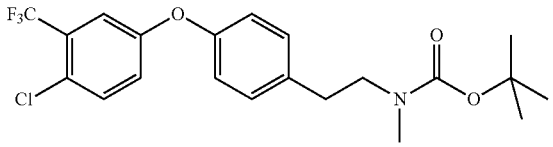 [SMILES: CN(CCc1ccc(Oc2ccc(Cl)c(C(F)(F)F)c2)cc1)C(=O)OC(C)(C)C]

{2-[4-(4-Chloro-3-trifluoromethyl-phenoxy)-phenyl]-ethyl)}-carbamic acid tert-butyl ester (1.1 g, 2.64 mmol, 1 eq) was dissolved in dry THF (18 ml) and NaH, 60% (316 mg, 7.92 mmol, 3 eq) was added. After 30 min, the reaction mixture was treated with methyl iodide (1.65 ml, 2.64 mmol, 10 eq) and was stirred for 3.5 h. The excess NaH was quenched by a slow addition of water, diluted with brine (40 ml) and extracted with Et$_2$O (3×40 ml). Combined organic layers were dried over anhydrous Na$_2$SO$_4$, filtered and evaporated to give a product without further purification {2-[4-(4-chloro-3-trifluoromethyl-phenoxy)-phenyl]-ethyl}-methyl-carbamic acid tert-butyl ester (1.08 g, yield=56.1%, purity=59%). [M+H]$^+$=430.87 $^1$H NMR (300 MHz; CDCl$_3$) δ/ppm 1.38-1.48 (s, 9H), 2.74-2.90 (m, 4H), 3.38-3.50 (m, 2H), 6.93-7.08 (m, 3H), 7.15-7.31 (m, 3H), 7.41 (t, J=8.43 Hz, 1H)

D218: {2-[4-(4-Chloro-3-trifluoromethyl-phenoxy)-phenyl]-ethyl}-methyl-amine

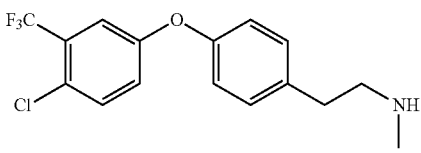 [SMILES: CNCCc1ccc(Oc2ccc(Cl)c(C(F)(F)F)c2)cc1]

{2-[4-(4-Chloro-3-trifluoromethyl-phenoxy)-phenyl]-ethyl)}-carbamic acid tert-butyl ester (1.08 g, 2.51 mmol, 1 eq) was dissolved in dry DCM (10 ml) under argon atmosphere and TFA (961 μl, 5 eq) was added. Reaction mixture was stirred for overnight. In the reaction mixture was added more DCM (15 ml) and was extracted with saturated NaHCO$_3$ (3×15 ml) and brine. Organic layer was dried over anhydrous Na$_2$SO$_4$, filtered and evaporated to give a crude product. Crude product was purified via Biotage SP-1 Snap Si 25 g; 25 ml/min; UV Wavelength (Collection: 254 nm; Monitor: 290 nm) in the gradient of MeOH in DCM: 2% for 1.5 CV, 2-10% for 20 CV. The appropriate fractions were combined and product 2-[4-(3-trifluoromethyl-phenoxy)-phenyl]-ethylamine (501 mg, yield=58.1%, purity 96%). [M+H]$^+$=330.75 $^1$H NMR (300 MHz; CDCl$_3$) δ/ppm 2.47 (s, 3H), 2.78-2.92 (m, 4H), 6.91-7.10 (m, 3H), 7.19-7.33 (m, 3H), 7.41 (d, J=8.99 Hz, 1H)

D219: 5-(2-methoxy-pyrimidin-5-ylmethyl)-2-methylsulfanyl-1H-pyrimidin-4-one

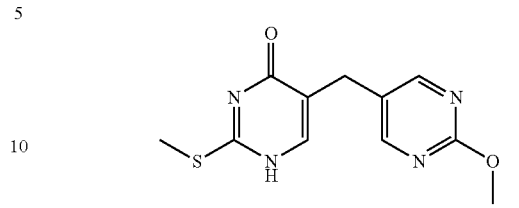

Into a stirred solution of sodium ethoxide (1.358 mmol, 2 eq) in EtOH (3 ml) was added 5-(2-methoxy-pyrimidin-5-ylmethyl)-2-thioxo-2,3-dihydro-1H-pyrimidin-4-one (0.679 mmol, 1 eq) at rt. After 30 min, the reaction mixture was treated with methyl iodide (1.358 mmol, 2 eq) and was stirred at rt overnight. Solvent was evaporated and a crude product was purified on Biotage SP1 Snap Si 10; 15 ml/min in the gradient of EtOAc in Cyclohexane: 0-10% in 30 CV. The appropriate fractions were combined and evaporated in vacuo to give the required product 5-(2-methoxy-pyrimidin-5-ylmethyl)-2-methylsulfanyl-1H-pyrimidin-4-one (0.568 mmol, yield=83%, purity=46%). [M+H]$^+$=265.25 $^1$H NMR (300 MHz, DMSO-d$_6$) δ/ppm 2.39 (s, 1H), 3.82-3.87 (m, 3H), 7.75 (s, 1H), 8.47 (s, 2H)

D220: 4-(5-trifluoromethyl-pyridin-2-yloxy)-benzaldehyde

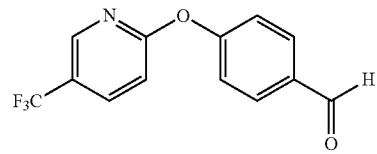 [SMILES: O=Cc1ccc(Oc2ccc(C(F)(F)F)cn2)cc1]

4-hydroxybenzaldehyde (4.094 mmol, 1 eq), 2-bromo-5-(trifluoromethyl)pyridine (4.094 mmol, 1 eq) and potassium carbonate (6.142 mmol, 1.5 eq) were suspended in N,N-dimethylformamide (15 ml). The reaction mixture was irradiated by microwave Biotage Initiator at 130° C. for 30 min. Reaction mixture was diluted with EtOAc (15 ml) and extraction with water followed (3×15 ml). Organic layers were combined, washed with brine, dried over MgSO$_4$, filtered and evaporated giving 4-(5-trifluoromethyl-pyridin-2-yloxy)-benzaldehyde (3.443 mmol, yield=84%, purity=94%). [M+H]$^+$=268.25 $^1$H NMR (300 MHz, DMSO-d$_6$) δ/ppm 7.33-7.38 (m, 1H), 7.43 (d, J=8.5 Hz, 2H), 7.99 (d, J=8.7 Hz, 2H), 8.26-8.33 (m, 1H), 8.57-8.62 (m, 1H)

D221: 2-[4-(2-nitro-vinyl)-phenoxy]-5-trifluoromethyl-pyridine

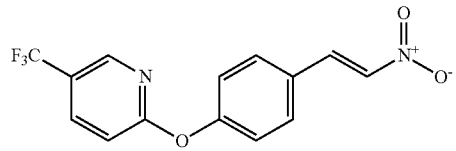 [SMILES: O=[N+]([O-])/C=C/c1ccc(Oc2ccc(C(F)(F)F)cn2)cc1]

Entire reaction was performed under argon using syringe septa technique. 4-(5-trifluoromethyl-pyridin-2-yloxy)-benzaldehyde (2.170 mmol, 1 eq) and ammonium acetate (1.736 mmol, 0.8 eq) were dissolved in nitromethane (3 ml) and reaction mixture was stirred at 95° C. overnight. The volatile was removed in vacuo and the residue was partitioned between DCM and water. Organic layers were combined, washed with brine, dried over MgSO$_4$, filtered and evaporated giving 2-[4-(2-nitro-vinyl)-phenoxy]-5-trifluoromethyl-pyridine (1.225 mmol, yield=56%, purity=95%). [M+H]$^+$=311.23 $^1$H NMR (300 MHz, DMSO-d$_6$) δ/ppm 7.27-7.36 (m, 3H), 7.91-7.98 (m, 2H), 8.24-8.30 (m, 1H), 8.55-8.62 (m, 1H)

D222: 2-[4-[5-trifluoromethyl-pyridin-2yloxy)phenyl]-ethylamine

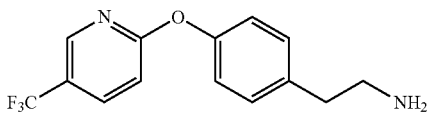

Entire reaction was performed under argon atmosphere using syringe septa technique. To a stirred suspension of LiAlH$_4$ (3.062 mmol, 2.5 eq) in dry tetrahydrofurane (20 ml) was added 2-[4-(2-nitro-vinyl)-phenoxy]-5-trifluoromethyl-pyridine (1.225 mmol, 1 eq) dissolved in dry tetrahydrofurane (10 ml) dropwise. Reaction mixture was stirred at rt for 2 h. Reaction mixture was quenched with 0.5 ml water. Celite and NaOH (3 ml, 5 N) were added and the mixture was filtered through Celite, rinsing the filter cake well with ether and DCM. Solvents were evaporated till dry. Crude product was purified on Biotage SP1 Snap Si 25; 25 ml/min in the gradient of MeOH in DCM: 0-5% for 3CV then from 5-40% for 30 CV. The appropriate fractions were combined and evaporated in vacuo to give the required product 2-[4-[5-trifluoromethyl-pyridin-2yloxy)phenyl]-ethylamine s yellow oil (0.443 mmol, yield=36%, purity=91%). [M+H]$^+$=283.30 $^1$H NMR (300 MHz, DMSO-d$_6$) δ/ppm 2.68 (d, 2H), 2.79 (d, J=7.5 Hz, 2H), 7.06-7.13 (m, 2H), 7.19 (d, J=8.7 Hz, 1H), 7.23-7.29 (m, 2H), 8.17-8.20 (m, 1H), 8.20-8.23 (m, 1H), 8.51-8.57 (m, 2H)

D223: {2-[4-(4-fluoro-phenoxy)-phenyl]-ethyl}-carbamic acid tert-butyl ester

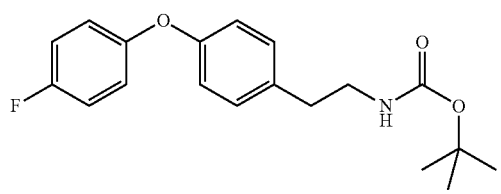 [SMILES: CC(C)(C)OC(=O)NCCc1ccc(Oc2ccc(F)cc2)cc1]

Entire reaction was performed under argon atmosphere using syringe septa technique. 4 Å molecular sievies were added to a stirred solution of para-4-fluorbenzene boronic acid (0.025 mmol, 1 eq) and [2-(4-hydroxy-phenyl)-ethyl]-carbamic acid tert butyl ester (0.051 mmol, 2 eq) in dry DCM (275 ml) at ambient temperature in a flame dried flask flushed with dry air. The reaction was stirred for 15 min. After that, copper (II) acetate (0.033 mol, 1.3 eq), triethylamine (0.126 mol, 5 eq) and pyridine (0.126 mol, 5 eq) were added in succession and the reaction was stirred for 50 hours. The reaction mixture was sequential washed with 0.5 M HCl (4×250 ml), water (3×150 ml) and brine (1×150 ml). Organic layers were combined, dried over Na$_2$SO$_4$/MgSO$_4$, filtered and evaporated. Crude product was purified on Biotage SP1 Snap Si 100; 40 ml/min in the gradient of EtOAc in cyclohexane: 0-30% in 25 CV. The appropriate fractions were combined and evaporated in vacuo to give the required product {2-[4-(4-fluoro-phenoxy)-phenyl]-sthyl}-carbamic acid tert-butyl ester (0.014 mol, yield=54%, purity=89%). [M+H]$^+$=276.26 $^1$H NMR (300 MHz, CDCl$_3$) δ/ppm 1.42 (s, 9H), 2.69-2.80 (m, 2H), 3.27-3.40 (m, 2H), 4.37-4.64 (m, 1H), 6.84-7.04 (m, 5H), 7.09-7.15 (m, 2H), 7.22-7.26 (m, 1H)

D224: 2-[4-(4-fluoro-phenoxy)-phenyl]ethylamine

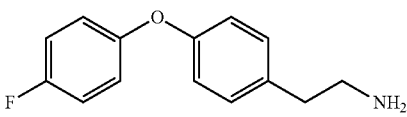 [SMILES: NCCc1ccc(Oc2ccc(F)cc2)cc1]

Entire reaction was performed under argon atmosphere using syringe septa technique. ({2-[4-(4-fluoro-phenoxy)-phenyl]-ethyl}-carbamic acid tert-butyl ester (3.018 mmol, 1 eq) was dissolved in dichloromethane (10 ml) and stirred at 0° C. for 5 min. TFA (15.088 mmol, 5 eq) was added and stirring was continued for overnight. Reaction mixture was diluted with 50 ml NaHCO$_3$ (sat.) and extraction with DCM (3×20 ml) followed. Organic layers were combined and evaporated in vacuo to give 2-[4-(4-fluoro-phenoxy)-phenyl]ethylamine (3.027 mmol, yield=94%, purity=94%). [M+H]$^+$=265.25 $^1$H NMR (300 MHz, CDCl$_3$) δ/ppm 2.86 (s, 2H), 3.09 (s, 2H), 7.01 (d, J=8.7 Hz, 5H), 7.24 (s, 2H), 7.37 (s, 1H)

D225: {2-[4-(4-fluoro-phenoxy)-phenyl]-ethyl}-methyl-carbamic acid tert-butyl ester

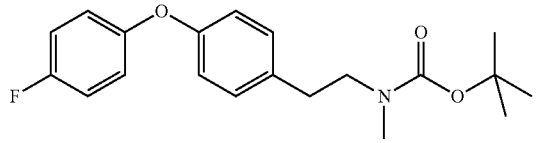 [SMILES: CN(CCc1ccc(Oc2ccc(F)cc2)cc1)C(=O)OC(C)(C)C]

{2-[4-(4-fluoro-phenoxy)-phenyl]-ethyl}-carbamic acid tert-butyl ester (3.018 mmol, 1 eq) was dissolved in dry THF (30 ml) and NaH (3.621 mmol, 1.2 eq) was added. After 30 min, the reaction mixture was treated with methyl iodide (30.176 mmol, 10 eq) and was stirred overnight. After overnight the excess NaH was quenched by a slow addition of water, diluted with brine (30 ml) and extracted with Et$_2$O (3×20 ml). Combined organic layers were dried over anhydrous Na$_2$SO$_4$, filtered and evaporated to give a product without further purification {2-[4-(4-fluoro-phenoxy)-phenyl]-ethyl}-methyl-carbamic acid tert-butyl ester (1.592 mmol, yield=53%, purity=97%). [M+H]$^+$=272.28 $^1$H NMR (300 MHz, CDCl$_3$) δ/ppm 1.55 (s, 9H), 7.24 (m, 5H), 3.39 (br. s., 2H), 6.83-7.03 (m, 5H), 7.06-7.17 (m, 2H), 7.24 (s, 2H)

D226: {2-[4-(4-fluoro-phenoxy)-phenyl]ethyl}-methyl-amine

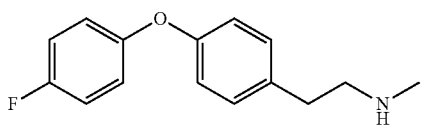 [SMILES: CNCCc1ccc(Oc2ccc(F)cc2)cc1]

Entire reaction was performed under argon atmosphere using syringe septa technique. {2-[4-(4-fluoro-phenoxy)-phenyl]-ethyl}-methyl-carbamic acid tert-butyl ester (1.578 mmol, 1 eq) was dissolved in dichloromethane (6 ml) and stirred at 0° C. for 5 min. TFA (15.778 mmol, 10 eq) was added and stirring was continued for 50 hours. Reaction mixture was diluted with 50 ml NaHCO$_3$ (sat.) and extraction with DCM (3×20 ml) followed. Organic layers were combined and evaporated. Crude product was put on a previously conditioned SCX column (5 g). Column was washed with MeOH (2×10 ml) and then with 2M NH$_3$/MeOH to retrieve the product, {2-[4-(4-fluoro-phenoxy)-phenyl]ethyl}-methyl-amine (1.468 mmol, yield=93%, purity=94%). [M+H]$^+$=246.22 $^1$H NMR (300 MHz, CDCl$_3$) δ/ppm 2.43 (s, 3H), 2.72-2.86 (m, 4H), 6.84-7.03 (m, 5H), 7.10-7.17 (m, 2H), 7.24 (s, 1H)

D227: 2-[3-bromo-4-(5-trifluoromethyl-pyridin-2-yloxy)-phenyl]-ethyl}-carbamic acid tert-butyl ester

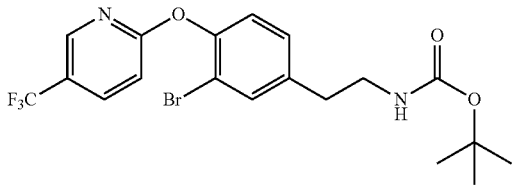 [SMILES: CC(C)(C)OC(=O)NCCc1ccc(Oc2ccc(C(F)(F)F)cn2)c(Br)c1]

[2-(3-bromo-4-hydroxy-phenyl)-ethyl]-carbamic acid tert-butyl ester (2.212 mmol, 1 eq), 2-bromo-5-(trifluoromethyl)-pyridine (2.212 mmol, 1 eq) and potassium carbonate (5.531 mmol, 1.5 eq) were suspended in dimethylsulfoxide (25 ml). The reaction mixture was stirred at 60° C. overnight. Reaction mixture was diluted with water (150 ml) and extraction with EtOAc followed (7×15 ml). Organic layers were combined, washed with brine, dried over MgSO$_4$, filtered and evaporated giving {2-[3-bromo-4-(5-trifluoromethyl-pyridin-2-yloxy)-phenyl]-ethyl)}-carbamic acid tert-butyl ester (1.734 mmol, yield=78%, purity=93%). [M+H]$^+$=461.29 $^1$H NMR (300 MHz, CDCl$_3$) δ/ppm 1.43 (s, 9H), 2.74-2.84 (m, 2H), 3.29-3.45 (m, 2H), 4.51-4.65 (m, 1H), 7.02-7.15 (m, 2H), 7.16-7.23 (m, 1H), 7.45-7.50 (m, 1H), 7.86-7.95 (m, 1H), 8.35-8.41 (m, 1H)

D228: {2-[3-cyano-4-(5-trifluoromethyl-pyridin-2-yloxy)-phenyl]-ethyl}-carbamic acid tert-butyl ester

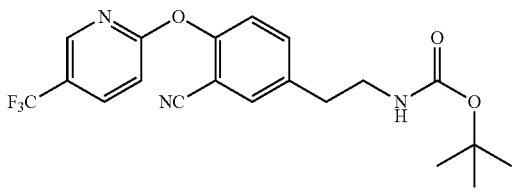 [SMILES: CC(C)(C)OC(=O)NCCc1ccc(Oc2ccc(C(F)(F)F)cn2)c(C#N)c1]

{2-[3-bromo-4-(5-trifluoromethyl-pyridin-2-yloxy)-phenyl]-ethyl}-carbamic acid tert-butyl ester (1.734 mmol, 1 eq), zinc cyanide (1.734 mmol, 1 eq), bis(tri-tbutylphosphine) palladium(0) (1.561 mmol, 0.9 eq) and zinc (0.173 mmol, 0.1 eq) were dissolved in N,N-dimethylformamide (48 ml) and heated in microwave Biotage Initiator at 120° C. for 3 min. Reaction mixture was diluted with water (200 ml) and extracted with EtOAc (7×15 ml). Crude product was purified on Biotage SP1 Snap Si 25; 25 ml/min in the gradient of MeOH in DCM: 0-30% for 30 CV. The appropriate fractions were combined and evaporated in vacuo to give the required product {2-[3-cyano-4-(5-trifluoromethyl-pyridin-2-yloxy)-phenyl]-ethyl}-carbamic acid tert-butyl ester (0.442 mmol, yield=25%, purity=91%). [M+H]=408.35 H NMR (300 MHz, CDCl$_3$) δ/ppm 1.38 (s, 9H), 2.84 (s, 2H), 3.31-3.46 (m, 2H), 4.53-4.70 (m, 1H), 7.22 (s, 2H), 7.43-7.54 (m, 2H), 7.91-8.00 (m, 1H), 8.34-8.41 (m, 1H)

D229: 5-(2-amino-ethyl)-2-(5-trifluoromethyl-pyridin-2-yloxy)benzonitrile

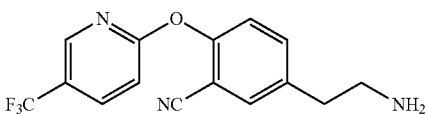 [SMILES: N#Cc1cc(CCN)ccc1Oc1ccc(C(F)(F)F)cn1]

Entire reaction was performed under argon atmosphere using syringe septa technique. {2-[3-cyano-4-(5-trifluoromethyl-pyridin-2-yloxy)-phenyl]-ethyl}-carbamic acid tert-butyl ester (0.425 mmol, 1 eq) was dissolved in dichloromethane (1.5 ml) and stirred at 0° C. for 5 min. TFA (2.213 mmol, 5 eq) was added and stirring was continued for 2 hours. Reaction mixture was diluted with 10 ml NaHCO$_3$ (sat.) and extraction with DCM (3×20 ml) followed. Organic layers were combined and evaporated in vacuo to give 5-(2-amino-ethyl)-2-(5-trifluoromethyl-pyridin-2-yloxy)benzonitrile (0.391 mmol, yield=92%, purity=80%). [M+H]$^+$=308.29 $^1$H NMR (300 MHz, CDCl$_3$) δ/ppm 2.79 (br. s., 2H), 2.94-3.07 (m, 2H), 7.21 (br. s., 2H), 7.49 (d, J=8.9 Hz, 1H), 7.54 (br. s., 1H), 7.90-8.05 (m, 1H), 8.38 (br. s., 1H)

D230: {2-[4-(3-chloro-4-trifluoromethyl-phenoxy)-phenyl]-ethyl}-carbamic acid tert-butyl ester

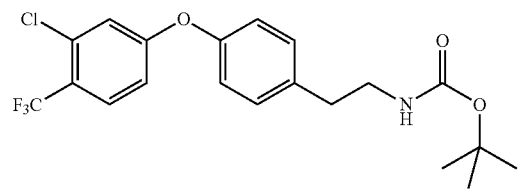 [SMILES: CC(C)(C)OC(=O)NCCc1ccc(Oc2ccc(C(F)(F)F)c(Cl)c2)cc1]

Entire reaction was performed under dry air using syringe septa technique. 4 Å molecular sievies were added to a stirred solution of 3-chloro-4-(trifluoromethyl)phenylboronic acid (0.021 mol, 2 eq) and [2-(4-hydroxy-phenyl)-ethyl]-carbamic acid tert butyl ester (0.011 mol, 1 eq) in dry DCM (105 ml) at ambient temperature in a flame dried flask flushed with dry air. The reaction was stirred for 15 min. After that, copper (II) acetate (0.011 mol, 1.01 eq), triethylamine (0.053 mol, 5 eq) and pyridine (0.053 mol, 5 eq) were added in succession and the reaction was stirred for 50 hours. The reaction mixture was sequential washed with 0.5 M HCl (4×250 ml), water (3×150 ml) and brine (1×150 ml). Organic layers were combined, dried over Na$_2$SO$_4$/MgSO$_4$, filtered and evaporated. Crude product was purified on Biotage SP1 Snap Si 100; 40 ml/min in the gradient of EtOAc in cyclohexan: 0-30% in 25 CV. The appropriate fractions were combined and evaporated in vacuo to give the required product {2-[4-(3-chloro-4-trifluoromethyl-phenoxy)-phenyl]-ethyl}-carbamic acid tert-butyl ester (3.703 mmol, yield=34%, purity=89%). [M+H]$^+$ =360.22 $^1$H NMR (300 MHz, CDCl$_3$) δ/ppm 1.42 (s, 9H), 2.75-2.84 (m, 2H), 3.31-3.43 (m, 2H), 4.55 (br. s., 1H), 6.84-6.90 (m, 1H), 6.94-7.01 (m, 2H), 7.02-7.06 (m, 1H), 7.18-7.23 (m, 3H), 7.55-7.61 (m, 1H)

D231: 2-[4-(3-chloro-4-trifluoromethyl-phenoxy)-phenyl]-ethylamine

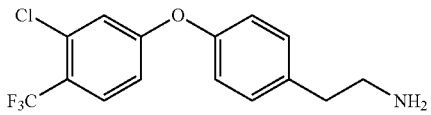 [SMILES: NCCc1ccc(Oc2ccc(C(F)(F)F)c(Cl)c2)cc1]

Entire reaction was performed under argon atmosphere using syringe septa technique. {2-[4-(3-chloro-4-trifluoromethyl-phenoxy)-phenyl]-ethyl}-carbamic acid tert-butyl ester (3.703 mmol, 1 eq) was dissolved in dichloromethane (20 ml) and stirred at 0° C. for 5 min. TFA (18.517 mmol, 5 eq) was added and stirring was continued overnight. Reaction mixture was diluted with 10 ml NaHCO$_3$ (sat.) and extraction with DCM (3×20 ml) followed. Organic layers were combined and evaporated in vacuo to give 2-[4-(3-chloro-4-trifluoromethyl-phenoxy)-phenyl]-ethylamine (2.661 mmol, yield=72%, purity=99%). [M+H]$^+$=316.21 $^1$H NMR (300 MHz, CDCl$_3$) δ/ppm 2.68-2.82 (m, 2H), 2.91-3.05 (m, 2H), 6.81-6.91 (m, 1H), 6.93-7.07 (m, 4H), 7.16-7.23 (m, 1H), 7.52-7.63 (m, 1H)

D232: 5-Bromo-2-methyl-pyrimidine

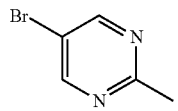

8 charges containing 1 g of 5-Bromo-2-iodo-pyrimidine (8 g, 28.08 mmol, 284.88 gmol$^{-1}$, 1 eq) dissolved in 10 ml of dry 1,4-dioxane with 41 mg Pd(0)tetrakis (0.01 eq, 325 mg) and 2.64 ml of trimethylaluminium, 2N solution in heptanes (1.5 eq, 21.06 ml) under argon atmosphere were heated in 10-20 ml vials for microwave synthesis in a microwave reactor at 115° C. for 1 hour. The charges were then poured into 400 ml of water. In the mixture was added 50 ml of 2 N NaOH water solution. The organic substances were extracted with EtOAc (3 times, 600 ml of EtOAc was used in total). The gathered EtOAc layers were dried and the solvent was evaporated. The obtained crude was purified by chromatography on BIOTAGE SP1 purification device using 100 g normal phase silica SNAP column and cyclohexane/EtOAc solvent system (gradient 3-15% of EtOAc in 20 column volumes). Solvent from the gathered fractions of appropriate composition was evaporated and obtained was 5-Bromo-2-methyl-pyrimidine (2.6 g, yield=53.5%, purity=95%). MS: [M+H]$^+$=173.01 $^1$H NMR (300 MHz; CDCl$_3$) δ/ppm 2.67 (s, 3H), 8.66 (s, 2H)

D233: 3-(2-Methyl-pyrimidin-5-yl)-acrylic acid methyl ester

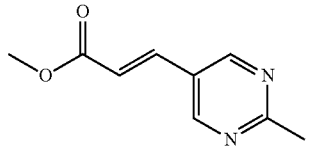

A sealed mixture of 5-Bromo-2-methyl-pyrimidine (2.6 g, 15.03 mmol, 1 eq), methyl acrylate (1.40 eq, 1.89 ml), palladium(II)-acetate (0.013 eq, 44 mg), triphenylphosphine (0.024 eq, 95 mg), and triethylamine (1.21 eq, 2.54 ml) was heated at 150° C. (temperature on display of heating device) for 16 hours. The mixture was cooled to ambient temperature and was poured into 200 ml of water. Organic substances were extracted with EtOAc (twice, 200 ml was used in total). The gathered EtOAc layers were filtered over celite pad, were dried and the solvent was evaporated. The resulting crude was purified by chromatography on BIOTAGE SP1 purification device using 50 g normal phase silica SNAP column and EtOAc/cyclohexane solvent system (gradient 30-80% of EtOAc in 20 column volumes). Solvent from the gathered fractions of appropriate composition was evaporated and obtained was 3-(2-Methyl-pyrimidin-5-yl)-acrylic acid methyl ester (450 mg, yield=16.80%, purity=95%). MS: [M+H]$^+$=179.13 $^1$H NMR (300 MHz; CDCl$_3$) δ/ppm 2.74 (s, 3H), 3.81 (s, 3H), 6.52 (d, J=16.60 Hz, 1H), 7.58 (d, J=16.60 Hz, 1H), 8.75 (s, 2H)

D234: 3-(2-Methyl-pyrimidin-5-yl)-propionic acid methyl ester

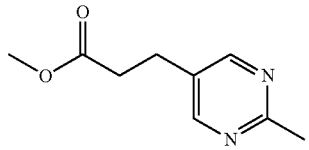

3-(2-Methyl-pyrimidin-5-yl)-acrylic acid methyl ester (450 mg, 2.53 mmol, 1 eq) and Pd/C, 10% (0.05 eq, 135 mg) were stirred in a DCM (4 ml)/ethanol (4 ml) mixture under hydrogen atmosphere at room temperature for 20 minutes. Pd/C was filtered off over a celite pad, the solvent was evaporated and obtained was 3-(2-methyl-pyrimidin-5-yl)-propionic acid methyl ester (450 mg, yield=90%, purity=88%). MS: [M+H]$^+$=181.14 $^1$H NMR (300 MHz; CDCl$_3$) δ/ppm 2.60 (t, d, J=7.66 Hz, 2H), 2.66 (s, 3H), 2.87 (t, J=7.66 Hz, 2H), 3.63 (s, 3H), 8.47 (s, 2H)

D235: 5-(2-Methyl-pyrimidin-5-ylmethyl)-2-thioxo-2,3-dihydro-1H-pyrimidin-4-one

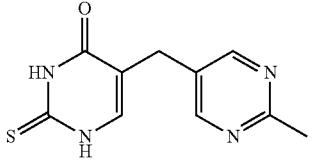 [SMILES: Cc1ncc(Cc2c[nH]c(=S)[nH]c2=O)cn1]

To the suspension of NaH, 60% (1.3 eq, 130 mg) in 600 μl of dry 1,2-dimethoxyethane, under argon atmosphere was carefully added, via syringe, a solution of 3-(2-Methyl-pyrimidin-5-yl)-propionic acid methyl ester (450 mg, 2.5 mmol, 1 eq) and methyl formate (4 eq, 616 μl) in 3 ml of dry 1,2-dimethoxyethane. The resulting suspension was stirred overnight (16 hours) at room temperature. In the reaction mixture was then added 3 ml of dry diethyl ether. The resulting precipitate was collected; it was washed with 3 ml of diethyl ether and dried. It was dissolved in 4 ml of absolute ethanol, thiourea (1.5 eq, 285 mg) was added and the reaction mixture was stirred at reflux under argon atmosphere for 8 hours. Solvent was then evaporated, the rest was dissolved in 3 ml of water and pH value of the solution was adjusted to 4.5-5 using 3N HCl water solution. The resulting precipitate was collected, it was washed with water and dried to afford 5-(2-Methyl-pyrimidin-5-ylmethyl)-2-thioxo-2,3-dihydro-1H-pyrimidin-4-one (210 mg, yield=35.9%, purity=95%) in form of white powder. MS: [M+H]$^+$=235.17 $^1$H NMR (300 MHz; DMSO-d$_6$) δ/ppm 2.54 (s, 3H), 3.50 (s, 2H), 7.48 (s, 1H), 8.55 (s, 2H), 12.38 (br.s., 2H)

D236: 5-(2-Methyl-pyrimidin-5-ylmethyl)-2-methylsulfanyl-1H-pyrimidin-4-one (MS109702-079K1)

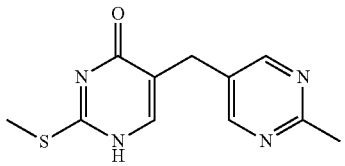

5-(2-Methyl-pyrimidin-5-ylmethyl)-2-thioxo-2,3-dihydro-1H-pyrimidin-4-one (210 mg, 234.28 gmol$^{-1}$, 0.90 mmol, 1 eq) and NaOEt (2 eq, 128 mg) were stirred in 5 ml of absolute ethanol at room temperature for 30 minutes. In the suspension was then added methyl iodide (2.5 eq, 140 μl) and the mixture was stirred for 35 hours. Solvent was then evaporated. In the mixture was added 3 ml of water and pH was adjusted to 5-6 range using 3N HCl water solution. The resulting precipitate was collected and dried to afford 5-(2-methyl-pyrimidin-5-ylmethyl)-2-methylsulfanyl-1H-pyrimidin-4-one (85 mg, yield=36.6%, purity=96%) in form of white powder. MS: [M+H]$^+$=249.22 $^1$H NMR (300 MHz; DMSO-d$_6$) δ/ppm 2.45 (s, 3H), 2.54 (s, 3H), 3.57 (s, 2H), 7.87 (br.s., 1H), 8.56 (s, 2H), 12.79 (br.s., 1H).

D237: {2-[4-(5-Trifluoromethyl-pyridin-2-yloxy)-phenyl]-ethyl}-carbamic acid tert-butyl ester

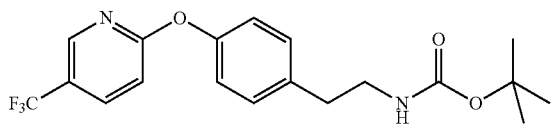 [SMILES: CC(C)(C)OC(=O)NCCc1ccc(Oc2ccc(C(F)(F)F)cn2)cc1]

2-Bromo-5-(trifluoromethyl) pyridine (3000 mg, 13.274 mmol), [2-(4-hydroxy-phenyl)ethyl]-carbamic acid tert-butyl ester (3150 mg, 13.274 mmol) and potassium carbonate anhydrous (2752 mg, 19.911 mmol) were dissolved in DMF (150 ml) and reaction was stirred at 60° C. overnight. The reaction mixture was washed with EtOAc and water (3×). Organic layers were combined and dried over phase separator filter tube affording the crude product which was purified on Biotage SP-1 system using 50 g Si SNAP column. The column containing sample was eluted with EtOAc/CyHex gradient (0-30% of EtOAc/30 CV). Fractions with desired product were gathered and solvent was evaporated to give the required product {2-[4-(5-trifluoromethyl-pyridin-2-yloxy)-phenyl]-ethyl}-carbamic acid tert-butyl ester as a white solid (2200 mg, yield=42.9%, purity 99%). [M+H]$^+$=383.39

D238: 2-[4-(5-Trifluoromethyl-pyridin-2-yloxy)-phenyl]-ethylamine

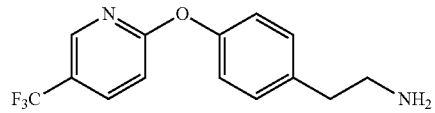 [SMILES: NCCc1ccc(Oc2ccc(C(F)(F)F)cn2)cc1]

{2-[4-(5-Trifluoromethyl-pyridin-2-yloxy)-phenyl]-ethyl}-carbamic acid tert-butyl ester (2200 mg, 1.135 mmol, 1 eq) was dissolved in dichloromethane (4 ml) and stirred at 0° C. for 5 min. TFA (3084 ml, 40.273 mmol, 7 eq) was added and stirring was continued at rt overnight. Reaction mixture was diluted with NaHCO$_3$ (sat.) and extracted with DCM (3×). Organic layers were combined and evaporated to give 2-[4-(5-trifluoromethyl-pyridin-2-yloxy)-phenyl]-ethylamine as white solid (1.6 g, yield=99%, purity 99%). [M+H]$^+$=283.26 1H NMR (DMSO-d$_6$, 300 MHz): 2.83-2.91 (m, 2H), 3.03-3.13 (m, 2H), 7.13-7.19 (d, 2H), 7.20-7.24 (d, 1H), 7.30-7.36 (d, 2H), 7.86 (bs, 2H), 8.19-8.25 (m, 1H), 8.53 (s, 1H)

D239: 2-methylsulfanyl-5-(2-oxo-1,2-dihydro-pyrimidin-5-ylmethyl)-1H-pyrimidin-4-one

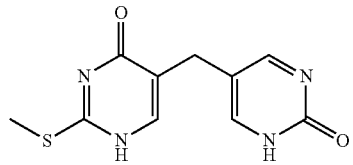 [SMILES: CSc1nc(=O)c(Cc2cnc(=O)[nH]c2)c[nH]1]

Entire reaction was performed under argon atmosphere using syringe septa technique. 5-(2-methoxy-pyrimidin-5-ylmethyl)-2-methylsulfanyl-1H-pyrimidin-4-one (0.984 mmol, 1 eq) was added in dry vessel. Boron tribromide (2.066 mmol, 2.1 eq) was added and reaction mixture was stirred at 0° C. After 30 min, reaction mixture was allowed to reach to room temperature and it was stirred overnight. Reaction mixture was diluted with water (2 ml). The resulting precipitate, 2-methylsulfanyl-5-(2-oxo-1,2-dihydro-pyrimidin-5-ylmethyl)-1H-pyrimidin-4-one (0.260 mmol, yield=26%) was obtained. $^1$H NMR (300 MHz, DMSO-d$_6$) δ/ppm 2.45 (s, 3H), 7.75-7.88 (m, 2H), 7.97-8.33 (m, 3H), 11.29-13.09 (m, 4H)

D240: 2-[(6-chloro-pyridin-3-yl)-hydroxymethyl]acrylic acid methyl ester

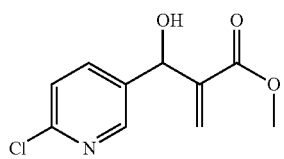

A mixture of 6-chloro-pyridin-3-carbaldehyde (7.064 mmol, 1 eq), DABCO (7.064 mmol, 1 eq) and methyl acyrlate (35.320 mmol, 5 eq) dissolved in 1,4-dioxane (50 ml)/water (50 ml) solvent mixture was stirred at room temperature overnight. The reaction mixture was poured in 200 ml brine and extraction with DCM (3×150 ml) followed. Organic layers were combined, dried over Na$_2$SO$_4$/MgSO$_4$ and evaporated to give crude 2-[(6-chloro-pyridin-3-yl)-hydroxymethyl]acrylic acid methyl ester. Crude product was purified on Biotage SP1 Snap Si 25; 25 ml/min in the gradient of EtOAc in cyclohexane: 10-45% in 15 CV. The appropriate fractions were combined and evaporated in vacuo to give the required product 2-[(6-chloro-pyridin-3-yl)-hydroxymethyl]acrylic acid methyl ester (4.788 mmol, yield=68%, purity=99%). [M+H]$^+$=228.14 $^1$H NMR (300 MHz, CDCl$_3$) δ/ppm 3.66 (s, 3H), 5.45-5.57 (m, 1H), 5.80-5.92 (m, 1H), 6.26-6.36 (m, 1H), 7.17-7.27 (m, 1H), 7.56-7.68 (m, 1H), 8.20-8.33 (m, 1H)

D241: 2-(acetoxy-(6-chloro-pyridin-3-yl)-methyl]-acrylic acid methyl ester

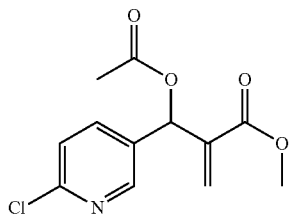 [SMILES: C=C(C(=O)OC)C(OC(C)=O)c1ccc(Cl)nc1]

To a solution of 2-[(6-chloro-pyridin-3-yl)-hydroxymethyl]acrylic acid methyl ester (4.788 mmol, 1 eq) in dichloromethane (10 ml), molecular sievies 4 Å and 4-DMAP (1.915 mmol, 0.4 eq) were added. Reaction mixture was cooled to 0° C. and acetic anhydride (7.182 mmol, 1.5 eq) was added. Mixture allowed to reach room temperature and stirred for 2 hours. The reaction mixture was poured in 50 ml NaHCO$_3$ (sat.) and extraction with DCM (3×100 ml) followed. Organic layers were combined and evaporated to give crude product which was purified on Biotage SP1 Snap Si 25; 25 ml/min in the gradient of EtOAc in Cyclohexan: 10-45% in 15 CV. The appropriate fractions were combined and evaporated in vacuo to give the required product 2-(acetoxy-(6-chloro-pyridin-3-yl)-methyl]-acrylic acid methyl ester (2.099 mmol, yield=44%, purity=100%). [M+H]$^+$=270.19 $^1$H NMR (300 MHz, CDCl$_3$) δ/ppm 2.10 (s, 3H), 3.69 (s, 3H), 5.97 (d, J=0.9 Hz, 1H), 6.44 (s, 1H), 6.62 (s, 1H), 7.19-7.33 (m, 1H), 7.58-7.70 (m, 1H), 8.35-8.44 (m, 1H)

D242: 5-(6-chloro-pyridin-3-ylmethyl)-2-methylsulfanyl-1H-pyrimidin-4-one

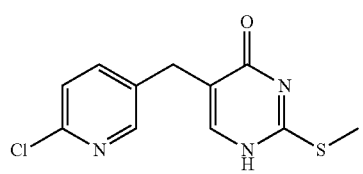 [SMILES: CSc1nc(=O)c(Cc2ccc(Cl)nc2)c[nH]1]

2-(acetoxy-(6-chloro-pyridin-3-yl)-methyl]-acrylic acid methyl ester (2.076 mmol, 1 eq) was added portionwise in suspension of carbamimidothionic acid-methylester-monohydriiodide (3.115 mmol, 1.1 eq) and triethylamine (4.568 mmol, 2.2 eq) in ethanol (2 ml) at 80° C. Reaction mixture was heated at that temperature for 6 hours. The solvent was evaporated to give crude product which was purified on Biotage SP1 Snap Si 25; 25 ml/min in the gradient of EtOAc in cyclohexan: 40-80% in 20 CV. The appropriate fractions were combined and evaporated in vacuo to give the required product 5-(6-chloro-pyridin-3-ylmethyl)-2-methylsulfanyl-1H-pyrimidin-4-one. (0.344 mmol, yield=16%, purity=85%). [M+H]$^+$=268.15 $^1$H NMR (300 MHz, CDCl$_3$) δ/ppm 1.55 (s, 3H), 3.68 (s, 2H), 7.16-7.21 (m, 1H), 7.53-7.63 (m, 1H), 7.72 (s, 1H), 8.31 (d, J=2.1 Hz, 1H)

D243: 3-pyridazine-4-yl-acrylic acid methyl ester

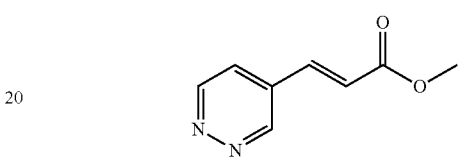

To a solution of pyridazine-4-carboxaldehyde (3.646 mmol, 1 eq) in dry dichloromethane (25 ml), (methoxycarbonylmethylene)triphenylphosphorane (5,550 mmol, 1.2 eq) was added portionwise. The reaction mixture was stirred at room temperature overnight. Reaction mixture was poured into water (200 ml) and extraction with DCM (3×100 ml) followed. Organic layers were combined, dried over phase separator cartridge to giving crude product which was purified on Biotage SP1 Snap Si 100; 40 ml/min in the gradient of MeOH in DCM: 0-10% in 30 CV. The appropriate fractions were combined and evaporated in vacuo to give the required product 3-pyridazine-4-yl-acrylic acid methyl ester (4.142 mmol, yield=89%, purity=96%). [M+H]$^+$=165.11 $^1$H NMR (300 MHz, CDCl$_3$) δ/ppm 3.82 (s, 3H), 6.64-6.68 (m, 1H), 6.72 (s, 1H), 9.22 (dd, J=5.3, 1.0 Hz, 1H), 9.27 (s, 2H)

D244: 3-pyridazine-4-yl)propionic acid methyl ester

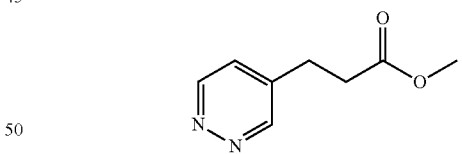

To a solution of 3-pyridazine-4-yl-acrylic acid methyl ester (3.959 mmol, 1 eq) dissolved in dichloromethane (9 ml) and ethanol (9 ml) Pd/C (0.198 mmol, 0.05 eq) was added. The resulting black suspension was shaken on a Parr apparatus under H$_2$ atmosphere (0.5 bar) for 45 minutes at rt. The suspension was filtered through Celite and evaporated to give crude product which was purified on Biotage SP1 Snap Si 25; 15 ml/min in the gradient of MeOH in DCM: 0-4% in 15 CV. The appropriate fractions were combined and evaporated in vacuo to give the required product 3-pyridazine-4-yl)propionic acid methyl ester. (1.715 mmol, yield=43%, purity=98%). [M+H]$^+$=167.09 $^1$H NMR (300 MHz, CDCl$_3$) δ/ppm 2.68 (s, 2H), 2.90-3.01 (m, 2H), 3.66 (s, 3H), 7.27-7.36 (m, 1H), 9.02-9.12 (m, 2H)

D245: 2-methylsulfanyl-5pyridazin-4-ylmethyl-1H-pyrimidin-4-one

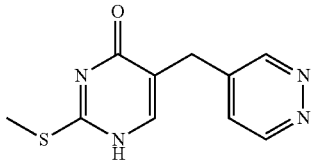 [SMILES: CSc1nc(=O)c(Cc2ccnnc2)c[nH]1]

A mixture of 3-pyridazin-4-yl-propionic acid methyl ester (1.685 mmol, 1 eq) and methyl formate (5.055 mmol, 3 eq) dissolved in dry 1,2-dimethoxyethane (4 ml) was added portionwise to a suspension of NaH (3.370 mmol, 2 eq) in dry 1,2-dimethoxyethane (2 ml). Reaction mixture was stirred overnight. The solvent was removed and the resulting crude was added portionwise in suspension of carbamimidothionic acid-methylester-monohydriiodide (1.685 mmol, 1 eq) and triethylamine (1.685 mmol, 1 eq) in ethanol at 80° C. Reaction mixture was heated at that temperature for 6 hours. After cooling the reaction mixture, solvent was evaporated to give crude product which was purified on Biotage SP1 Snap NH 10; 15 ml/min in the gradient of MeOH in DCM: 5-30% in 15 CV. The appropriate fractions were combined and evaporated in vacuo to give the required product 2-methylsulfanyl-5pyridazin-4-ylmethyl-1H-pyrimidin-4-one (0.341 mmol, yield=20%, purity=98%). [M+H]=235.17 H NMR (300 MHz, DMSO-$d_6$) δ/ppm 2.49 (s, 3H), 3.69 (s, 2H), 7.46-7.57 (m, 1H), 7.90-8.01 (m, 1H), 9.04-9.12 (m, 1H), 9.16 (d, J=0.7 Hz, 1H), 12.69-13.03 (m, 1H)

D246: 2-{2-[4-(4-Chloro-3-trifluoromethyl-phenoxy)-phenyl]-ethylamino}-1H-pyrimidin-4-one

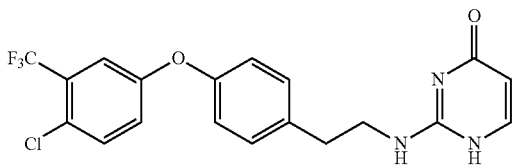 [SMILES: O=c1cc[nH]c(NCCc2ccc(Oc3ccc(Cl)c(C(F)(F)F)c3)cc2)n1]

2-Methylsulfanyl-1H-pyrimidin-4-one (70 mg, 0.492 mmol, 1.41 eq) and 2-[4-(4-chloro-3-trifluoromethyl-phenoxy)-phenyl]-ethylamine (110 mg, 0.348 mmol, 1 eq) were heated in a sealed vial at 150° C. in 400 μl of dry pyridine for 16 hours. Solvent was then evaporated and the resulting crude was purified by chromatography on BIOTAGE SP1 purification device using 10 g normal phase silica SNAP column and DCM/30% MEOH in DCM solvent system (gradient 2-20% of 30% MeOH in DCM in 20 column volumes). Solvent from the gathered fractions of appropriate composition was evaporated and the resulting crude was triturated with diisopropyl ether and cyclohexane to afford 2-{2-[4-(4-chloro-3-trifluoromethyl-phenoxy)-phenyl]-ethylamino}-1H-pyrimidin-4-one (111 mg, yield=73.8%, purity=95%) as a white powder. MS: [M+H]$^+$=410.33 $^1$H NMR (300 MHz; CDCl$_3$) δ/ppm 2.92 (t, J=6.95 Hz, 2H), 3.61-3.72 (m, 2H), 5.59 (d, J=6.38 Hz, 1H), 6.18 (br.s, 1H), 6.95 (d, J=8.51 Hz, 2H), 7.03 (dd, J=9.07 Hz, J=2.69 Hz, 1H), 7.24 (d, J=8.51 Hz, 1H), 7.30 (d, J=2.69 Hz, 1H), 7.41 (d, J=8.80 Hz, 1H), 7.77 (d, J=6.38 Hz, 1H), 11.77 (br.s, 1H)

D247: 5-Methyl-2-methylsulfanyl-1H-pyrimidin-4-one

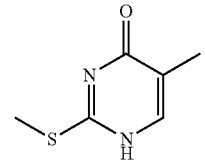

5-methyl-2-thiouracil (2 g, 98%, 13.78 mmol, 1 eq) and KOH, 85%, (1.05 eq, 995 mg) were suspended in 25 ml of absolute ethanol and the mixture was stirred for 1 hour at room temperature. In the suspension was then added MeI (1.05 eq, 905 μl) dropwise and the suspension was heated at 65° C. (temperature on display of heating device) for 2 hours. Solvent was then evaporated. In the rest was added 100 ml of water and using ultrasound was suspended. The obtained precipitate was collected by filtration, it was dried and obtained was 5-methyl-2-methylsulfanyl-1H-pyrimidin-4-one (1.7 g, yield=71.9%, purity=93%) in form of a white powder. MS: [M+H]$^+$=157.08 $^1$H NMR (300 MHz; DMSO-$d_6$) δ/ppm 1.90 (s, 3H), 2.50 (s, 3H), 7.78 (s, 1H)

D248: 2-[3-Bromo-4-(5-trifluoromethyl-pyridin-2-yloxy)-phenyl]-ethylamine

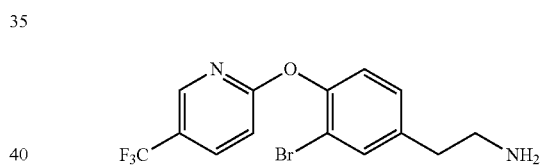

{2-[3-bromo-(5-trifluoromethyl-pyridin-2-yloxy)-phenyl]-ethyl}-carbamic acid tert-butyl ester (1.3 g, 2.818 mmol) was dissolved in dichloromethane (10 ml) and stirred at 0° C. for 5 min. TFA (1.08 ml, 14.091 mmol, 5 eq) was added and stirring was continued overnight. Reaction mixture was diluted with 10 ml NaHCO$_3$ (sat.) and extraction with DCM (3×20 ml) followed. Organic layers were combined and evaporated in vacuo to give 2-[3-bromo-(5-trifluoromethyl-pyridin-2-yloxy)-phenyl]-ethylamine (1.01 g, 2.796 mmol, yield=99%, purity=100%). [M+H]$^+$=361.17

D249: 5-(2-Amino-ethyl)-2-(5-trifluoromethyl-pyridin-2-yloxy)-benzonitrile

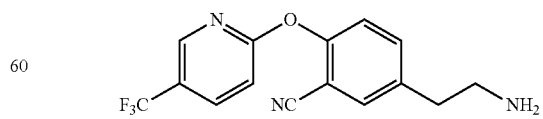

A mixture of 2-[3-bromo-(5-trifluoromethyl-pyridin-2-yloxy)-phenyl]-ethylamine (950 mg, 2.059 mmol) and copper(I)cyanide (239.78 mg, 2.677 mmol, 1.3 eq) were suspended in N-methylpyrrolidone (2.1 ml) was irradiated in microwave Biotage Initiator at 200° C. for 20 min. After cooling, water (20 ml) was added and extraction with EtOAc (3×15 ml) followed. Organic layers were combined, dried over Na₂SO₄/MgSO₄, filtered off and evaporated in vacuo to give crude 5-(2-amino-ethyl)-2-(5-trifluoromethyl-pyridin-2-yloxy)-benzonitrile. Crude product was put on a previously conditioned SCX column (5 g). The column was washed with MeOH (2×10 ml) and then with 2N NH₃/MeOH (2×10 ml) to retrieve the product 5-(2-amino-ethyl)-2-(5-trifluoromethyl-pyridin-2-yloxy)-benzonitrile (245 mg, 0.797 mmol, yield=38%, purity=91%). [M+H]=308.23 H NMR (300 MHz, CDCl₃) δ/ppm 2.79 (br. s., 2H), 2.94-3.07 (m, 2H), 7.21 (br. s., 2H), 7.49 (d, J=8.9 Hz, 1H), 7.54 (br. s., 1H), 7.90-8.05 (m, 1H), 8.38 (br. s., 1H)

D250: 2-[Hydroxy-(2-methyl-pyrimidin-5-yl)-methyl]-acrylic acid methyl ester

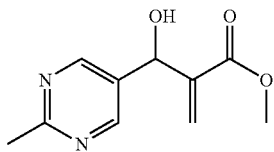

A mixture of 2-methylpyrimidine-5-carbaldehyde (1 g, 8.18 mmol, 1 eq), DABCO (1 eq, 935 mg) and methyl acrylate (5 eq, 3 68 ml) dissolved in a 1,4-dioxane (40 ml/H₂O (40 ml) mixture was stirred at room temperature for 2 hours. The mixture was then poured into 300 ml of brine and the organic substances were extracted with DCM (3 times, 300 ml was used in total). The gathered DCM layers were dried, the solvent was evaporated and the obtained crude oil was triturated with diethyl ether to afford 2-[hydroxy-(2-methyl-pyrimidin-5-yl)-methyl]-acrylic acid methyl ester (1.58 g, yield=83.40%, purity=90%) in form of white powder. MS: [M+H]⁺=209.18 ¹H NMR (300 MHz; CDCl₃) δ/ppm 2.72 (s, 3H), 3.61 (br.s., 1H), 3.75 (s, 3H), 5.58 (s, 1H), 5.97 (s, 1H), 6.43 (s, 1H) 8.64 (s, 2H)

D251: 2-[Acetoxy-(2-methyl-pyrimidin-5-yl)-methyl]-acrylic acid methyl ester

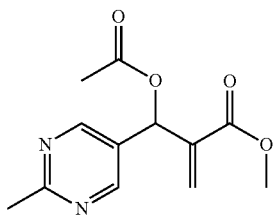 [SMILES: C=C(C(=O)OC)C(OC(C)=O)c1cnc(C)nc1]

2-[Hydroxy-(2-methyl-pyrimidin-5-yl)-methyl]-acrylic acid methyl ester (1.58 g, 7.58 mmol, 1 eq) and 4-DMAP (0.4 eq, 370 mg) were dissolved in 30 ml of dry DCM under argon atmosphere. To the mixture, cooled at 0° C., was added acetic anhydride (1.5 eq, 1.07 ml) dropwise, during 2 minutes. The mixture was warmed-up to room temperature and was stirred overnight (16 hours). The mixture was then poured into 150 ml of NaHCO₃ saturated water solution and organic substances were extracted with DCM (3 times, 150 ml of DCM was used in total). The gathered DCM layers were dried, the solvent was evaporated and obtained was 2-[acetoxy-(2-methyl-pyrimidin-5-yl)-methyl]-acrylic acid methyl ester (1.16 g, yield=61.1%, purity=90%) in form of orange transparent oil. MS: [M+H]⁺=251.25 ¹H NMR (300 MHz; CDCl₃) δ/ppm 2.73 (s, 3H), 3.72 (s, 2H), 6.05 (s, 1H), 6.49 (s, 1H), 6.61 (s, 1H) 8.65 (s, 2H)

D252: 5-(2-Methyl-pyrimidin-5-ylmethyl)-2-methyl-sulfanyl-1H-pyrimidin-4-one

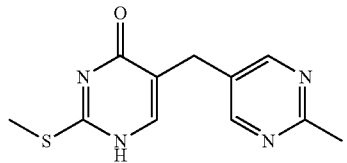

To a solution of carbamimidothionic acid, methyl ester monohydriiodide (1.1 eq, 878 mg) and dry triethylamine (2.2 eq, 1.22 ml) in 5 ml of dry ethanol heated at 90° C. (temperature on display of heating device), sealed with septa, was added a solution of 2-[acetoxy-(2-methyl-pyrimidin-5-yl)-methyl]-acrylic acid methyl ester (1.0 g, 3.99 mmol, 1 eq) in 2 ml of dry ethanol. The mixture was stirred at 90° C. for 3 hours. The solvent was then evaporated, the residue was dissolved in 15 ml of water and pH value of the solution was adjusted to 4.5-5.5 range. Organic substances were extracted with DCM (5 times, 100 ml of DCM was used in total). The gathered DCM layers were dried, the solvent was evaporated and the resulting crude was purified by chromatography on Biotage SP1 purification device using 25 g normal phase silica SNAP column and DCM/20% MeOH in DCM solvent system (gradient 5-35% of 20% MeOH in DCM in 20 column volumes). Solvent from the gathered fractions of appropriate composition was evaporated and obtained was 5-(2-Methyl-pyrimidin-5-ylmethyl)-2-methylsulfanyl-1H-pyrimidin-4-one (400 mg, yield=40.3%, purity=95%). MS: [M+H]⁺= 249.22 ¹H NMR (300 MHz; CDCl₃) δ/ppm 2.54 (s, 3H), 2.67 (s, 3H), 3.64 (s, 2H), 7.76 (s, 1H), 8.58 (s, 2H), 11.85 (br. s., 1H)

D253: 5-(2-Amino-ethyl)-2-(4-chloro-3-trifluoromethyl-phenoxy)-benzonitrile

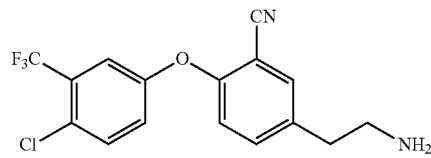 [SMILES: N#Cc1cc(CCN)ccc1Oc1ccc(Cl)c(C(F)(F)F)c1]

2-(4-Chloro-3-trifluoromethyl-phenoxy)-5-(2-hydroxy-ethyl)-benzonitrile (592 mg, 1.732 mmol) was dissolved in DCM (2 ml) and TEA (0.6 ml) was added. Methanesulfonyl chloride (175 μl, 2.252 mmol, 1.3 eq) was added drop-wise under ice-cold conditions and the reaction was stirred for 2 h at RT. The mixture was poured into cold water (3 ml). The organic layers was separated and washed with NaHCO₃ (sat.), 1% aqueous HCl and brine solution. The organic layers was dried over phase tube separator and concentrated. The residue was dissolved in acetonitrile (25 ml) and it was added in to aqueous NH₄OH (5 ml). The reaction mixture was stirred at RT for over weekend. Aqueous NH₄OH (10 ml) was added and the reaction was stirred for another 48 h. Then aqueous NH₄OH (5 ml) was added and the reaction was stirred for another 48 h. Acetonitrile was evaporated and product 5-(2-Amino-ethyl)-2-(4-chloro-3-trifluoromethyl-phenoxy)-benzonitrile was obtained. Raw product was purified by SCX cartridge (5 g). Cartridge was first equilibrated with MeOH. Raw product was dissolved in MeOH. Desired product was eluted from the column with 2M NH$_3$ in MeOH. MeOH fractions were concentrated under reduced pressure to give crude product with some impurities. It was purified on Biotage SP-1 system using 10 g Si SNAP column. The column containing sample was eluted with DCM/MeOH gradient (0-10% of MeOH/20 CV). Fractions with desired product were gathered and solvent was evaporated. Product 5-(2-Amino-ethyl)-2-(4-chloro-3-trifluoromethyl-phenoxy)-benzonitrile was obtained as yellow oil (250 mg, yield=40.24%, purity=95%). MS: [M+H]$^+$=341.74 1H NMR (DMSO-d$_6$, 300 MHz): 7.26 (d, 2H), 7.45-7.52 (m, 1H), 7.61 (d, 1H), 7.80 (d, 1H), 7.99 (d, 2H), 9.99 (s, 1H)

D254: 2-[Hydroxy-(6-methyl-pyridin-3-yl)-methyl]-acrylic acid methyl ester

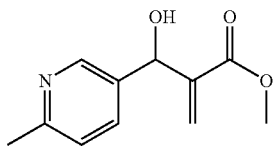

A mixture of 6-methylpyridine-3-carboxaldehyde, 97% (500 mg, 4.0 mmol, 1 eq), DABCO (458 mg, 1 eq) and methyl acrylate (1.80 ml, 5 eq) in a 1,4-dioxane (20 ml)/water (20 ml) solvent mixture was stirred at room temperature for 4 days. The resulting mixture was poured in 150 ml of brine and the organics were extracted with DCM (3×300 ml). The gathered DCM layers were dried, solvent was evaporated and the obtained crude was purified by chromatography on Biotage SP1 purification device using 25 g normal phase silica SNAP column and DCM/MeOH solvent system (gradient 1-6% of MeOH in 20 CV). Solvent from gathered fractions of appropriate composition was evaporated and the resulting crude was triturated with cyclohexane to obtain 2-[hydroxy-(6-methyl-pyridin-3-yl)-methyl]-acrylic acid methyl ester in form of white powder (375 mg, yield=43.8%, purity=95%). MS: [M+H]$^+$=208.17 $^1$H NMR (300 MHz; CDCl$_3$) δ/ppm 2.55 (s, 3H), 3.11 (d, J=5.86 Hz, 1H), 3.74 (s, 3H), 5.58 (d, J=5.58 Hz, 1H), 5.87 (s, 1H), 6.38 (s, 1H), 7.15 (d, J=8.13 Hz, 1H), 7.61 (dd, J=8.13 Hz, J=2.45 Hz, 1H), 8.48 (d, J=2.45 Hz, 1H)

D255: 2-[Acetoxy-(6-methyl-pyridin-3-yl)-methyl]-acrylic acid methyl ester

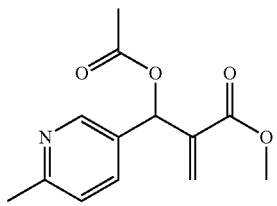 [SMILES: C=C(C(=O)OC)C(OC(C)=O)c1ccc(C)nc1]

To a solution of 2-[hydroxy-(6-methyl-pyridin-3-yl)-methyl]-acrylic acid methyl ester (375 mg, 1.80 mmol, 1 eq) and 4-DMAP (88 mg, 0.72 mmol, 0.4 eq) in dry DCM (10 ml) under argon atmosphere, cooled at 0° C. was added acetic anhydride (0.255 ml, 1.5 eq) dropwise during 2 minutes. The mixture was warmed up to room temperature and was stirred for 16 h. The reaction mixture was poured into 50 ml of NaHCO$_3$ saturated solution. The organic substances were extracted with DCM (2×100 ml). The gathered DCM layers were dried, the solvent was evaporated and the resulting crude was purified on Biotage SP1 purification device using 10 g normal phase silica SNAP column and cyclohexane/EtOAc solvent system (gradient 50-80% of EtOAc in 20 CV). Solvent from gathered fractions of appropriate composition was evaporated and obtained was 2-[acetoxy-(6-methyl-pyridin-3-yl)-methyl]-acrylic acid methyl ester in form of transparent orange oil (280 mg, yield=62.21%, purity=95%). MS: [M+H]$^+$=250.24 $^1$H NMR (300 MHz; CDCl$_3$) δ/ppm 2.11 (s, 3H), 2.55 (s, 3H), 3.71 (s, 3H), 5.95 (s, 1H), 6.44 (s, 1H), 6.65 (s, 1H), 7.14 (d, J=7.98 Hz, 1H), 7.60 (dd, J=7.98 Hz, J=2.23 Hz, 1H), 8.52 (d, J=2.23 Hz, 1H)

D256: 5-(6-Methyl-pyridin-3-ylmethyl)-2-methylsulfanyl-1H-pyrimidin-4-one

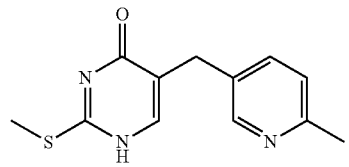

To a solution of carbamimidothionic acid, methyl ester monohydroiodide (1.1 eq, 270 mg) and dry triethylamine (2.2 eq, 0.342 ml) in 2 ml of dry ethanol heated at 90° C. (temperature on display of heating device), sealed with septa, was added a solution of 2-[acetoxy-(6-methyl-pyridin-3-yl)-methyl]-acrylic acid methyl ester (280 mg, 1.12 mmol, 1 eq) in 1 ml of dry ethanol. The mixture was stirred at 90° C. for 4 hours. The solvent was then evaporated and the rest was dissolved in 10 ml of water. pH value of the solution was adjusted to 6.5-7 range and the organic substances were extracted with DCM (5 times, 50 ml of DCM was used in total). The gathered DCM layers were dried, solvent was evaporated and the resulting crude was purified by chromatography on Biotage SP1 purification device using 10 g normal phase silica SNAP column and DCM/30% MeOH in DCM solvent system (gradient 3-32% of 30% MeOH in DCM in 20 CV). Solvent from the gathered fractions of appropriate composition was evaporated and the rest was triturated with diethyl ether and hexane to obtain 5-(6-Methyl-pyridin-3-ylmethyl)-2-methylsulfanyl-1H-pyrimidin-4-one (76 mg, yield=27.36%, purity=95%). MS: [M+H]$^+$= 248.20 $^1$H NMR (300 MHz; CDCl$_3$) δ/ppm 2.52 (s, 3H), 2.55 (s, 3H), 3.70 (s, 2H), 7.08 (d, J=7.97 Hz, 1H), 7.53 (dd, J=7.97 Hz, J=2.15 Hz, 1H), 7.68 (s, 1H), 8.44 (d, J=2.15 Hz, 1H)

D257: 6-Methoxy-pyridine-3-carbaldehyde

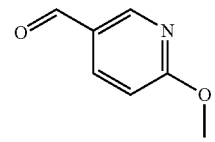

N-butyllithium, 1.6 M solution in hexanes (1.05 eq, 7.0 ml) was added dropwise to a solution of 5-bromo-2-methoxypyridine (2 g, 10.63 mmol) in THF, Acros dry (25 ml) under argon atmosphere at −78° C. After complete addition the mixture was stirred for another 90 minutes at −78° C. at which time DMF, acros dry (2 eq, 1.65 ml) was added dropwise. The mixture was then stirred at −78° C. for another 90 minutes. The mixture was then warmed-up to room temperature and poured into 150 ml of NaHCO₃ saturated water solution. The organics were extracted with 3×70 ml of diethyl ether. The gathered ether layers were dried over Na₂SO₄ the solvent was evaporated and the obtained crude was purified by chromatography on BIOTAGE SP1 purification device using 25 g normal phase silica SNAP coloumn and cyclohexane/EtOAc solvent system (gradient 1-10% of EtOAc in 20 coloumn volumes) Solvent from the gathered fractions of appropriate composition was evaporated and obtained was 6-methoxy-pyridine-3-carbaldehyde (1.04 g, yield=71.2%, purity=95%) in form of white crystals. MS: [M+H]⁺=138.09 ¹H NMR (300 MHz; CDCl₃) δ/ppm 4.04 (s, 3H), 6.85 (d, J=8.70 Hz, 1H), 8.07 (dd, J=8.70 Hz, J=2.34 Hz, 1H), 8.64 (d, J=2.34 Hz, 1H), 9.96 (s, 1H)

D258: 3-(6-Methoxy-pyridin-3-yl)-acrylic acid methyl ester

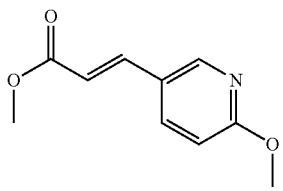

To a solution of 6-methoxy-pyridine-3-carbaldehyde (1 g, 7.29 mmol, 1 eq) in 50 ml of dry DCM was added portionwise (methoxycarbonylmethylene)triphenylphosphorane (1.05 eq, 2.56 g). The mixture was stirred at room temperature for 16 hours (overnight). The mixture was then poured into 200 ml of water and the organic substances were extracted with DCM (twice, 150 ml of DCM was used in total) The gathered DCM layers were dried and the resulting crude was purified by chromatography on BIOTAGE SP1 purification device using 100 g normal phase silica SNAP coloumn and cyclohexane/EtOAc solvent system (gradient 3-22% of EtOAc in 20 coloumn volumes). Solvent from the gathered fractions of appropriate composition was evaporated and obtained was 3-(6-methoxy-pyridin-3-yl)-acrylic acid methyl ester (1.04 g, yield=73.8%, purity=95%). MS: [M+H]⁺=194.17 ¹H NMR (300 MHz; CDCl₃) δ/ppm 3.81 (s, 3H), 3.97 (s, 3H), 6.34 (d, J=16.02 Hz, 1H), 6.77 (d, J=8.79 Hz, 1H), 7.65 (d, J=16.02 Hz, 1H), 7.77 (dd, J=8.70 Hz, J=2.40 Hz, 1H), 8.27 (d, J=2.40 Hz, 1H)

D259: 3-(6-Methoxy-pyridin-3-yl)-propionic acid methyl ester

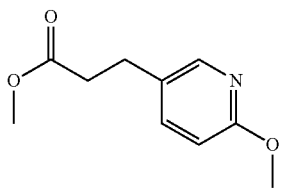

A suspension of 3-(6-methoxy-pyridin-3-yl)-acrylic acid methyl ester (1.2 g, 6.21 mmol, 1 eq) and Pd/C, 10% (330 mg, 0.05 eq, 10%) was stirred in a DCM (15 ml)/absolute EtOH (15 ml) solvent mixture under hydrogen atmosphere for 1 hour at room temperature. Palladium was filtered off over a celite pad, the solvent was evaporated and obtained was 3-(6-methoxy-pyridin-3-yl)-propionic acid methyl ester (1.18 g, yield=93%, purity=95%) in form of yellowish oil. MS: [M+H]⁺=196.15 ¹H NMR (300 MHz; CDCl₃) δ/ppm 2.59 (t, J=7.75 Hz, 2H), 2.88 (t, J=7.75 Hz, 2H), 3.67 (s, 3H), 3.91 (s, 3H), 6.68 (d, J=8.46 Hz, 1H), 7.42 (dd, J=7.42 Hz, J=2.40 Hz, 1H), 8.00 (d, J=2.40 Hz, 1H)

D260: 5-(6-Methoxy-pyridin-3-ylmethyl)-2-thioxo-2,3-dihydro-1H-pyrimidin-4-one

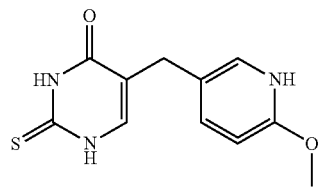 [SMILES: COC1=C=CC(Cc2c[nH]c(=S)[nH]c2=O)=CN1]

To a suspension of NaH, 60% dispersion on mineral oil (1.3 eq, 110 mg, 60%) in 700 µl of dry 1,2-dimethoxyethane under argon atmosphere was added a solution of 3-(6-Methoxy-pyridin-3-yl)-propionic acid methyl ester (590 mg, 3.02 mmol, 1 eq) and methyl formate (2 eq, 380 µl) in 4 ml of dry 1,2-dimethoxyethane. The sealed mixture was stirred at room temperature for 16 hours (overnight). Solvent from the mixture was then evaporated. In the rest was added 15 ml of diethyl ether and using ultrasound bath the precipitate was formed. The liquor was removed and in the rest was triturated once more with diethyl ether. The precipitate was dried and was dissolved in 5 ml of absolute ethanol, thiourea (1.5 eq, 345 mg) was added and the resulting mixture was heated at 90° C. (temperature on display of heating device) for 2 hours. The solvent was evaporated and the rest was dissolved in 5 ml of water. pH of the solution was adjusted to 6-7 and the formed precipitate was collected by filtration and was dried to afford 5-(6-methoxy-pyridin-3-ylmethyl)-2-thioxo-2,3-dihydro-1H-pyrimidin-4-one (395 mg, yield=49.8%, purity=95%). MS: [M+H]⁺=250.18 ¹H NMR (300 MHz; DMSO-d₆) δ/ppm 3.45 (s, 2H), 3.80 (s, 3H), 6.70 (d, J=8.36 Hz, 1H), 7.42 (s, 1H), 7.55 (dd, J=8.36 Hz, J=2.40 Hz, 1H), 8.05 (d, J=2.40 Hz, 1H), 12.10-12.60 (m, 2H)

D261: 5-(6-Oxo-1,6-dihydro-pyridin-3-ylmethyl)-2-thioxo-2,3-dihydro-1H-pyrimidin-4-one

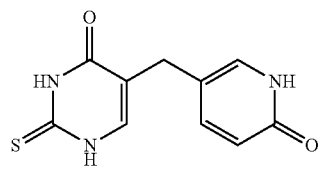 [SMILES: O=c1ccc(Cc2c[nH]c(=S)[nH]c2=O)c[nH]1]

5-(6-methoxy-pyridin-3-ylmethyl)-2-thioxo-2,3-dihydro-1H-pyrimidin-4-one (395 mg, 1.58 mmol, 1 eq) was refluxed in an acetic acid, glacial (5 ml)/HCl conc. (5 ml) mixture for 16 hours. (150° C. on display of heating device). Solvent from the mixture was evaporated as much as possible. In the mixture was added 10 ml of water. pH of the mixture was adjusted to 4-5. The resulting precipitate was collected and was dried. It was obtained 5-(6-oxo-1,6-dihydro-pyridin-3-ylmethyl)-2-thioxo-2,3-dihydro-1H-pyrimidin-4-one (285 mg, yield=61.3%, purity=90%) in form of grey powder. MS: [M+H]⁺=236.20 ¹H NMR (300 MHz; DMSO-d₆) δ/ppm 3.24 (s, 2H), 6.25 (d, J=9.36 Hz, 1H), 7.28-7-36 (m, 2H), 11.39 (br.s, 1H), 12.23 (br.s, 1H), 12.46 (br.s, 1H)

D262: 2-Methylsulfanyl-5-(6-oxo-1,6-dihydro-pyridin-3-ylmethyl)-1H-pyrimidin-4-one

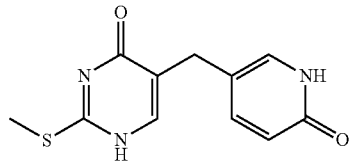 [SMILES: CSc1nc(=O)c(Cc2ccc(=O)[nH]c2)c[nH]1]

A suspension of 5-(6-oxo-1,6-dihydro-pyridin-3-ylmethyl)-2-thioxo-2,3-dihydro-1H-pyrimidin-4-one (130 mg, 0.55 mmol, 1 eq) and KOH, 85% (1.2 eq, 44 mg) in 5 ml of absolute ethanol was stirred with ultrasound bath at room temperature for 1 hour. In the suspension was then added MeI (1.2 eq, 42 µl) dropwise and the mixture was stirred in a sealed vial at 70° C. (temperature on display of heating device) for 20 hours (overnight). The solvent was then evaporated. In the crude was added 10 ml of water and pH of the solution was adjusted to 7-7.5. The resulting suspension was filtered over filter paper. The filtrate was washed with chloroform (3 times, 30 ml was used in total). pH of the water layer was adjusted to 5-5.5 and using ultrasound bath precipitate was formed. The precipitate was collected, it was dried and obtained was 2-methylsulfanyl-5-(6-oxo-1,6-dihydro-pyridin-3-ylmethyl)-1H-pyrimidin-4-one (22 mg, yield=15.9%, purity=95%) in form of white powder. MS: [M+H]⁺=250.18 ¹H NMR (300 MHz; DMSO-d₆) δ/ppm 2.46 (s, 3H), 3.31 (s, 2H), 6.25 (d, J=9.37 Hz, 1H), 7.19 (d, J=2.06 Hz, 1H), 7.35 (dd, J=9.37 Hz, J=2.45 Hz, 1H), 7.77 (s, 1H)

D263: 3-(2-Methoxy-pyridin-4-yl)-acrylic acid methyl ester

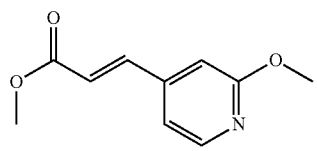

To a solution of 2-Methoxy-pyridine-4-carbaldehyde (1 g, 7.29 mmol, 1 eq) in 50 ml of dry DCM was added portionwise (methoxycarbonylmethylene)triphenylphosphorane (1.05 eq, 2.56 g). The mixture was stirred at room temperature for 2 hours. The mixture was then poured into 200 ml of water and the organic substances were extracted with DCM (twice, 150 ml of DCM was used in total) The gathered DCM layers were dried and the resulting crude was purified by chromatography on BIOTAGE SP1 purification device using 50 g normal phase silica SNAP coloumn and cyclohexane/EtOAc solvent system (gradient 2-20% of EtOAc in 20 coloumn volumes). Solvent from the gathered fractions of appropriate composition was evaporated and obtained was 3-(2-methoxy-pyridin-4-yl)-acrylic acid methyl ester (1.3 g, yield=87.6%, purity=95%). MS: [M+H]⁺=194.14 ¹H NMR (300 MHz; CDCl₃) δ/ppm 3.82 (s, 3H), 3.95 (s, 3H), 6.54 (d, J=16.0 Hz, 1H), 6.80 (s, 1H), 6.97 (dd, J=5.38 Hz, J=1.31 Hz, 1H), 7.55 (d, J=16.0 Hz, 1H), 8.18 (d, J=5.38 Hz, 1H)

D264: 3-(2-Methoxy-pyridin-4-yl)-propionic acid methyl ester

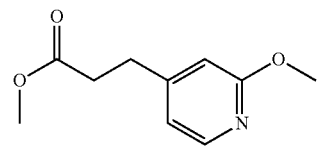

A suspension of 3-(2-methoxy-pyridin-4-yl)-acrylic acid methyl ester (1.3 g, 6.72 mmol, 1 eq) and Pd/C, 10% (357 mg, 0.05 eq, 10%) was stirred in a DCM (15 ml)/absolute EtOH (15 ml) solvent mixture under hydrogen atmosphere for 1 hour at room temperature. Palladium was filtered off over a celite pad, the solvent was evaporated and obtained crude was purified by chromatography on BIOTAGE SP1 purification device using 25 g normal phase silica SNAP coloumn and cyclohexane/EtOAc solvent system (gradient 3-30% of EtOAc in 20 coloumn volumes). Solvent from the gathered fractions of appropriate composition was evaporated and obtained was 3-(2-methoxy-pyridin-4-yl)-propionic acid methyl ester (1.22 g, yield=88.2%, purity=95%) in form of transparent colourless oil. MS: [M+H]⁺=196.14 ¹H NMR (300 MHz; CDCl₃) δ/ppm 2.63 (t, J=7.91 Hz, 2H), 2.90 (t, J=7.91 Hz, 2H), 3.68 (s, 3H), 3.92 (s, 3H), 6.57 (s, 1H), 6.72 (dd, J=5.33 Hz, J=1.29 Hz, 1H), 8.06 (d, J=5.33 Hz, 1H)

D265: 5-(2-Methoxy-pyridin-4-ylmethyl)-2-thioxo-2,3-dihydro-1H-pyrimidin-4-one

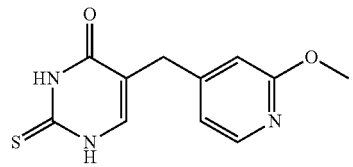 [SMILES: COc1cc(Cc2c[nH]c(=S)[nH]c2=O)ccn1]

To a suspension of NaH, 60% dispersion on mineral oil (1.3 eq, 320 mg, 60%) in 1.5 ml of dry 1,2-dimethoxyethane under argon atmosphere was added a solution of 3-(2-methoxy-pyridin-4-yl)-propionic acid methyl ester (1.2 g, 6.14 mmol, 1 eq) and methyl formate (2 eq, 760 µl) in 8 ml of dry 1,2-dimethoxyethane. The sealed mixture was stirred at room temperature for 16 hours (overnight). Solvent from the mixture was then evaporated. In the rest was added 15 ml of diethyl ether and using ultrasound bath the precipitate was formed. Mother liquor was removed and in the rest was triturated once more with diethyl ether. The precipitate was dried and was dissolved in 10 ml of absolute ethanol, thiourea (1.5 eq, 700 mg) and triethylamine (1.1 eq, 936 µl) were added and the resulting mixture was heated at 90° C. (temperature on display of heating device) for 2 hours. The solvent was evaporated and the rest was dissolved in 10 ml of water. pH of the solution was adjusted to 6-7 and the formed precipitate was collected by filtration and was dried to 5-(2-methoxy-pyridin-4-ylmethyl)-2-thioxo-2,3-dihydro-1H-pyrimidin-4-one (900 mg, yield=58.7%, purity=95%). MS: [M+H]⁺=250.15 ¹H NMR (300 MHz; DMSO-d₆) δ/ppm 3.51 (s, 2H), 3.81 (s, 3H), 6.65 (s, 1H), 6.85 (dd, J=5.42 Hz, J=1.03 Hz 1H), 7.42 (s, 1H), 8.03 (d, J=5.42 Hz, 1H), 12.02-12.76 (m, 2H)

D266: 5-(2-Oxo-1,2-dihydro-pyridin-4-ylmethyl)-2-thioxo-2,3-dihydro-1H-pyrimidin-4-one

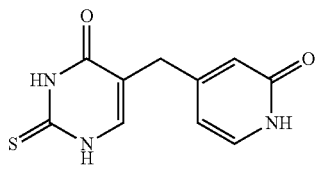 [SMILES: O=c1cc(Cc2c[nH]c(=S)[nH]c2=O)cc[nH]1]

5-(2-Methoxy-pyridin-4-ylmethyl)-2-thioxo-2,3-dihydro-1H-pyrimidin-4-one (900 mg, 3.61 mmol, 1 eq) was refluxed in an acetic acid, glacial (12 ml)/HCl conc. (12 ml) mixture for 7 hours. (150° C. on display of heating device). Solvent from the mixture was evaporated as much as possible. In the mixture was added 20 ml of water. pH of the mixture was adjusted to 4-5. The resulting precipitate was collected and was dried. It was obtained 5-(2-Oxo-1,2-dihydro-pyridin-4-ylmethyl)-2-thioxo-2,3-dihydro-1H-pyrimidin-4-one (645 mg, yield=72.1%, purity=95%) in form of white powder. MS: [M+H]$^+$=236.15 $^1$H NMR (300 MHz; DMSO-$d_6$) δ/ppm 3.36 (s, 2H), 6.06 (dd, J=6.81 Hz, J=1.60 Hz, 1H), 6.11 (s, 1H), 7.24 (d, J=6.81 Hz, 1H), 7.43 (d, J=5.66 Hz, 1H), 11.36 (br.s, 1H), 12.30 (d, J=4.89 Hz, 1H), 12.52 (br.s, 1H)

D267: 2-Methylsulfanyl-5-(2-oxo-1,2-dihydro-pyridin-4-ylmethyl)-1H-pyrimidin-4-one

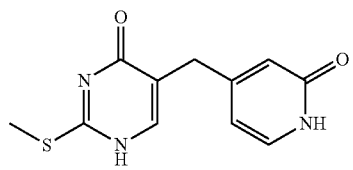 [SMILES: CSc1nc(=O)c(Cc2cc[nH]c(=O)c2)c[nH]1]

A suspension of 5-(2-Oxo-1,2-dihydro-pyridin-4-ylmethyl)-2-thioxo-2,3-dihydro-1H-pyrimidin-4-one (640 mg, 2.72 mmol, 1 eq) and KOH, 85% (1.05 eq, 190 mg) in 15 ml of absolute ethanol was stirred with at 80° C. for 1 hour. In the suspension was then added MeI (1.1 eq, 187 µl) dropwise and the mixture was stirred for another 2 hours. The solvent was then evaporated. In the crude was added 10 ml of water and pH of the solution was adjusted to 5.5-6.5. The precipitate was collected, it was dried and obtained was 2-Methylsulfanyl-5-(2-oxo-1,2-dihydro-pyridin-4-ylmethyl)-1H-pyrimidin-4-one (394 mg, yield=48.2%, purity=83%) in form of white powder. MS: [M+H]$^+$=250.15 $^1$H NMR (300 MHz; DMSO-$d_6$) δ/ppm 2.46 (s, 3H), 3.31 (s, 2H), 6.05-6.10 (m, 2H), 7.25 (d, J=6.6 Hz, 1H), 7.84 (s, 1H)

D268: 2-(Acetoxy-thiazol-2-yl-methyl)-acrylic acid methyl ester

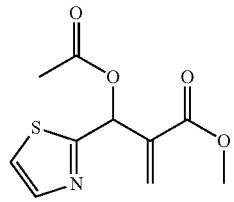 [SMILES: C=C(C(=O)OC)C(OC(C)=O)c1nccs1]

Thiazole-2-carbaldehyde (1 g, 9 mmol, 1 eq) was dissolved in 45 ml of water and 45 ml dioxane. Methyl acrylate (2.32 g, 27 mmol, 3 eq) and DABCO (1 g, 9 mmol, 1 eq) were added. Reaction mixture was stirred at room temperature for 1 h. Then, it was diluted with saturated solution of NaCl (800 ml) and extracted with DCM (7×200 ml). Combined organic layers were dried over anhydrous Na$_2$SO$_4$, filtered and evaporated to give 1.66 g of oily residue. Oily residue was dissolved in dry DCM (10 ml). Molecular sieves and DMAP (0.44 g, 3.6 mmol, 0.4 eq) were added. Reaction mixture was cooled at 0° C. and acetic anhydride (1.38 g, 13.6 mmol, 1.5 eq) was added. Reaction mixture was stirred at room temperature for 1 h. Then, it was washed with saturated solution of NaHCO$_3$. Organic layer was evaporated and purified via Biotage SP1 Snap 25 g, 25 ml/min; in system EtOAc/Cyclohexane 10-100% EtOAc in 50 CV. It was obtained 1.3 g of desired product 2-(acetoxy-thiazol-2-yl-methyl)-acrylic acid methyl ester without further analysis.

D269: 2-Methylsulfanyl-5-thiazol-2-ylmethyl-3H-pyrimidin-4-one

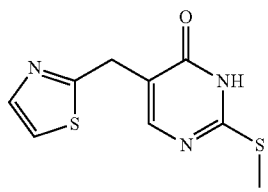

Methyl thiourea (0.492 g, 2.28 mmol, 1.1 eq) was dissolved in EtOH (dried over mol. sieves) (2 ml) and triethyl amine (0.633 ml, 2.2 eq) was added. Reaction mixture was heated to 70° C. and 2-(acetoxy-thiazol-2-yl-methyl)-acrylic acid methyl ester (0.5 g, 2.07 mmol, 1 eq) dissolved in EtOH (dried over mol. sieves) (2 ml), was added. It was heated at 70° C. for 8 h and then, it was cooled and filtered. Filtrate was evaporated to dryness and purified via Biotage SP1 Snap 25 g, 25 ml/min; in system MeOH/DCM 1-30% MeOH in 30 CV. Appropriate fractions were combined and evaporated to give 250 mg of brown powder.

E1: 2-[2-(4-{[4-Chloro-3-(trifluoromethyl)phenyl]oxy}phenyl)ethyl]-5-(5-pyrimidinylmethyl)-4(1H)-pyrimidinone

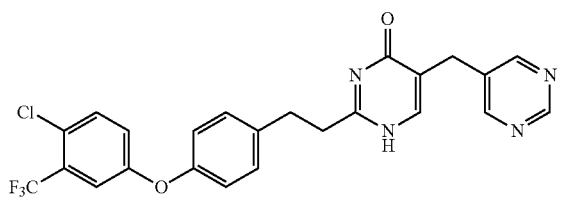

A mixture of 3-(4-{[4-chloro-3-(trifluoromethyl)phenyl]oxy}phenyl)propanimidamide (150 mg, 0.316 mmol), K$_2$CO$_3$ (131 mg, 0.949 mmol) and methyl 2-formyl-3-(5-pyrim-idinyl)propanoate (188 mg, 0.633 mmol) in NMP (1.5 mL) was heated with a microwave reactor at 120° C. for 2 h. Purification via a reverse phase Biotage then afforded the title compound as a white solid. LCMS: rt=3.13 min, [M+H$^+$]= 487

E2: 2-(4-(4-Chloro-3-(trifluoromethyl)phenoxy) phenethyl)-5-((2-methoxypyrimidin-5-yl)methyl) pyrimidin-4(1H)-one

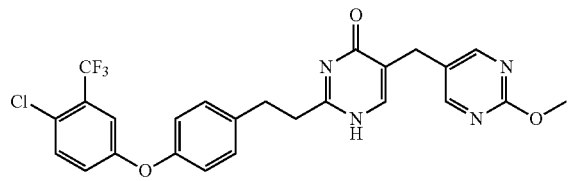 [SMILES: COc1ncc(Cc2c[nH]c(CCc3ccc(Oc4ccc(Cl)c(C(F)(F)F)c4)cc3)nc2=O)cn1]

The suspension of 3-(4-(4-chloro-3-(trifluoromethyl)phenoxy)phenyl)propanimidamide hydrochloride (5.9 g, 15.56 mmol), methyl 3-hydroxy-2-((2-methoxypyrimidin-5-yl)methyl)acrylate (3.49 g, 15.56 mmol) and potassium acetate (4.58 g, 46.7 mmol) in toluene (100 mL) was heated under reflux overnight. Dean-Stark apparatus was used to remove water formed in the reaction. The residue was recrystallized in ethyl acetate and washed with ether to provide the title compound (3.4 g, 42%). LCMS: rt=1.71 min, [M+H$^+$]=517

E3: 2-[2-(4-{[4-Chloro-3-(trifluoromethyl)phenyl] oxy}phenyl)ethyl]-1-methyl-5-{[2-(methyloxy)-5-pyrimidinyl]methyl}-4(1H)-pyrimidinone

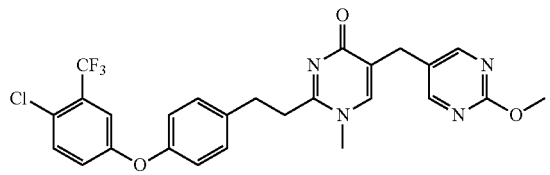 [SMILES: COc1ncc(Cc2cn(C)c(CCc3ccc(Oc4ccc(Cl)c(C(F)(F)F)c4)cc3)nc2=O)cn1]

To the solution of 2-(4-(4-chloro-3-(trifluoromethyl)phenoxy)phenethyl)-5-((2-methoxypyrimidin-5-yl)methyl)pyrimidin-4(1H)-one (308 mg, 0.596 mmol) in dichloroethane (8 mL) was added DIPEA (0.208 mL, 1.192 mmol) and MeI (0.045 mL, 0.715 mmol). The reaction mixture was stirred at room temp overnight. Concentration and purification via MDAP then provided the title compound (50 mg, 15.81% yield). LCMS: rt=3.09 min, [M+H$^+$]=531

E4: 2-[2-(4-{[4-Chloro-3-(trifluoromethyl)phenyl] oxy}phenyl)ethyl]-1-methyl-5-(5-pyrimidinylmethyl)-4(1H)-pyrimidinone

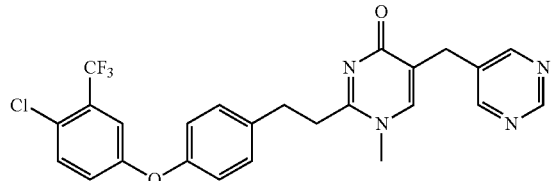

To the solution of 2-[2-(4-{[4-chloro-3-(trifluoromethyl)phenyl]oxy}phenyl)ethyl]-5-(5-pyrimidinylmethyl)-4(1H)-pyrimidinone (200 mg, 0.411 mmol) in dichloroethane (5 ml) was added DIPEA (0.143 ml, 0.822 mmol). It was stirred at rt for 30 min, mixed with MeI (0.031 ml, 0.493 mmol) dropwise, then stirred at r.t. overnight. Purification via MDAP then afforded the title compound (16 mg, 7.8%). LCMS: rt=3.04 min, [M+H$^+$]=501

E5: 2-[2-(4-{[4-Chloro-3-(trifluoromethyl)phenyl] oxy}phenyl)ethyl]-5-[(1-methyl-1H-pyrazol-4-yl) methyl]-4(1H)-pyrimidinone

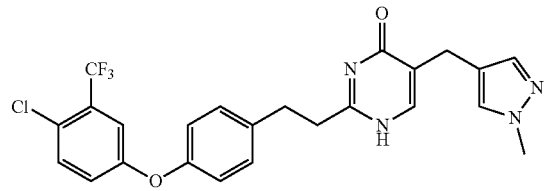 [SMILES: Cn1cc(Cc2c[nH]c(CCc3ccc(Oc4ccc(Cl)c(C(F)(F)F)c4)cc3)nc2=O)cn1]

The mixture of 3-(4-{[4-chloro-3-(trifluoromethyl)phenyl]oxy}phenyl)propanimidamide (699 mg, 1.427 mmol), K$_2$CO$_3$ (300 mg, 2.171 mmol) and 3-(4-{[4-chloro-3-(trifluoromethyl)phenyl]oxy}phenyl)propanimidamide (699 mg, 1.427 mmol) in NMP (3 mL) was heated with a microwave reactor at 120° C. for 2 h. Purification via MDAP then afforded the title compound as a white solid (215 mg, 24.99% yield). LCMS: rt=3.13 min, [M+H$^+$]=489

E6: 2-[2-(4-{[4-Chloro-3-(trifluoromethyl)phenyl] oxy}phenyl)ethyl]-1-methyl-5-[(1-methyl-1H-pyrazol-4-yl)methyl]-4(1H)-pyrimidinone trifluoroacetate

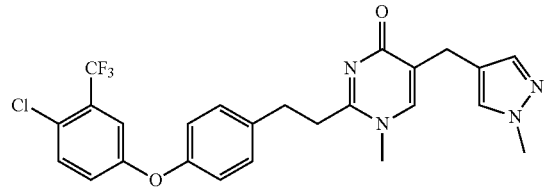 [SMILES: Cn1cc(Cc2cn(C)c(CCc3ccc(Oc4ccc(Cl)c(C(F)(F)F)c4)cc3)nc2=O)cn1]

To the solution of 2-[2-(4-{[4-chloro-3-(trifluoromethyl)phenyl]oxy}phenyl)ethyl]-5-[(1-methyl-1H-pyrazol-4-yl)methyl]-4(1H)-pyrimidinone (200 mg, 0.409 mmol) and DIPEA (0.214 mL, 1.227 mmol) in CH$_3$CN (2 mL) and NMP (0.5 mL) was added MeI (0.028 mL, 0.450 mmol). It was stirred at 60° C. for 4 h. Purification via MDAP then afforded the title compound as a white solid (20 mg, 7.92% yield). LCMS: rt=3.07 min, [M+H$^+$]=503

E7: 2-{[4-Chloro-3-(trifluoromethyl)phenyl]oxy}-5-[2-(5-{[2-(methyloxy)-5-pyrimidinyl]methyl}-4-oxo-1,4-dihydro-2-pyrimidinyl)ethyl]benzonitrile

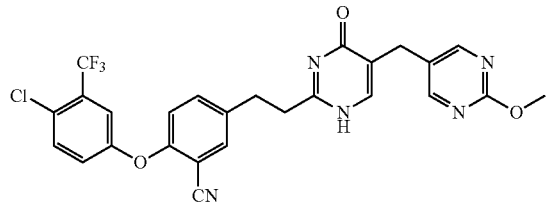 [SMILES: COc1ncc(Cc2c[nH]c(CCc3ccc(Oc4ccc(Cl)c(C(F)(F)F)c4)c(C#N)c3)nc2=O)cn1]

To a solution of 2-fluoro-5-[2-(5-{[2-(methyloxy)-5-pyrimidinyl]methyl}-4-oxo-1,4-dihydro-2-pyrimidinyl)ethyl] benzonitrile (80 mg, 0.219 mmol) and 4-chloro-3-(trifluoromethyl)phenol (64.6 mg, 0.328 mmol) in NMP (2 mL), K$_2$CO$_3$ (60.5 mg, 0.438 mmol) was added. The reaction vessel was sealed and stirred at room temp for 10 min, and heated by microwave to 150° C. for 2 h. Purification via MDAP then afforded the title compound as a white solid (30 mg, 25.3% yield). LCMS: rt=3.19 min, [M+H$^+$]=542

E8: 2-(4-Chloro-3-(trifluoromethyl)phenoxy)-5-(2-(4-oxo-5-(pyrimidin-5-ylmethyl)-1,4-dihydropyrimidin-2-yl)ethyl)benzonitrile

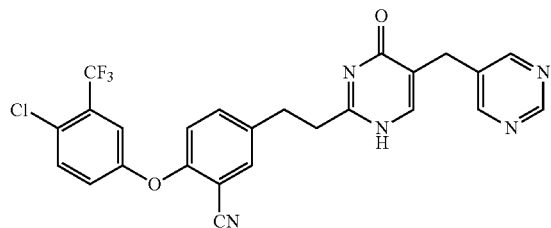 [SMILES: N#Cc1cc(CCc2nc(=O)c(Cc3cncnc3)c[nH]2)ccc1Oc1ccc(Cl)c(C(F)(F)F)c1]

A mixture of 2-fluoro-5-(2-(4-oxo-5-(pyrimidin-5-ylmethyl)-1,4-dihydropyrimidin-2-yl)ethyl)benzonitrile (1.0 g, 2.68 mmol), 4-chloro-3-(trifluoromethyl)phenol (0.633 g, 3.22 mmol) and K$_2$CO$_3$ (0.556 g, 4.03 mmol) in NMP (5 mL) was heated with a microwave reactor at 150° C. for 1.5 h. Purification via MDAP then afforded the title compound as a white solid (210 mg, 15% yield). LCMS: rt=1.65 min, [M+H$^+$]=512

E9: 2-{[2-(4-{[4-Chloro-3-(trifluoromethyl)phenyl]oxy}phenyl)ethyl]amino}-5-{[2-(methyloxy)-5-pyrimidinyl]methyl}-4(1H)-pyrimidinone

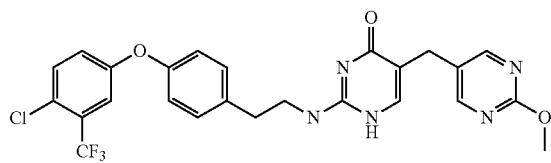

To the solution of 5-{[2-(methyloxy)-5-pyrimidinyl]methyl}-2-(nitroamino)-4(1H)-pyrimidinone (100 mg, 0.359 mmol) in ethanol (5 mL) was added neat 2-(4-{[4-chloro-3-(trifluoromethyl)-phenyl]oxy}phenyl)ethanamine (189 mg, 0.599 mmol). It was heated with a microwave reactor at 100° C. overnight. Purification via MDAP then afforded the title compound (92 mg, 35.6% yield). LCMS: rt=3.04 min, [M+H$^+$]=532.2

E10: 2-{[2-(4-{[4-Chloro-3-(trifluoromethyl)phenyl]oxy}phenyl)ethyl]amino}-5-[(1-methyl-1H-pyrazol-4-yl)methyl]-4(1H)-pyrimidinone

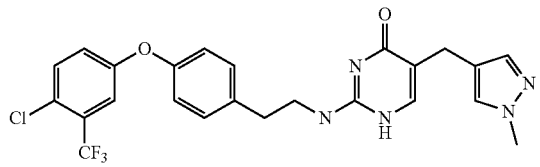 [SMILES: Cn1cc(Cc2c[nH]c(NCCc3ccc(Oc4ccc(Cl)c(C(F)(F)F)c4)cc3)nc2=O)cn1]

To the solution of 5-[(1-methyl-1H-pyrazol-4-yl)methyl]-2-(nitroamino)-4(1H)-pyrimidinone (100 mg, 0.400 mmol) in ethanol (5 mL) was added neat [2-(4-{[4-chloro-3-(trifluoromethyl)-phenyl]oxy}phenyl)ethyl]amine 2-(4-{[4-chloro-3-(trifluoromethyl)phenyl]oxy}-phenyl)ethanamine (189 mg, 0.599 mmol). The reaction mixture was heated with a microwave reactor at 100° C. overnight. Purification via MDAP then afforded the title compound as a white solid (87 mg, 35.2% yield). LCMS: rt=2.95 min, [M+H$^+$]=504.2

E11: 2-{[2-(4-{[4-Chloro-3-(trifluoromethyl)phenyl]oxy}phenyl)ethyl]amino}-5-(5-pyrimidinylmethyl)-4(1H)-pyrimidinone

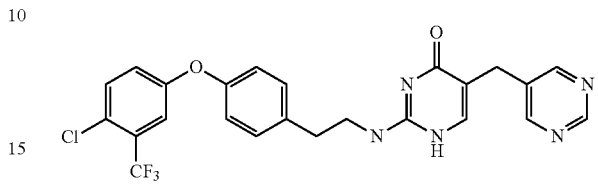

To the solution of [2-(4-{[4-chloro-3-(trifluoromethyl)phenyl]oxy}phenyl)ethyl]amine 2-(4-{[4-chloro-3-(trifluoromethyl)phenyl]oxy}phenyl)ethanamine (191 mg, 0.604 mmol) in ethanol (1 mL) was added neat 2-(nitroamino)-5-(5-pyrimidinylmethyl)-4(1H)-pyrimidinone (100 mg, 0.403 mmol). The reaction mixture was heated with a microwave reactor at 120° C. for 1 hr. Purification via MDAP then afforded the title compound as a white solid (31 mg, 12.4% yield). LCMS: rt=2.96 min, [M+H$^+$]=502.1

E12: 2-{[2-(4-{[4-Chloro-3-(trifluoromethyl)phenyl]oxy}phenyl)ethyl]amino}-1-methyl-5-{[2-(methyloxy)-5-pyrimidinyl]methyl}-4(1H)-pyrimidinone

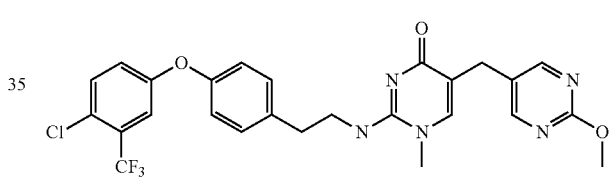

To the solution of 1-methyl-5-{[2-(methyloxy)-5-pyrimidinyl]methyl}-2-(nitroamino)-4(1H)-pyrimidinone (18.4 mg, 0.063 mmol) in ethanol (1 mL) was added neat [2-(4-{[4-chloro-3-(trifluoromethyl)phenyl]oxy}phenyl)ethyl]amine 2-(4-{[4-chloro-3-(trifluoromethyl)phenyl]oxy}-phenyl)ethanamine (29.8 mg, 0.094 mmol). The reaction mixture was heated with a microwave at 100° C. overnight. Purification via MDAP then afforded the title compound as a white solid (10.2 mg, 24.5% yield). LCMS: rt=3.03 min, [M+H$^+$]= 546.0

E13: 2-{[2-(4-{[4-Chloro-3-(trifluoromethyl)phenyl]oxy}phenyl)ethyl]amino}-1-methyl-5-[(1-methyl-1H-pyrazol-4-yl)methyl]-4(1H)-pyrimidinone

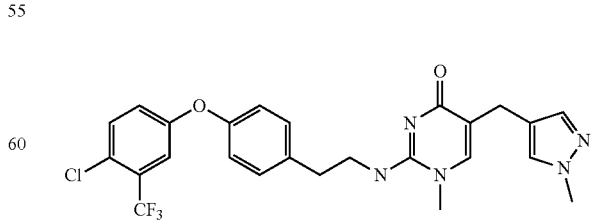

To the solution of [2-(4-{[4-chloro-3-(trifluoromethyl)phenyl]oxy}phenyl)ethyl]amine 2-(4-{[4-chloro-3-(trifluoromethyl)phenyl]oxy}phenyl)ethanamine (179 mg, 0.568 mmol) in ethanol (3 mL) was added neat 1-methyl-5-[(1-methyl-1H-pyrazol-4-yl)methyl]-2-(nitroamino)-4(1H)-pyrimidinone (100 mg, 0.378 mmol). The reaction mixture was heated with a microwave reactor at 120° C. overnight. Purification via MDAP then afforded the title compound as a white solid (23 mg, 9.6% yield). LCMS: rt=3.26 min, [M+H$^+$]=518.2

E14: 2-[[2-(4-{[4-Chloro-3-(trifluoromethyl)phenyl]oxy}phenyl)ethyl](methyl)amino]-5-[(1-methyl-1H-pyrazol-4-yl)methyl]-4(1H)-pyrimidinone

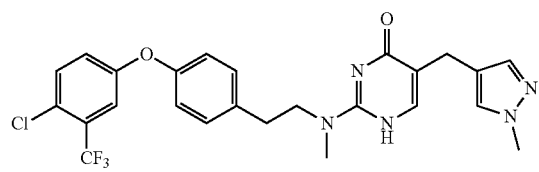 [SMILES: CN(CCc1ccc(Oc2ccc(Cl)c(C(F)(F)F)c2)cc1)c1nc(=O)c(Cc2cnn(C)c2)c[nH]1]

To the mixture of methyl 2-formyl-3-(1-methyl-1H-pyrazol-4-yl)propanoate (68.6 mg, 0.350 mmol) and K$_2$CO$_3$ (112 mg, 0.807 mmol) in NMP (5 mL) was added neat N-[2-(4-{[4-chloro-3-(trifluoromethyl)phenyl]oxy}phenyl)ethyl]-N-methylguanidine (100 mg, 0.269 mmol). The reaction mixture was heated with a microwave reactor at 200° C. for 2 h. Purification via MDAP then afforded the title compound as a white solid (35 mg, 0.055 mmol, 20.5% yield). LCMS: rt=3.00 min, [M+H$^+$]=518.0

E15: 2-[[2-(4-{[4-Chloro-3-(trifluoromethyl)phenyl]oxy}phenyl)ethyl](methyl)amino]-5-{[2-(methyloxy)-5-pyrimidinyl]methyl}-4(1H)-pyrimidinone

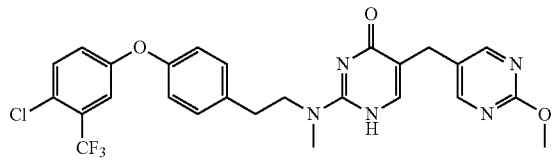

To the solution of N-[2-(4-{[4-chloro-3-(trifluoromethyl)phenyl]oxy}phenyl)ethyl]-N-methylguanidine (100 mg, 0.269 mmol), methyl 2-formyl-3-[2-(methyloxy)-5-pyrimidinyl]propanoate (78 mg, 0.350 mmol) in NMP (5 mL) was added neat N-[2-(4-{[4-chloro-3-(trifluoromethyl)phenyl]oxy}phenyl)ethyl]-N-methylguanidine (100 mg, 0.269 mmol). The reaction mixture was heated with a microwave reactor at 200° C. for 2 h. Purification via MDAP then afforded the title compound as a white solid (33 mg, 0.050 mmol, 18.5% yield). LCMS: rt=3.14 min, [M+H$^+$]=545.9

E16: 2-[[2-(4-{[4-Chloro-3-(trifluoromethyl)phenyl]oxy}phenyl)ethyl](methyl)amino]-5-(5-pyrimidinylmethyl)-4(1H)-pyrimidinone

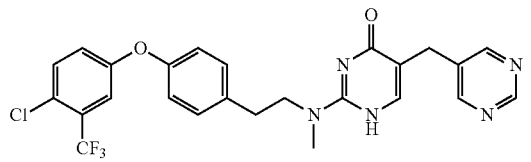 [SMILES: CN(CCc1ccc(Oc2ccc(Cl)c(C(F)(F)F)c2)cc1)c1nc(=O)c(Cc2cncnc2)c[nH]1]

To the mixture of methyl 2-formyl-3-(5-pyrimidinyl)propanoate (67.9 mg, 0.350 mmol) and K$_2$CO$_3$ (149 mg, 1.076 mmol) in NMP (2 mL) was added neat N-[2-(4-{[4-chloro-3-(trifluoromethyl)phenyl]oxy}phenyl)ethyl]-N-methylguanidine (100 mg, 0.269 mmol). The reaction mixture was heated with a microwave reactor at 200° C. for 3 h. Purification via MDAP then afforded the title compound as a white solid (38 mg, 22.4% yield). LCMS: rt=3.02 min, [M+H$^+$]=516.0

E17: 4-[(2-{[2-(4-{[4-Chloro-3-(trifluoromethyl)phenyl]oxy}phenyl)ethyl]oxy}-4-oxo-1,4-dihydro-5-pyrimidinyl)methyl]benzonitrile

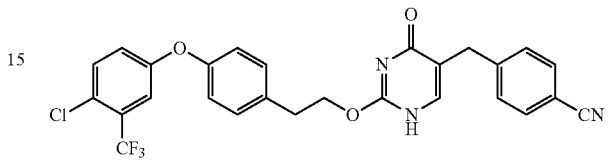

The mixture of 2-(4-{[4-chloro-3-(trifluoromethyl)phenyl]oxy}phenyl)ethyl imidocarbamate triflate (120 mg, 0.236 mmol), ethyl 3-(4-cyanophenyl)-2-formylpropanoate (137 mg, 0.591 mmol) and K$_2$CO$_3$ (98 mg, 0.709 mmol) in DMA (5 mL) was heated with a microwave reactor at 160° C. for 1 hour. Purification via MDAP then afforded the title compound as a pale yellow solid (38 mg, 29.0% yield). LCMS: rt=3.90 min, [M+H$^+$]=526.2

E18: 2-{[2-(4-{[4-Chloro-3-(trifluoromethyl)phenyl]oxy}phenyl)ethyl]oxy}-5-(phenylmethyl)-4(1H)-pyrimidinone

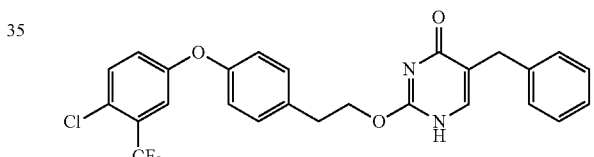

The mixture of 2-(4-{[4-chloro-3-(trifluoromethyl)phenyl]oxy}phenyl)ethyl imidocarbamate triflate (120 mg, 0.236 mmol), ethyl 2-formyl-3-phenylpropanoate (122 mg, 0.591 mmol) and K$_2$CO$_3$ (98 mg, 0.709 mmol) in DMA (5 mL) was heated with a microwave reactor at 160° C. for 1 hour. Purification via MDAP then afforded the title compound as an off-white solid (47 mg, 39.7% yield). LCMS: rt=4.08 min, [M+H$^+$]=501.2

E19: 2-{[2-(4-{[4-Chloro-3-(trifluoromethyl)phenyl]oxy}phenyl)ethyl]oxy}-5-[(2,4-difluoro-6-hydroxyphenyl)methyl]-4(1H)-pyrimidinone

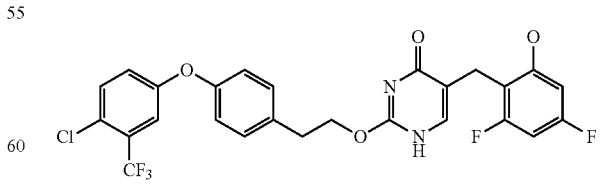

The mixture of 2-(4-{[4-chloro-3-(trifluoromethyl)phenyl]oxy}phenyl)ethyl imidocarbamate triflate (120 mg, 0.236 mmol), ethyl 2-formyl-3-(2,4,6-trifluorophenyl)propanoate (154 mg, 0.591 mmol) and K$_2$CO$_3$ (98 mg, 0.709 mmol) in DMA (5 mL) was heated with a microwave reactor at 160° C. for 1 hour. Purification via MDAP then afforded the title compound (44 mg, 32.0% yield). LCMS: rt=4.14 min, [M+H+]=553.2

E20: 2-{[2-(4-{[4-Chloro-3-(trifluoromethyl)phenyl]oxy}phenyl)ethyl]oxy}-5-(5-pyrimidinylmethyl)-4(1H)-pyrimidinone

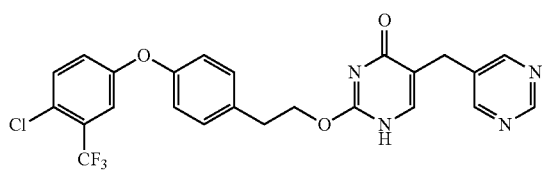 [SMILES: O=c1nc(OCCc2ccc(Oc3ccc(Cl)c(C(F)(F)F)c3)cc2)[nH]cc1Cc1cncnc1]

(a) To the suspension of methyl (2E)-3-hydroxy-2-(5-pyrimidinylmethyl)-2-propenoate (302 mg, 1.557 mmol) and 2-(4-{[4-chloro-3-(trifluoromethyl)phenyl]oxy}phenyl)ethyl imidocarbamate triflate (527 mg, 1.038 mmol) in NMP (12 mL) was added K₂CO₃ (430 mg, 3.11 mmol). The mixture was heated with a microwave reactor at 160° C. for 1 h. Purification via MDAP then afforded the title compound (130 mg, 24.91% yield). LCMS: rt=3.43 min, [M+H+]=503

(b) An alternative synthesis was provided to prepare the compound of Example 20. A suspension of 2-(4-{[4-chloro-3-(trifluoromethyl)phenyl]oxy}phenyl)ethyl imidocarbamate triflate (17.29 g, 34.0 mmol), methyl (2Z)-3-hydroxy-2-(5-pyrimidinylmethyl)-2-propenoate (5.5 g, 28.3 mmol) and potassium acetate (5.56 g, 56.6 mmol) in toluene (200 mL) was stirred at room temperature for 2 min. and then heated to reflux for 3 h. The mixture was filtered off and concentrated to dryness, which was then dissolved in DMF and purified by MDAP with TFA. The purified fractions were combined and neutrallized with ammonia. The organic solvent was removed under vacuo and the water layer was extracted with EA. The organic layer was combined and dried over Na₂SO₄ which was concentrated to give the white solid. The solid was recrystallized in MeCN to afford the title compound (3.0 g, 21.06% yield) LCMS: rt=3.43 min, [M+H+]=503.

E21: 2-{[2-(4-{[4-Chloro-3-(trifluoromethyl)phenyl]oxy}phenyl)ethyl]oxy}-1-methyl-5-(5-pyrimidinylmethyl)-4(1H)-pyrimidinone

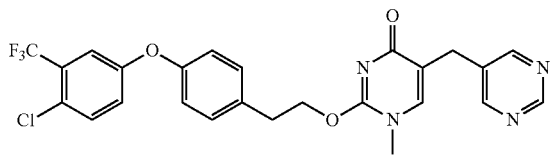 [SMILES: Cn1cc(Cc2cncnc2)c(=O)nc1OCCc1ccc(Oc2ccc(Cl)c(C(F)(F)F)c2)cc1]

To a solution of 2-{[2-(4-{[4-chloro-3-(trifluoromethyl)phenyl]oxy}phenyl)ethyl]oxy}-5-(5-pyrimidinylmethyl)-4(1H)-pyrimidinone (45 mg, 0.089 mmol) in dichloromethane (DCM) (2 mL) was added DIPEA (0.031 mL, 0.179 mmol) and MeI (8.39 µL, 0.134 mmol). The mixture was purified by reverse phase biotage affording 2-{[2-(4-{[4-chloro-3-(trifluoromethyl)phenyl]oxy})phenyl)ethyl]oxy}-1-methyl-5-(5-pyrimidinylmethyl)-4(1H)-pyrimidinone (20 mg, 0.039 mmol, 43.2% yield) LCMS: rt=3.37 min, [M+H+]=517

E22: 2-{[2-(4-{[4-Chloro-3-(trifluoromethyl)phenyl]oxy}phenyl)ethyl]oxy}-5-[(1-methyl-1H-pyrazol-4-yl)methyl]-4(1H)-pyrimidinone trifluoroacetate

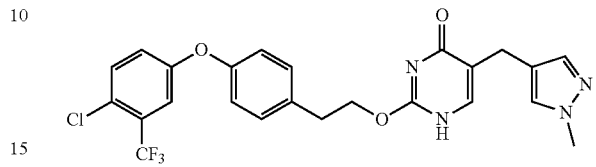

To a suspension of methyl (2Z)-3-hydroxy-2-[(1-methyl-1H-pyrazol-4-yl)methyl]-2-propenoate (125 mg, 0.636 mmol) and 2-(4-{[4-chloro-3-(trifluoromethyl)phenyl]oxy}phenyl)ethyl imidocarbamate (190 mg, 0.530 mmol) in toluene (4 mL) was added K₂CO₃ (220 mg, 1.589 mmol). The mixture was heated with a microwave reactor at 130° C. for 1 h. Purification via MDAP then afforded the title compound (55 mg, 16.78% yield). LCMS: rt=3.45 min, [M+H+]=505

E23: 2-{[2-(4-{[4-Chloro-3-(trifluoromethyl)phenyl]oxy}phenyl)ethyl]oxy}-1-methyl-5-[(1-methyl-1H-pyrazol-4-yl)methyl]-4(1H)-pyrimidinone

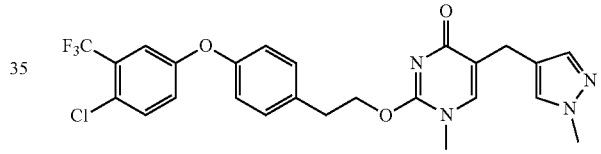

To the solution of 2-{[2-(4-{[4-chloro-3-(trifluoromethyl)phenyl]oxy}phenyl)ethyl]oxy}-5-[(1-methyl-1H-pyrazol-4-yl)methyl]-4(1H)-pyrimidinone (71 mg, 0.109 mmol) in DCM (1.5 mL) was added DIPEA (0.038 mL, 0.217 mmol) and MeI (10.18 µL, 0.163 mmol). The mixture was stirred at room temp overnight. Purification via MDAP then afforded the title compound (34 mg, 60.3% yield). LCMS: rt=3.35 min, [M+H+]=519

E24: 2-{[2-(4-{[4-Chloro-3-(trifluoromethyl)phenyl]oxy}phenyl)ethyl]oxy}-5-{[2-(methyloxy)-5-pyrimidinyl]methyl}-4(1H)-pyrimidinone

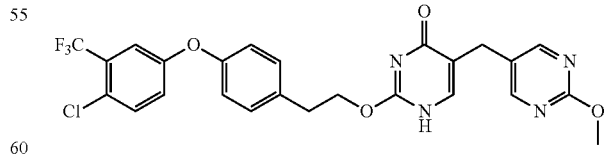

To the solution of methyl (2E)-3-hydroxy-2-{[2-(methyloxy)-5-pyrimidinyl]methyl}-2-propenoate (177 mg, 0.789 mmol) and 2-(4-{[4-chloro-3-(trifluoromethyl)phenyl]oxy}phenyl)ethyl imidocarbamate triflate (267 mg, 0.526 mmol) in NMP (10 mL) was added K₂CO₃ (218 mg, 1.577 mmol). The mixture was heated with a microwave reactor at 160° C.

for 1 h. Purification via MDAP then afforded the title compound (60 mg, 21.41% yield). LCMS: rt=3.58 min, [M+H+]=532.9

E25: 2-{[2-(4-{[4-Chloro-3-(trifluoromethyl)phenyl]oxy}phenyl)ethyl]oxy}-1-methyl-5-{[2-(methyloxy)-5-pyrimidinyl]methyl}-4(1H)-pyrimidinone

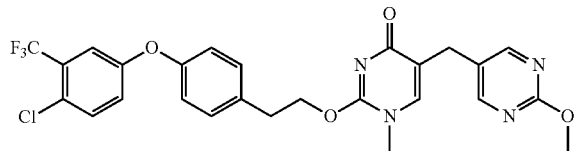 [SMILES: COc1ncc(Cc2cn(C)c(OCCc3ccc(Oc4ccc(Cl)c(C(F)(F)F)c4)cc3)nc2=O)cn1]

To the solution of 2-{[2-(4-{[4-chloro-3-(trifluoromethyl)phenyl]oxy}phenyl)ethyl]oxy}-5-{[2-(methyloxy)-5-pyrimidinyl]methyl}-4(1H)-pyrimidinone (crude) (410 mg, 0.769 mmol) in DCM (1.5 mL) was added DIPEA (0.269 mL, 1.539 mmol) and MeI (0.072 mL, 1.154 mmol). The mixture was stirred at room temp overnight. Purification via MDAP then afforded the title compound (120 mg, 28.5% yield). LCMS: rt=3.48 min, [M+H+]=547

E26: 5-[(4-oxo-2-{[2-(4-{[3-(trifluoromethyl)phenyl]oxy}phenyl)ethyl]oxy}-1,4-dihydro-5-pyrimidinyl)methyl]pyrimidine

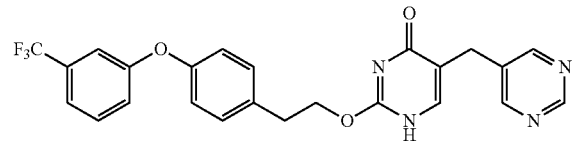 [SMILES: O=c1nc(OCCc2ccc(Oc3cccc(C(F)(F)F)c3)cc2)[nH]cc1Cc1cncnc1]

To the suspension of methyl (2E)-3-hydroxy-2-(5-pyrimidinylmethyl)-2-propenoate (105 mg, 0.542 mmol) and 2-(4-{[3-(trifluoromethyl)phenyl]oxy}phenyl)ethyl imidocarbamate (171 mg, 0.361 mmol) in NMP (4 mL) was added K₂CO₃ (150 mg, 1.084 mmol). The mixture was heated with a microwave reactor at 160° C. for 1 h. Purification via MDAP then afforded the title compound (48 mg, 28.4% yield). LCMS: rt=3.258 min, [M+H+]=469

E27: 2-{[2-(4-{[4-Chloro-3-(trifluoromethyl)phenyl]oxy}phenyl)ethyl]oxy}-5-ethyl-4(1H)-pyrimidinone

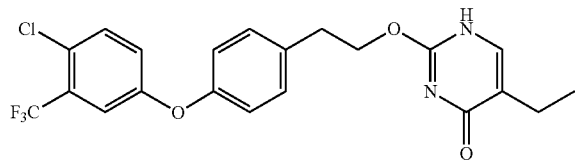 [SMILES: CCc1c[nH]c(OCCc2ccc(Oc3ccc(Cl)c(C(F)(F)F)c3)cc2)nc1=O]

To the suspension of ethyl (2Z)-2-ethyl-3-hydroxy-2-propenoate (281 mg, 1.951 mmol) and K₂CO₃ (270 mg, 1.951 mmol) in NMP (10 mL) was added 2-(4-{[4-chloro-3-(trifluoromethyl)phenyl]oxy}phenyl)ethyl imidocarbamate (350 mg, 0.976 mmol). The reaction mixture was heated with a microwave reactor at 160° C. for 1.5 h. Purification via MDAP then afforded the title compound (165 mg, 38.5% yield). LCMS: rt=3.89 min, [M+H+]=439

E28: 2-{[2-(4-{[4-Chloro-3-(trifluoromethyl)phenyl]oxy}phenyl)ethyl]oxy}-5-ethyl-1-methyl-4(1H)-pyrimidinone

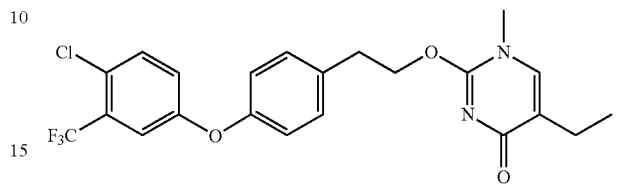

To the solution of 2-{[2-(4-{[4-chloro-3-(trifluoromethyl)phenyl]oxy}phenyl)ethyl]oxy}-5-ethyl-4(1H)-pyrimidinone (123 mg, 0.280 mmol) and DIPEA (0.490 mL, 2.80 mmol) in DCM (3.0 mL) was added MeI (0.175 mL, 2.80 mmol) dropwise. The reaction mixture was stirred at rt for 3 h. Purification via MDAP then afforded the title compound (40 mg, 29.9% yield). LCMS: rt=3.60 min, [M+H+]=453

E29: 2-{[2-(4-{[4-Chloro-3-(trifluoromethyl)phenyl]oxy}-3,5-difluorophenyl)ethyl]oxy}-5-(5-pyrimidinylmethyl)-4(1H)-pyrimidinone

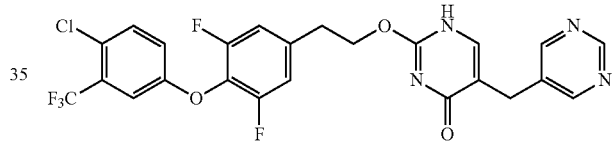

The mixture of 2-(4-{[4-chloro-3-(trifluoromethyl)phenyl]oxy}-3,5-difluorophenyl)ethyl imidocarbamate (450 mg, 0.826 mmol), methyl (2Z)-3-hydroxy-2-(5-pyrimidinylmethyl)-2-propenoate (321 mg, 1.652 mmol) and K₂CO₃ (228 mg, 1.652 mmol) in NMP (5 mL) was heated with a microwave reactor at 160° C. for 1.5 h. Purification via MDAP then afforded the title compound (120 mg, 22.25% yield). LCMS: rt=3.46 min, [M+H+]=539

E30: 2-{[2-(4-{[4-Chloro-3-(trifluoromethyl)phenyl]oxy}-3,5-difluorophenyl)ethyl]oxy}-1-methyl-5-(5-pyrimidinylmethyl)-4(1H)-pyrimidinone

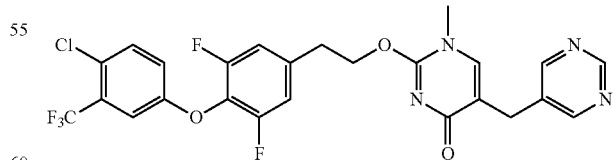

To the solution of 2-{[2-(4-{[4-chloro-3-(trifluoromethyl)phenyl]oxy}-3,5-difluorophenyl)ethyl]oxy}-5-(5-pyrimidinylmethyl)-4(1H)-pyrimidinone (80 mg, 0.148 mmol) and DIPEA (0.078 mL, 0.445 mmol) in DCM (3.0 mL) was added MeI (0.019 mL, 0.297 mmol) dropwise. The reaction mixture was stirred at room 25° C. for 3 h. Purification via MDAP then afforded the title compound (5 mg, 9.04 mol, 6.0% yield). LCMS: rt=3.46 min, [M+H]=553

E31: 2-{[2-(4-{[4-Chloro-3-(trifluoromethyl)phenyl]oxy}-3-fluorophenyl)ethyl]oxy}-5-(5-pyrimidinylmethyl)-4(1H)-pyrimidinone trifluoroacetate

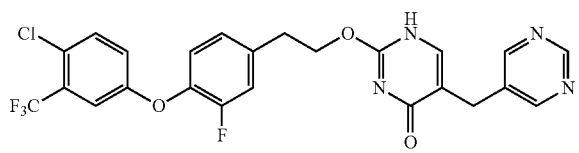 [SMILES: O=c1nc(OCCc2ccc(Oc3ccc(Cl)c(C(F)(F)F)c3)c(F)c2)[nH]cc1Cc1cncnc1]

The mixture of 2-(4-{[4-chloro-3-(trifluoromethyl)phenyl]oxy}-3-fluorophenyl)ethyl imidocarbamate (200 mg, 0.380 mmol), methyl (2Z)-3-hydroxy-2-(5-pyrimidinylmethyl)-2-propenoate (147 mg, 0.759 mmol) and $K_2CO_3$ (105 mg, 0.759 mmol) in NMP (5 mL) was heated with a microwave reactor at 160° C. for 1.5 h. Purification via MDAP then afforded the title compound (100 mg, 41.5% yield). LCMS: rt=3.42 min, [M+H$^+$]=521

E32: 2-{[(4-{[4-Chloro-3-(trifluoromethyl)phenyl]oxy}phenyl)methyl]amino}-5-(5-pyrimidinylmethyl)-4(1H)-pyrimidinone trifluoroacetate

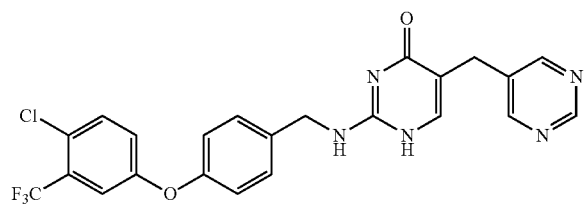

The mixture of N-[(4-{[4-chloro-3-(trifluoromethyl)phenyl]oxy}phenyl)methyl]guanidine (50 mg, 0.109 mmol), methyl (2Z)-3-hydroxy-2-(5-pyrimidinylmethyl)-2-propenoate (33 mg, 0.170 mmol) and $Cs_2CO_3$ (143 mg, 0.438 mmol) in NMP (1 mL) was heated with a microwave reactor at 130° C. for 1 h. Purification via MDAP then afforded the title compound (5 mg, 7.60% yield). LCMS: rt=2.93 min, [M+H]=488

E33: 2-[[(4-{[4-Chloro-3-(trifluoromethyl)phenyl]oxy}phenyl)methyl](methyl)amino]-5-[(1-methyl-1H-pyrazol-4-yl)methyl]-4(1H)-pyrimidinone trifluoroacetate

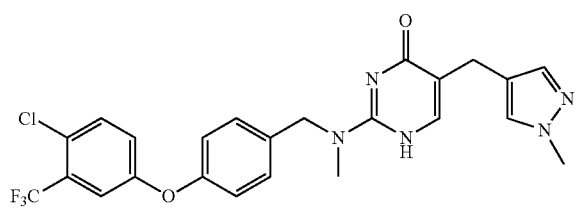 [SMILES: CN(Cc1ccc(Oc2ccc(Cl)c(C(F)(F)F)c2)cc1)c1nc(=O)c(Cc2cnn(C)c2)c[nH]1]

To the mixture of N-[(4-{[4-chloro-3-(trifluoromethyl)phenyl]oxy}phenyl)methyl]-N-methylguanidine (50 mg, 0.140 mmol) and $Cs_2CO_3$ (182 mg, 0.559 mmol) in NMP (1 mL), was added methyl (2Z)-3-hydroxy-2-[(1-methyl-1H-pyrazol-4-yl)methyl]-2-propenoate (40 mg, 0.204 mmol). It was heated with a microwave reactor at 130° C. for 1 h.

Purification via MDAP then afforded the title compound as a white solid (13 mg, 15.1% yield). LCMS: rt=3.03 min, [M+H$^+$]=504

E34: 2-[[(4-{[4-Chloro-3-(trifluoromethyl)phenyl]oxy}phenyl)methyl](methyl)amino]-5-(5-pyrimidinylmethyl)-4(1H)-pyrimidinone trifluoroacetate

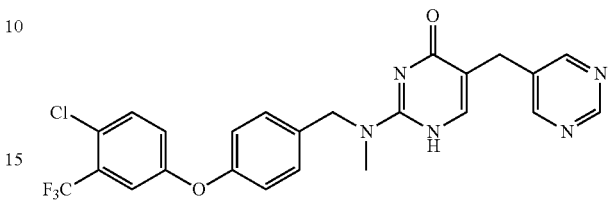

To the mixture of N-[(4-{[4-chloro-3-(trifluoromethyl)phenyl]oxy}phenyl)methyl]-N-methylguanidine (50 mg, 0.106 mmol) and $Cs_2CO_3$ (138 mg, 0.425 mmol) in NMP (1 mL) was added methyl (2Z)-3-hydroxy-2-(5-pyrimidinylmethyl)-2-propenoate (25 mg, 0.129 mmol). It was heated with a microwave reactor at 130° C. for 1 h. Purification via MDAP then afforded the title compound as a white solid (5 mg, 7.6%, yield). LCMS: rt=3.12 min, [M+H$^+$]=502

E35: 2-{[(4-{[4-Chloro-3-(trifluoromethyl)phenyl]oxy}phenyl)methyl]amino}-5-[(1-methyl-1H-pyrazol-4-yl)methyl]-4(1H)-pyrimidinone trifluoroacetate

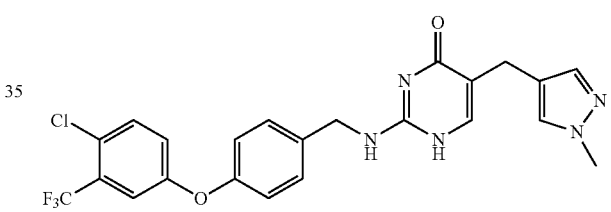

To the mixture of N-[(4-{[4-chloro-3-(trifluoromethyl)phenyl]oxy}phenyl)methyl]guanidine (150 mg, 0.328 mmol) and $Cs_2CO_3$ (428 mg, 1.314 mmol) in NMP (1.5 mL) was added methyl (2Z)-3-hydroxy-2-[(1-methyl-1H-pyrazol-4-yl)methyl]-2-propenoate (77 mg, 0.394 mmol). It was heated with a microwave reactor at 130° C. for 1 h. Purification via MDAP then afforded the title compound as a white solid (54 mg, 27.3% yield). LCMS: rt=2.88 min, [M+H$^+$]=490

E36: 2-[[(4-{[4-Chloro-3-(trifluoromethyl)phenyl]oxy}phenyl)methyl](methyl)amino]-5-{[2-(methyloxy)-5-pyrimidinyl]methyl}-4(1H)-pyrimidinone

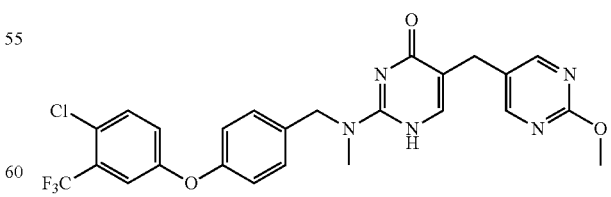

To the solution of N-[(4-{[4-chloro-3-(trifluoromethyl)phenyl]oxy}phenyl)methyl]-N-methylguanidine (100 mg, 0.212 mmol) and methyl (2Z)-3-hydroxy-2-{[2-(methyloxy)-5-pyrimidinyl]methyl}-2-propenoate (57.2 mg, 0.255 mmol) in NMP (1 ml) was added $K_2CO_3$ (117 mg, 0.850 mmol). It was heated with a microwave reactor at 130° C. for 1.5 h. Purification via MDAP then afforded the title compound as a white solid (10 mg, 8.8% yield). LCMS: rt=3.14 min, [M+H⁺]=532

E37: 5-ethyl-2-(4-(3-(trifluoromethyl)phenoxy)phenethyl)pyrimidin-4(1H)-one

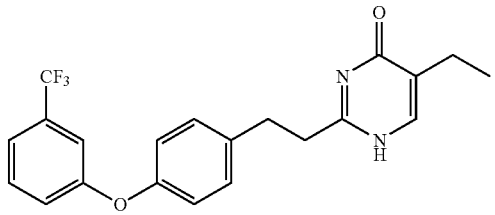 [SMILES: CCc1c[nH]c(CCc2ccc(Oc3cccc(C(F)(F)F)c3)cc2)nc1=O]

To a solution of 3-(4-(3-(trifluoromethyl)phenoxy)phenyl)propanimidamide (200 mg, 0.580 mmol) in THF (4 mL) were added methyl 2-(hydroxymethylene)butanoate (151 mg, 0.580 mmol) and potassium acetate (171 mg, 1.740 mmol). The mixture was stirred with a microwave condition at 100° C. for 1 h under nitrogen. The reaction mixture was cooled to room temperature; the solvent was removed in vacuo. The residue was purified MDAP to afford the title compound (36.7 mg, 16.29% yield) as a white solid. LCMS: rt=1.67 min, [M+H]=389.

E38: 5-(pyrimidin-5-ylmethyl)-2-(4-(3-(trifluoromethyl)phenoxy)phenethyl)pyrimidin-4(1H)-one

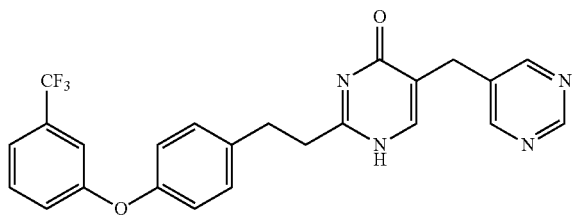 [SMILES: O=c1nc(CCc2ccc(Oc3cccc(C(F)(F)F)c3)cc2)[nH]cc1Cc1cncnc1]

To a solution of 3-(4-(3-(trifluoromethyl)phenoxy)phenyl)propanimidamide (200 mg, 0.580 mmol) in Toluene (10 mL) were added methyl 3-hydroxy-2-(pyrimidin-5-ylmethyl)acrylate (113 mg, 0.580 mmol) and potassium acetate (171 mg, 1.740 mmol). The mixture was heated at 120° C. overnight. The mixture was filtered at hot, and the solid was washed with toluene. The filtrate was concentrated. The residue was triturated with diethyl ether to afford the title compound (144 mg, 53.9% yield). LCMS: rt=8.51 min, [M+H⁺]=453.

E39: 2-(4-(4-fluorophenoxy)phenethyl)-5-(pyrimidin-5-ylmethyl)pyrimidin-4(1H)-one

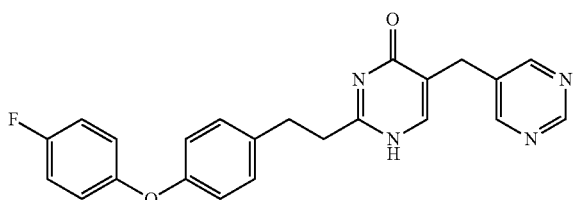

The same procedure as E38 from (Z)-methyl 3-hydroxy-2-(pyrimidin-5-ylmethyl) acrylate (194 mg, 1 mmol), 3-(4-(4-fluorophenoxy)phenyl)propanimidamide (258 mg, 1 mmol) and potassium acetate (294 mg, 3 mmol) in Toluene (10 mL) to afford the title compound (250 mg, 62.1% yield) as a yellow solid. LCMS: rt=1.528 min, [M+H⁺]=403.

E40: 1-methyl-5-(pyrimidin-5-ylmethyl)-2-(4-(3-(trifluoromethyl)phenoxy)phenethyl)pyrimidin-4(1H)-one

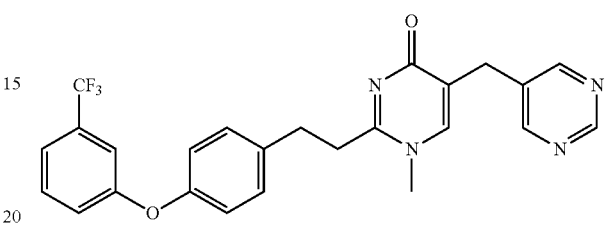

To the solution of 5-(pyrimidin-5-ylmethyl)-2-(4-(3-(trifluoromethyl)phenoxy)phenethyl) pyrimidin-4(1H)-one (200 mg, 0.442 mmol) in DCM (10 mL) was added MeI (4.42 mL, 4.42 mmol) (1.0 M in DCM) and DIPEA (0.772 mL, 4.42 mmol) at 25° C. The mixture was stirred at room temperature for 2 days. The solvent was removed in vacuo. Purification via MDAP then afforded the title compound (87.6 mg, 40.8% yield) as a white solid. LCMS: rt=1.59 min, [M+H⁺]=467.

E41: 2-(4-(4-fluorophenoxy)phenethyl)-1-methyl-5-(pyrimidin-5-ylmethyl)pyrimidin-4(1H)-one

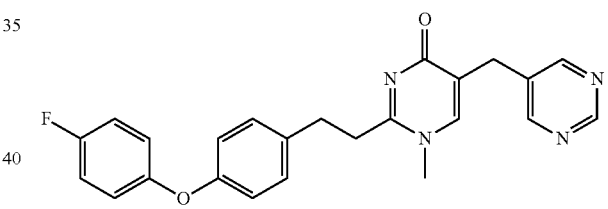

The same procedure as E40 from 2-(4-(4-fluorophenoxy)phenethyl)-5-(pyrimidin-5-ylmethyl)pyrimidin-4(1H)-one (130 mg, 0.323 mmol), MeI (459 mg, 3.23 mmol) and DIPEA (418 mg, 3.23 mmol) in DCM (20 ml) to afford the title compound (30 mg) as a yellow solid. LCMS: rt=1.496 min, [M+H⁺]=417.

E42: 2-(4-(4-fluorophenoxy)phenethyl)-5-((2-methoxypyrimidin-5-yl)methyl)pyrimidin-4(1H)-one

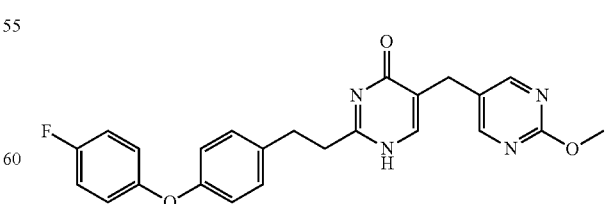

The same procedure as E38 from (Z)-methyl 3-hydroxy-2-((2-methoxypyrimidin-5-yl)methyl)acrylate (224 mg, 1 mmol), 3-(4-(4-fluorophenoxy)phenyl)propanimidamide (258 mg, 1 mmol) and potassium acetate (294 mg, 3 mmol) in Toluene (10 mL) to afford the title compound (250 mg, 57.8% yield) as a yellow solid. LCMS: rt=1.584 min, [M+H⁺]=433.

E43: 2-(4-(4-fluorophenoxy)phenethyl)-5-((2-methoxypyrimidin-5-yl)methyl)-1-methylpyrimidin-4(1H)-one

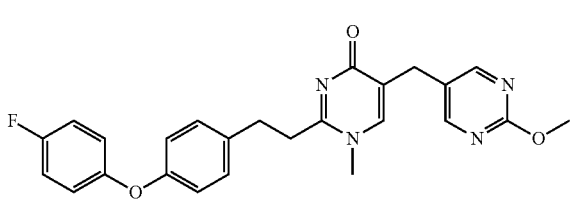 [SMILES: COc1ncc(Cc2cn(C)c(CCc3ccc(Oc4ccc(F)cc4)cc3)nc2=O)cn1]

The same procedure as E40 from 2-(4-(4-fluorophenoxy)phenethyl)-5-((2-methoxypyrimidin-5-yl)methyl) pyrimidin-4(1H)-one (141 mg, 0.326 mmol), MeI (463 mg, 3.26 mmol) and DIPEA (421 mg, 3.26 mmol) in DCM (20 ml) to afford the title compound (30 mg) as a yellow solid. LCMS: rt=1.540 min, [M+H⁺]=447.

E44: 2-(4-(4-fluorophenoxy)phenethyl)-5-((1-methyl-1H-pyrazol-4-yl)methyl)pyrimidin-4(1H)-one

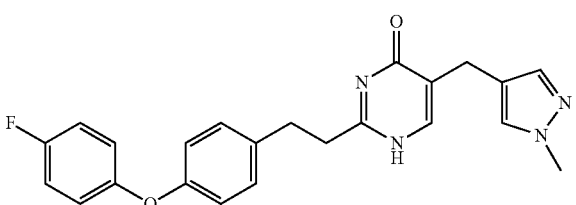

The same procedure as E38 from (Z)-methyl 3-hydroxy-2-((1-methyl-1H-pyrazol-4-yl)methyl)acrylate (196 mg, 1 mmol), 3-(4-(4-fluorophenoxy)phenyl) propanimidamide (258 mg, 1 mmol) and potassium acetate (294 mg, 3 mmol) in toluene (10 mL) to afford the title compound (32 mg, 7.91% yield) as a yellow solid. LCMS: rt=1.580 min, [M+H⁺]=405.

E45: 2-(4-(4-fluorophenoxy)phenethyl)-1-methyl-5-((1-methyl-1H-pyrazol-4-yl)methyl)pyrimidin-4(1H)-one

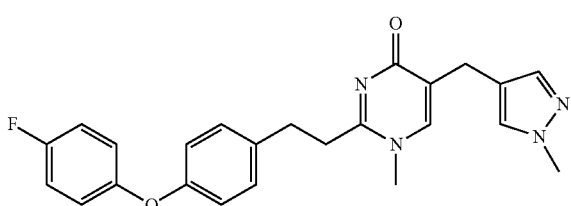

The same procedure as E40 from 2-(4-(4-fluorophenoxy)phenethyl)-5-((1-methyl-1H-pyrazol-4-yl)methyl)pyrimidin-4(1H)-one (380 mg, 0.94 mmol), MeI (1334 mg, 9.4 mmol), and DIPEA (1214 mg, 9.4 mmol) in DCM (20 ml) to afford the title compound (12 mg) as a yellow solid. LCMS: rt=1.491 min, [M+H⁺]=419.

E46: 5-ethyl-2-(4-(4-fluorophenoxy)phenethyl)pyrimidin-4(1H)-one

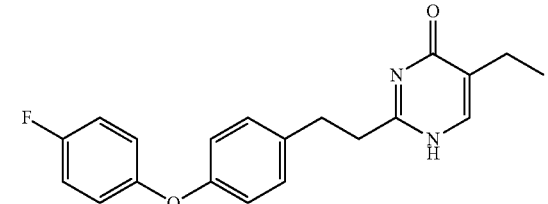

The same procedure as E38 from (Z)-methyl 2-(hydroxymethylene) butanoate (195 mg, 1.5 mmol), 3-(4-(4-fluorophenoxy)phenyl)propanimidamide (387 mg, 1.5 mmol) and potassium acetate (442 mg, 4.5 mmol) in toluene (10 mL) to afford the title compound (100 mg, 19.7% yield) as a yellow solid. LCMS: rt=1.570 min, [M+H⁺]=339.

E47: 2-(4-(4-chloro-3-(trifluoromethyl)phenoxy)phenethyl)-5-ethylpyrimidin-4(1H)-one

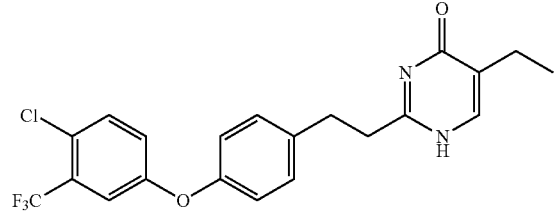 [SMILES: CCc1c[nH]c(CCc2ccc(Oc3ccc(Cl)c(C(F)(F)F)c3)cc2)nc1=O]

The same procedure as E38 from (Z)-methyl 2-(hydroxymethylene) butanoate (130 mg, 1 mmol), 3-(4-(4-chloro-3-(trifluoromethyl)phenoxy)phenyl) propanimidamide (343 mg, 1 mmol) and potassium acetate (294 mg, 3 mmol) in toluene (20 mL) to afford the title compound (40 mg, 9.46% yield) as a yellow solid. LCMS: rt=1.728 mins, [M+H⁺]=423, 425.

E48: 5-((2-methoxypyrimidin-5-yl)methyl)-2-(4-(3-(trifluoromethyl)phenoxy)phenethyl)pyrimidin-4(1H)-one

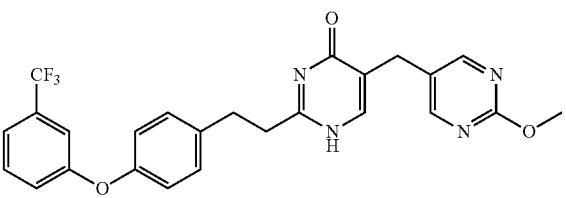 [SMILES: COc1ncc(Cc2c[nH]c(CCc3ccc(Oc4cccc(C(F)(F)F)c4)cc3)nc2=O)cn1]

The same procedure as E38 from a mixture of 3-(4-(3-(trifluoromethyl) phenoxy)phenyl)propanimidamide (200 mg, 0.580 mmol), methyl 3-hydroxy-2-((2-methoxypyrimidin-5-yl)methyl)acrylate (130 mg, 0.580 mmol) and potassium acetate (171 mg, 1.740 mmol) in toluene (10 mL) to afford the title compound (180 mg, 61.1% yield) as a yellow solid. LCMS: rt=8.88 min, [M+H]=483.

E49: 5-((2-methoxypyrimidin-5-yl)methyl)-1-methyl-2-(4-(3-(trifluoromethyl)phenoxy)phenethyl)pyrimidin-4(1H)-one

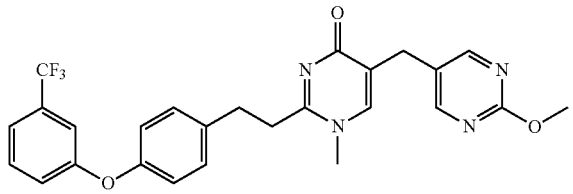 [SMILES: COc1ncc(Cc2cn(C)c(CCc3ccc(Oc4cccc(C(F)(F)F)c4)cc3)nc2=O)cn1]

The same procedure as E40 from 5-((2-methoxypyrimidin-5-yl)methyl)-2-(4-(3-(trifluoromethyl)phenoxy)phenethyl)pyrimidin-4(1H)-one (120 mg, 0.249 mmol) MeI (6.22 mL, 1.244 mmol) (0.2 M in DCM) and DIPEA (0.043 mL, 0.249 mmol) in DCM (5 mL) to afford the title compound (13.2 mg, 10.41% yield) as a colorless oil. LCMS: rt=1.63 min, [M+H]=497.

E50: 5-((1-methyl-1H-pyrazol-4-yl)methyl)-2-(4-(3-(trifluoromethyl)phenoxy)phenethyl)pyrimidin-4(1H)-one

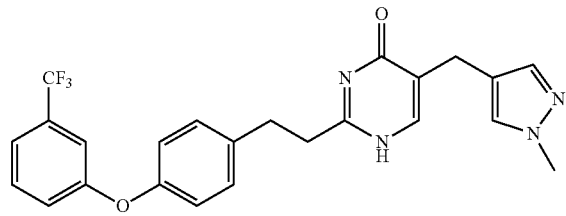 [SMILES: Cn1cc(Cc2c[nH]c(CCc3ccc(Oc4cccc(C(F)(F)F)c4)cc3)nc2=O)cn1]

The same procedure as E38 from 3-(4-(3-(trifluoromethyl)phenoxy)phenyl) propanimidamide (200 mg, 0.580 mmol), methyl (2Z)-3-hydroxy-2-[(1-methyl-1H-pyrazol-4-yl)methyl]-2-propenoate (126 mg, 0.638 mmol) and KOAc (171 mg, 1.740 mmol) in toluene (8 mL) to afford the title compound (18.3 mg, 6.66% yield) as a white solid. LCMS: rt=1.65 min, [M+H]=455.

E51: 1-methyl-5-((1-methyl-1H-pyrazol-4-yl)methyl)-2-(4-(3-(trifluoromethyl)phenoxy)phenethyl)pyrimidin-4(1H)-one

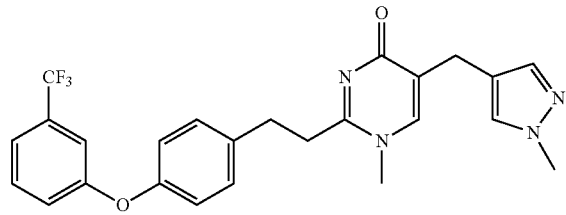 [SMILES: Cn1cc(Cc2cn(C)c(CCc3ccc(Oc4cccc(C(F)(F)F)c4)cc3)nc2=O)cn1]

The same procedure as E40 from 5-((1-methyl-1H-pyrazol-4-yl)methyl)-2-(4-(3-(trifluoromethyl)phenoxy)phenethyl)pyrimidin-4(1H)-one (200 mg, 0.440 mmol), MeI (7.04 mL, 3.52 mmol) (0.5 M in DCM) and DIPEA (0.615 mL, 3.52 mmol) in DCM (8 mL) to afford the title compound (13.8 mg, 6.46% yield) as a colorless oil. LCMS: rt=1.57 min, [M+H]=469.

E52: 2-((4-(4-fluorophenoxy)benzyl)thio)-5-((2-methoxypyrimidin-5-yl)methyl)pyrimidin-4(1H)-one

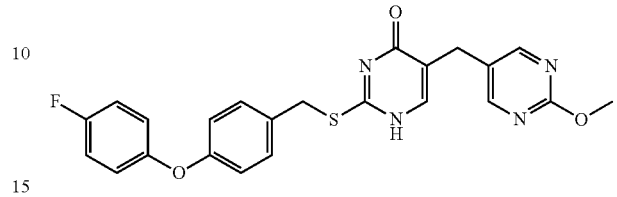

A mixture of 5-((2-methoxypyrimidin-5-yl)methyl)-2-thioxo-2,3-dihydropyrimidin-4(1H)-one (2.75 g, 10.99 mmol), 1-(chloromethyl)-4-(4-fluorophenoxy)benzene (2.6 g, 10.99 mmol) and diisopropylamine (3.34 g, 33.0 mmol) in DCM (50 mL) was heated at 60° C. overnight. After cooling to room temperature, the mixture was washed with brine, the organic phase was dried over Na$_2$SO$_4$, filtered and concentrated to leave the crude product, which was slurred in EA (20 mL) for 10 min, filtered, washed with EA and concentrated in vacuo to afford the title compound (2.75 g, 51.4% yield) as white solid. LCMS: rt=1.47 min, [M+H]=451.0

E53: 2-[({4-[(4-fluorophenyl)oxy]phenyl}methyl)thio]-1-methyl-5-{[2-(methyloxy)-5-pyrimidinyl]methyl}-4(1H)-pyrimidinone

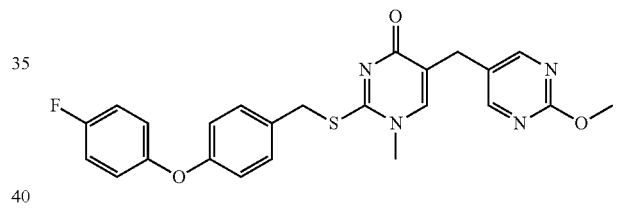

To a solution of 2-(4-(4-fluorophenoxy)benzylthio)-5-((2-methoxypyrimidin-5-yl)methyl) pyrimidin-4(1H)-one (100 mg, 0.222 mmol) and Hunig's base (0.058 mL, 0.333 mmol) in DCM (4 mL) was added MeI (0.021 mL, 0.333 mmol). The mixture was heated at 50° C. for 2 h. Purification via reverse phase flash chromatography then afforded the title compound (30 mg, 29.1% yield). LCMS: rt=3.05 min, [M+H]=465.

E54: 1-ethyl-2-[({4-[(4-fluorophenyl)oxy]phenyl}methyl)thio]-5-{[2-(methyloxy)-5-pyrimidinyl]methyl}-4(1H)-pyrimidinone

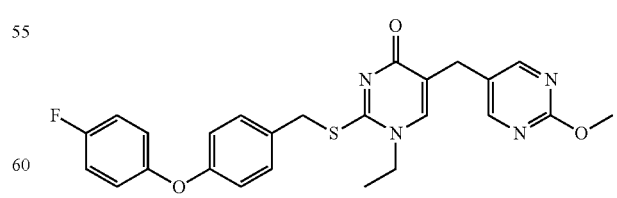

To a solution of 2-((4-(4-fluorophenoxy)benzyl)thio)-5-((2-methoxypyrimidin-5-yl)methyl)pyrimidin-4(1H)-one (167 mg, 0.371 mmol) in DCE (5 mL) was added Hunig's base (0.194 mL, 1.112 mmol) and EtI (0.045 mL, 0.556 mmol). The mixture was heated at 55° C. for 2 days. Purification via reverse phase flash chromatography then afforded the title compound (10 mg, 5.64% yield). LCMS: rt=3.24 min, [M+H⁺]=479

E55: 2-[({4-[(4-fluorophenyl)oxy]phenyl}methyl)thio]-5-{[2-(methyloxy)-5-pyrimidinyl]methyl}-1-propyl-4(1H)-pyrimidinone

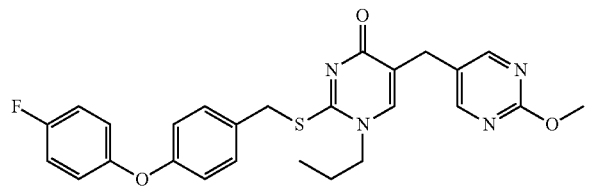 [SMILES: CCCn1cc(Cc2cnc(OC)nc2)c(=O)nc1SCc1ccc(Oc2ccc(F)cc2)cc1]

The same procedure as E54 from 2-((4-(4-fluorophenoxy)benzyl)thio)-5-((2-methoxypyrimidin-5-yl)methyl)pyrimidin-4(1H)-one (146.6 mg, 0.325 mmol), Hunig's base (0.171 mL, 0.976 mmol) and 1-bromopropane (80 mg, 0.651 mmol) in DCE (5 mL), except that the time was prolonged to 3 days, to afford the title compound (50 mg, 0.102 mmol, 31.2% yield). LCMS: rt=3.41 min, [M+H⁺]=493

E56: 2-{[(4-{[4-chloro-3-(trifluoromethyl)phenyl]oxy}phenyl)methyl]thio}-5-(5-pyrimidinylmethyl)-4(1H)-pyrimidinone

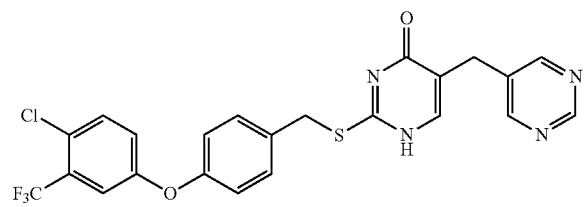

To a suspension of 5-(5-pyrimidinylmethyl)-2-thioxo-2,3-dihydro-4(1H)-pyrimidinone (75 mg, 0.343 mmol) and DIPEA (0.163 ml, 0.934 mmol) in DCM (2 mL) was added 1-chloro-4-{[4-(chloromethyl)phenyl]oxy}-2-(trifluoromethyl)benzene (100 mg, 0.311 mmol). The solution was heated at 60° C. overnight. Purification via MDAP then afforded the title compound (42 mg, 26.7% yield). LCMS: rt=3.49 min, [M+H⁺]=505

E57: 2-{[(4-{[4-chloro-3-(trifluoromethyl)phenyl]oxy}phenyl)methyl]thio}-1-methyl-5-(5-pyrimidinylmethyl)-4(1H)-pyrimidinone

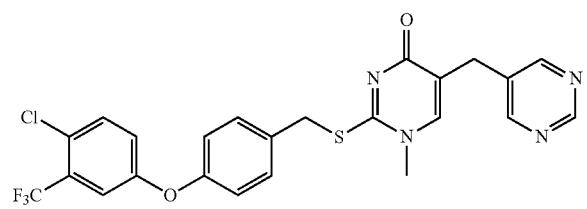 [SMILES: Cn1cc(Cc2cncnc2)c(=O)nc1SCc1ccc(Oc2ccc(Cl)c(C(F)(F)F)c2)cc1]

To a solution of 5-(5-pyrimidinylmethyl)-2-thioxo-2,3-dihydro-4(1H)-pyrimidinone (70 mg, 0.318 mmol) and DIPEA (0.083 ml, 0.477 mmol) in DCM (2 ml) was added 1-chloro-4-{[4-(chloromethyl)phenyl]oxy}-2-(trifluoromethyl)benzene (110 mg, 0.343 mmol). The reaction mixture was heated at 60° C. overnight. After removing the solvent by nitrogen, the residue was dissolved in MeCN (4 ml), and NMP (1.5 ml), and ZnBr₂ (107 mg, 0.477 mmol) and DIPEA (0.083 ml, 0.477 mmol) were added. The mixture was then stirred at 60° C. for 10 min and MeI (0.020 ml, 0.318 mmol) was added dropwise, then stirred at 60° C. for 1.5 h. Purification via MDAP then afforded the title compound (12 mg, 5.97% yield). LCMS: rt=3.38 min, [M+H⁺]=519

E58: 2-(4-chloro-3-(trifluoromethyl)phenoxy)-5-(((5-((1-methyl-1H-pyrazol-4-yl)methyl)-4-oxo-1,4-dihydropyrimidin-2-yl)thio)methyl)benzonitrile, trifluoroacetic acid salt

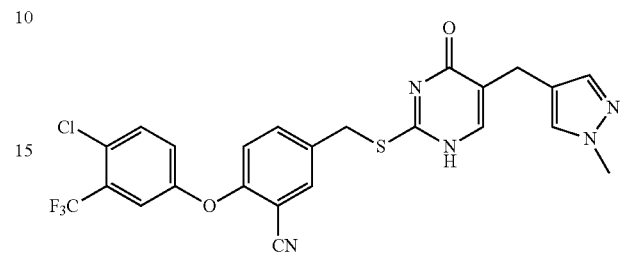

To a solution of 5-[(1-methyl-1H-pyrazol-4-yl)methyl]-2-thioxo-2,3-dihydro-4(1H)-pyrimidinone (104 mg, 0.468 mmol) and 2-(4-chloro-3-(trifluoromethyl)phenoxy)-5-(chloromethyl)benzonitrile (180 mg, 0.520 mmol) in chloroform (2 mL) was added DIPEA (0.454 mL, 2.60 mmol). The mixture was heated at 60° C. overnight. Purification via MDAP then afforded the title compound (89 mg, 26.5% yield). LCMS: rt=3.33 min, [M+H⁺]=532

E59: 2-((4-(4-chloro-3-(trifluoromethyl)phenoxy)benzyl)thio)-5-((1-methyl-1H-pyrazol-4-yl)methyl)pyrimidin-4(1H)-one, trifluoroacetic acid salt

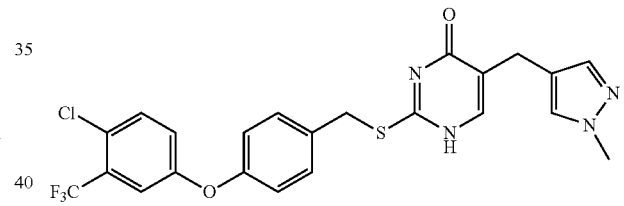

The same procedure as E58 from 5-[(1-methyl-1H-pyrazol-4-yl)methyl]-2-thioxo-2,3-dihydro-4(1H)-pyrimidinone (104 mg, 0.468 mmol) and 1-chloro-4-{[4-(chloromethyl)phenyl]oxy}-2-(trifluoromethyl)benzene (167 mg, 0.520 mmol) and DIPEA (0.454 mL, 2.60 mmol) in chloroform (2 mL) to afford the title compound (92 mg, 0.148 mmol, 28.5% yield). LCMS: rt=3.54 min, [M+H⁺]=507

E60: 2-(4-fluoro-3-(trifluoromethyl)phenoxy)-5-(((1-methyl-5-((1-methyl-1H-pyrazol-4-yl)methyl)-4-oxo-1,4-dihydropyrimidin-2-yl)thio)methyl)benzonitrile, trifluoroacetic acid salt

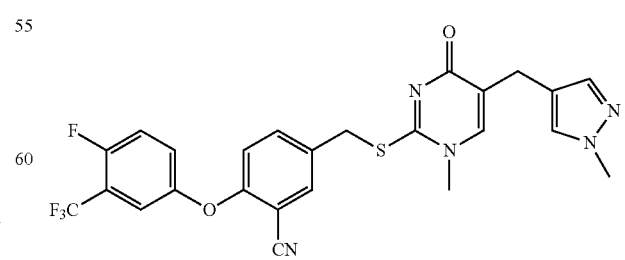

To a solution of 2-{[4-fluoro-3-(trifluoromethyl)phenyl]oxy}-5-[({5-[(1-methyl-1H-pyrazol-4-yl)methyl]-4-oxo-1,4-dihydro-2-pyrimidinyl}thio)methyl]benzonitrile (123 mg, 0.239 mmol) and DIPEA (0.125 mL, 0.716 mmol) in MeCN (2 mL) and NMP (0.5 mL) was added MeI (0.018 mL, 0.286 mmol). The mixture was heated at 60 OC for 2 h. Purification via MDAP then afforded the title compound (18 mg, 0.028 mmol, 11.72% yield). LCMS: rt=3.06 min, [M+H$^+$]=530

E61: 2-{[(4-{[4-chloro-3-(trifluoromethyl)phenyl]oxy}phenyl)methyl]thio}-1-methyl-5-[(1-methyl-1H-pyrazol-4-yl)methyl]-4(1H)-pyrimidinone, trifluoroacetic acid salt

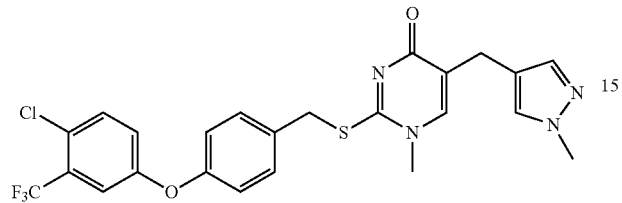

The same procedure as E60 from 2-{[(4-{[4-chloro-3-(trifluoromethyl)phenyl]oxy})phenyl)methyl]thio}-5-[(1-methyl-1H-pyrazol-4-yl)methyl]-4(1H)-pyrimidinone (89 mg, 0.176 mmol), DIPEA (0.092 mL, 0.527 mmol) and MeI (0.013 mL, 0.211 mmol) in MeCN (2 mL) to afford the title compound (24 mg, 0.038 mmol, 21.53% yield). LCMS: rt=3.37 min, [M+H$^+$]=521

E62: 4-[(2-{[(4-{[4-chloro-3-(trifluoromethyl)phenyl]oxy}phenyl)methyl]thio}-4-oxo-1,4-dihydro-5-pyrimidinyl)methyl]benzonitrile

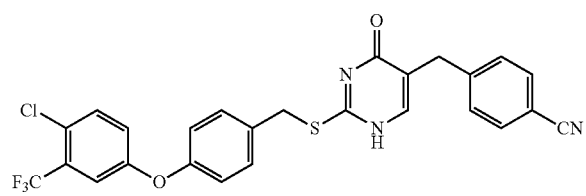 [SMILES: N#Cc1ccc(Cc2c[nH]c(SCc3ccc(Oc4ccc(Cl)c(C(F)(F)F)c4)cc3)nc2=O)cc1]

To a suspension of 4-[(4-oxo-2-thioxo-1,2,3,4-tetrahydro-5-pyrimidinyl)methyl]benzonitrile (70 mg, 0.288 mmol) and K$_2$CO$_3$ (41.3 mg, 0.299 mmol) in acetone (6 mL), which was stirred at room temperature for 5 min was added 1-chloro-4-{[4-(chloromethyl)phenyl]oxy}-2-(trifluoromethyl)benzene (60 mg, 0.187 mmol) under argon. The mixture was heated at 60° C. for 3 h. Purification via MDAP then afforded the title compound (31 mg, 0.059 mmol, 31.4% yield). LCMS: rt=3.98 min, [M+H$^+$]=528

E63: 2-{[(4-{[4-chloro-3-(trifluoromethyl)phenyl]oxy}phenyl)methyl]thio}-5-ethyl-4(1H)-pyrimidinone

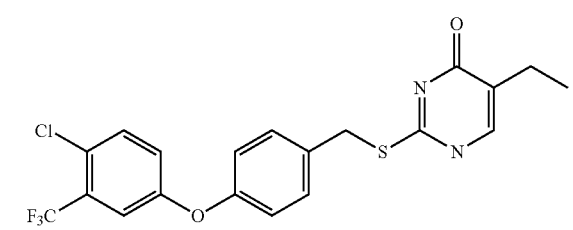

A mixture of 1-chloro-4-{[4-(chloromethyl)phenyl]oxy}-2-(trifluoromethyl)benzene (65 mg, 0.202 mmol), 5-ethyl-2-thioxo-2,3-dihydro-4(1H)-pyrimidinone (47.4 mg, 0.304 mmol) and DIPEA (0.163 mL, 0.933 mmol) in DCE (3.0 mL) was sealed in a vessel and stirred at room temperature for 5 min, then was heated with a microwave condition at 80° C. for 30 min. After cooling, the reaction was quenched with water, extracted with EA, the combined organic layers were dried with sodium sulfate, concentrated, and purified via MDAP to afford the title compound (41 mg, 45.9% yield). LCMS: rt=3.94 min, [M+H$^+$]=441

E64: 2-{[4-chloro-3-(trifluoromethyl)phenyl]oxy}-5-{[(5-ethyl-1-methyl-4-oxo-1,4-dihydro-2-pyrimidinyl)thio]methyl}benzonitrile

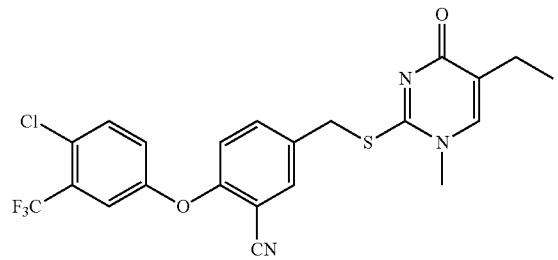 [SMILES: CCc1cn(C)c(SCc2ccc(Oc3ccc(Cl)c(C(F)(F)F)c3)c(C#N)c2)nc1=O]

To a suspension of 2-{[4-chloro-3-(trifluoromethyl)phenyl]oxy}-5-{[(5-ethyl-4-oxo-1,4-dihydro-2-pyrimidinyl)thio]methyl}benzonitrile (120 mg, 0.258 mmol) and DIPEA (0.090 ml, 0.515 mmol) in DCM (2 mL) was added MeI (0.02416 ml, 0.386 mmol). The mixture was stirred at room temperature for 2 h. The reaction was then quenched with water, extracted with EA. The combined organic layers were dried with Na$_2$SO$_4$, filtered, concentrated and purified via reverse phase flash chromatography to afford the title compound (40 mg, 32.4% yield). LCMS: rt=3.44 min, [M+H$^+$]= 480

E65: 2-{[(4-{[4-chloro-3-(trifluoromethyl)phenyl]oxy}phenyl)methyl]thio}-5-ethyl-1-methyl-4(1H)-pyrimidinone

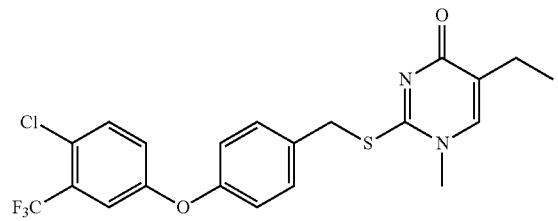

The same procedure as E64 from 2-{[(4-{[4-chloro-3-(trifluoromethyl)phenyl]oxy}phenyl)methyl]thio}-5-ethyl-4(1H)-pyrimidinone (60 mg, 0.136 mmol), DIPEA (0.048 mL, 0.272 mmol) and MeI (0.013 mL, 0.204 mmol) in DCM (2 mL) to afford the title compound (35 mg, 56.5% yield). LCMS: rt=3.62 min, [M+H$^+$]=455

E66: 2-{[(4-{[4-Chloro-3-(trifluoromethyl)phenyl]oxy}phenyl)methyl]thio}-5-(1H-indol-1-ylmethyl)-4(1H)-pyrimidinone

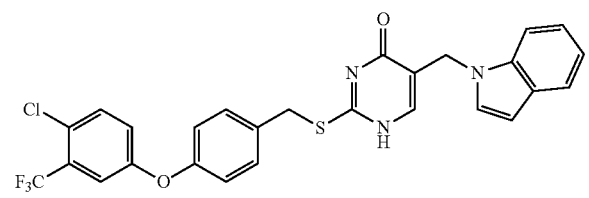 [SMILES: O=c1nc(SCc2ccc(Oc3ccc(Cl)c(C(F)(F)F)c3)cc2)[nH]cc1Cn1ccc2ccccc21]

A mixture of 1-chloro-4-(4-(chloromethyl)phenoxy)-2-(trifluoromethyl)benzene (200 mg, 0.623 mmol), 5-(1H-indol-1-ylmethyl)-2-thioxo-2,3-dihydro-4(1H)-pyrimidinone (160 mg, 0.623 mmol), and K$_2$CO$_3$ (200 mg, 1.447 mmol) in DMF (5 mL) was heated at 80° C. for 3 h. Purification via MDAP then afforded the title compound (30 mg, 8.44% yield). LCMS: rt=4.19 min, [M+H$^+$]=542

E67: 2-((4-(4-chloro-3-(trifluoromethyl)phenoxy)benzyl)thio)-5-((1-methyl-1H-indol-2-yl)methyl)pyrimidin-4(1H)-one

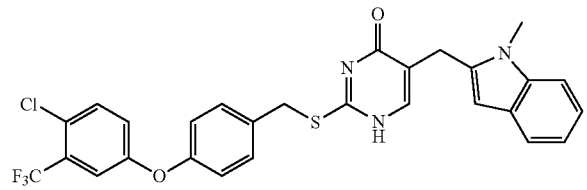 [SMILES: Cn1c(Cc2c[nH]c(SCc3ccc(Oc4ccc(Cl)c(C(F)(F)F)c4)cc3)nc2=O)cc2ccccc21]

The same procedure as E66 from 5-[(1-methyl-1H-indol-2-yl)methyl]-2-thioxo-2,3-dihydro-4(1H)-pyrimidinone (84 mg, 0.311 mmol), 1-chloro-4-(4-(chloromethyl)phenoxy)-2-(trifluoromethyl)benzene (100 mg, 0.311 mmol), and K$_2$CO$_3$ (150 mg, 1.085 mmol) in DMF (3 mL) to afford the title compound (23 mg, 12.89% yield). LCMS: rt=4.27 min, [M+H$^+$]=556

E68: 2-{[(4-{[4-Chloro-3-(trifluoromethyl)phenyl]oxy}phenyl)methyl]thio}-5-[(1-methyl-1H-indol-3-yl)methyl]-4(1H)-pyrimidinone

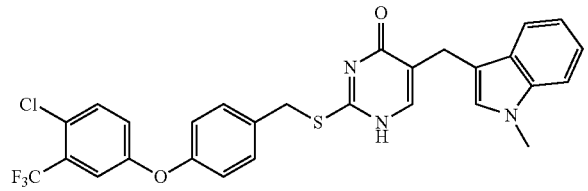 [SMILES: Cn1cc(Cc2c[nH]c(SCc3ccc(Oc4ccc(Cl)c(C(F)(F)F)c4)cc3)nc2=O)c2ccccc21]

A mixture of 5-[(1-methyl-1H-indol-3-yl)methyl]-2-thioxo-2,3-dihydro-4(1H)-pyrimidinone (95 mg, 0.349 mmol), 1-chloro-4-(4-(chloromethyl)phenoxy)-2-(trifluoromethyl)benzene (112 mg, 0.349 mmol), and K$_2$CO$_3$ (90 mg, 0.651 mmol) in DMF (2 mL) was heated at 80° C. for 3 h. The reaction mixture was diluted with EA (10 mL) and filtered through a silica pad to remove the solid suspension. The clear filtrate was concentrated under reduced pressure and purification via MDAP then afforded the title compound (50 mg, 24.75% yield). LCMS: rt=4.79 min, [M+H$^+$]=556

E69: 2-{[(4-{[4-chloro-3-(trifluoromethyl)phenyl]oxy}phenyl)methyl]thio}-5-(1-piperidinylmethyl)-4(1H)-pyrimidinone

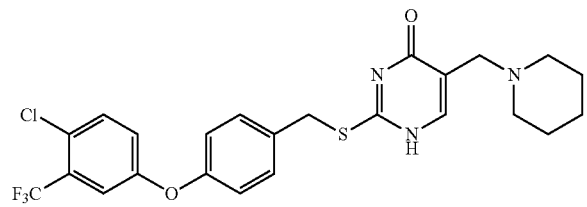 [SMILES: O=c1nc(SCc2ccc(Oc3ccc(Cl)c(C(F)(F)F)c3)cc2)[nH]cc1CN1CCCCC1]

To a solution of 2-{[(4-{[4-chloro-3-(trifluoromethyl)phenyl]oxy}phenyl)methyl]thio)}-5-(hydroxymethyl)-4(1H)-pyrimidinone (51 mg, 0.115 mmol) in dry DMF (3 mL) was added DIAD (0.034 mL, 0.173 mmol), triphenylphosphine (45.3 mg, 0.173 mmol) and piperizine (19.61 mg, 0.230 mmol) under argon. The mixture was heated with a microwave reactor at 45° C. for 0.5 h. Purification via MDAP then afforded the title compound (28 mg, 47.7% yield). LCMS: rt=3.02 min, [M+H$^+$]=510

E70: 2-{[(4-{[4-chloro-3-(trifluoromethyl)phenyl]oxy}phenyl)methyl]thio}-5-[(4-methyl-1-piperazinyl)methyl]-4(1H)-pyrimidinone trifluoroacetate, trifluoroacetic acid salt

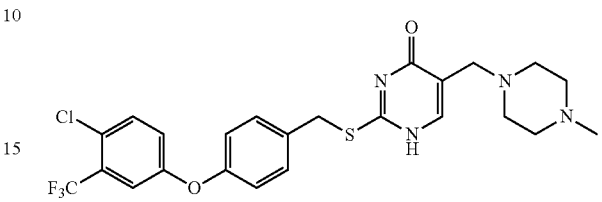

The same procedure as E69 from 2-{[(4-{[4-chloro-3-(trifluoromethyl)phenyl]oxy}phenyl)methyl]thio}-5-(hydroxymethyl)-4(1H)-pyrimidinone (56 mg, 0.126 mmol), triphenylphosphine (49.8 mg, 0.190 mmol), N-methylpiperazine (25.3 mg, 0.253 mmol) and DIAD (0.037 mL, 0.190 mmol) in dry DMF (3 mL) to afford the title compound (26 mg, 27.3% yield). LCMS: rt=2.71 min, [M+H$^+$]=525

E71: 2-{[(4-{[4-chloro-3-(trifluoromethyl)phenyl]oxy}phenyl)methyl]thio}-5-(1-pyrrolidinylmethyl)-4(1H)-pyrimidinone

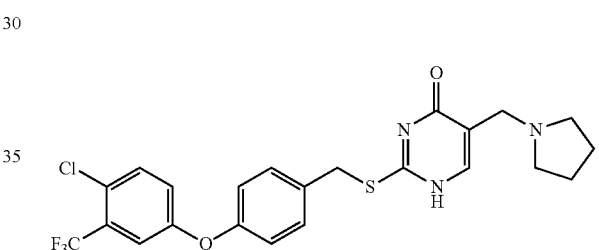

The same procedure as E69 from 2-{[(4-{[4-chloro-3-(trifluoromethyl)phenyl]oxy}phenyl)methyl]thio)}-5-(hydroxymethyl)-4(1H)-pyrimidinone (53 mg, 0.120 mmol), DIAD (0.035 mL, 0.180 mmol), triphenylphosphine (47.1 mg, 0.180 mmol) and pyrrolidine (25.5 mg, 0.359 mmol) in DMF (2 mL), except that the temperature was up to 50° C., to afford the title compound (8 mg, 13.48% yield). LCMS: rt=3.06 min, [M+H$^+$]=496

E72: 2-{[(4-{[4-chloro-3-(trifluoromethyl)phenyl]oxy}phenyl)methyl]thio}-5-{[(3S)-3-fluoro-1-pyrrolidinyl]methyl}-4(1H)-pyrimidinone

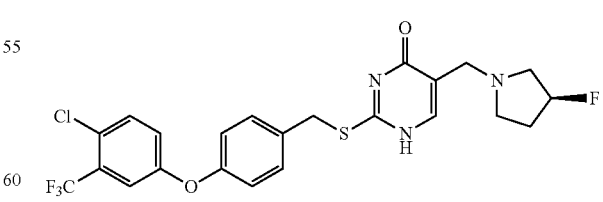

The same procedure as E69 from 2-{[(4-{[4-chloro-3-(trifluoromethyl)phenyl]oxy}phenyl)methyl]thio}-5-(hydroxymethyl)-4(1H)-pyrimidinone (109 mg, 0.246 mmol), DIAD (0.072 mL, 0.369 mmol), triphenylphosphine (97 mg, 0.369 mmol), Hunig's base (0.129 mL, 0.738 mmol) and (3S)-3-fluoropyrrolidine hydrochloride (93 mg, 0.738 mmol)

in dry DMF (3 mL) to afford the title compound (20 mg, 15.81% yield). LCMS: rt=3.07 min, [M+H⁺]=514

E73: 5-({[4-oxo-5-(5-pyrimidinylmethyl)-1,4-dihydro-2-pyrimidinyl]thio}methyl)-2-{[5-(trifluoromethyl)-2-pyridinyl]oxy}benzonitrile

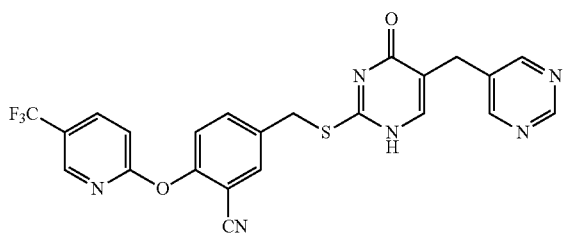

To the suspension of 5-(5-pyrimidinylmethyl)-2-thioxo-2,3-dihydro-4(1H)-pyrimidinone (40 mg, 0.182 mmol) and DIPEA (0.08 mL, 0.458 mmol) in DCM (1 mL) was added 5-(chloromethyl)-2-{[5-(trifluoromethyl)-2-pyridinyl]oxy}) benzonitrile (50 mg, 0.160 mmol). The solution was heated at 60° C. overnight. Purification via reverse phase flash chromatography then afforded the title compound (33 mg, 41.6% yield). LCMS: rt=2.92 min, [M+H⁺]=497

E74: 2-{[(4-{[4-chloro-3-(trifluoromethyl)phenyl]oxy}phenyl)methyl]thio}-5-{[2-(methyloxy)-5-pyrimidinyl]methyl}-4(1H)-pyrimidinone

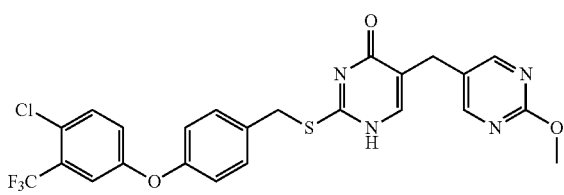

The same procedure as E73 from 5-((2-methoxypyrimidin-5-yl)methyl)-2-thioxo-2,3-dihydropyrimidin-4(1H)-one (2 g, 7.99 mmol), 4-(4-(bromomethyl)phenoxy)-1-chloro-2-(trifluoromethyl)benzene (2.92 g, 7.99 mmol) and diisopropylamine (2.426 g, 23.97 mmol) in DCM (50 mL) to afford the title compound (2.6 g, 58.5% yield) as white solid. LCMS: rt=1.624 min, [M+H⁺]=535, 537.

E75: 2-{[(4-{[4-chloro-3-(trifluoromethyl)phenyl]oxy}phenyl)methyl]thio}-1-methyl-5-{[2-(methyloxy)-5-pyrimidinyl]methyl}-4(1H)-pyrimidinone

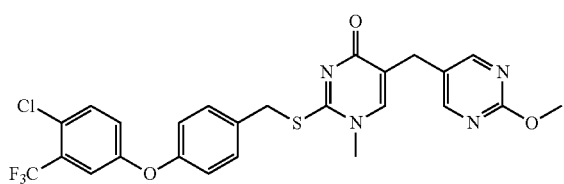 [SMILES: COc1ncc(Cc2cn(C)c(SCc3ccc(Oc4ccc(Cl)c(C(F)(F)F)c4)cc3)nc2=O)cn1]

To a solution of 2-{[(4-{[4-chloro-3-(trifluoromethyl)phenyl]oxy}phenyl)methyl]thio}-5-{[2-(methyloxy)-5-pyrimidinyl]methyl}-4(1H)-pyrimidinone (300 mg, 0.561 mmol) and DIPEA (0.294 mL, 1.682 mmol) in DCM (15 mL) was added MeI (0.053 ml, 0.841 mmol). The mixture was stirred at room temperature overnight. Purification via reverse phase flash chromatography then afforded the title compound (100 mg, 32.5% yield). LCMS: rt=3.49 min, [M+H⁺]=549

E76: 5-[(2-{[(4-{[4-chloro-3-(trifluoromethyl)phenyl]oxy}phenyl)methyl]thio}-4-oxo-1,4-dihydro-5-pyrimidinyl)methyl]-2(1H)-pyrimidinone

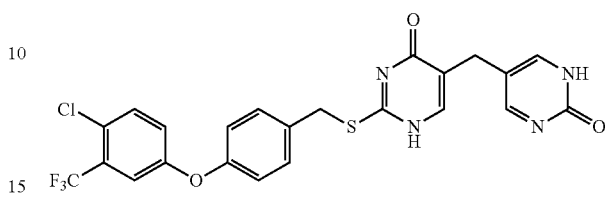

A mixture of 2-{[(4-{[4-chloro-3-(trifluoromethyl)phenyl]oxy}phenyl)methyl]thio)}-5-{[2-(methyloxy)-5-pyrimidinyl]methyl}-4(1H)-pyrimidinone and B-bromocatecholborane (357 mg, 1.795 mmol) in DCM (10 mL) was stirred at room temperature for 24 h. Purification via MDAP then afforded the title compound (24 mg, 25.3% yield). LCMS: rt=3.01 min, [M+H⁺]=521

E77: 2-{[1-(4-{[4-chloro-3-(trifluoromethyl)phenyl]oxy}phenyl)ethyl]thio}-5-[(1-methyl-1H-pyrazol-4-yl)methyl]-4(1H)-pyrimidinone

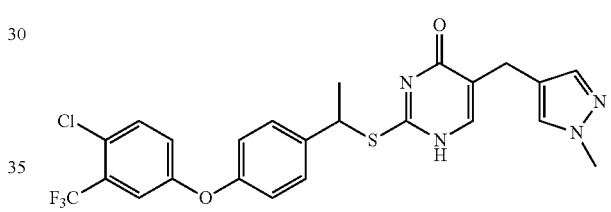

To a suspension of 1-chloro-4-{[4-(1-chloroethyl)phenyl]oxy}-2-(trifluoromethyl)benzene (150 mg, 0.448 mmol) and K₂CO₃ (124 mg, 0.895 mmol) in DMF (3 mL) was added 5-[(1-methyl-1H-pyrazol-4-yl)methyl]-2-thioxo-2,3-dihydro-4(1H)-pyrimidinone (99 mg, 0.448 mmol). The mixture was heated with a microwave reactor at 130° C. for 15 min. Purification via reverse phase flash chromatography and MDAP then afforded the title compound (13 mg, 5.58% yield). LCMS: rt=3.65 min, [M+H⁺]=521

E78: 2-{[4-chloro-3-(trifluoromethyl)phenyl]oxy}-5-({[4-oxo-5-(5-pyrimidinylmethyl)-1,4-dihydro-2-pyrimidinyl]thio}methyl)benzonitrile

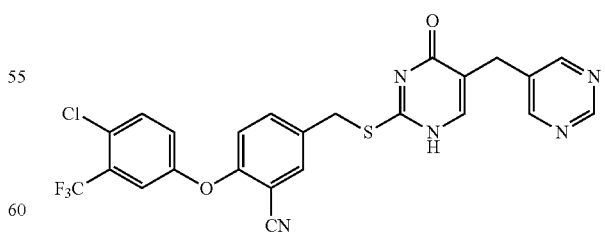

To a suspension of 5-(5-pyrimidinylmethyl)-2-thioxo-2,3-dihydro-4(1H)-pyrimidinone (35.0 mg, 0.159 mmol) and DIPEA (0.08 mL, 0.458 mmol) in DCM (1 mL) was added 2-(4-chloro-3-(trifluoromethyl)phenoxy)-5-(chloromethyl) benzonitrile (50 mg, 0.144 mmol). The solution was heated at 60° C. overnight. Purification via MDAP then afforded the title compound (33 mg, 43.1% yield). LCMS: rt=3.28 min, [M+H⁺]=531

E79: 2-{[4-chloro-3-(trifluoromethyl)phenyl]oxy}-5-({[1-methyl-4-oxo-5-(5-pyrimidinylmethyl)-1,4-dihydro-2-pyrimidinyl]thio}methyl)benzonitrile

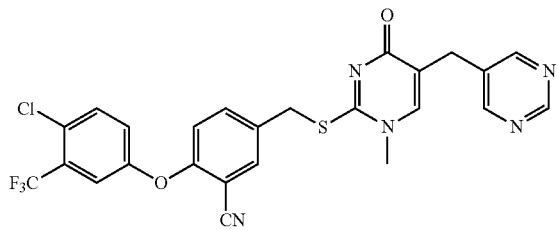 [SMILES: Cn1cc(Cc2cncnc2)c(=O)nc1SCc1ccc(Oc2ccc(Cl)c(C(F)(F)F)c2)c(C#N)c1]

To a solution of 5-(5-pyrimidinylmethyl)-2-thioxo-2,3-dihydro-4(1H)-pyrimidinone (70 mg, 0.318 mmol) and DIPEA (0.083 ml, 0.477 mmol) in DCM (2 ml), was added 5-(chloromethyl)-2-{[4-chloro-3-(trifluoromethyl)phenyl]oxy}benzonitrile (110 mg, 0.318 mmol). The mixture was stirred at 60° C. overnight. After removing the solvent by nitrogen, the residue was dissolved in MeCN (4 ml), and NMP (1.5 ml), and ZnBr₂ (107 mg, 0.477 mmol) and DIPEA (0.083 ml, 0.477 mmol) were added. The mixture was then heated at 60° C. for 10 min. And MeI (0.020 ml, 0.318 mmol) was added dropwise, then stirred at 60° C. for 1.5 h. Purification via MDAP then afforded the title compound (24 mg, 11.49% yield). LCMS: rt=3.20 min, [M+H⁺]=544

E80: 5-(((5-((1-methyl-1H-pyrazol-4-yl)methyl)-4-oxo-1,4-dihydropyrimidin-2-yl)thio)methyl)-2-((5-(trifluoromethyl)pyridin-2-yl)oxy)benzonitrile

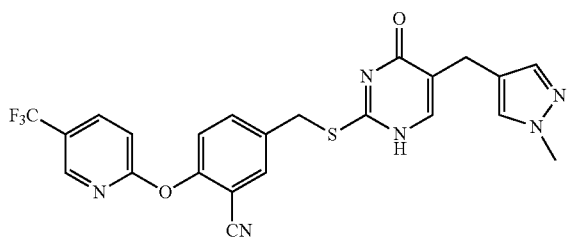 [SMILES: Cn1cc(Cc2c[nH]c(SCc3ccc(Oc4ccc(C(F)(F)F)cn4)c(C#N)c3)nc2=O)cn1]

To a solution of 5-(chloromethyl)-2-{[5-(trifluoromethyl)-2-pyridinyl]oxy}benzonitrile (97 mg, 0.310 mmol) and 5-[(1-methyl-1H-pyrazol-4-yl)methyl]-2-thioxo-2,3-dihydro-4(1H)-pyrimidinone (76 mg, 0.341 mmol) in chloroform (2 mL) was added dropwise DIPEA (0.163 mL, 0.931 mmol) at 0° C. The mixture was heated at 60° C. for 2 h. Purification via reverse phase flash chromatography then afforded the title compound (65 mg, 42.0% yield). LCMS: rt=2.98 min, [M+H⁺]=499

E81: 2-(4-chloro-3-(trifluoromethyl)phenoxy)-5-(((5-((1-methyl-1H-indol-3-yl)methyl)-4-oxo-1,4-dihydropyrimidin-2-yl)thio)methyl)benzonitrile

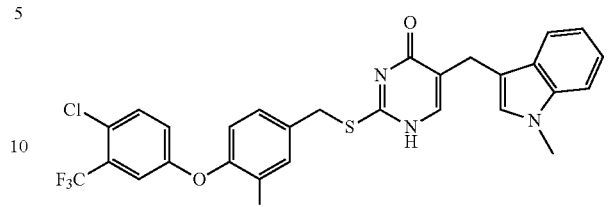

The same procedure as E80 from 5-[(1-methyl-1H-indol-3-yl)methyl]-2-thioxo-2,3-dihydro-4(1H)-pyrimidinone (50 mg, 0.184 mmol), 2-(4-chloro-3-(trifluoromethyl)phenoxy)-5-(chloromethyl)benzonitrile (77 mg, 0.221 mmol) and DIPEA (0.097 mL, 0.553 mmol) in chloroform (2 mL) was added to afford the title compound (76 mg, 71.0% yield). LCMS: rt=3.99 min, [M+H⁺]=581

E82: 2-(4-chloro-3-(trifluoromethyl)phenoxy)-5-(((1-methyl-5-((1-methyl-1H-indol-3-yl)methyl)-4-oxo-1,4-dihydropyrimidin-2-yl)thio)methyl)benzonitrile

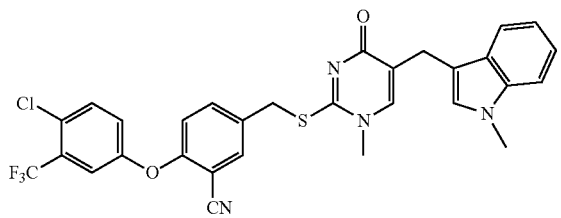 [SMILES: Cn1cc(Cc2cn(C)c3ccccc23)c(=O)nc1SCc1ccc(Oc2ccc(Cl)c(C(F)(F)F)c2)c(C#N)c1]

To a solution of 2-{[4-chloro-3-(trifluoromethyl)phenyl]oxy}-5-[({5-[(1-methyl-1H-indol-3-yl)methyl]-4-oxo-1,4-dihydro-2-pyrimidinyl}thio)methyl]benzonitrile (60 mg, 0.103 mmol), DIPEA (0.054 mL, 0.310 mmol) and zinc bromide (23.26 mg, 0.103 mmol) in chloroform (2 mL) was added MeI (0.013 mL, 0.207 mmol). The mixture was heated at 60° C. for 1 h. Purification via reverse phase flash chromatography then afforded the title compound (8.3 mg, 13.51% yield). LCMS: rt=3.78 min, [M+H⁺]=595

E83: 2-{[4-chloro-3-(trifluoromethyl)phenyl]oxy}-5-{[(5-ethyl-4-oxo-1,4-dihydro-2-pyrimidinyl)thio]methyl}benzonitrile

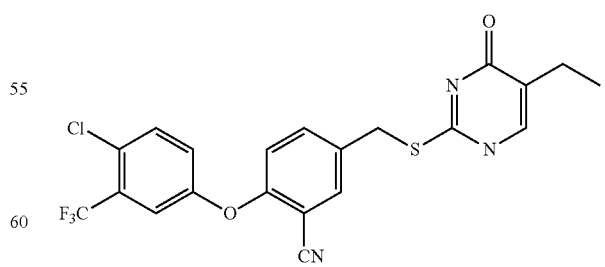

The same procedure as E63 from 2-(4-chloro-3-(trifluoromethyl)phenoxy)-5-(chloromethyl)benzonitrile (450 mg, 1.300 mmol), 5-ethyl-2-thioxo-2,3-dihydro-4(1H)-pyrimidinone (305 mg, 1.950 mmol) and DIPEA (0.303 mL, 1.735 mmol) in DCE (3 mL) to afford the title compound (140 mg, 0.301 mmol, 23.11% yield). LCMS: rt=3.68 min, [M+H⁺]= 466

E84: 2-{[4-chloro-3-(trifluoromethyl)phenyl]oxy}-5-{[(5-{[2-(methyloxy)-5-pyrimidinyl]methyl}-4-oxo-1,4-dihydro-2-pyrimidinyl)thio]methyl}benzonitrile

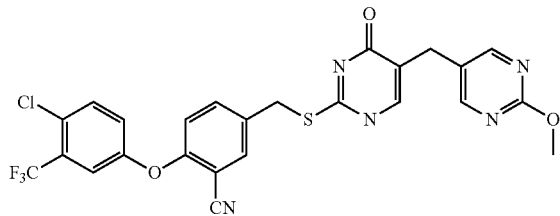 [SMILES: COc1ncc(Cc2c[nH]c(SCc3ccc(Oc4ccc(Cl)c(C(F)(F)F)c4)c(C#N)c3)nc2=O)cn1]

The same procedure as E63 from 2-(4-chloro-3-(trifluoromethyl)phenoxy)-5-(chloromethyl)benzonitrile (200 mg, 0.578 mmol), 5-{[2-(methyloxy)-5-pyrimidinyl]methyl}-2-thioxo-2,3-dihydro-4(1H)-pyrimidinone (174 mg, 0.693 mmol) and DIPEA (0.303 mL, 1.733 mmol) in DCE (3.0 mL), except that the reaction time was prolonged to 1.5 h, to afford the title compound (70 mg, 21.64% yield). LCMS: rt=3.44 min, [M+H⁺]=560

E85: 2-{[4-chloro-3-(trifluoromethyl)phenyl]oxy}-5-{[(1-methyl-5-{[2-(methyloxy)-5-pyrimidinyl]methyl}-4-oxo-1,4-dihydro-2-pyrimidinyl)thio]methyl}benzonitrile

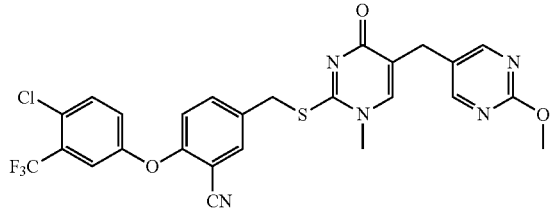 [SMILES: COc1ncc(Cc2cn(C)c(SCc3ccc(Oc4ccc(Cl)c(C(F)(F)F)c4)c(C#N)c3)nc2=O)cn1]

To a solution of 2-{[4-chloro-3-(trifluoromethyl)phenyl]oxy}-5-{[(5-{[2-(methyloxy)-5-pyrimidinyl]methyl}-4-oxo-1,4-dihydro-2-pyrimidinyl)thio]methyl}benzonitrile (100 mg, 0.179 mmol) and Hunig's base (0.062 mL, 0.357 mmol) in DCM (3 mL) was added MeI (0.013 mL, 0.214 mmol). The mixture was stirred at room temperature overnight, and quenched by ice water. Purification via MDAP afforded the title compound (8 mg, 7.80% yield). LCMS: rt=3.29 min, [M+H⁺]=575

E86: 2-(4-fluoro-3-(trifluoromethyl)phenoxy)-5-(((5-((1-methyl-1H-pyrazol-4-yl)methyl)-4-oxo-1,4-dihydropyrimidin-2-yl)thio)methyl)benzonitrile, trifluoroacetic acid salt

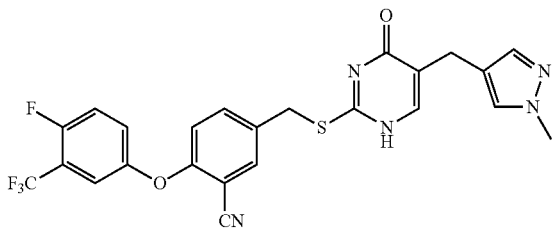 [SMILES: Cn1cc(Cc2c[nH]c(SCc3ccc(Oc4ccc(F)c(C(F)(F)F)c4)c(C#N)c3)nc2=O)cn1]

The same procedure as E58 from 5-[(1-methyl-1H-pyrazol-4-yl)methyl]-2-thioxo-2,3-dihydro-4(1H)-pyrimidinone (234 mg, 1.054 mmol), 5-(chloromethyl)-2-{[4-fluoro-3-(trifluoromethyl)phenyl]oxy}benzonitrile (386 mg, 1.171 mmol) and DIPEA (1.022 mL, 5.85 mmol) in chloroform (2 mL) to afford the title compound (152 mg, 0.241 mmol, 20.62% yield). LCMS: rt=3.19 min, [M+H⁺]=516

E87: 2-{[4-fluoro-3-(trifluoromethyl)phenyl]oxy}-5-({[4-oxo-5-(5-pyrimidinylmethyl)-1,4-dihydro-2-pyrimidinyl]thio}methyl)benzonitrile

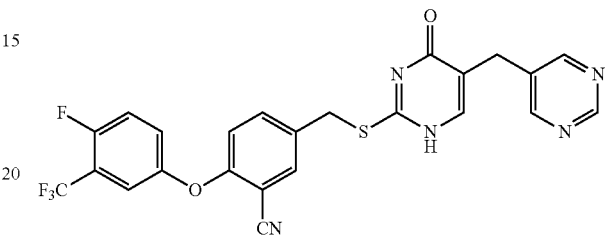

To a suspension of 5-(5-pyrimidinylmethyl)-2-thioxo-2,3-dihydro-4(1H)-pyrimidinone (38 mg, 0.173 mmol) and DIPEA (0.079 mL, 0.455 mmol) in DCM (1 mL), was added 5-(chloromethyl)-2-{[4-fluoro-3-(trifluoromethyl)phenyl]oxy}benzonitrile (50 mg, 0.152 mmol). The solution was heated at 60° C. overnight. Purification via MDAP then afforded the title compound (30 mg, 38.5% yield). LCMS: rt=3.14 min, [M+H⁺]=514

E88: 2-{[4-fluoro-3-(trifluoromethyl)phenyl]oxy}-5-({[1-methyl-4-oxo-5-(5-pyrimidinylmethyl)-1,4-dihydro-2-pyrimidinyl]thio}methyl)benzonitrile

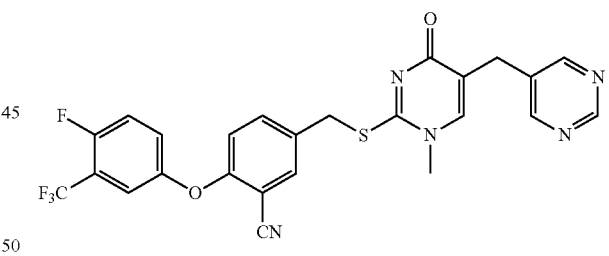

To a solution of 5-(5-pyrimidinylmethyl)-2-thioxo-2,3-dihydro-4(1H)-pyrimidinone (70 mg, 0.318 mmol) and DIPEA (0.083 ml, 0.477 mmol) in DCM (2 mL) was added 5-(chloromethyl)-2-{[4-fluoro-3-(trifluoromethyl)phenyl]oxy}benzonitrile (105 mg, 0.318 mmol). The reaction mixture was heated at 60° C. overnight. After removing the solvent by nitrogen, the residue was dissolved in MeCN (4 ml), and NMP (1.5 mL), and ZnBr₂ (107 mg, 0.477 mmol) and DIPEA (0.083 mL, 0.477 mmol) were added. The mixture was then stirred at 60° C. for 10 min. And MeI (0.020 mL, 0.318 mmol) was added dropwise, then stirred at 60° C. for 1.5 h. Purification via MDAP then afforded the title compound (25 mg, 12.28% yield). LCMS: rt=3.07 min, [M+H⁺]=528

E89: 2-{[4-fluoro-3-(trifluoromethyl)phenyl]oxy}-5-{[(5-{[2-(methyloxy)-5-pyrimidinyl]methyl}-4-oxo-1,4-dihydro-2-pyrimidinyl)thio]methyl}benzonitrile

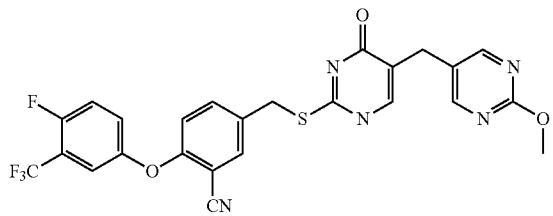 [SMILES: COc1ncc(Cc2c[nH]c(SCc3ccc(Oc4ccc(F)c(C(F)(F)F)c4)c(C#N)c3)nc2=O)cn1]

The same procedure as E63 from 5-(chloromethyl)-2-{[4-fluoro-3-(trifluoromethyl)phenyl]oxy}benzonitrile (198 mg, 0.599 mmol), 5-{[2-(methyloxy)-5-pyrimidinyl]methyl}-2-thioxo-2,3-dihydro-4(1H)-pyrimidinone (150 mg, 0.599 mmol) and $K_2CO_3$ (166 mg, 1.199 mmol) in DMF (3 mL), except that the reaction time was prolonged to 1.5 h, to afford the title compound (108 mg, 33.2% yield). LCMS: rt=3.32 min, [M+H+]=544

E90: 2-{[4-fluoro-3-(trifluoromethyl)phenyl]oxy}-5-{[(1-methyl-5-{[2-(methyloxy)-5-pyrimidinyl]methyl}-4-oxo-1,4-dihydro-2-pyrimidinyl)thio]methyl}benzonitrile

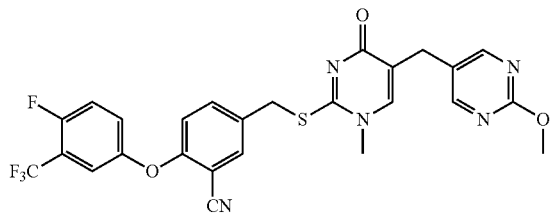 [SMILES: COc1ncc(Cc2cn(C)c(SCc3ccc(Oc4ccc(F)c(C(F)(F)F)c4)c(C#N)c3)nc2=O)cn1]

The same procedure as E85 from 2-{[4-fluoro-3-(trifluoromethyl)phenyl]oxy}-5-{[(5-{[2-(methyloxy)-5-pyrimidinyl]methyl}-4-oxo-1,4-dihydro-2-pyrimidinyl)thio]methyl}benzonitrile (100 mg, 0.184 mmol), Hunig's base (0.064 mL, 0.368 mmol) and MeI (0.014 mL, 0.221 mmol) in DCM (4 mL) to afford the title compound (8 mg, 7.80% yield). LCMS: rt=3.29 min, [M+H+]=575

E91: 2-[({4-[(4-chloro-2-pyridinyl)oxy]phenyl}methyl)thio]-5-[(1-methyl-1H-pyrazol-4-yl)methyl]-4(1H)-pyrimidinone

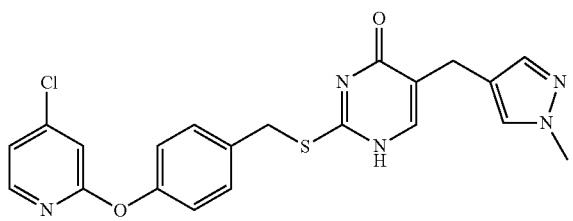 [SMILES: Cn1cc(Cc2cn(C)c(SCc3ccc(Oc4cc(Cl)ccn4)cc3)nc2=O)cn1]

To a solution of 4-[(4-chloro-2-pyridinyl)oxy]benzaldehyde (120 mg, 0.514 mmol), (which may be prepared according to procedures described in the International Patent Application Publication No. WO 199847869) in methanol (2.0 mL) was added $NaBH_4$ (23.32 mg, 0.616 mmol). After the suspended solution turned clear, it was quenched with water. The mixture was extracted with EA and concentrated. After removing the solvent, thionyl chloride (0.187 mL, 2.57 mmol) and DCM (2 mL) was added, and stirring continued overnight. Then 5-[(1-methyl-1H-pyrazol-4-yl)methyl]-2-thioxo-2,3-dihydro-4(1H)-pyrimidinone (114 mg, 0.514 mmol) was added. The reaction mixture was heated at 60° C. for 0.5 h. Purification via MDAP then afforded the title compound (132 mg, 58.4% yield). LCMS: rt=2.84 min, [M+H+]=440

E92: 5-[2-({1-methyl-5-[(1-methyl-1H-pyrazol-4-yl)methyl]-4-oxo-1,4-dihydro-2-pyrimidinyl}thio)ethyl]-2-{[3-(trifluoromethyl)phenyl]oxy}benzonitrile, trifluoroacetic acid salt

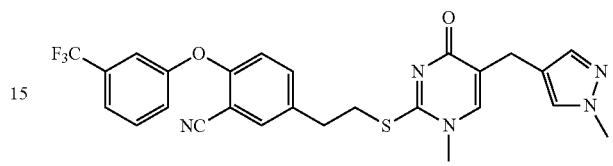

To a solution of 5-[2-({5-[(1-methyl-1H-pyrazol-4-yl)methyl]-4-oxo-1,4-dihydro-2-pyrimidinyl}thio)ethyl]-2-{[3-(trifluoromethyl)phenyl]oxy}benzonitrile (81 mg, 0.158 mmol) and DIPEA (0.083 mL, 0.475 mmol) in DCM (2 mL) was added MeI (0.012 mL, 0.190 mmol). The reaction mixture was heated at 60° C. for 0.5 h. Purification via MDAP then afforded the title compound (12.8 mg, 12.64% yield). LCMS: rt=3.09 min, [M+H+]=526

E93: 2-[({4-[(4-chloro-2-pyridinyl)oxy]phenyl}methyl)thio]-1-methyl-5-[(1-methyl-1H-pyrazol-4-yl)methyl]-4(1H)-pyrimidinone

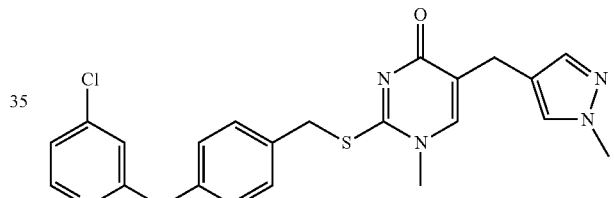

The same procedure as E92 from 2-[({4-[(4-chloro-2-pyridinyl)oxy]phenyl}methyl)thio]-5-[(1-methyl-1H-pyrazol-4-yl)methyl]-4(1H)-pyrimidinone (100 mg, 0.227 mmol), DIPEA (0.199 mL, 1.137 mmol) and MeI (0.017 mL, 0.273 mmol) in DCM (2 mL) to afford the title compound (17.1 mg, 0.038 mmol, 16.57% yield). LCMS: rt=2.66 min, [M+H]=454

E94: 5-(((5-((1-methyl-1H-pyrazol-4-yl)methyl)-4-oxo-1,4-dihydropyrimidin-2-yl)thio)methyl)-2-(3-(trifluoromethyl)phenoxy)benzonitrile, trifluoroacetic acid salt

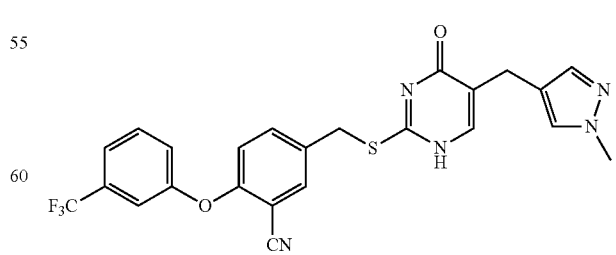

The same procedure as E58 from 5-[(1-methyl-1H-pyrazol-4-yl)methyl]-2-thioxo-2,3-dihydro-4(1H)-pyrimidinone (128 mg, 0.578 mmol), 5-(chloromethyl)-2-{[3-(trifluoromethyl)phenyl]oxy}benzonitrile (200 mg, 0.642 mmol) and DIPEA (0.336 mL, 1.925 mmol) in Chloroform (2 mL) to afford the title compound (104 mg, 26.5% yield). LCMS: rt=3.17 min, [M+H+]=498

E95: 5-(((1-methyl-5-((1-methyl-1H-pyrazol-4-yl) methyl)-4-oxo-1,4-dihydropyrimidin-2-yl)thio)methyl)-2-(3-(trifluoromethyl)phenoxy)benzonitrile, trifluoroacetic acid salt

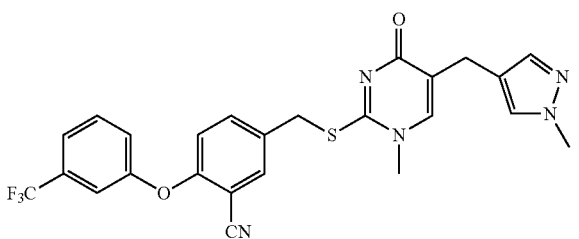 [SMILES: Cn1cc(Cc2cn(C)c(SCc3ccc(Oc4cccc(C(F)(F)F)c4)c(C#N)c3)nc2=O)cn1]

To a solution of 5-[({5-[(1-methyl-1H-pyrazol-4-yl)methyl]-4-oxo-1,4-dihydro-2-pyrimidinyl}thio)methyl]-2-{[3-(trifluoromethyl)phenyl]oxy}benzonitrile (85 mg, 0.171 mmol) and DIPEA (0.090 mL, 0.513 mmol) in DCE (2 mL) was added MeI (0.021 mL, 0.342 mmol). The mixture was heated at 60° C. for 1 h. Purification via MDAP then afforded the title compound (35 mg, 32.7% yield). LCMS: rt=3.03 min, [M+H+]=512

E96: 5-({[4-oxo-5-(5-pyrimidinylmethyl)-1,4-dihydro-2-pyrimidinyl]thio}methyl)-2-{[3-(trifluoromethyl)phenyl]oxy}benzonitrile

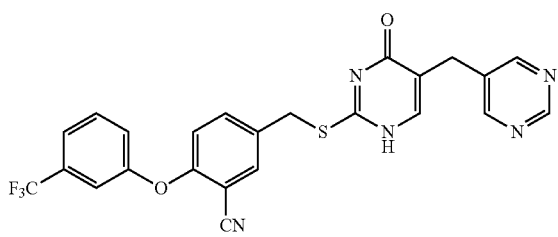

To a suspension of 5-(5-pyrimidinylmethyl)-2-thioxo-2,3-dihydro-4(1H)-pyrimidinone (38.9 mg, 0.176 mmol) and DIPEA (0.08 mL, 0.458 mmol) in DCM (1 mL) was added 5-(chloromethyl)-2-{[3-(trifluoromethyl)phenyl]oxy})benzonitrile (50 mg, 0.160 mmol). The solution was heated at 60° C. overnight. Purification via MDAP then afforded the title compound (36 mg, 45.3% yield). LCMS: rt=3.11 min, [M+H+]=496

E97: 5-({[1-methyl-4-oxo-5-(5-pyrimidinylmethyl)-1,4-dihydro-2-pyrimidinyl]thio}methyl)-2-{[3-(trifluoromethyl)phenyl]oxy}benzonitrile

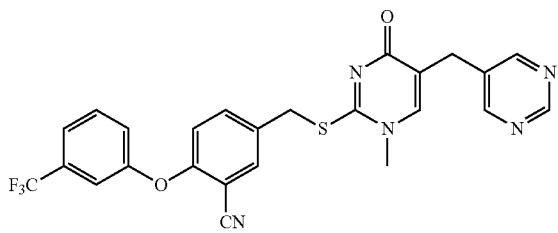

To a solution of 5-(5-pyrimidinylmethyl)-2-thioxo-2,3-dihydro-4(1H)-pyrimidinone (70.7 mg, 0.321 mmol) and DIPEA (0.084 ml, 0.481 mmol) in DCM (2 ml) was added 5-(chloromethyl)-2-{[3-(trifluoromethyl)phenyl]oxy}benzonitrile (100 mg, 0.321 mmol). The reaction mixture was heated at 60° C. overnight. After removing the solvent by nitrogen, the residue was dissolved in MeCN (4 ml), and NMP (1.5 ml), and ZnBr₂ (107 mg, 0.477 mmol) and DIPEA (0.083 ml, 0.477 mmol) were added. The mixture was then stirred at 60° C. for 10 min. And MeI (0.022 mL, 0.353 mmol) was added dropwise, then stirred at 60° C. for 1.5 h. Purification via MDAP then afforded the title compound (16 mg, 8.01% yield). LCMS: rt=2.96 min, [M+H+]=510

E98: 5-{[(5-ethyl-4-oxo-1,4-dihydro-2-pyrimidinyl)thio]methyl}-2-{[3-(trifluoromethyl)phenyl]oxy}benzonitrile

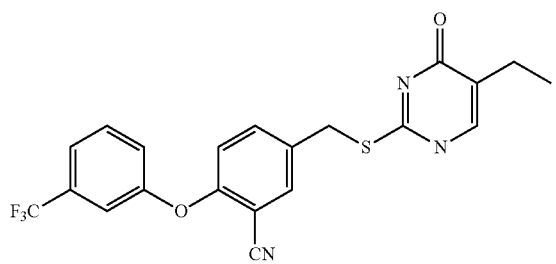 [SMILES: CCc1c[nH]c(SCc2ccc(Oc3cccc(C(F)(F)F)c3)c(C#N)c2)nc1=O]

The same procedure as E63 from 5-(chloromethyl)-2-{[3-(trifluoromethyl)phenyl]oxy}benzonitrile (200 mg, 0.642 mmol), 5-ethyl-2-thioxo-2,3-dihydro-4(1H)-pyrimidinone (150 mg, 0.962 mmol) and DIPEA (0.280 mL, 1.603 mmol) in DCE (3.0 mL) to afford the title compound (140 mg, 0.325 mmol, 50.6% yield). LCMS: rt=3.51 min, [M+H+]=432

E99: 5-{[(5-ethyl-1-methyl-4-oxo-1,4-dihydro-2-pyrimidinyl)thio]methyl}-2-{[3-(trifluoromethyl)phenyl]oxy}benzonitrile

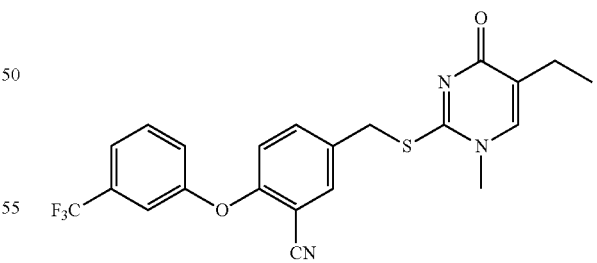

The same procedure as E64 from 5-{[(5-ethyl-4-oxo-1,4-dihydro-2-pyrimidinyl)thio]methyl}-2-{[3-(trifluoromethyl)phenyl]oxy})benzonitrile (250 mg, 0.579 mmol), DIPEA (0.202 mL, 1.159 mmol) and MeI (0.054 mL, 0.869 mmol) in DCM (2 mL). to afford the title compound (100 mg, 38.7% yield). LCMS: rt=3.25 min, [M+H+]=446

E100: 5-{[(5-{[2-(methyloxy)-5-pyrimidinyl]methyl}-4-oxo-1,4-dihydro-2-pyrimidinyl)thio]methyl}-2-{[3-(trifluoromethyl)phenyl]oxy}benzonitrile

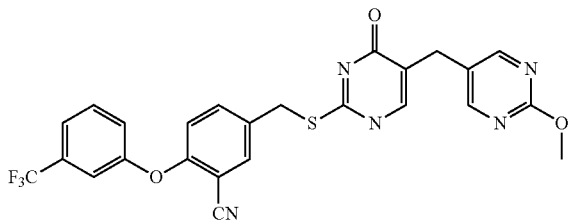 [SMILES: COc1ncc(Cc2c[nH]c(SCc3ccc(Oc4cccc(C(F)(F)F)c4)c(C#N)c3)nc2=O)cn1]

The same procedure as E63 from 5-(chloromethyl)-2-{[3-(trifluoromethyl)phenyl]oxy}benzonitrile (224 mg, 0.719 mmol), 5-{[2-(methyloxy)-5-pyrimidinyl]methyl}-2-thioxo-2,3-dihydro-4(1H)-pyrimidinone (150 mg, 0.599 mmol) and DIPEA (0.209 mL, 1.199 mmol) in DCE (3.0 mL), except that the reaction time was prolonged to 1.5 h, to afford the title compound (35 mg, 11.11% yield). LCMS: rt=3.30 min, [M+H$^+$]=526

E101: Methyl 3-(2-{[(3-cyano-4-{[3-(trifluoromethyl)phenyl]oxy}phenyl)methyl]thio}-4-oxo-1,4-dihydro-5-pyrimidinyl)propanoate

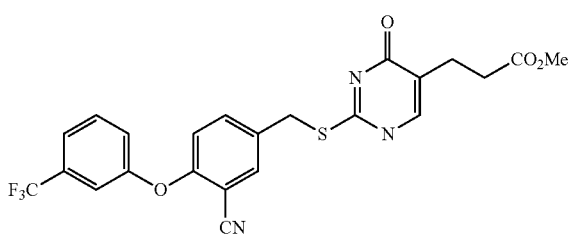 [SMILES: COC(=O)CCc1c[nH]c(SCc2ccc(Oc3cccc(C(F)(F)F)c3)c(C#N)c2)nc1=O]

A mixture of 5-(chloromethyl)-2-(3-(trifluoromethyl)phenoxy)benzonitrile (286 mg, 0.919 mmol), methyl 3-(4-oxo-2-thioxo-1,2,3,4-tetrahydro-5-pyrimidinyl)propanoate (164 mg, 0.765 mmol) and DIPEA (0.267 mL, 1.531 mmol) in DCE (2 mL) was heated with a microwave reactor at 80° C. for 0.5 h. Purification via reverse phase flash chromatography then afforded the title compound (35 mg, 9.34% yield). LCMS: rt=3.38 min, [M+H$^+$]=490

E102: 2-((3-methoxy-4-(3-(trifluoromethyl)phenoxy)benzyl)thio)-5-((1-methyl-1H-pyrazol-4-yl)methyl)pyrimidin-4(1H)-one

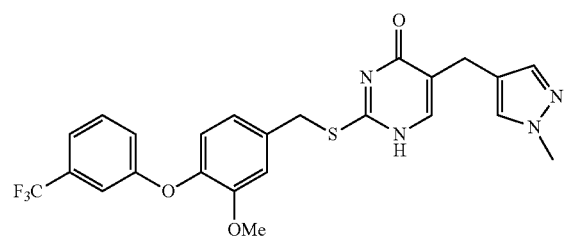 [SMILES: COc1cc(CSc2nc(=O)c(Cc3cnn(C)c3)c[nH]2)ccc1Oc1cccc(C(F)(F)F)c1]

A mixture of (3-(methyloxy)-4-{[3-(trifluoromethyl)phenyl]oxy}phenyl)methanol (200 mg, 0.671 mmol) and thionyl chloride (0.657 mL, 9.00 mmol) in Chloroform (2 mL) was stirred at room temperature for 2 h. After removing the solvent and excess thionyl chloride, a solution of 5-[(1-methyl-1H-pyrazol-4-yl)methyl]-2-thioxo-2,3-dihydro-4(1H)-pyrimidinone (100 mg, 0.450 mmol) and DIPEA (0.393 mL, 2.250 mmol) in chloroform (2 mL) was added into the mixture. The mixture was heated at 60° C. for 1 h. Purification via reverse phase flash chromatography then afforded the title compound (103 mg, 45.6% yield). LCMS: rt=3.29 min, [M+H$^+$]=503

E103: 2-((3-methoxy-4-(3-(trifluoromethyl)phenoxy)benzyl)thio)-5-((1-methyl-1H-pyrazol-4-yl)methyl)pyrimidin-4(1H)-one, trifluoroacetic acid salt

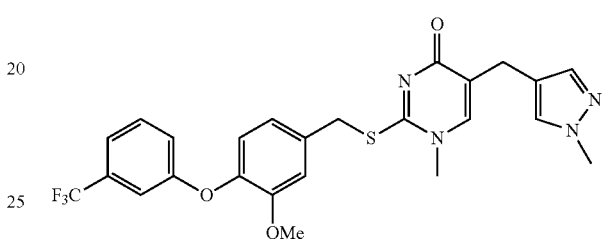

To a solution of 2-{[(3-(methyloxy)-4-{[3-(trifluoromethyl)phenyl]oxy}phenyl)methyl]thio}-5-[(1-methyl-1H-pyrazol-4-yl)methyl]-4(1H)-pyrimidinone (72 mg, 0.143 mmol), DIPEA (0.075 mL, 0.430 mmol) and ZnBr$_2$ (32.3 mg, 0.143 mmol) in chloroform (2 mL) was added MeI (0.018 mL, 0.287 mmol). The mixture was heated at 60° C. for 1 h. Purification via reverse phase flash chromatography then afforded the title compound (26 mg, 0.041 mmol, 28.8% yield). LCMS: rt=3.16 min, [M+H$^+$]=517

E104: 5-{[2-(methyloxy)-5-pyrimidinyl]methyl}-2-{[(3-(trifluoromethyl)-4-{[3-(trifluoromethyl)phenyl]oxy}phenyl)methyl]thio}-4(1H)-pyrimidinone

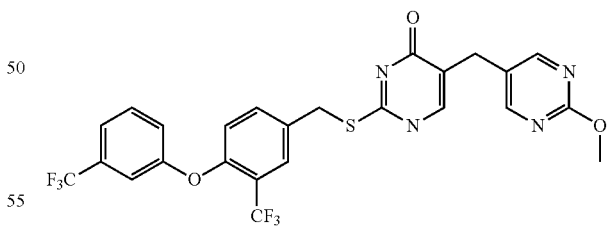

The same procedure as E63 from 4-(chloromethyl)-2-(trifluoromethyl)-1-{[3-(trifluoromethyl)phenyl]oxy})benzene (425 mg, 1.199 mmol), 5-{[2-(methyloxy)-5-pyrimidinyl]methyl}-2-thioxo-2,3-dihydro-4(1H)-pyrimidinone (200 mg, 0.799 mmol) and DIPEA (0.279 mL, 1.598 mmol) in DCE (3.0 mL), except that the reaction time was prolonged to 1.5 h, to afford the title compound (20 mg, 4.40% yield). LCMS: rt=3.66 min, [M+H$^+$]=569

E105: 5-({[1-methyl-4-oxo-5-(5-pyrimidinylmethyl)-1,4-dihydro-2-pyrimidinyl]thio}methyl)-2-{[5-(trifluoromethyl)-2-pyridinyl]oxy}benzonitrile

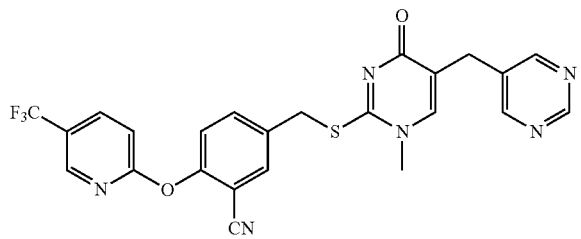 [SMILES: Cn1cc(Cc2cncnc2)c(=O)nc1SCc1ccc(Oc2ccc(C(F)(F)F)cn2)c(C#N)c1]

To a solution of 5-(5-pyrimidinylmethyl)-2-thioxo-2,3-dihydro-4(1H)-pyrimidinone (40 mg, 0.182 mmol) and DIPEA (0.095 mL, 0.545 mmol) in DCM (2 mL) was added 5-(chloromethyl)-2-{[5-(trifluoromethyl)-2-pyridinyl]oxy})benzonitrile (60 mg, 0.192 mmol). The solution was heated at 60° C. overnight. To the solution, was added MeI (0.017 ml, 0.272 mmol). The mixture was stirred at rt overnight. Purification via MDAP then afforded the title compound (7 mg, 6.18% yield). LCMS: rt=2.80 min, [M+H⁺]=511

E106: 5-[2-({5-[(1-methyl-1H-pyrazol-4-yl)methyl]-4-oxo-1,4-dihydro-2-pyrimidinyl}thio)ethyl]-2-{[3-(trifluoromethyl)phenyl]oxy}benzonitrile

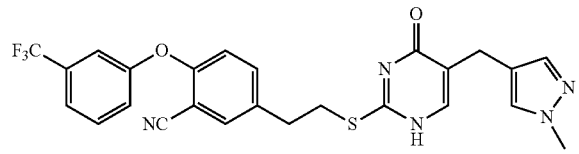 [SMILES: Cn1cc(Cc2c[nH]c(SCCc3ccc(Oc4cccc(C(F)(F)F)c4)c(C#N)c3)nc2=O)cn1]

To a solution of 5-[(1-methyl-1H-pyrazol-4-yl)methyl]-2-thioxo-2,3-dihydro-4(1H)-pyrimidinone (128 mg, 0.575 mmol) and 5-(2-iodoethyl)-2-{[3-(trifluoromethyl)phenyl]oxy}benzonitrile (200 mg, 0.479 mmol) in DCM (2 mL) was added DIPEA (0.251 mL, 1.438 mmol). The reaction mixture was heated at 60° C. for 0.5 h. Purification via reverse phase flash chromatography then afforded the title compound (105 mg, 42.8% yield). LCMS: rt=3.24 min, [M+H⁺]=512

E107: 5-(2-{[4-oxo-5-(5-pyrimidinylmethyl)-1,4-dihydro-2-pyrimidinyl]thio}ethyl)-2-{[3-(trifluoromethyl)phenyl]oxy}benzonitrile

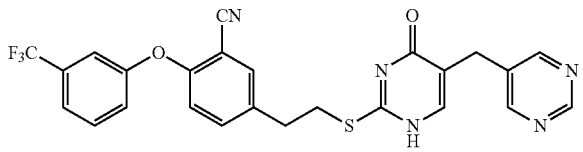 [SMILES: N#Cc1cc(CCSc2nc(=O)c(Cc3cncnc3)c[nH]2)ccc1Oc1cccc(C(F)(F)F)c1]

A mixture of 5-(2-iodoethyl)-2-{[3-(trifluoromethyl)phenyl]oxy})benzonitrile (200 mg, 0.479 mmol), 5-(5-pyrimidinylmethyl)-2-thioxo-2,3-dihydro-4(1H)-pyrimidinone (116 mg, 0.527 mmol), and K₂CO₃ (133 mg, 0.959 mmol) in DMF (3 mL) was heated with a microwave reactor at 130° C. for 10 min. Purification via reverse phase flash chromatography then afforded the title compound (134 mg, 54.9% yield). LCMS: rt=3.19 min, [M+H⁺]=510

E108: 2-{[2-(4-{[4-chloro-3-(trifluoromethyl)phenyl]oxy}phenyl)ethyl]thio}-5-{[2-(methyloxy)-5-pyrimidinyl]methyl}-4(1H)-pyrimidinone

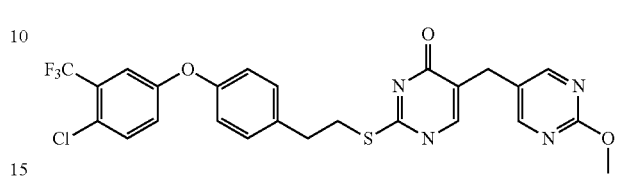

A mixture of 1-chloro-4-{[4-(2-iodoethyl)phenyl]oxy}-2-(trifluoromethyl)benzene (400 mg, 0.938 mmol), 5-{[2-(methyloxy)-5-pyrimidinyl]methyl}-2-thioxo-2,3-dihydro-4(1H)-pyrimidinone (258 mg, 1.031 mmol) and K₂CO₃ (259 mg, 1.875 mmol) in DMF (3 mL) was heated with a microwave reactor at 50° C. for 15 min. Purification via reverse phase flash chromatography then afforded the title compound (44 mg, 0.080 mmol, 8.55% yield). LCMS: rt=3.76 min, [M+H⁺]=549

E109: 5-{2-[(5-{[2-(methyloxy)-5-pyrimidinyl]methyl}-4-oxo-1,4-dihydro-2-pyrimidinyl)thio]ethyl}-2-{[3-(trifluoromethyl)phenyl]oxy}benzonitrile

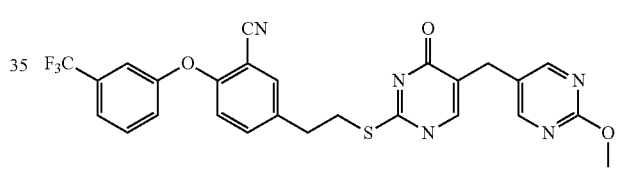

The same procedure as E108 from 5-(2-iodoethyl)-2-{[3-(trifluoromethyl)phenyl]oxy}benzonitrile (200 mg, 0.479 mmol), 5-{[2-(methyloxy)-5-pyrimidinyl]methyl}-2-thioxo-2,3-dihydro-4(1H)-pyrimidinone (144 mg, 0.575 mmol) and K₂CO₃ (133 mg, 0.959 mmol) in DMF (3 mL) to afford the title compound (120 mg, 46.4% yield). LCMS: rt=3.35 min, [M+H⁺]=540

E110: 2-{[2-(4-{[4-chloro-3-(trifluoromethyl)phenyl]oxy}phenyl)ethyl]thio}-1-methyl-5-{[2-(methyloxy)-5-pyrimidinyl]methyl}-4(1H)-pyrimidinone

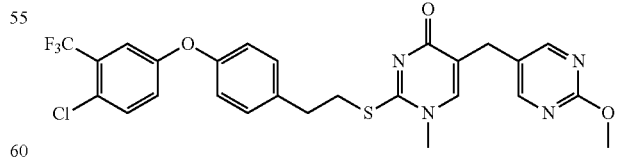

To a suspension of 2-{[2-(4-{[4-chloro-3-(trifluoromethyl)phenyl]oxy}phenyl)ethyl]thio}-5-{[2-(methyloxy)-5-pyrimidinyl]methyl}-4(1H)-pyrimidinone (135 mg, 0.246 mmol) and Hunig's base (0.086 ml, 0.492 mmol) in DCM (3 mL). was added MeI (0.020 ml, 0.320 mmol). The mixture was stirred at room temperature for 3 h, and quenched with water. Purification via reverse phase flash chromatography then afforded the title compound (20 mg, 12.01% yield). LCMS: rt=3.60 min, [M+H⁺]=563

E111: 5-{2-[(l-methyl-5-{[2-(methyloxy)-5-pyrimidinyl]methyl}-4-oxo-1,4-dihydro-2-pyrimidinyl)thio]ethyl}-2-{[3-(trifluoromethyl)phenyl]oxy}benzonitrile

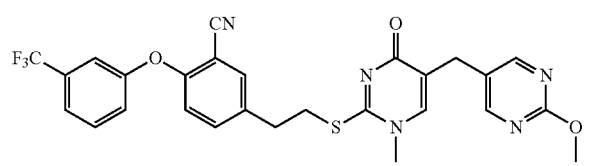 [SMILES: COc1ncc(Cc2cn(C)c(SCCc3ccc(Oc4cccc(C(F)(F)F)c4)c(C#N)c3)nc2=O)cn1]

The same procedure as E110 from 5-{2-[(5-{[2-(methyloxy)-5-pyrimidinyl]methyl}-4-oxo-1,4-dihydro-2-pyrimidinyl)thio]ethyl}-2-{[3-(trifluoromethyl)phenyl]oxy})benzonitrile (130 mg, 0.241 mmol), Hunig's base (0.084 ml, 0.482 mmol) and MeI (0.01959 ml, 0.313 mmol) in DCM (3 mL) to afford the title compound (18 mg, 11.19% yield). LCMS: rt=3.22 min, [M+H⁺]=554

E112: 2-((4-(4-chloro-3-(trifluoromethyl)phenoxy)phenethyl)thio)-5-((l-methyl-1H-pyrazol-4-yl)methyl)pyrimidin-4(1H)-one

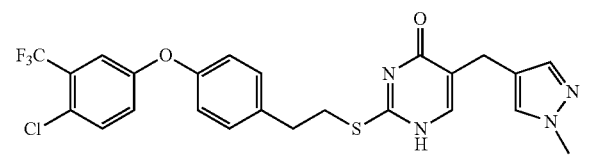 [SMILES: Cn1cc(Cc2c[nH]c(SCCc3ccc(Oc4ccc(Cl)c(C(F)(F)F)c4)cc3)nc2=O)cn1]

A mixture of 5-[(1-methyl-1H-pyrazol-4-yl)methyl]-2-thioxo-2,3-dihydro-4(1H)-pyrimidinone (98 mg, 0.442 mmol), 4-chloro-3-(trifluoromethyl)phenyl 4-(2-iodoethyl)phenyl ether (157 mg, 0.368 mmol) and DIPEA (0.193 mL, 1.104 mmol) in chloroform (2 mL) was heated with a microwave reactor at 120° C. for 0.5 h. Purification via reverse phase flash chromatography then afforded the title compound (42 mg, 21.91% yield). LCMS: rt=3.63 min, [M+H⁺]=521

E113: 2-{[2-(4-{[4-chloro-3-(trifluoromethyl)phenyl]oxy}phenyl)ethyl]thio}-1-methyl-5-[(1-methyl-1H-pyrazol-4-yl)methyl]-4(1H)-pyrimidinone

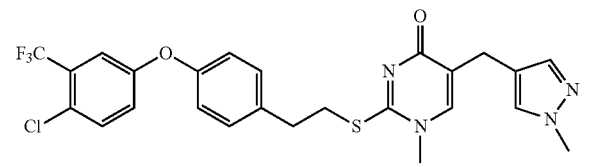 [SMILES: Cn1cc(Cc2cn(C)c(SCCc3ccc(Oc4ccc(Cl)c(C(F)(F)F)c4)cc3)nc2=O)cn1]

To a solution of 2-{[2-(4-{[4-chloro-3-(trifluoromethyl)phenyl]oxy}phenyl)ethyl]thio}-1-methyl-5-[(1-methyl-1H-pyrazol-4-yl)methyl]-4(1H)-pyrimidinone (102 mg, 0.157 mmol) in Methanol (2 mL) was added NaOH (0.262 mL, 0.786 mmol). The mixture was stirred at room temperature for 1 h. Purification via reverse phase flash chromatography then afforded the title compound (30.5 mg, 0.057 mmol, 36.3% yield). LCMS: rt=3.49 min, [M+H⁺]=535

E114: 4-[(2-{[2-(4-{[4-chloro-3-(trifluoromethyl)phenyl]oxy}phenyl)ethyl]thio}-4-oxo-1,4-dihydro-5-pyrimidinyl)methyl]benzonitrile

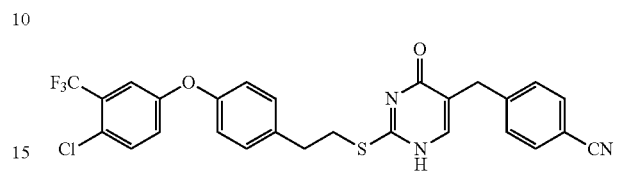

To a suspension of 4-[(4-oxo-2-thioxo-1,2,3,4-tetrahydro-5-pyrimidinyl)methyl]benzonitrile (40 mg, 0.164 mmol) and K₂CO₃ (25 mg, 0.181 mmol) in Acetone (5 mL), which was stirred at room temperature for 5 min was added 1-chloro-4-{[4-(2-iodoethyl)phenyl]oxy}-2-(trifluoromethyl)benzene (42 mg, 0.098 mmol) under argon. The mixture was heated with a microwave reactor at 80° C. for 45 min. Purification via MDAP then afforded the title compound (321 mg, 37.4% yield). LCMS: rt=4.07 min, [M+H]=542

E115: 2-{[2-(4-{[4-chloro-3-(trifluoromethyl)phenyl]oxy}phenyl)ethyl]thio}-5-(5-pyrimidinylmethyl)-4(1H)-pyrimidinone

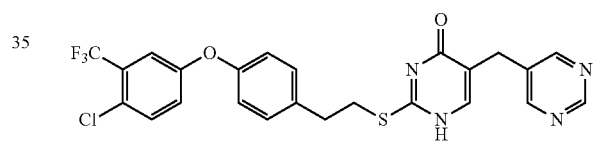

A mixture of 1-chloro-4-{[4-(2-iodoethyl)phenyl]oxy}-2-(trifluoromethyl)benzene (50 mg, 0.117 mmol), K₂CO₃ (32.4 mg, 0.234 mmol), and 5-(5-pyrimidinylmethyl)-2-thioxo-2,3-dihydro-4(1H)-pyrimidinone (26 mg, 0.118 mmol) in DMF (1 mL) was heated with a microwave reactor at 60° C. for 0.5 h. Purification via MDAP then afforded the title compound (15 mg, 24.66% yield). LCMS: rt=3.62 min, [M+H⁺]=519

E116: 2-{[2-(4-{[4-chloro-3-(trifluoromethyl)phenyl]oxy}phenyl)ethyl]thio}-1-methyl-5-(5-pyrimidinylmethyl)-4(1H)-pyrimidinone

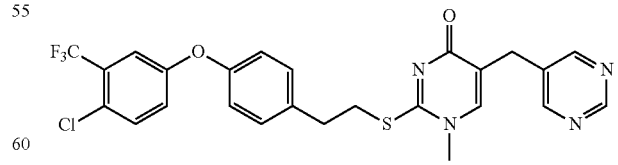

To the solution of 2-{[2-(4-{[4-chloro-3-(trifluoromethyl)phenyl]oxy}phenyl)ethyl]thio}-5-(5-pyrimidinylmethyl)-4 (1H)-pyrimidinone (75 mg, 0.145 mmol) and DIPEA (0.08 mL, 0.458 mmol) in DCM (2 ml) was added MeI (0.014 mL, 0.217 mmol). The solution was stirred at room temperature overnight. Purification via MDAP then afforded the title compound (13 mg, 16.88% yield). LCMS: rt=3.45 min, [M+H⁺]=533

E117: 2-(4-chloro-3-(trifluoromethyl)phenoxy)-5-(2-((5-((1-methyl-1H-pyrazol-4-yl)methyl)-4-oxo-1,4-dihydropyrimidin-2-yl)thio)ethyl)benzonitrile

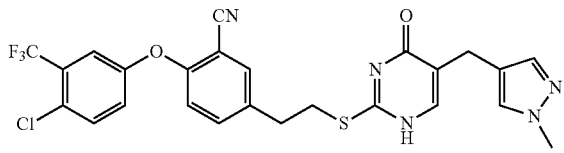 [SMILES: Cn1cc(Cc2c[nH]c(SCCc3ccc(Oc4ccc(Cl)c(C(F)(F)F)c4)c(C#N)c3)nc2=O)cn1]

The same procedure as E112 from 5-[(1-methyl-1H-pyrazol-4-yl)methyl]-2-thioxo-2,3-dihydro-4(1H)-pyrimidinone (80 mg, 0.360 mmol), 2-{[4-chloro-3-(trifluoromethyl)phenyl]oxy}-5-(2-iodoethyl)benzonitrile (163 mg, 0.360 mmol) and DIPEA (0.063 mL, 0.360 mmol) in Chloroform (2 mL) to afford the title compound (63 mg, 32.1% yield). LCMS: rt=3.38 min, [M+H]=546

E118: 2-{[4-chloro-3-(trifluoromethyl)phenyl]oxy}-5-(2-{[4-oxo-5-(5-pyrimidinylmethyl)-1,4-dihydro-2-pyrimidinyl]thio}ethyl)benzonitrile

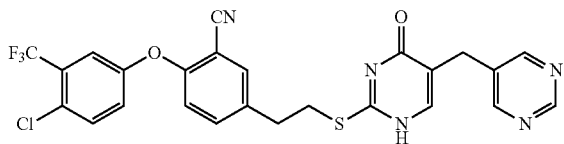 [SMILES: N#Cc1cc(CCSc2nc(=O)c(Cc3cncnc3)c[nH]2)ccc1Oc1ccc(Cl)c(C(F)(F)F)c1]

A mixture of 2-{[4-chloro-3-(trifluoromethyl)phenyl]oxy}-5-(2-iodoethyl)benzonitrile (200 mg, 0.443 mmol), K₂CO₃ (122 mg, 0.886 mmol), and 5-(5-pyrimidinylmethyl)-2-thioxo-2,3-dihydro-4(1H)-pyrimidinone (107 mg, 0.487 mmol) in DMF (4 mL) was heated with a microwave reactor at 60° C. for 15 min. Purification via reverse phase flash chromatography then afforded the title compound (148 mg, 61.4% yield). LCMS: rt=3.34 min, [M+H⁺]=544

E119: 2-{[4-chloro-3-(trifluoromethyl)phenyl]oxy}-5-{2-[(5-{[2-(methyloxy)-5-pyrimidinyl]methyl}-4-oxo-1,4-dihydro-2-pyrimidinyl)thio]ethyl}benzonitrile

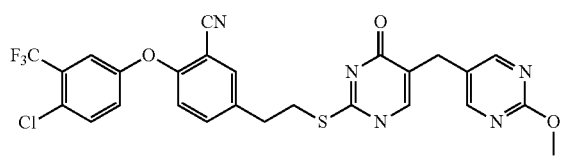 [SMILES: COc1ncc(Cc2c[nH]c(SCCc3ccc(Oc4ccc(Cl)c(C(F)(F)F)c4)c(C#N)c3)nc2=O)cn1]

The same procedure as E108 from 2-{[4-chloro-3-(trifluoromethyl)phenyl]oxy}-5-(2-iodoethyl)benzonitrile (62 mg, 0.137 mmol), 5-{[2-(methyloxy)-5-pyrimidinyl]methyl}-2-thioxo-2,3-dihydro-4(1H)-pyrimidinone (37.8 mg, 0.151 mmol) and K₂CO₃ (37.9 mg, 0.275 mmol) in DMF (3 mL) to afford the title compound (32 mg, 40.6% yield). LCMS: rt=3.50 min, [M+H+]=574

E120: 2-{[4-chloro-3-(trifluoromethyl)phenyl]oxy}-5-{2-[(1-methyl-5-{[2-(methyloxy)-5-pyrimidinyl]methyl}-4-oxo-1,4-dihydro-2-pyrimidinyl)thio]ethyl}benzonitrile

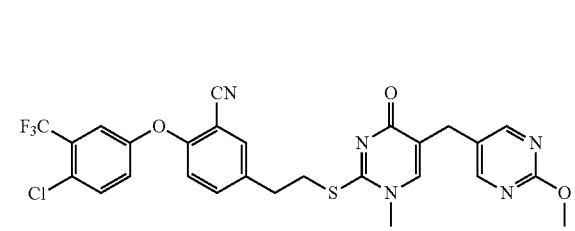 [SMILES: COc1ncc(Cc2cn(C)c(SCCc3ccc(Oc4ccc(Cl)c(C(F)(F)F)c4)c(C#N)c3)nc2=O)cn1]

The same procedure as E110 from 2-{[4-chloro-3-(trifluoromethyl)phenyl]oxy}-5-{2-[(5-{[2-(methyloxy)-5-pyrimidinyl]methyl}-4-oxo-1,4-dihydro-2-pyrimidinyl)thio]ethyl}benzonitrile (130 mg, 0.226 mmol), Hunig's base (0.079 ml, 0.453 mmol) and MeI (0.01841 ml, 0.294 mmol) in DCM (3 mL) to afford the title compound (32 mg, 20.13% yield), LCMS: rt=3.38 min, [M+H⁺]=588

E121: 2-(4-(4-fluorophenoxy)phenethoxy)-5-((2-methoxypyrimidin-5-yl)methyl)pyrimidin-4(1H)-one

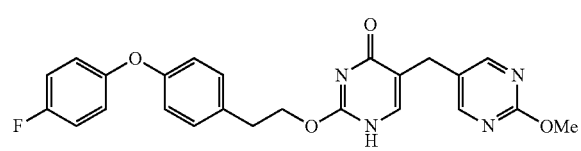 [SMILES: COc1ncc(Cc2c[nH]c(OCCc3ccc(Oc4ccc(F)cc4)cc3)nc2=O)cn1]

A mixture of 4-(4-fluorophenoxy)phenethyl carbamimidate (50 mg, 0.182 mmol), methyl 2-formyl-3-[2-(methyloxy)-5-pyrimidinyl]propanoate (49.0 mg, 0.219 mmol) and K₂CO₃ (101 mg, 0.729 mmol) in NMP (2 mL) was heated with a microwave reactor at 135° C. for 2 h. Purification via MDAP then afforded the title compound (15 mg, 18.35% yield). LCMS: rt=3.14 min, [M+H⁺]=449

E122: 2-[(2-{4-[(4-fluorophenyl)oxy]phenyl}ethyl)oxy]-5-[(1-methyl-1H-pyrazol-4-yl)methyl]-4(1H)-pyrimidinone, trifluoroacetic acid salt

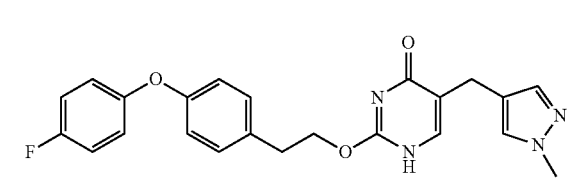 [SMILES: Cn1cc(Cc2c[nH]c(OCCc3ccc(Oc4ccc(F)cc4)cc3)nc2=O)cn1]

The same procedure as E121 from 4-(4-fluorophenoxy)phenethyl carbamimidate (100 mg, 0.365 mmol), methyl 2-formyl-3-(1-methyl-1H-pyrazol-4-yl)propanoate (71.5 mg, 0.365 mmol) and K₂CO₃ (202 mg, 1.458 mmol) in NMP (2 mL) to afford the title compound (17 mg, 8.72% yield). LCMS: rt=3.02 min, [M+H⁺]=421

E123: 5-{[2-(methyloxy)-5-pyrimidinyl]methyl}-2-{[2-(4-{[4-(trifluoromethyl)phenyl]oxy}phenyl)ethyl]oxy}-4(1H)-pyrimidinone

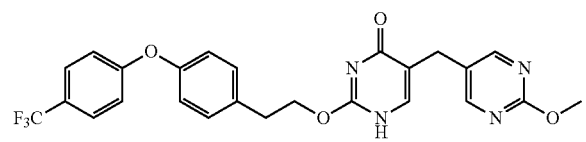 [SMILES: COc1ncc(Cc2c[nH]c(OCCc3ccc(Oc4ccc(C(F)(F)F)cc4)cc3)nc2=O)cn1]

To the solution of 2-(4-{[4-(trifluoromethyl)phenyl]oxy}phenyl)ethyl imidocarbamate (100 mg, 0.229 mmol) and methyl 2-formyl-3-[2-(methyloxy)-5-pyrimidinyl]propanoate (61.5 mg, 0.274 mmol) in NMP (1.5 mL), was added $K_2CO_3$ (126 mg, 0.915 mmol). The mixture was heated with a microwave reactor at 115° C. for 4 h. Purification via MDAP then afforded the title compound (10 mg, 8.77% yield). LCMS: rt=3.44 min, [M+H⁺]=499

E124: 5-[(1-methyl-1H-pyrazol-4-yl)methyl]-2-{[2-(4-{[4-(trifluoromethyl)phenyl]oxy}phenyl)ethyl]oxy}-4(1H)-pyrimidinone

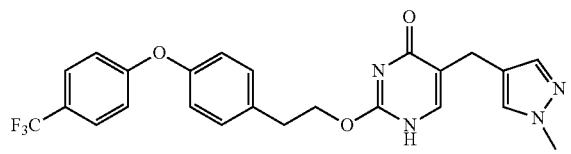 [SMILES: Cn1cc(Cc2c[nH]c(OCCc3ccc(Oc4ccc(C(F)(F)F)cc4)cc3)nc2=O)cn1]

To the solution of 2-(4-{[4-(trifluoromethyl)phenyl]oxy}phenyl)ethyl imidocarbamate (50 mg, 0.114 mmol) and methyl 2-formyl-3-(1-methyl-1H-pyrazol-4-yl)propanoate (27 mg, 0.138 mmol) in NMP (1 mL), was added $K_2CO_3$ (60 mg, 0.434 mmol). The mixture was was heated with a microwave reactor at 110° C. for 1 h. Purification via MDAP then afforded the title compound (6.8 mg, 10.19% yield). LCMS: rt=3.30 min, [M+H⁺]=471

E125: 2-{[2-(4-{[4-chloro-3-(trifluoromethyl)phenyl]oxy}-3,5-difluorophenyl)ethyl]oxy}-5-ethyl-4(1H)-pyrimidinone

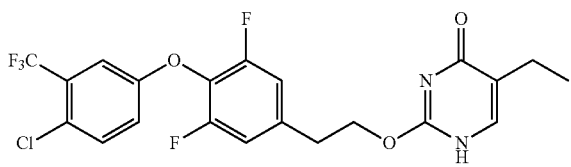 [SMILES: CCc1c[nH]c(OCCc2cc(F)c(Oc3ccc(Cl)c(C(F)(F)F)c3)c(F)c2)nc1=O]

A mixture of 2-(4-{[4-chloro-3-(trifluoromethyl)phenyl]oxy}-3,5-difluorophenyl)ethyl imidocarbamate (250 mg, 0.459 mmol), ethyl (2Z)-2-ethyl-3-hydroxy-2-propenoate (132 mg, 0.918 mmol) and $K_2CO_3$ (127 mg, 0.918 mmol) in DMF (3 mL) was heated with a microwave condition at 110° C. for 1.5 h. Purification via MDAP afforded the title compound (60 mg, 27.5% yield). LCMS: rt=3.83 min, [M+H⁺]=475

E126: 2-{[2-(4-{[4-chloro-3-(trifluoromethyl)phenyl]oxy}phenyl)ethyl]oxy}-5-{[2-(trifluoromethyl)-5-pyrimidinyl]methyl}-4(1H)-pyrimidinone

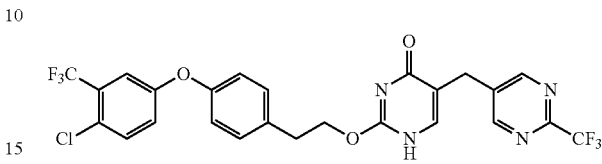

The same procedure as E125 from 2-(4-{[4-chloro-3-(trifluoromethyl)phenyl]oxy}phenyl)ethyl imidocarbamate (460 mg, 1.282 mmol), methyl (2Z)-3-hydroxy-2-{[2-(trifluoromethyl)-5-pyrimidinyl]methyl}-2-propenoate (280 mg, 1.068 mmol) and $K_2CO_3$ (295 mg, 2.136 mmol) in DMF (3 mL), except that the reaction temperature was 150° C., to afford the title compound (20 mg, 0.035 mmol, 3.28% yield) as white solid. LCMS: rt=3.89 min, [M+H]=571

E127: 2-(4-(4-chloro-3-(trifluoromethyl)phenoxy)phenethoxy)-5-(2,2,2-trifluoroethyl)pyrimidin-4(1H)-one

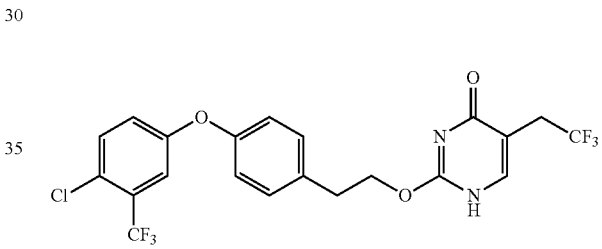

To a suspension of (E)-methyl 4,4,4-trifluoro-2-(hydroxymethylene)butanoate (400 mg, 2.173 mmol) and 4-(4-chloro-3-(trifluoromethyl)phenoxy)phenethyl carbamimidate, trifluoromethanesulphonate (552 mg, 1.086 mmol) in toluene (25 mL) was added KOAc (213 mg, 2.173 mmol). The mixture was heated to reflux for 4 h. Purification via reverse phase flash chromatography then afforded the title compound (95 mg, 17.75% yield). LCMS: rt=3.87 min, [M+H⁺]=493

E128: 2-(4-(4-chloro-3-(trifluoromethyl)phenoxy)phenethoxy)-1-methyl-5-(2,2,2-trifluoroethyl)pyrimidin-4(1H)-one

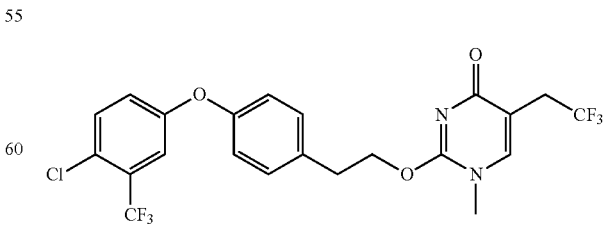

To a solution of 2-(4-(4-chloro-3-(trifluoromethyl)phenoxy)phenethoxy)-5-(2,2,2-trifluoroethyl)pyrimidin-4(1H)-one (66 mg, 0.134 mmol) in DCM (10 mL) was added DIPEA (0.070 mL, 0.402 mmol) and MeI (0.013 mL, 0.201 mmol). The mixture was stirred at room temperature for 3 h. Purification via reverse phase flash chromatography then afforded the title compound (28 mg, 41.3% yield). LCMS: rt=3.73 min, [M+H$^+$]=507

E129: 2-{[2-(4-{[4-chloro-3-(trifluoromethyl)phenyl]oxy}phenyl)ethyl]oxy}-5-[(2,4,6-trifluorophenyl)methyl]-4(1H)-pyrimidinone

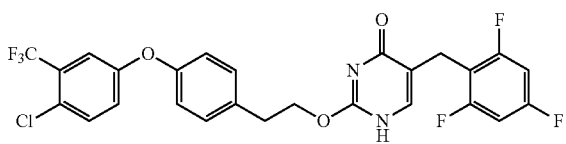 [SMILES: O=c1nc(OCCc2ccc(Oc3ccc(Cl)c(C(F)(F)F)c3)cc2)[nH]cc1Cc1c(F)cc(F)cc1F]

A mixture of 2-(4-{[4-chloro-3-(trifluoromethyl)phenyl]oxy}phenyl)ethyl imidocarbamate (130 mg, 0.275 mmol), ethyl 2-formyl-3-(2,4,6-trifluorophenyl)propanoate (130 mg, 0.500 mmol) and Cs$_2$CO$_3$ (2.00 g, 6.14 mmol) in toluene (60 mL) was heated at reflux with a Dean-Stark apparatus for 12 h. After cooling, the mixture was filtered through celite pad and washed with EA. Purification via MDAP then afforded the title compound (9.5 mg, 6.23% yield). LCMS: rt=4.13 min, [M+H]=555

E130: 2-{[2-(4-{[4-chloro-3-(trifluoromethyl)phenyl]oxy}phenyl)ethyl]oxy}-1,5-diethyl-4(1H)-pyrimidinone

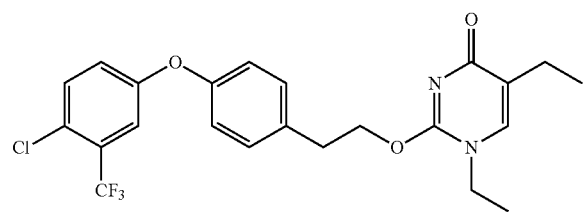 [SMILES: CCc1cn(CC)c(OCCc2ccc(Oc3ccc(Cl)c(C(F)(F)F)c3)cc2)nc1=O]

To a solution of 2-{[2-(4-{[4-chloro-3-(trifluoromethyl)phenyl]oxy}phenyl)ethyl]oxy}-5-ethyl-4(1H)-pyrimidinone (60 mg, 0.137 mmol), DIPEA (0.036 mL, 0.205 mmol) in DCE (2 mL) was added EtI (0.013 mL, 0.164 mmol). The mixture was heated at 40° C. for 1 h. Purification via reverse phase flash chromatography then afforded the title compound (25 mg, 0.054 mmol, 39.2% yield). LCMS: rt=3.80 min, [M+H$^+$]=467

E131: (2-{[2-(4-{[4-chloro-3-(trifluoromethyl)phenyl]oxy}phenyl)ethyl]oxy}-4-oxo-1,4-dihydro-5-pyrimidinyl)acetic acid

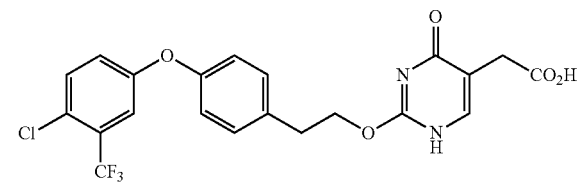 [SMILES: O=C(O)Cc1c[nH]c(OCCc2ccc(Oc3ccc(Cl)c(C(F)(F)F)c3)cc2)nc1=O]

To a solution of methyl (2-{[2-(4-{[4-chloro-3-(trifluoromethyl)phenyl]oxy}phenyl)ethyl]oxy}-4-oxo-1,4-dihydro-5-pyrimidinyl)acetate (102 mg, 0.211 mmol) in ethanol (8 mL) and Water (3 mL) was added NaOH (3M in water) (2 mL, 6.00 mmol). The mixture was stirred at room temperature overnight. The mixture was neutralized by HCl and the solvent was removed. Purification via reverse phase flash chromatography then afforded the title compound (66 mg, 66.6% yield). LCMS: rt=3.29 min, [M+H$^+$]=469

E132: 2-{[2-(4-{[4-chloro-3-(trifluoromethyl)phenyl]oxy}phenyl)ethyl]oxy}-5-{2-[(3S)-3-fluoro-1-pyrrolidinyl]-2-oxoethyl}-4(1H)-pyrimidinone, trifluoroacetic acid salt

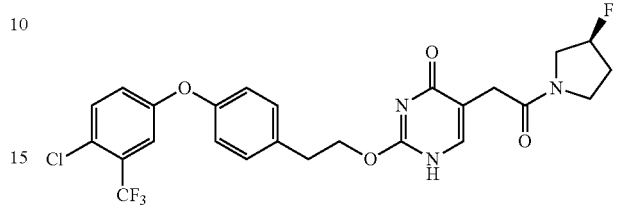

To a solution of (2-{[2-(4-{[4-chloro-3-(trifluoromethyl)phenyl]oxy}phenyl)ethyl]oxy}-4-oxo-1,4-dihydro-5-pyrimidinyl)acetic acid (44 mg, 0.094 mmol) in DCM (5 mL) was added DIPEA (0.049 mL, 0.282 mmol) and HATU (42.8 mg, 0.113 mmol). The mixture was stirred at room temperature for 10 min then (3S)-3-fluoropyrrolidine hydrochloride (17.68 mg, 0.141 mmol) was added. Stirring continued for 1 h. Purification via MDAP then afforded the title compound (20 mg, 32.6% yield). LCMS: rt=3.39 min, [M+H$^+$]=540

E133: 2-{[2-(4-{[4-chloro-3-(trifluoromethyl)phenyl]oxy}phenyl)ethyl]oxy}-5-[(3-methyl-1,2,4-oxadiazol-5-yl)methyl]-4(1H)-pyrimidinone

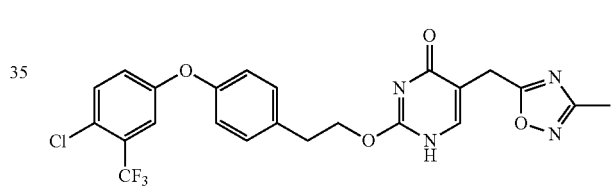

To a solution of (2-{[2-(4-{[4-chloro-3-(trifluoromethyl)phenyl])phenyl)ethyl]oxy}-4-oxo-1,4-dihydro-5-pyrimidinyl)acetic acid (81 mg, 0.173 mmol) in THF (5 mL) was added EDC (99 mg, 0.518 mmol) and HOBT (52.9 mg, 0.346 mmol). The mixture was stirred at room temperature for 10 min then acetamide oxime (19.20 mg, 0.259 mmol) was added. After stirring continued for another 20 min, TBAF (181 mg, 0.691 mmol) was added. The mixture was heated with a microwave reactor at 120° C. for 0.5 h. Purification via MDAP then afforded the title compound (16 mg, 18.27% yield). LCMS: rt=3.59 min, [M+H$^+$]=507

E134: 2-{[2-(4-{[4-chloro-3-(trifluoromethyl)phenyl]oxy}phenyl)ethyl]oxy}-5-[(5-methyl-1,3,4-oxadiazol-2-yl)methyl]-4(1H)-pyrimidinone

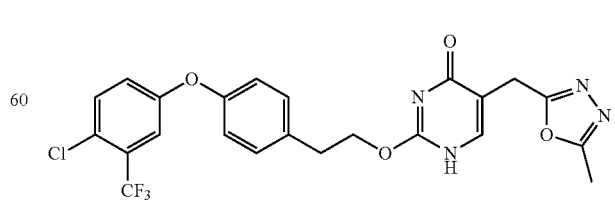

To a solution of N'-acetyl-2-(2-{[2-(4-{[4-chloro-3-(trifluoromethyl)phenyl]oxy}phenyl)ethyl]oxy}-4-oxo-1,4-dihydro-5-pyrimidinyl)acetohydrazide (26 mg, 0.050 mmol) in THF (5 mL) was added Burgess reagent (17.71 mg, 0.074 mmol). The mixture was heated with a microwave reactor at 130° C. for 0.5 h. Purification via MDAP then afforded the title compound (10 mg, 9.8% yield). LCMS: rt=3.38 min, [M+H⁺]=507

E135: 5-(pyrimidin-5-ylmethyl)-2-(4-((6-(trifluoromethyl)pyridin-2-yl)oxy)phenethoxy)pyrimidin-4(1H)-one, Trifluoroacetate

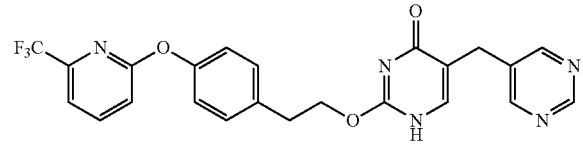 [SMILES: O=c1nc(OCCc2ccc(Oc3cccc(C(F)(F)F)n3)cc2)[nH]cc1Cc1cncnc1]

To the solution of 4-((6-(trifluoromethyl)pyridin-2-yl)oxy)phenethyl carbamimidate, Trifluoroacetate (200 mg, 0.456 mmol) and methyl 2-formyl-3-(pyrimidin-5-yl)propanoate (177 mg, 0.913 mmol) in NMP (2 mL) was added K₂CO₃ (252 mg, 1.825 mmol). The mixture was heated with a microwave reactor at 130° C. for 2 h. Purification via MDAP then afforded the title compound (14.6 mg, 5.49% yield). LCMS: rt=2.93 min, [M+H]=470

E136: 5-((2-methoxypyrimidin-5-yl)methyl)-2-(4-((6-(trifluoromethyl)pyridin-2-yl)oxy)phenethoxy)pyrimidin-4(1H)-one

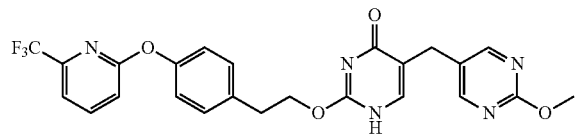 [SMILES: COc1ncc(Cc2c[nH]c(OCCc3ccc(Oc4cccc(C(F)(F)F)n4)cc3)nc2=O)cn1]

To the solution of 4-((6-(trifluoromethyl)pyridin-2-yl)oxy)phenethyl carbamimidate, Trifluoroacetate (200 mg, 0.456 mmol) and methyl 2-formyl-3-[2-(methyloxy)-5-pyrimidinyl]propanoate (205 mg, 0.913 mmol) in NMP (3 mL) was added K₂CO₃ (252 mg, 1.825 mmol). The mixture was heated with a microwave reactor at 130° C. for 1 h. Purification via MDAP then afforded the title compound (14 mg, 6.14% yield). LCMS: rt=3.11 min, [M+H⁺]=500

E137: 5-((2-methoxypyrimidin-5-yl)methyl)-2-(4-((5-(trifluoromethyl)pyridin-2-yl)oxy)phenethoxy)pyrimidin-4(1H)-one

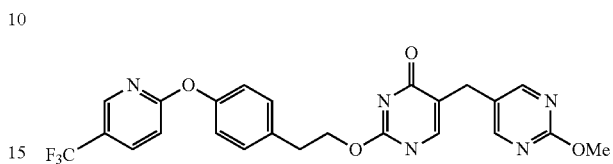

To the solution of 4-((5-(trifluoromethyl)pyridin-2-yl)oxy)phenethyl carbamimidate, Trifluoroacetate (600 mg, 1.369 mmol) and methyl 2-formyl-3-(2-methoxypyrimidin-5-yl)propanoate (246 mg, 1.095 mmol) in 1,4-dioxane (6 mL) was added K₂CO₃ (757 mg, 5.48 mmol). The mixture was heated with a microwave reactor at 80° C. for 0.5 h. Purification via MDAP then afforded the title compound (2 mg, 0.293 yield). LCMS: rt=3.09 min, [M+H⁺]=500

E138: 5-[(1-methyl-1H-pyrazol-4-yl)methyl]-2-{[2-(4-{[6-(trifluoromethyl)-3-pyridinyl]oxy}phenyl)ethyl]oxy}-4(1H)-pyrimidinone

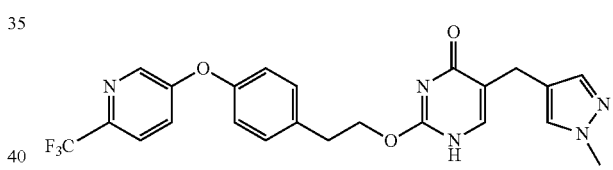

To the solution of 2-(4-{[6-(trifluoromethyl)-3-pyridinyl]oxy}phenyl)ethyl imidocarbamate (200 mg, 0.456 mmol) and methyl 2-formyl-3-(1-methyl-1H-pyrazol-4-yl)propanoate (107 mg, 0.548 mmol) in NMP (3 mL) was added K₂CO₃ (252 mg, 1.825 mmol). The mixture was heated with a microwave reactor at 130° C. for 0.5 h. Purification via MDAP then afforded the title compound (53 mg, 0.112 mmol, 24.64% yield). LCMS: rt=2.92 min, [M+H⁺]=472

E139: 5-{[2-(methyloxy)-5-pyrimidinyl]methyl}-2-{[2-(4-{[6-(trifluoromethyl)-3-pyridinyl]oxy}phenyl)ethyl]oxy}-4(1H)-pyrimidinone

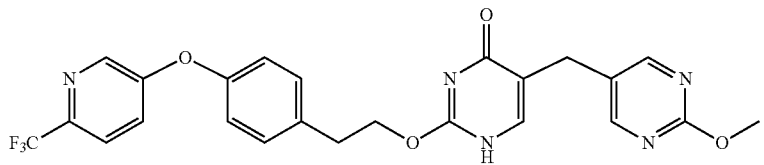 [SMILES: COc1ncc(Cc2c[nH]c(OCCc3ccc(Oc4ccc(C(F)(F)F)nc4)cc3)nc2=O)cn1]

To the solution of 2-(4-{[6-(trifluoromethyl)-3-pyridinyl]oxy}phenyl)ethyl imidocarbamate (400 mg, 0.913 mmol) and methyl 2-formyl-3-[2-(methyloxy)-5-pyrimidinyl]propanoate (246 mg, 1.095 mmol) in NMP (3 mL) was added K$_2$CO$_3$ (505 mg, 3.65 mmol). The mixture was heated with a microwave reactor at 130° C. for 1 h. Purification via MDAP then afforded the title compound (44 mg, 9.65% yield). LCMS: rt=3.10 min, [M+H$^+$]=500

E140: 5-ethyl-2-{[2-(4-{[6-(trifluoromethyl)-3-pyridinyl]oxy}phenyl)ethyl]oxy}-4(1H)-pyrimidinone

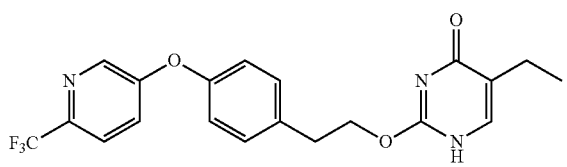 [SMILES: CCc1c[nH]c(OCCc2ccc(Oc3ccc(C(F)(F)F)nc3)cc2)nc1=O]

The same procedure as E125 from 2-(4-{[6-(trifluoromethyl)-3-pyridinyl]oxy}phenyl) ethyl imidocarbamate (300 mg, 0.922 mmol), ethyl (2Z)-2-ethyl-3-hydroxy-2-propenoate (199 mg, 1.383 mmol) and K$_2$CO$_3$ (319 mg, 2.306 mmol) in DMF (3.0 mL), except that the reaction temperature was 160° C., to afford the title compound (100 mg, 0.247 mmol, 26.7% yield) as white solid. LCMS: rt=3.28 min, [M+H]=406

E141: 2-{[2-(4-{[4-chloro-3-(trifluoromethyl)phenyl]oxy}-3-fluorophenyl)ethyl]oxy}-1-methyl-5-(5-pyrimidinylmethyl)-4(1H)-pyrimidinone

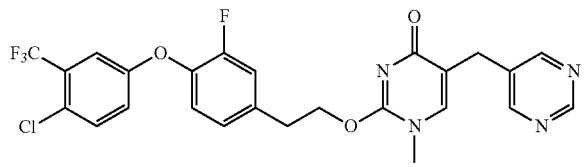 [SMILES: Cn1cc(Cc2cncnc2)c(=O)nc1OCCc1ccc(Oc2ccc(Cl)c(C(F)(F)F)c2)c(F)c1]

To a solution of 2-{[2-(4-{[4-chloro-3-(trifluoromethyl)phenyl]oxy}-3-fluorophenyl)ethyl]oxy}-5-(5-pyrimidinylmethyl)-4(1H)-pyrimidinone (80 mg, 0.154 mmol) and Hunig's base (0.040 mL, 0.230 mmol) in DCM (3.0 mL) was added MeI (0.019 mL, 0.307 mmol) dropwise. The mixture was stirred at room temperature for 2 h. Purification via reverse phase flash chromatography afforded the title compound (15 mg, 18.26% yield). LCMS: rt=3.32 min, [M+H$^+$]=535

E142: 5-ethyl-1-methyl-2-{[2-(4-{[6-(trifluoromethyl)-3-pyridinyl]oxy}phenyl)ethyl]oxy}-4(1H)-pyrimidinone

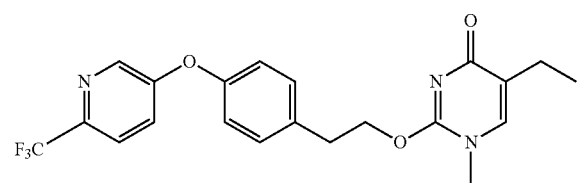 [SMILES: CCc1cn(C)c(OCCc2ccc(Oc3cnc(C(F)(F)F)nc3)cc2)nc1=O]

The same procedure as E141 from 5-ethyl-2-{[2-(4-{[6-(trifluoromethyl)-3-pyridinyl]oxy}phenyl)ethyl]oxy}-4 (1H)-pyrimidinone (90 mg, 0.222 mmol), DIPEA (0.097 mL, 0.555 mmol) and MeI (0.028 mL, 0.444 mmol) in DCM (2 mL), except that the reaction time was 3 h, to afford the title compound (50 mg, 53.7% yield) as white solid. LCMS: rt=3.09 min, [M+H$^+$]=420

E143: 5-{[2-(methyloxy)-5-pyrimidinyl]methyl}-2-{[2-(4-{[2-(trifluoromethyl)-5-pyrimidinyl]oxy}phenyl)ethyl]oxy}-4(1H)-pyrimidinone

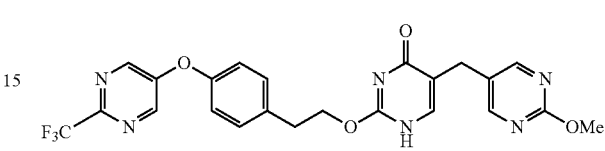

The same procedure as E121 from 2-(4-{[2-(trifluoromethyl)-5-pyrimidinyl]oxy}phenyl) ethyl imidocarbamate (60 mg, 0.184 mmol), methyl 2-formyl-3-[2-(methyloxy)-5-pyrimidinyl]propanoate (49.5 mg, 0.221 mmol) and K$_2$CO$_3$ (102 mg, 0.736 mmol) in NMP (1 mL), except that the temperature was 130° C. and the reaction time was 1 h, to afford the title compound (2.8 mg, 5.60 mol, 3.04% yield). LCMS: rt=1.29 min, [M+H$^+$]=501

E144: 5-ethyl-1-methyl-2-(4-((2-(trifluoromethyl)pyrimidin-5-yl)oxy)phenethoxy)pyrimidin-4(1H)-one, trifluoroacetic acid salt

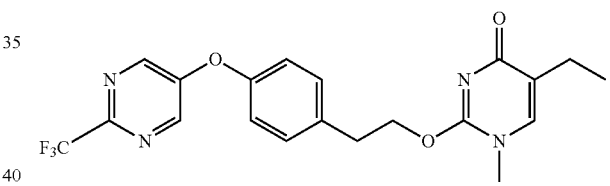

To a solution of 5-ethyl-2-(4-((2-(trifluoromethyl)pyrimidin-5-yl)oxy)phenethoxy) pyrimidin-4(1H)-one (30 mg, 0.074 mmol) and DIPEA (0.052 mL, 0.295 mmol) in DCM (2 mL) was added MeI (6.00 µL, 0.096 mmol). The mixture was stirred at room temperature overnight. Purification via MDAP then afforded the title compound (3.2 mg, 5.99 mol, 8.11% yield). LCMS: rt=3.00 min, [M+H$^+$]=421

E145: 2-(4-((5-chloropyrimidin-2-yl)oxy)phenethoxy)-5-((2-methoxypyrimidin-5-yl)methyl)pyrimidin-4(1H)-one, Trifluoroacetic acid salt

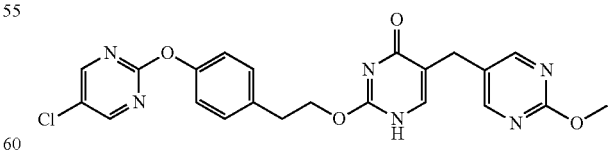

To a solution of 4-((5-chloropyrimidin-2-yl)oxy)phenethyl carbamimidate, Trifluoromethanesulphonate (136 mg, 0.308 mmol) in DMF (5 mL) was added (Z)-methyl 3-hydroxy-2-((2-methoxypyrimidin-5-yl)methyl)acrylate (138 mg, 0.616 mmol) and Cs$_2$CO$_3$ (301 mg, 0.924 mmol). The mixture was heated with a microwave reactor at 130° C. for 1 h. Purification via MDAP then afforded the title compound (20 mg, 0.034 mmol, 11.18% yield). LCMS: rt=2.66 min, [M+H⁺]= 467

E146: 5-((2-methoxypyrimidin-5-yl)methyl)-2-(4-((5-(trifluoromethyl)pyrimidin-2-yl)oxy)phenethoxy)pyrimidin-4(1H)-one

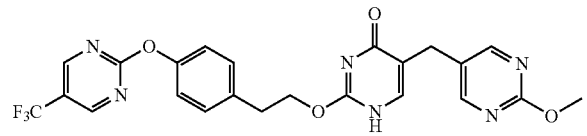 [SMILES: COc1ncc(Cc2c[nH]c(OCCc3ccc(Oc4ncc(C(F)(F)F)cn4)cc3)nc2=O)cn1]

The same procedure as E145 from 4-((5-(trifluoromethyl)pyrimidin-2-yl)oxy)phenethyl carbamimidate, trifluoromethanesulphonate (275 mg, 0.579 mmol), (Z)-methyl 3-hydroxy-2-((2-methoxypyrimidin-5-yl)methyl)acrylate (259 mg, 1.157 mmol) and Cs₂CO₃ (565 mg, 1.736 mmol) in 1,4-dioxane (10 mL) to afford the title compound (20 mg, 6.91% yield). LCMS: rt=2.85 min, [M+H⁺]=501

E147: 5-((2-methoxypyrimidin-5-yl)methyl)-2-(4-(pyrimidin-2-yloxy)phenethoxy)pyrimidin-4(1H)-one

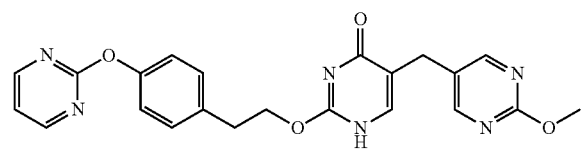 [SMILES: COc1ncc(Cc2c[nH]c(OCCc3ccc(Oc4ncccn4)cc3)nc2=O)cn1]

The same procedure as E145 from 4-(pyrimidin-2-yloxy)phenethyl carbamimidate, trifluoromethanesulphonate (307 mg, 0.754 mmol), (Z)-methyl 3-hydroxy-2-((2-methoxypyrimidin-5-yl)methyl)acrylate (338 mg, 1.507 mmol) and Cs₂CO₃ (737 mg, 2.261 mmol) in DMF (5 mL) to afford the title compound (15 mg, 4.60% yield). LCMS: rt=2.28 min, [M+H⁺]=433

E148: 2-(4-((6-chloropyridazin-3-yl)oxy)phenethoxy)-5-((2-methoxypyrimidin-5-yl)methyl)pyrimidin-4(1H)-one

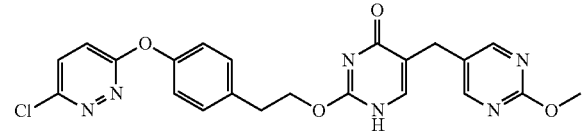 [SMILES: COc1ncc(Cc2c[nH]c(OCCc3ccc(Oc4ccc(Cl)nn4)cc3)nc2=O)cn1]

The same procedure as E145 from 4-((6-chloropyridazin-3-yl)oxy)phenethyl carbamimidate, trifluoromethanesulphonate (87.8 mg, 0.199 mmol), (Z)-methyl 3-hydroxy-2-((2-methoxypyrimidin-5-yl)methyl)acrylate (89 mg, 0.397 mmol) and K₂CO₃ (82 mg, 0.596 mmol) in DMF (5 mL) to afford the title compound (15 mg, 16.17% yield). LCMS: rt=2.55 min, [M+H⁺]=467

E149: 2-[(2-{4-[(3-chloro-4-methylphenyl)oxy]phenyl}ethyl)oxy]-5-[(1-methyl-1H-pyrazol-4-yl)methyl]-4(1H)-pyrimidinone

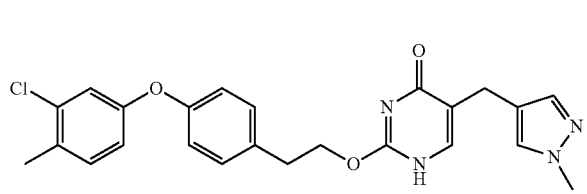 [SMILES: Cc1ccc(Oc2ccc(CCOc3nc(=O)c(Cc4cnn(C)c4)c[nH]3)cc2)cc1Cl]

To the solution of 2-{4-[(3-chloro-4-methylphenyl)oxy]phenyl}) ethyl imidocarbamate (150 mg, 0.359 mmol) and methyl 2-formyl-3-(1-methyl-1H-pyrazol-4-yl)propanoate (85 mg, 0.431 mmol) in NMP (2 mL), was added K₂CO₃ (198 mg, 1.436 mmol). The mixture was heated with a microwave reactor at 130° C. for 1 h. Purification via MDAP then afforded the title compound (24 mg, 14.82% yield). LCMS: rt=3.35 min, [M+H⁺]=451

E150: 2-[(2-{4-[(3-chloro-4-methylphenyl)oxy]phenyl}ethyl)oxy]-5-[pyrimidin-5-ylmethyl]-4(1H)-pyrimidinone

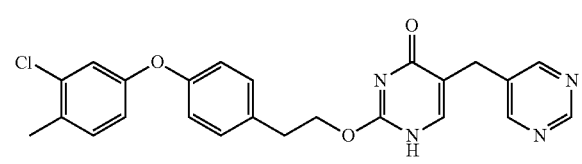 [SMILES: Cc1ccc(Oc2ccc(CCOc3nc(=O)c(Cc4cncnc4)c[nH]3)cc2)cc1Cl]

Prepared in a manner similar to that described for E149 using 2-{4-[(3-chloro-4-methylphenyl)oxy]phenyl}) ethyl imidocarbamate (150 mg, 0.359 mmol) and methyl 2-formyl-3-(5-pyrimidinyl)propanoate (84 mg, 0.431 mmol) and K₂CO₃ (198 mg, 1.436 mmol) in NMP (2 ml), to afford the title compound (11 mg, 6.83% yield). LCMS: rt=3.33 min, [M+H⁺]=449

E151: 2-[(2-{4-[(3-chloro-4-methylphenyl)oxy]phenyl}ethyl)oxy]-5-{[2-(methyloxy)-5-pyrimidinyl]methyl}-4(1H)-pyrimidinone

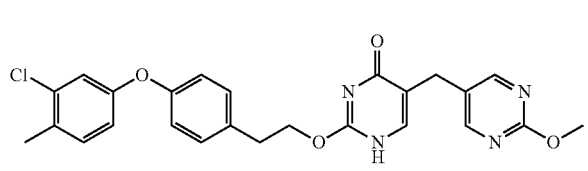

To the solution of 2-{4-[(3-chloro-4-methylphenyl)oxy]phenyl}) ethyl imidocarbamate (150 mg, 0.359 mmol) and methyl 2-formyl-3-[2-(methyloxy)-5-pyrimidinyl]propanoate (89 mg, 0.395 mmol) in NMP (2 mL), was added K₂CO₃ (198 mg, 1.436 mmol). The mixture was heated with a microwave reactor at 130° C. for 1 h. Purification via MDAP then afforded the title compound (4 mg, 2.33% yield). LCMS: rt=3.54 min, [M+H⁺]=479

E152: 2-[(2-{4-[(4-chloro-3-methylphenyl)oxy]phenyl}ethyl)oxy]-5-[(1-methyl-1H-pyrazol-4-yl)methyl]-4(1H)-pyrimidinone

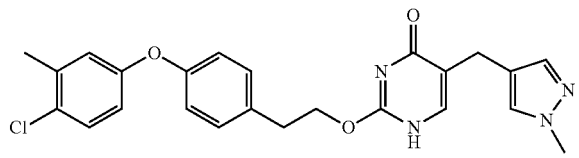 [SMILES: Cc1cc(Oc2ccc(CCOc3nc(=O)c(Cc4cnn(C)c4)c[nH]3)cc2)ccc1Cl]

To the solution of 2-{4-[(4-chloro-3-methylphenyl)oxy]phenyl}ethyl imidocarbamate (50 mg, 0.120 mmol) and methyl 2-formyl-3-(1-methyl-1H-pyrazol-4-yl)propanoate (30 mg, 0.153 mmol) in NMP (2 mL), was added $K_2CO_3$ (50 mg, 0.362 mmol). The mixture was heated with a microwave reactor at 130° C. for 1 h. Purification via MDAP then afforded the title compound (3 mg, 5.56% yield). LCMS: rt=3.39 min, [M+H]=451

E153: 2-[(2-{4-[(4-chloro-3-methylphenyl)oxy]phenyl}ethyl)oxy]-5-(5-pyrimidinylmethyl)-4(1H)-pyrimidinone, trifluoroacetic acid salt

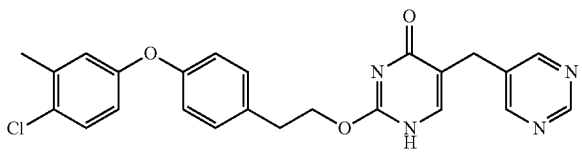 [SMILES: Cc1cc(Oc2ccc(CCOc3nc(=O)c(Cc4cncnc4)c[nH]3)cc2)ccc1Cl]

To the solution of 2-{4-[(4-chloro-3-methylphenyl)oxy]phenyl}ethyl imidocarbamate (50 mg, 0.120 mmol) and methyl 2-formyl-3-(5-pyrimidinyl)propanoate (27 mg, 0.139 mmol) in NMP (1 mL), was added $K_2CO_3$ (60 mg, 0.434 mmol). The mixture was heated with a microwave reactor at 130° C. for 1 h. Purification via MDAP then afforded the title compound (3.7 mg, 5.50% yield). LCMS: rt=3.35 min, [M+H]=449

E154: 2-[(2-{4-[(4-chloro-3-methylphenyl)oxy]phenyl}ethyl)oxy]-5-{[2-(methyloxy)-5-pyrimidinyl]methyl}-4(1H)-pyrimidinone

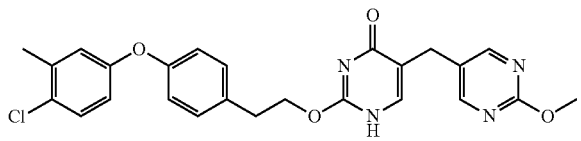 [SMILES: COc1ncc(Cc2c[nH]c(OCCc3ccc(Oc4ccc(Cl)c(C)c4)cc3)nc2=O)cn1]

To the solution of 2-{4-[(4-chloro-3-methylphenyl)oxy]phenyl}ethyl imidocarbamate (100 mg, 0.239 mmol) and methyl 2-formyl-3-[2-(methyloxy)-5-pyrimidinyl]propanoate (64.4 mg, 0.287 mmol) in NMP (1 mL) was added $K_2CO_3$ (132 mg, 0.957 mmol). The mixture was heated with a microwave reactor at 130° C. for 1 h. Purification via MDAP then afforded the title compound (9 mg, 7.85% yield). LCMS: rt=3.54 min, [M+H⁺]=479

E155: 2-[(2-{4-[(3-fluoro-4-methylphenyl)oxy]phenyl}ethyl)oxy]-5-[(1-methyl-1H-pyrazol-4-yl)methyl]-4(1H)-pyrimidinone

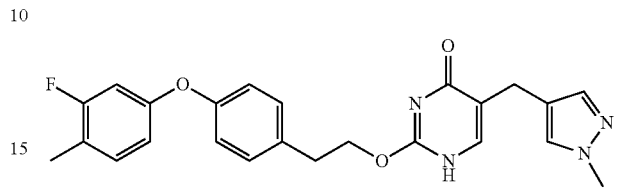

To the solution of 2-{4-[(3-fluoro-4-methylphenyl)oxy]phenyl}) ethyl imidocarbamate (150 mg, 0.374 mmol) and methyl 2-formyl-3-(1-methyl-1H-pyrazol-4-yl)propanoate (88 mg, 0.449 mmol) in NMP (2.5 mL) was added $K_2CO_3$ (207 mg, 1.495 mmol). The mixture was heated with a microwave reactor at 115° C. for 1 h. Purification via MDAP then afforded the title compound (13 mg, 8.01% yield). LCMS: rt=3.24 min, [M+H⁺]=435

E156: 2-[(2-{4-[(3-fluoro-4-methylphenyl)oxy]phenyl}ethyl)oxy]-5-(5-pyrimidinylmethyl)-4(1H)-pyrimidinone

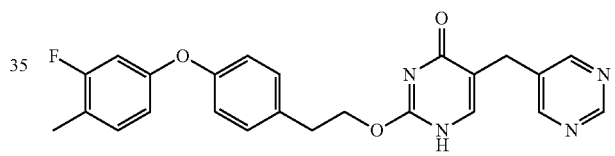

To the solution of 2-{4-[(3-fluoro-4-methylphenyl)oxy]phenyl}) ethyl imidocarbamate (100 mg, 0.249 mmol) and methyl 2-formyl-3-(5-pyrimidinyl)propanoate (58 mg, 0.299 mmol) in NMP (2 mL) was added $K_2CO_3$ (138 mg, 0.997 mmol). The mixture was heated with a microwave reactor at 115° C. for 2 h. Purification via MDAP then afforded the title compound (4 mg, 3.71% yield). LCMS: rt=3.19 min, [M+H⁺]=433

E157: 2-[(2-{4-[(3-fluoro-4-methylphenyl)oxy]phenyl}ethyl)oxy]-5-{[2-(methyloxy)-5-pyrimidinyl]methyl}-4(1H)-pyrimidinone

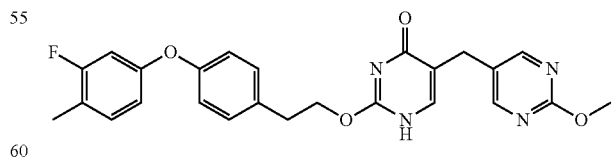

To the solution of 2-{4-[(3-fluoro-4-methylphenyl)oxy]phenyl}) ethyl imidocarbamate (100 mg, 0.347 mmol) and methyl 2-formyl-3-[2-(methyloxy)-5-pyrimidinyl]propanoate (93 mg, 0.416 mmol) in NMP (1.5 mL), was added $K_2CO_3$ (192 mg, 1.387 mmol). The mixture was heated with a microwave reactor at 115° C. for 2 h. Purification via MDAP then afforded the title compound (10 mg, 6.23% yield). LCMS: rt=3.30 min, [M+H+]=463

E158: 5-[(1-methyl-1H-pyrazol-4-yl)methyl]-2-[(2-{4-[(6-methyl-2-pyridinyl)oxy]phenyl}ethyl)oxy]-4(1H)-pyrimidinone

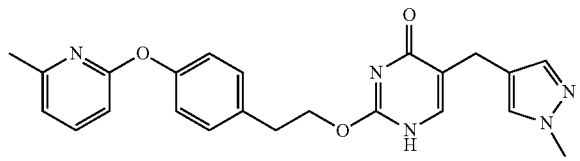 [SMILES: Cc1cccc(Oc2ccc(CCOc3nc(=O)c(Cc4cnn(C)c4)c[nH]3)cc2)n1]

To the solution of 2-{4-[(6-methyl-2-pyridinyl)oxy]phenyl}ethyl imidocarbamate (200 mg, 0.737 mmol) and methyl 2-formyl-3-(1-methyl-1H-pyrazol-4-yl)propanoate (174 mg, 0.885 mmol) in NMP (3 mL) was added $K_2CO_3$ (408 mg, 2.95 mmol). The mixture was heated with a microwave reactor at 130° C. for 0.5 h. Purification via MDAP then afforded the title compound (22 mg, 7.15% yield). LCMS: rt=2.38 min, [M+H+]=418

E159: 5-{[2-(methyloxy)-5-pyrimidinyl]methyl}-2-[(2-{4-[(6-methyl-2-pyridinyl)oxy]phenyl}ethyl)oxy]-4(1H)-pyrimidinone

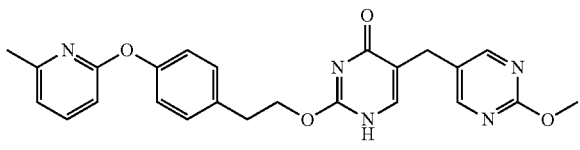

To the solution of 2-{4-[(6-methyl-2-pyridinyl)oxy]phenyl}ethyl imidocarbamate (200 mg, 0.737 mmol) and methyl 2-formyl-3-[2-(methyloxy)-5-pyrimidinyl]propanoate (182 mg, 0.811 mmol) in NMP (3 mL) was added $K_2CO_3$ (408 mg, 2.95 mmol). The mixture was heated with a microwave reactor at 130° C. for 1 h. Purification via MDAP then afforded the title compound (15 mg, 4.57% yield). LCMS: rt=2.54 min, [M+H+]=447

E160: 5-ethyl-2-[(2-{4-[(6-methyl-2-pyridinyl)oxy]phenyl}ethyl)oxy]-4(1H)-pyrimidinone

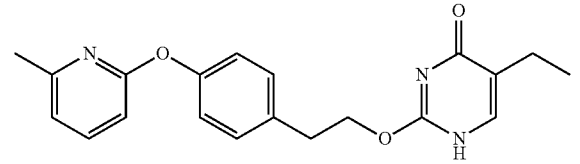 [SMILES: CCc1c[nH]c(OCCc2ccc(Oc3cccc(C)n3)cc2)nc1=O]

The same procedure as E125 from 2-{4-[(6-methyl-2-pyridinyl)oxy]phenyl}ethyl imidocarbamate (120 mg, 0.442 mmol), ethyl (2Z)-2-ethyl-3-hydroxy-2-propenoate (63.8 mg, 0.442 mmol) and $K_2CO_3$ (122 mg, 0.885 mmol) in DMF (3 mL) to afford the title compound (26 mg, 12.63% yield) as white solid. LCMS: rt=2.66 min, [M+H+]=466

E161: 2-(4-((5-chloro-6-(trifluoromethyl)pyridin-2-yl)oxy)phenethoxy)-5-((2-methoxypyrimidin-5-yl)methyl)pyrimidin-4(1H)-one

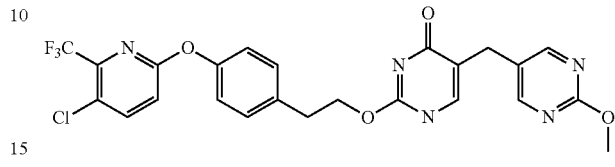

To the solution of 4-((5-chloro-6-(trifluoromethyl)pyridin-2-yl)oxy)phenethyl carbamimidate, trifluoroacetate (250 mg, 0.264 mmol) and methyl 2-formyl-3-(2-methoxypyrimidin-5-yl)propanoate (71.1 mg, 0.317 mmol) in 1,4-dioxane (2 mL) was added $K_2CO_3$ (110 mg, 0.793 mmol). The mixture was heated with a microwave reactor at 80° C. for 0.5 h. Purification via MDAP then afforded the title compound (3.6 mg, 6.74 mol, 2.55% yield). LCMS: rt=3.31 min, [M+H+]=534

E162: 2-{[2-(4-{[3-chloro-5-(trifluoromethyl)phenyl]oxy}phenyl)ethyl]oxy}-5-[(1-methyl-1H-pyrazol-4-yl)methyl]-4(1H)-pyrimidinone

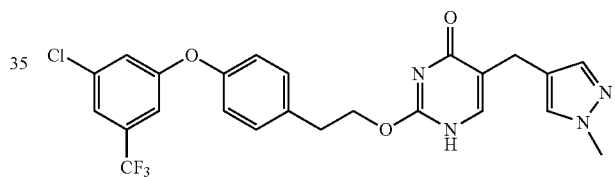

To the solution of 2-(4-{[3-chloro-5-(trifluoromethyl)phenyl]oxy}phenyl)ethyl imidocarbamate (200 mg, 0.424 mmol) and methyl 2-formyl-3-(1-methyl-1H-pyrazol-4-yl)propanoate (100 mg, 0.509 mmol) in NMP (3 mL) was added $K_2CO_3$ (234 mg, 1.696 mmol). The mixture was heated with a microwave reactor at 130° C. for 0.5 h. Purification via MDAP then afforded the title compound (54 mg, 25.2% % yield). LCMS: rt=3.57 min, [M+H]=505

E163: 2-{[2-(4-{[3-chloro-5-(trifluoromethyl)phenyl]oxy}phenyl)ethyl]oxy}-5-ethyl-4(1H)-pyrimidinone

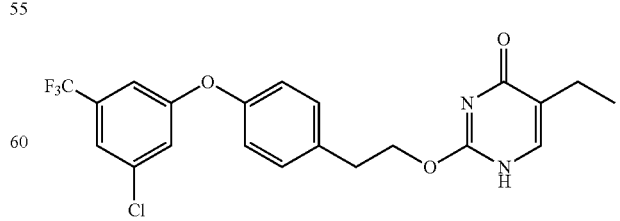

The same procedure as E125 from 2-(4-{[3-chloro-5-(1-fluoro-1-methylethyl)phenyl]oxy}phenyl)ethyl imidocarbamate (300 mg, 0.836 mmol), ethyl (2Z)-2-ethyl-3-hydroxy-2-propenoate (181 mg, 1.254 mmol) and K$_2$CO$_3$ (289 mg, 2.091 mmol) in DMF (3.0 mL), except that the reaction temperature was 130° C., to afford the title compound (110 mg, 0.251 mmol, 30.0% yield) as white solid. LCMS: rt=3.93 min, [M+H]=439

E164: 2-{[2-(4-{[3-chloro-5-(trifluoromethyl)phenyl]oxy}phenyl)ethyl]oxy}-5-ethyl-1-methyl-4(1H)-pyrimidinone

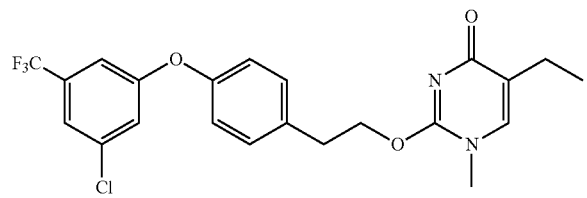 [SMILES: CCc1cn(C)c(OCCc2ccc(Oc3cc(Cl)cc(C(F)(F)F)c3)cc2)nc1=O]

The same procedure as E141 from 2-{[2-(4-{[3-chloro-5-(trifluoromethyl)phenyl]oxy}phenyl)ethyl]oxy}-5-ethyl-4(1H)-pyrimidinone (100 mg, 0.228 mmol), DIPEA (0.099 mL, 0.570 mmol) and MeI (0.028 mL, 0.456 mmol) in DCM (2 mL), except that the reaction time was 3 h, to afford the title compound (18 mg, 0.032 mmol, 13.93% yield). LCMS: rt=3.68 min, [M+H]=453

E165: 2-{[2-(4-{[3-chloro-5-(trifluoromethyl)phenyl]oxy}phenyl)ethyl]oxy}-5-{[2-(methyloxy)-5-pyrimidinyl]methyl}-4(1H)-pyrimidinone

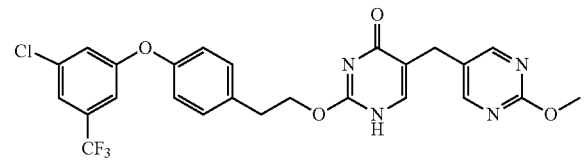 [SMILES: COc1ncc(Cc2c[nH]c(OCCc3ccc(Oc4cc(Cl)cc(C(F)(F)F)c4)cc3)nc2=O)cn1]

To the solution of 2-(4-{[3-chloro-5-(trifluoromethyl)phenyl]oxy}phenyl)ethyl imidocarbamate (230 mg, 0.488 mmol) and methyl 2-formyl-3-[2-(methyloxy)-5-pyrimidinyl]propanoate (131 mg, 0.585 mmol) in NMP (3 mL) was added K$_2$CO$_3$ (270 mg, 1.950 mmol). The mixture was heated with a microwave reactor at 130° C. for 1 h. Purification via MDAP then afforded the title compound (38 mg, 0.071 mmol, 14.63% yield). LCMS: rt=3.68 min, [M+H$^+$]=533

E166: 2-{[2-(3-fluoro-4-{[6-(trifluoromethyl)-2-pyridinyl]oxy}phenyl)ethyl]oxy}-5-{[2-(methyloxy)-5-pyrimidinyl]methyl}-4(1H)-pyrimidinone

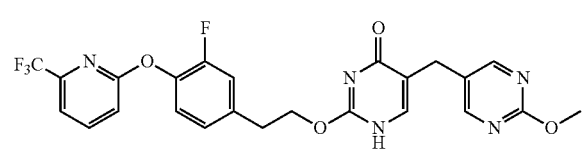 [SMILES: COc1ncc(Cc2c[nH]c(OCCc3ccc(Oc4cccc(C(F)(F)F)n4)c(F)c3)nc2=O)cn1]

A mixture of 2-(3-fluoro-4-{[6-(trifluoromethyl)-2-pyridinyl]oxy}phenyl)ethyl imidocarbamate (44 mg, 0.089 mmol), methyl (2E)-3-hydroxy-2-{[2-(methyloxy)-5-pyrimidinyl]methyl}-2-propenoate (30.1 mg, 0.134 mmol), and K$_2$CO$_3$ (37.1 mg, 0.268 mmol) in NMP (15 mL) was heated with a microwave reactor at 160° C. for 1 h. Purification via reverse phase flash chromatography then afforded the title compound (10 mg, 21.63% yield). LCMS: rt=3.13 min, [M+H]=518

E167: 2-(3-fluoro-4-((2-(trifluoromethyl)pyrimidin-5-yl)oxy)phenethoxy)-5-((2-methoxypyrimidin-5-yl)methyl)pyrimidin-4(1H)-one

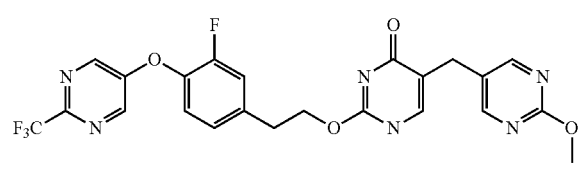 [SMILES: COc1ncc(Cc2c[nH]c(OCCc3ccc(Oc4cnc(C(F)(F)F)nc4)c(F)c3)nc2=O)cn1]

To the solution of 3-fluoro-4-((2-(trifluoromethyl)pyrimidin-5-yl)oxy)phenethyl carbamimidate, trifluoroacetate (50 mg, 0.109 mmol) and methyl 2-formyl-3-(2-methoxypyrimidin-5-yl)propanoate (30 mg, 0.134 mmol) in 1,4-dioxane (1 mL) was added K$_2$CO$_3$ (60 mg, 0.434 mmol). The mixture was heated with a microwave reactor at 100° C. for 0.5 h. Purification via MDAP then afforded the title compound (13.5 mg, 23.82 yield). LCMS: rt=2.97 min, [M+H+]=519

E168: 2-(3,5-difluoro-4-((2-(trifluoromethyl)pyrimidin-5-yl)oxy)phenethoxy)-5-(pyrimidin-5-ylmethyl)pyrimidin-4(1H)-one

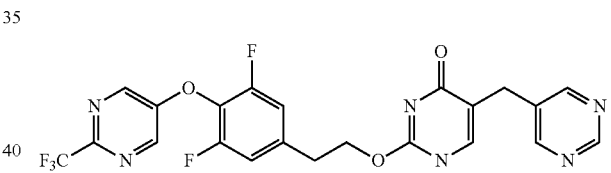

To the solution of 3,5-difluoro-4-((2-(trifluoromethyl)pyrimidin-5-yl)oxy)phenethyl carbamimidate, trifluoroacetate (100 mg, 0.210 mmol) and methyl 2-formyl-3-(pyrimidin-5-yl)propanoate (60 mg, 0.309 mmol) in 1,4-dioxane (1 mL) was added K$_2$CO$_3$ (116 mg, 0.842 mmol). The mixture was heated with a microwave reactor at 80° C. for 0.5 h. Purification via MDAP then afforded the title compound (36 mg, 0.071 mmol, 33.8% yield). LCMS: rt=2.82 min, [M+H]=507

E169: 2-(3,5-difluoro-4-((2-(trifluoromethyl)pyrimidin-5-yl)oxy)phenethoxy)-5-((2-methoxypyrimidin-5-yl)methyl)pyrimidin-4(1H)-one

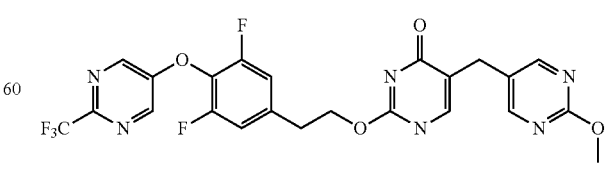

To the solution of 3,5-difluoro-4-((2-(trifluoromethyl)pyrimidin-5-yl)oxy)phenethyl carbamimidate, trifluoroacetate (200 mg, 0.421 mmol) and methyl 2-formyl-3-(2-methoxypyrimidin-5-yl)propanoate (113 mg, 0.505 mmol) in 1,4-dioxane (2 mL) was added K$_2$CO$_3$ (233 mg, 1.683 mmol). The mixture was heated with a microwave reactor at 80° C. for 0.5 h. Purification via MDAP then afforded the title compound (65 mg, 28.8% yield). LCMS: rt=3.05 min, [M+H]=537

E170: 2-(3,5-difluoro-4-((2-(trifluoromethyl)pyrimidin-5-yl)oxy)phenethoxy)-5-ethylpyrimidin-4(1H)-one

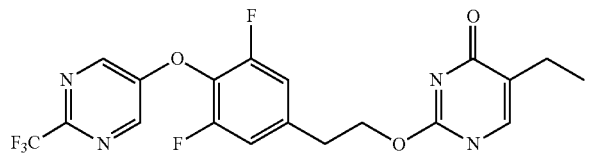 [SMILES: CCc1c[nH]c(OCCc2cc(F)c(Oc3cnc(C(F)(F)F)nc3)c(F)c2)nc1=O]

To the solution of 3,5-difluoro-4-((2-(trifluoromethyl)pyrimidin-5-yl)oxy)phenethyl carbamimidate, trifluoroacetate (50 mg, 0.105 mmol) and methyl 2-formylbutanoate (17 mg, 0.131 mmol) in 1,4-dioxane (0.5 mL) was added K$_2$CO$_3$ (58.2 mg, 0.421 mmol). The mixture was heated with a microwave reactor at 80° C. for 1 h. Purification via reverse phase flash chromatography then afforded the title compound (14.6 mg, 31.4% yield). LCMS: rt=3.15 min, [M+H$^+$]=443

E171: 2-(3,5-difluoro-4-((2-(trifluoromethyl)pyrimidin-5-yl)oxy)phenethoxy)-5-ethyl-1-methylpyrimidin-4(1H)-one

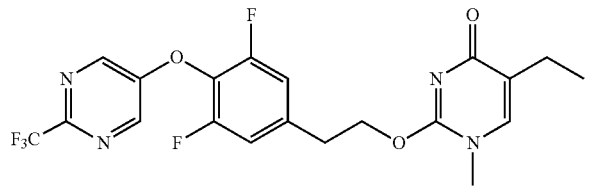 [SMILES: CCc1cn(C)c(OCCc2cc(F)c(Oc3cnc(C(F)(F)F)nc3)c(F)c2)nc1=O]

To the solution of 2-(3,5-difluoro-4-((2-(trifluoromethyl)pyrimidin-5-yl)oxy)phenethoxy)-5-ethylpyrimidin-4(1H)-one (30 mg, 0.068 mmol) and DIPEA (0.03 ml, 0.172 mmol) in DCM (1.5 ml) was added MeI (0.025 ml, 0.407 mmol). The solution was stirred at room temperature overnight. Purification via reverse phase flash chromatography then afforded the title compound (12 mg, 0.026 mmol, 38.8% yield). LCMS: rt=3.10 min, [M+H]=457

E172: 2-{[2-(4-{[4-chloro-3-(trifluoromethyl)phenyl]oxy}-3-fluorophenyl)ethyl]oxy}-5-{[2-(methyloxy)-5-pyrimidinyl]methyl}-4(1H)-pyrimidinone

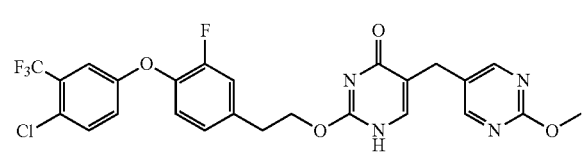 [SMILES: COc1ncc(Cc2c[nH]c(OCCc3ccc(Oc4ccc(Cl)c(C(F)(F)F)c4)c(F)c3)nc2=O)cn1]

A mixture of 2-(4-{[4-chloro-3-(trifluoromethyl)phenyl]oxy}-3-fluorophenyl)ethyl imidocarbamate (200 mg, 0.380 mmol), methyl (2Z)-3-hydroxy-2-{[2-(methyloxy)-5-pyrimidinyl]methyl}-2-propenoate (170 mg, 0.759 mmol) and K$_2$CO$_3$ (115 mg, 0.835 mmol) in NMP (5 mL) was heated with a microwave condition at 160° C. for 1.5 h. Purification via reverse phase flash chromatography afforded the title compound (32 mg, 0.055 mmol, 14.54% yield). LCMS: rt=3.53 min, [M+H]=551

E173: 2-{[2-(4-{[4-chloro-3-(trifluoromethyl)phenyl]oxy}-3-fluorophenyl)ethyl]oxy}-5-ethyl-4(1H)-pyrimidinone

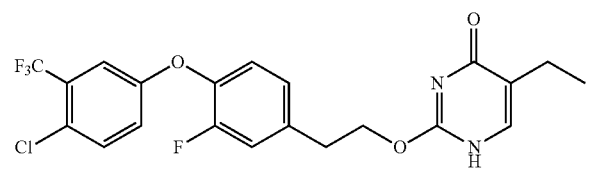 [SMILES: CCc1c[nH]c(OCCc2ccc(Oc3ccc(Cl)c(C(F)(F)F)c3)c(F)c2)nc1=O]

The same procedure as E125 from 2-(4-{[4-chloro-3-(trifluoromethyl)phenyl]oxy}-3-fluorophenyl)ethyl imidocarbamate (250 mg, 0.664 mmol), ethyl (2Z)-2-ethyl-3-hydroxy-2-propenoate (191 mg, 1.327 mmol) and K$_2$CO$_3$ (183 mg, 1.327 mmol) in DMF (3 mL) to afford the title compound (60 mg, 0.131 mmol, 19.79% yield) as white solid. LCMS: rt=3.80 min, [M+H$^+$]=457

E174: 2-{[2-(4-{[4-chloro-3-(trifluoromethyl)phenyl]oxy}-3-fluorophenyl)ethyl]oxy}-5-ethyl-1-methyl-4(1H)-pyrimidinone

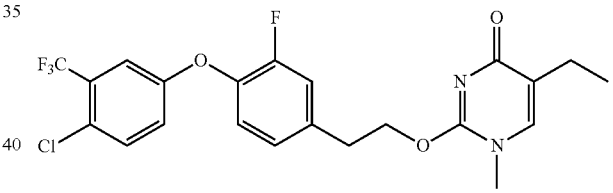

The same procedure as E141 from 2-{[2-(4-{[4-chloro-3-(trifluoromethyl)phenyl]oxy}-3-fluorophenyl)ethyl]oxy}-5-ethyl-4(1H)-pyrimidinone (60 mg, 0.131 mmol), DIPEA (0.046 mL, 0.263 mmol) and MeI (0.012 mL, 0.197 mmol) in DCM (2 mL), except that the reaction time was 3 h, to afford the title compound (13 mg, 0.022 mmol, 16.92% yield). LCMS: rt=3.59 min, [M+H$^+$]=471

E175: 2-{[2-(4-{[4-chloro-3-(trifluoromethyl)phenyl]oxy}-3,5-difluorophenyl)ethyl]oxy}-5-ethyl-1-methyl-4(1H)-pyrimidinone

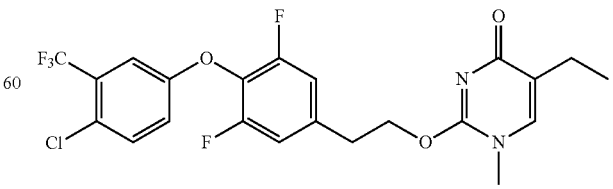

The same procedure as E141 from 2-{[2-(4-{[4-chloro-3-(trifluoromethyl)phenyl]oxy}-3,5-difluorophenyl)ethyl]

oxy}-5-ethyl-4(1H)-pyrimidinone (60 mg, 0.126 mmol), DIPEA (0.044 mL, 0.253 mmol) and MeI (0.012 mL, 0.190 mmol) in DCM (2 mL), except that the reaction time was 3 h, to afford the title compound (11 mg, 0.018 mmol, 14.44% yield). LCMS: rt=3.62 min, [M+H+]=489

E176: 2-{[2-(4-{[4-chloro-3-(trifluoromethyl)phenyl]oxy}-3,5-difluorophenyl)ethyl]oxy}-5-{[2-(methyloxy)-5-pyrimidinyl]methyl}-4(1H)-pyrimidinone

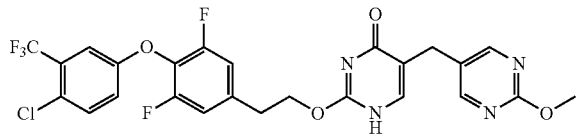 [SMILES: COc1ncc(Cc2c[nH]c(OCCc3cc(F)c(Oc4ccc(Cl)c(C(F)(F)F)c4)c(F)c3)nc2=O)cn1]

The same procedure as E125 from 2-(4-{[4-chloro-3-(trifluoromethyl)phenyl]oxy}-3,5-difluorophenyl)ethyl imidocarbamate (143 mg, 0.362 mmol), ethyl (2Z)-3-hydroxy-2-{[2-(methyloxy)-5-pyrimidinyl]methyl}-2-propenoate (129 mg, 0.543 mmol) and $K_2CO_3$ (125 mg, 0.906 mmol) in DMF (3 mL), except that the reaction temperature was 130° C., to afford the title compound (31 mg, 0.054 mmol, 15.04% yield) as white solid. LCMS: rt=3.61 min, [M+H+]=569

E177: 2-(4-(4-chloro-3-(trifluoromethoxy)phenoxy)phenethoxy)-5-(pyrimidin-5-ylmethyl)pyrimidin-4(1H)-one

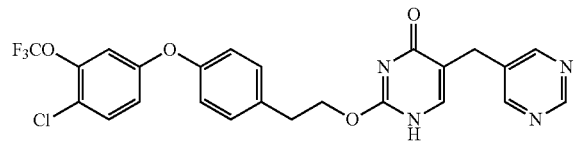 [SMILES: O=c1nc(OCCc2ccc(Oc3ccc(Cl)c(OC(F)(F)F)c3)cc2)[nH]cc1Cc1cncnc1]

A mixture of 4-(4-chloro-3-(trifluoromethoxy)phenoxy)phenethyl carbamimidate (80 mg, 0.213 mmol), (Z)-methyl 3-hydroxy-2-(pyrimidin-5-ylmethyl)acrylate (124 mg, 0.640 mmol) and $Cs_2CO_3$ (174 mg, 0.534 mmol) in 1,4-dioxane (2 mL) was heated with a microwave condition at 110° C. for 2 h. After cooling, the mixture was filtered through the celite. The filtrate was concentrated and purified via reverse phase flash chromatography to afford the title compound (48 mg, 0.093 mmol, 43.3% yield). LCMS: rt=3.48 min, [M+H+]=519

E178: 2-(4-(4-chloro-3-(trifluoromethoxy)phenoxy)phenethoxy)-5-((2-methoxypyrimidin-5-yl)methyl)pyrimidin-4(1H)-one

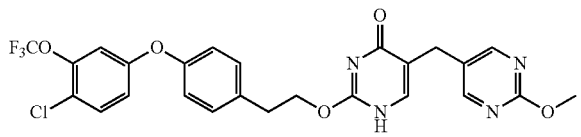 [SMILES: COc1ncc(Cc2c[nH]c(OCCc3ccc(Oc4ccc(Cl)c(OC(F)(F)F)c4)cc3)nc2=O)cn1]

The same procedure as E177 from 4-(4-chloro-3-(trifluoromethoxy)phenoxy)phenethyl carbamimidate (100 mg, 0.267 mmol), (Z)-methyl 3-hydroxy-2-((2-methoxypyrimidin-5-yl)methyl)acrylate (180 mg, 0.803 mmol) and $Cs_2CO_3$ (260 mg, 0.798 mmol) in 1,4-dioxane (2 mL), except that the reaction temperature was 120° C. and the time was 4 h, to afford the title compound (28 mg, 0.042 mmol, 15.83% yield). LCMS: rt=3.63 min, [M+H+]=549

E179: 2-(4-(4-chloro-3-(trifluoromethoxy)phenoxy)phenethoxy)-5-ethyl)pyrimidin-4(1H)-one

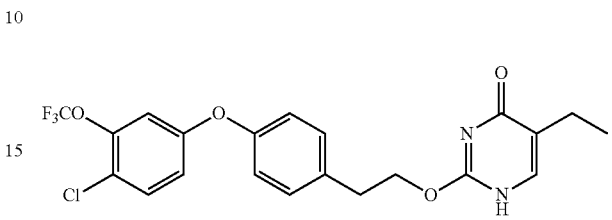

The same procedure as E177 from 4-(4-chloro-3-(trifluoromethoxy)phenoxy) phenethylcarbamimidate (35 mg, 0.093 mmol), (Z)-methyl 2-(hydroxymethylene)butanoate (24.31 mg, 0.187 mmol) and $Cs_2CO_3$ (60.9 mg, 0.187 mmol) in 1,4-dioxane (2 mL), except that the reaction temperature was 100° C. and the time was 1.5 h, to afford the title compound (22 mg, 0.039 mmol, 41.4% yield). LCMS: rt=3.85 min, [M+H+]=455

E180: 2-(4-(4-chloro-2,6-difluorophenoxy)phenethoxy)-5-ethylpyrimidin-4(1H)-one

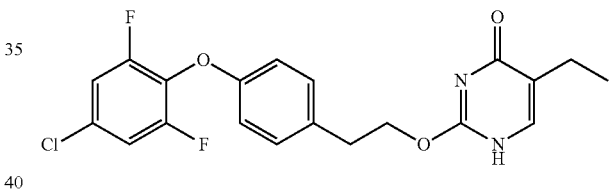

The same procedure as E177 from 4-(4-chloro-2,6-difluorophenoxy)phenethyl carbamimidate, trifluoromethanesulphonic acid salt (200 mg, 0.419 mmol), (Z)-methyl 2-(hydroxymethylene)butanoate (110 mg, 0.845 mmol) and $Cs_2CO_3$ (280 mg, 0.859 mmol) in 1,4-dioxane (2 mL), except that the reaction temperature was 100° C., to afford the title compound (56 mg, 0.138 mmol, 32.8% yield). LCMS: rt=3.61 min, [M+H+]=407

E181: 2-(4-(4-chloro-2,6-difluorophenoxy)phenethoxy)-5-((2-methoxypyrimidin-5-yl)methyl)pyrimidin-4(1H)-one

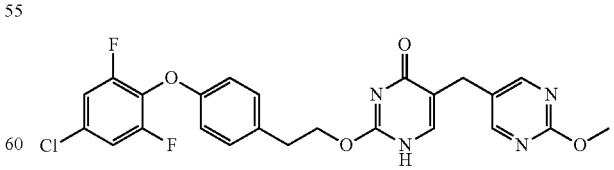

The same procedure as E177 from 4-(4-chloro-2,6-difluorophenoxy)phenethyl carbamimidate, trifluoromethanesulphonic acid salt (100 mg, 0.210 mmol), (Z)-methyl 3-hydroxy-2-((2-methoxypyrimidin-5-yl)methyl)acrylate (100 mg, 0.446 mmol) and $Cs_2CO_3$ (140 mg, 0.430 mmol) in 1,4-Dioxane (2 mL) to afford the title compound (60 mg, 0.120 mmol, 57.1% yield). LCMS: rt=3.39 min, [M+H⁺]= 501

E182: 2-(4-(4-chloro-2,6-difluorophenoxy)phenethoxy)-5-(pyrimidin-5-ylmethyl)pyrimidin-4(1H)-one

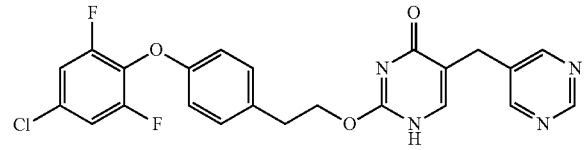 [SMILES: O=c1nc(OCCc2ccc(Oc3c(F)cc(Cl)cc3F)cc2)[nH]cc1Cc1cncnc1]

The same procedure as E177 from 4-(4-chloro-2,6-difluorophenoxy)phenethyl carbamimidate, trifluoromethanesulphonic acid salt (100 mg, 0.210 mmol), (Z)-methyl 3-hydroxy-2-(pyrimidin-5-ylmethyl)acrylate (85 mg, 0.438 mmol) and Cs₂CO₃ (140 mg, 0.430 mmol) in 1,4-dioxane (2 mL) to afford the title compound (48 mg, 0.102 mmol, 48.6% yield). LCMS: rt=3.20 min, [M+H⁺]=471

E183: 2-[(2-{4-[(4-chloro-3-methylphenyl)oxy]phenyl}ethyl)oxy]-5-ethyl-4(1H)-pyrimidinone

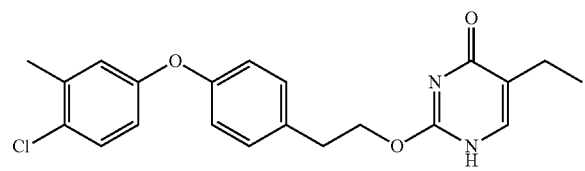 [SMILES: CCc1c[nH]c(OCCc2ccc(Oc3ccc(Cl)c(C)c3)cc2)nc1=O]

A mixture of 2-{4-[(4-chloro-3-methylphenyl)oxy]phenyl}ethyl imidocarbamate (130 mg, 0.427 mmol), ethyl (2Z)-2-ethyl-3-hydroxy-2-propenoate (123 mg, 0.853 mmol) and K₂CO₃ (118 mg, 0.853 mmol) in DMF (3 mL) was heated with a microwave condition at 110° C. for 1.5 h. After cooling, the mixture was filtered, and purified via MDAP to afford the title compound (50 mg, 30.5% yield) as white solid. LCMS: rt=3.80 min, [M+H⁺]=385

E184: 2-[(2-{4-[(4-chloro-3-methylphenyl)oxy]phenyl}ethyl)oxy]-5-ethyl-1-methyl-4(1H)-pyrimidinone

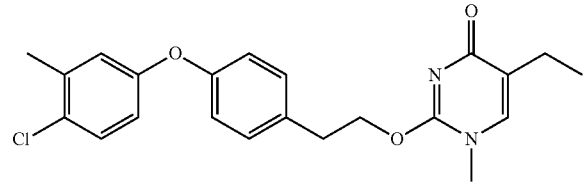 [SMILES: CCc1cn(C)c(OCCc2ccc(Oc3ccc(Cl)c(C)c3)cc2)nc1=O]

A mixture solution of 2-[(2-{4-[(4-chloro-3-methylphenyl)oxy]phenyl}ethyl)oxy]-5-ethyl-4(1H)-pyrimidinone (30 mg, 0.078 mmol) and DIPEA (0.027 mL, 0.156 mmol) in DCM (2 mL) was added MeI (9.75 µL, 0.156 mmol). The mixture was stirred at room temperature for 3 h, and quenched with water. The aqueous layer was extracted with DCM. The combined organic layers was dried with anhydrous Na₂SO₄, filtered, concentrated, and purified via MDAP to afford the title compound (8 mg, 25.7% yield) as oil. LCMS: rt=3.56 min, [M+H⁺]=399

E185: 5-Pyrimidin-5-ylmethyl-2-{2-[4-(3-trifluoromethyl-phenoxy)-phenyl]-ethylamino}-1H-pyrimidin-4-one

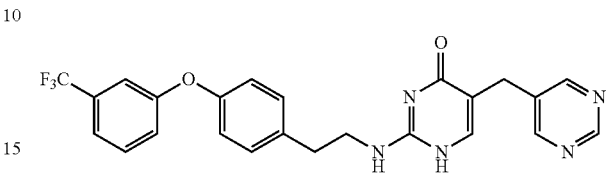

2-Methylsulfanyl-5-pyrimidin-5-ylmethyl-1H-pyrimidin-4-one (40 mg, 0.171 mmol, 1 eq) and 2-[4-(3-trifluoromethyl-phenoxy)-phenyl]-ethylamine (53 mg, 0.188 mmol, 1.1 eq) were dissolved in dry ethanol (300 µl) and stirred at 120° C. for 6 h. Ethanol was evaporated during the reaction and in the mixture was added pyridine (300 µl) and reaction was stirred for 3 h. Pyridine was evaporated and 0.5 ml of EtOH was added. Precipitate was formed and it was starting material. Mother liquor was evaporated and purified via Biotage SP-1 Snap Si 10 g in the gradient of MeOH in DCM: 1% for 1 CV, 1-5% for 18 CV; 5-10% for 20 CV. The appropriate fractions were combined and evaporated in vacuo to give the required product which was not pure enough and it was sent to HPLC/MS Purification. After HPLC/MS purification combined fractions of desired product were collected and put on lyophilisation to obtain 5-pyrimidin-5-ylmethyl-2-{2-[4-(3-trifluoromethyl-phenoxy)-phenyl]-ethylamino}-1H-pyrimidin-4-one (0.0087 mmol; yield: 5.1%, HPLC-MS/UV: [M+H]⁺= 468.45; rt: 10.90 min; purity: 94.9%). ¹H NMR (300 MHz; DMSO-d6) δ/ppm 2.78 (t, J=7.17 Hz, 2H), 3.41-3.47 (m, 2H), 3.50 (s, 2H), 6.99 (d, J=8.40 Hz, 2H), 7.22 (d, J=8.34 Hz, 1H), 7.24-7.31 (m, 3H), 7.44 (d, J=7.82 Hz, 1H), 7.56 (s, J=7.92 Hz, 1H), 7.60 (s, 1H), 8.66 (s, 2H), 8.94 (s, 1H)

E186: 5-(2-methoxy-pyrimidin-5-ylmethyl)-2-{2-[4-(5-trifluoromethyl-pyridin-2-yloxy)phenyl]-ethylamino}-1H-pyrimidin-4-one

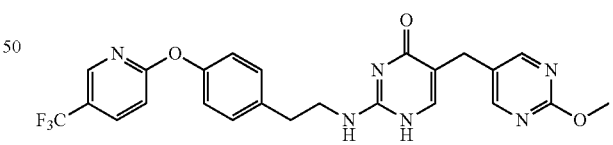

2-[4-(5-trifluoromethyl-pyridin-2-yloxy)-phenyl]ethylamine (0.246 mmol, 1.3 eq) and 5-(2-methoxy-pyrimidin-5-ylmethyl)-2-methylsulfanyl-1H-pyrimidin-4-one (0.189 mmol, 1 eq) were dissolved in dry ethanol (300 µL) and stirred at 125° C. for 16 hours. Solvent was evaporated and crude product was purified by Waters Mass Direct Autopurification system giving 5-(2-methoxy-pyrimidin-5-ylmethyl)-2-{2-[4-(5-trifluoromethyl-pyridin-2-yloxy)phenyl]-ethylamino}-1H-pyrimidin-4-one (0.090 mmol; yield: 36%, HPLC-MS/UV: [M+H]=499.34; rt: 10.40 min; purity: 94%). ¹H NMR (300 MHz; CDCl₃) δ/ppm 2.93 (t, J=7.05, 2H), 3.51 (s, 2H), 3.58-3.74 (m, 2H), 3.95 (s, 1H), 5.31 (br.s., 1H), 6.98-7.13 (m, 3H), 7.22-7.32 (m, 2H), 7.61-7.67 (m, 1H), 7.89 (dd, J=8.50, J=2.64, 1H), 8.38 (m, 1H)

E187: 2-(Methyl-{2-[4-(3-trifluoromethyl-phenoxy)-phenyl]-ethyl}-amino)-5-pyrimidin-5-ylmethyl-1H-pyrimidin-4-one

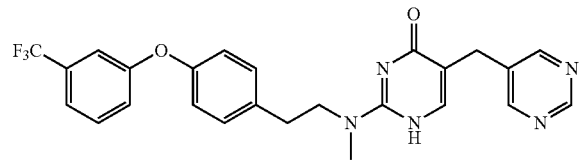 [SMILES: CN(CCc1ccc(Oc2cccc(C(F)(F)F)c2)cc1)c1nc(=O)c(Cc2cncnc2)c[nH]1]

2-Methylsulfanyl-5-pyrimidin-5-ylmethyl-1H-pyrimidin-4-one (30 mg, 0.128 mmol, 1 eq) and methyl-{2-[4-(3-trifluoromethyl-phenoxy)-phenyl]-ethyl}-amine (56.7 mg, 0.192 mmol, 1.5 eq) were dissolved in dry ethanol (300 µl) and stirred at 125° C. for overnight. Reaction mixture was evaporated and crude residue was sent to HPLC/MS Purification. After HPLC/MS purification combined fractions of desired product were collected and put on lyophilisation to obtain 2-(methyl-{2-[4-(3-trifluoromethyl-phenoxy)-phenyl]-ethyl}-amino)-5-pyrimidin-5-ylmethyl-1H-pyrimidin-4-one (0.069 mmol; yield: 54%, HPLC-MS/UV: [M+H]=482.48; rt: 11.27 min; purity: 96%). $^1$H NMR (300 MHz; DMSO-d6) δ/ppm 2.80 (t, J=6.68 Hz, 2H), 2.94 (s, 3H), 3.52 (s, 2H), 3.69 (t, J=7.09 Hz, 2H), 7.00 (d, J=8.76 Hz, 2H), 7.19 (d, J=8.10 Hz, 1H), 7.24 (s, 1H), 7.30 (d, J=8.45 Hz, 2H), 7.44 (d, J=7.75 Hz, 1H), 7.58 (t, J=8.10 Hz, 1H), 7.66 (s, 1H), 8.66 (s, 2H), 8.95 (s, 1H)

E188: 2-{2-[4-(4-Fluoro-phenoxy)-phenyl]-ethylamino}-5-pyrimidin-5-ylmethyl-1H-pyrimidin-4-one

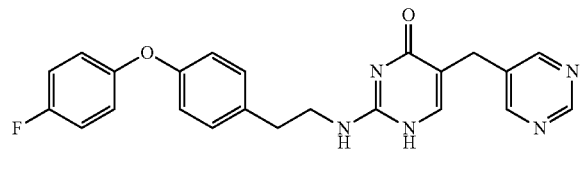 [SMILES: O=c1nc(NCCc2ccc(Oc3ccc(F)cc3)cc2)[nH]cc1Cc1cncnc1]

2-Methylsulfanyl-5-pyrimidin-5-ylmethyl-1H-pyrimidin-4-one (30 mg, 0.128 mmol, 1 eq) and 2-[4-(4-Fluoro-phenoxy)-phenyl]-ethylamine (44.4 mg, 0.192 mmol, 1.5 eq) were dissolved in dry ethanol (300 µl) and stirred at 125° C. for overnight. Reaction mixture was evaporated and crude residue was sent to HPLC/MS Purification. After HPLC/MS purification combined fractions of desired product were collected and put on lyophilisation to obtain 2-{2-[4-(4-fluoro-phenoxy)-phenyl]-ethylamino}-5-pyrimidin-5-ylmethyl-1H-pyrimidin-4-one (0.068 mmol; yield: 53.1%, HPLC-MS/UV: [M+H]$^+$=418.45; rt: 9.78 min; purity: 98%). $^1$H NMR (300 MHz; DMSO-d6) δ/ppm 2.75 (t, J=7.50 Hz, 2H), 3.39-3.49 (m, 2H), 3.51 (s, 2H), 6.46 (br.s, 1H), 6.90 (d, J=8.57 Hz, 2H), 6.97-7.05 (m 2H), 7.15-7.25 (m, 4H), 7.66 (s, 1H), 8.66 (s, 2H), 8.97 (s, 1H), 10.92 (br.s., 1H)

E189: 2-{2-[4-(4-Chloro-3-trifluoromethyl-phenoxy)-phenyl]-ethylamino}-1-methyl-5-pyrimidin-5-ylmethyl-1H-pyrimidin-4-one

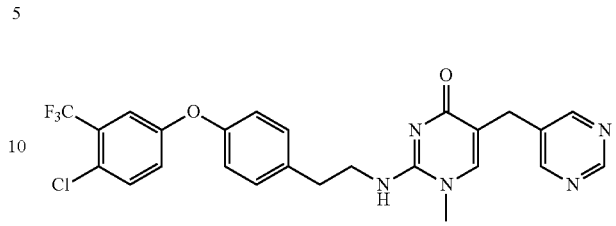

2-Methylsulfanyl-5-pyrimidin-5-ylmethyl-1H-pyrimidin-4-one (18.6 mg, 0.079 mmol, 1 eq) and 2-[4-(4-Chloro-3-trifluoromethyl-phenoxy)-phenyl]-ethylamine (39.3 mg, 0.119 mmol, 1.5 eq) were dissolved in dry ethanol (300 µl) and stirred at 125° C. for 48 h. Reaction mixture was evaporated and crude residue was purified via Biotage SP-1 Snap Si 10 g; 15 ml/min in the gradient of MeOH in DCM: 1% for 1 CV then from 1-5% for 20 CV. The appropriate fractions were combined and evaporated in vacuo to give the required product which was not pure enough and it was sent to HPLC/MS Purification. After HPLC/MS purification combined fractions of desired product were collected and put on lyophilisation to obtain 2-{2-[4-(4-Chloro-3-trifluoromethyl-phenoxy)-phenyl]-ethylamino}-1-methyl-5-pyrimidin-5-ylmethyl-1H-pyrimidin-4-one (0.0095 mmol; yield: 10%, HPLC-MS/UV: [M+H]$^+$=516.93; rt: 11.49 min; purity: 96%). $^1$H NMR (300 MHz; DMSO-d6) δ/ppm 2.82 (t, J=8.17 Hz, 2H), 3.40-3.52 (m, 4H), 6.92 (m, 1H), 7.05 (d, J=8.59 Hz, 2H), 7.22 (dd, J=9.11, J=2.72, 1H), 7.28 (d, J=8.29, 2H), 7.38-7.44 (m, 2H), 7.67 (d, J=8.84, 1H), 8.67 (s, 2H), 8.97 (s, 1H)

E190: 2-{2-[4-(4-fluoro-phenoxy)phenyl]-ethylamino}-5-(2-methoxy-pyrimidin-5-ylmethyl)-1H-pyrimidin-4-one

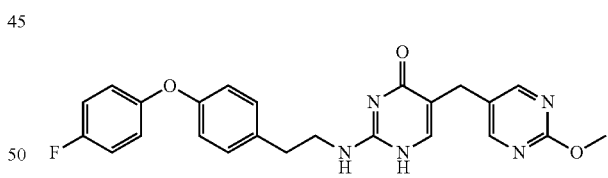

2-[4-(4-fluoro-phenoxy)-phenyl]ethylamine (0.216 mmol, 1 eq) and 5-(2-methoxy-pyrimidin-5-ylmethyl)-2-methylsulfanyl-1H-pyrimidin-4-one (0.108 mmol, 0.5 eq) were dissolved in dry ethanol (300 µL) and stirred at 125° C. for 16 hours. Solvent was evaporated and crude product was purified by Waters Mass Direct Autopurification system giving 2-{2-[4-(4-fluoro-phenoxy)phenyl]-ethylamino}-5-(2-methoxy-pyrimidin-5-ylmethyl)-1H-pyrimidin-4-one (0.090 mmol; yield: 18%, HPLC-MS/UV: [M+H]=448.34; rt: 10.25 min; purity: 94%). $^1$H NMR (300 MHz; CDCl$_3$) δ/ppm 2.88 (t, J=7.17, 2H), 3.51 (s, 2H), 3.55-3.67 (m, 2H), 3.95 (s, 3H), 5.11 (br.s., 1H), 6.87-7.05 (m, 5H), 7.14-7.21 (m, 2H), 7.23-7.30 (m, 1H), 7.65 (s, 1H), 8.39 (s, 1H)

E191: 2-({2-[4-(4-fluoro-phenoxy)phenyl]-ethyl}-methyl-amino)-5-(2-methoxy-pyrimidin-5-ylmethyl)-1H-pyrimidin-4-one

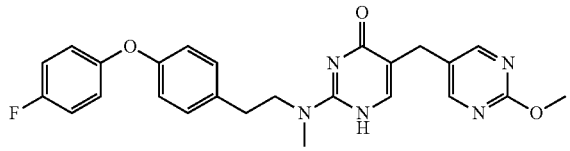 [SMILES: COc1ncc(Cc2c[nH]c(N(C)CCc3ccc(Oc4ccc(F)cc4)cc3)nc2=O)cn1]

2-[4-(4-fluoro-phenoxy)-phenyl]ethylamine (0.204 mmol, 1 eq) and 5-(2-methoxy-pyrimidin-5-ylmethyl)-2-methylsulfanyl-1H-pyrimidin-4-one (0.082 mmol, 0.4 eq) were dissolved in dry ethanol (200 μL) and stirred at 125° C. for 16 hours. Solvent was evaporated and crude product was purified by Waters Mass Direct Autopurification system giving 2-({2-[4-(4-fluoro-phenoxy)phenyl]-ethyl}-methyl-amino)-5-(2-methoxy-pyrimidin-5-ylmethyl)-1H-pyrimidin-4-one (0.039 mmol, yield: 19%, HPLC-MS/UV: [M+H]$^+$=462.24; rt: 10.59 min; purity: 99%). $^1$H NMR (300 MHz; CDCl$_3$) δ/ppm 2.85 (t, J=7.17, 2H), 2.98 (s, 2H), 3.51 (s, 2H), 3.73 (t, J=6.72, 2H), 3.95 (s, 3H), 6.85-7.05 (m, 5H), 7.11-7.17 (m, 2H), 7.23-7.28 (m, 1H), 7.65 (s, 1H), 8.37 (s, 1H), 10.09 (br.s., 1H)

E192: 2-{2-[4-(4-fluoro-phenoxy)phenyl]-ethyl-methyl-amino}-5-pyrimidin-5-ylmethyl-1H-pyrimidin-4-one

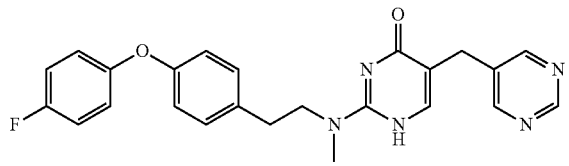 [SMILES: CN(CCc1ccc(Oc2ccc(F)cc2)cc1)c1nc(=O)c(Cc2cncnc2)c[nH]1]

2-[4-(4-fluoro-phenoxy)-phenyl]-ethyl-methyl amine (0.204 mmol, 1 eq) and 2-methylsulfanyl-5-pyrimidin-5-ylmethyl-1H-pyrimidin-4-one (0.082 mmol, 0.4 eq) were dissolved in dry ethanol (200 μL) and stirred at 125° C. for 16 hours. Solvent was evaporated and crude product was purified on Biotage SP1 Snap Si 25; 25 ml/min in the gradient of MeOH in DCM: 0-10% in 30CV. The appropriate fractions were combined and evaporated in vacuo to give the required product 2-{2-[4-(4-fluoro-phenoxy)phenyl]-ethyl-methyl-amino}-5-pyrimidin-5-ylmethyl-1H-pyrimidin-4-one (0.042 mmol, yield: 20%, HPLC-MS/UV: [M+H]=432.14; rt: 10.14 mins; purity: 97%). $^1$H NMR (300 MHz; CDCl$_3$) δ/ppm 2.89 (t, J=7.17, 2H), 3.59 (s, 2H), 3.69-3.77 (m, 2H), 6.86-7.05 (m, 5H), 7.10-7.18 (m, 2H), 7.23-7.30 (m, 2H), 7.69 (s, 1H), 8.61 (s, 1H), 9.02-9.05 (m, 1H), 9.95 (br.s., 1H)

E193: 5-(2-methoxy-pyrimidin-5-ylmethyl)-2-{2-[4-(3-trifluoromethyl-phenoxy)phenyl]-ethylamino}-1H-pyrimidin-4-one

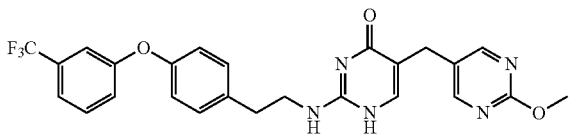 [SMILES: COc1ncc(Cc2c[nH]c(NCCc3ccc(Oc4cccc(C(F)(F)F)c4)cc3)nc2=O)cn1]

2-[4-(3-fluoromethyl-phenoxy)-phenyl]ethylamine (0.178 mmo, 1 eq) and 5-(2-methoxy-pyrimidin-5-ylmethyl)-2-methylsulfanyl-1H-pyrimidin-4-one (0.089 mmol, 0.5 eq) were dissolved in dry ethanol (300 μL) and stirred at 125° C. for 16 hours. Solvent was evaporated and crude product was purified by Waters Mass Direct Autopurification system giving 5-(2-methoxy-pyrimidin-5-ylmethyl)-2-{2-[4-(3-trifluoromethyl-phenoxy)phenyl]-ethylamino}-1H-pyrimidin-4-one (0.030 mmol, yield: 17%, HPLC-MS/UV: [M+H]$^+$=498.13; rt: 11.19 min; purity: 94%). $^1$H NMR (300 MHz; CDCl$_3$) δ/ppm 2.91 (t, J=7.56, 2H), 3.51 (s, 1H), 3.58-3.67 (m, 2H), 3.94 (s, 3H), 5.28 (br.s., 1H), 6.93-7.01 (m, 2H), 7.08-7.14 (m, 1H), 7.17-7.24 (m, 2H), 7.29-7.45 (m, 3H), 7.66 (s, 1H), 8.39 (s, 1H), 12.07 (br.s., 1H)

E194: 2-{2-[4-(4-Chloro-phenoxy)-phenyl]-ethylamino}-5-pyrimidin-5-ylmethyl-1H-pyrimidin-4-one

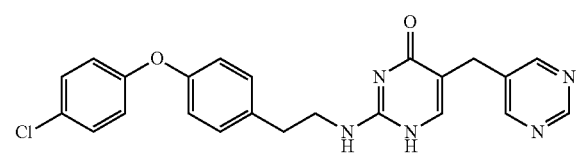 [SMILES: O=c1nc(NCCc2ccc(Oc3ccc(Cl)cc3)cc2)[nH]cc1Cc1cncnc1]

2-Methylsulfanyl-5-pyrimidin-5-ylmethyl-1H-pyrimidin-4-one (30 mg, 0.128 mmol, 1 eq) and 2-[4-(4-Chloro-phenoxy)-phenyl]-ethylamine (47.5 mg, 0.192 mmol, 1.5 eq) were dissolved in dry ethanol (300 μl) and stirred at 130° C. for overnight. Reaction mixture was evaporated and crude residue was purified via Biotage SP-1 Snap Si 10 g; 15 ml/min; UV Wavelength (Collection: 254 nm; Monitor: 290 nm) in the gradient of MeOH in DCM: 0% for 1 CV, 0-8% for 15 CV. The appropriate fractions were combined and product was triturated with cyclohexane to give 2-{2-[4-(4-Chloro-phenoxy)-phenyl]-ethylamino}-5-pyrimidin-5-ylmethyl-1H-pyrimidin-4-one (0.077 mmol; yield: 60.2%, HPLC-MS/UV: [M+H]$^+$=434.90; rt: 10.52 min; purity: 95%). $^1$H NMR (300 MHz; DMSO-d6) δ/ppm 2.77 (t, J=7.12 Hz, 2H), 3.40-3.50 (m, 2H), 3.52 (s, 2H), 6.34 (br.s., 1H), 6.90-7.03 (m, 4H), 7.25 (d, J=7.63, 2H), 7.40 (d, J=8.65, 2H), 7.68 (s, 1H), 8.66 (s, 2H), 8.97 (s, 1H), 10.85 (br.s., 1H)

E195: 2-{2-[4-(4-Chloro-3-trifluoromethyl-phenoxy)-phenyl]-ethylamino}-5-(2-methyl-pyrimidin-5-ylmethyl)-1H-pyrimidin-4-one

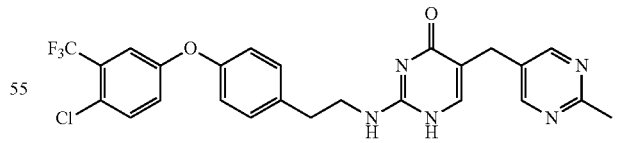

5-(2-Methyl-pyrimidin-5-ylmethyl)-2-methylsulfanyl-1H-pyrimidin-4-one (30 mg, 248.31 gmol$^{-1}$, 0.12 mmol, 1 eq) and 2-[4-(4-Chloro-3-trifluoromethyl-phenoxy)-phenyl]-ethylamine (57 mg, 315.73 gmol$^{-1}$ 0.18 mmol, 1.5 eq) were stirred in 300 μl of absolute ethanol at 125° C. for 50 hours. Solvent from the reaction mixture was evaporated and the resulting crude was purified by preparative HPLC-MS. The gathered fractions of appropriate composition were lyophilized and the resulting oily product was triturated with DCM and diethyl ether to afford 2-{2-[4-(4-Chloro-3-trifluoromethyl-phenoxy)-phenyl]-ethylamino}-5-(2-methyl-pyrimidin-5-ylmethyl)-1H-pyrimidin-4-one (43 mg, yield=65.5%, purity=95%) MS: [M+H]⁺=516.38. ¹H NMR (300 MHz; CDCl₃) δ/ppm 2.64 (s, 3H), 2.89 (t, J=7.0 Hz, 2H), 3.52 (s, 2H), 3.57-3.66 (m, 2H), 5.20 (br.s., 1H), 6.94 (d, J=7.75 Hz, 2H), 7.02 (d, J=9.26 Hz, 1H), 7.17-7.30 (m, 3H), 7.39 (d, J=8.70 Hz, 1H), 7.67 (s, 1H), 8.49 (s, 2H), 12.18 (br.s., 1H).

E196: 2-({2-[4-(4-Chloro-3-trifluoromethyl-phenoxy)-phenyl]-ethyl}-methyl-amino)-1-methyl-5-pyrimidin-5-ylmethyl-1H-pyrimidin-4-one

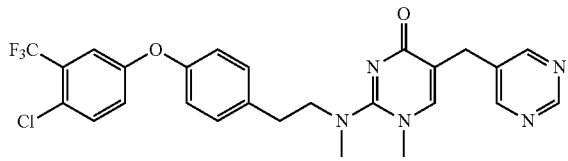 [SMILES: CN(CCc1ccc(Oc2ccc(Cl)c(C(F)(F)F)c2)cc1)c1nc(=O)c(Cc2cncnc2)cn1C]

1-Methyl-2-methylsulfanyl-5-pyrimidin-5-ylmethyl-1H-pyrimidin-4-one (50 mg, 0.201 mmol, 1 eq) and {2-[4-(4-Chloro-3-trifluoromethyl-phenoxy)-phenyl]-ethyl}-methyl-amine (99.4 mg, 0.302 mmol, 1.5 eq) were dissolved in dry ethanol (300 µl) and stirred at 130° C. for 48 h. Reaction mixture was evaporated and crude residue was purified via Biotage SP-1 Snap Si 10 g; 15 ml/min; UV Wavelength (Collection: 254 nm; Monitor: 290 nm) in the gradient of MeOH in DCM: 0% for 1 CV, 0-8% for 25 CV. The appropriate fractions were combined and product was not pure enough and it was sent to HPLC/MS Purification. After HPLC/MS purification combined fractions of desired product were collected and put on lyophilisation to obtain 2-({2-[4-(4-chloro-3-trifluoromethyl-phenoxy)-phenyl]-ethyl}-methyl-amino)-1-methyl-5-pyrimidin-5-ylmethyl-1H-pyrimidin-4-one (0.058 mmol; yield: 28.9%, HPLC-MS/UV: [M+H]⁺=530.95; rt: 12.13 min; purity: 99%). ¹H NMR (300 MHz; DMSO-d6) δ/ppm 1.38 (s, 3H), 2.81 (s, 3H), 2.87 (t, J=6.73 Hz, 2H), 3.38 (t, J=7.20 Hz, 2H), 3.50 (s, 2H), 7.02 (d, J=7.20 Hz, 2H), 7.18 (d, J=8.17 Hz, 1H), 7.31 (d, J=8.17 Hz, 2H), 7.37 (s, 1H), 7.50 (s, 1H), 7.67 (d, J=8.65 Hz, 1H), 8.67 (s, 2H), 8.97 (s, 1H)

E197: 2-{2-[4-(4-Chloro-phenoxy)-phenyl]-ethylamino}-5-(2-methoxy-pyrimidin-5-ylmethyl)-1H-pyrimidin-4-one

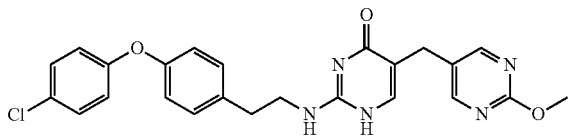 [SMILES: COc1ncc(Cc2c[nH]c(NCCc3ccc(Oc4ccc(Cl)cc4)cc3)nc2=O)cn1]

5-(2-Methoxy-pyrimidin-5-ylmethyl)-2-methylsulfanyl-1H-pyrimidin-4-one (30 mg, 0.114 mmol, 1 eq) and 2-[4-(4-Chloro-phenoxy)-phenyl]-ethylamine (42.6 mg, 0.171 mmol, 1.5 eq) were dissolved in dry ethanol (300 µl) and stirred at 130° C. for overnight. Reaction mixture was evaporated and crude residue (72 mg) was sent to HPLC/MS Purification. After HPLC/MS purification combined fractions of desired product were collected and put on lyophilisation to obtain 2-{2-[4-(4-Chloro-phenoxy)-phenyl]-ethylamino}-5-(2-methoxy-pyrimidin-5-ylmethyl)-1H-pyrimidin-4-one (0.020 mmol; yield: 17.5%, HPLC-MS/UV: [M+H]⁺= 464.93; rt: 10.93 min; purity: 95%). ¹H NMR (300 MHz; DMSO-d6) δ/ppm 2.77 (t, J=7.02 Hz, 2H), 3.39-3.52 (m, 4H), 3.84 (s, 3H), 6.49 (br.s., 1H), 6.88-7.03 (m, 4H), 7.24 (d, J=7.72 Hz, 2H), 7.40 (d, J=7.02 Hz, 2H), 7.61 (s, 1H), 8.44 (s, 2H), 10.92 (br.s., 1H)

E198: 2-{2-[4-(4-Chloro-3-trifluoromethyl-phenoxy)-phenyl]-ethylamino}-5-methyl-1H-pyrimidin-4-one

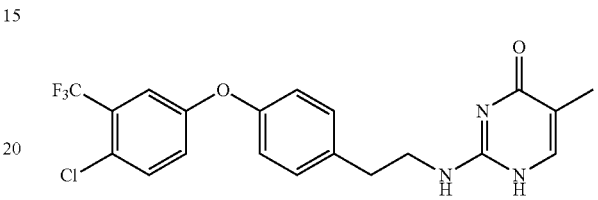

5-Methyl-2-methylsulfanyl-1H-pyrimidin-4-one (25 mg, 0.16 mmol, 1 eq) and 2-[4-(4-chloro-3-trifluoromethyl-phenoxy)-phenyl]-ethylamine (60 mg, 0.192 mmol, 1.2 eq) were stirred in 300 µl of absolute ethanol for 50 hours. Solvent was then evaporated and the resulting crude was purified by chromatography on BIOTAGE SP1 purification device using 11 g normal phase silica KP—NH column and DCM/MeOH solvent system (gradient 0-7% of MeOH in 20 column volumes). Solvent from the gathered fractions of appropriate composition was evaporated and the crude was triturated with cyclohexane to obtain 2-{2-[4-(4-chloro-3-trifluoromethyl-phenoxy)-phenyl]-ethylamino}-5-methyl-1H-pyrimidin-4-one (24 mg, yield=33.9%, purity=96%) in form of white powder. MS: [M+H]⁺=424.31. ¹H NMR (300 MHz; CDCl₃) δ/ppm 1.79 (s, 3H), 2.90 (t, J=6.24 Hz, 2H), 3.52 (s, 2H), 3.56-3.67 (m, 2H), 6.23 (br.s., 1H), 6.92 (d, J=7.56 Hz, 2H), 7.00 (d, J=7.95 Hz, 1H), 7.21 (d, J=7.56 Hz, 2H), 7.28 (s, 1H) 7.38 (d, J=8.32 Hz, 1H), 7.63 (s, 1H), 11.62 (br.s., 1H).

E199: 2-{2-[4-(4-Fluoro-phenoxy)-phenyl]ethylamino}-5-thiazol-2-ylmethyl-1Hpyrimidin-4-one

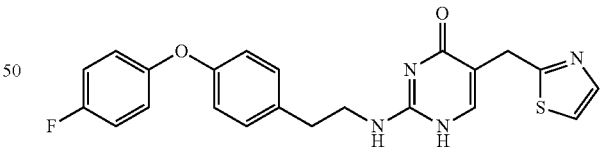

A mixture of 2-methylsulfanyl-5-thiazol-2-ylmethyl-3H-pyrimidin-4-one (30 mg, 0.125 mmol) and 2-[4-(4-Fluoro-phenoxy)-phenyl]-ethylamine (44 mg, 0.188 mmol) were heated in a sealed vial at 125° C. in ethanol (0.3 mL) overnight.

Reaction mixture was checked by UPLC-MS, which showed desired product [M+H]⁺=423.36. The mixture was poured into 15 mL of DCM and 15 mL water and extracted. Organic layer was washed with water and brine, filtered through phase separator and solvent evaporated under reduced pressure. Crude product was then purified on Solid-Prep purification system on a 5 g silicagel column in the solvent system DCM:MeOH 10:1 (isocratic). After evaporation of the solvent, 12 mg of product was isolated. [M+H]⁺ = 423.15 (yield=23%, purity=93%). ¹H NMR (600 MHz; DMSO) δ/ppm 2.78 (t, J=7.0 Hz, 2H), 3.48 (q, J=6.7 Hz 2H), 3.87 (s, 2H), 6.40 (br.s., 1H), 6.92 (d, J=8.5 Hz, 2H), 7.01 (m, 2H), 7.20 (m, J=8.7 Hz, 2H), 7.23 (d, J=8.5 Hz, 2H), 7.48 (d, J=3.3 Hz, 1H), 7.63 (d, J=3.3 Hz 1H), 7.67 (s, 1H), 10.91 (br.s., 1H)

E200: 2-{2-[4-(4-Chloro-3-trifluoromethylphenoxy)phenyl]-ethylamino}-5-thiazol-2-ylmethyl-1H-pyrimidin-4-one

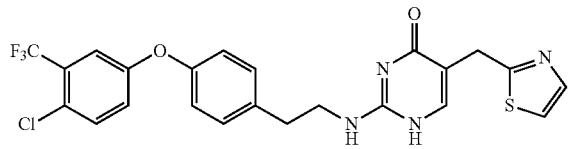 [SMILES: O=c1nc(NCCc2ccc(Oc3ccc(Cl)c(C(F)(F)F)c3)cc2)[nH]cc1Cc1nccs1]

A mixture of 2-methylsulfanyl-5-thiazol-2-ylmethyl-3H-pyrimidin-4-one (30 mg, 0.125 mmol) and 2-[4-(4-Chloro-3-trifluoromethyl-phenoxy)-phenyl]-ethylamine (59 mg, 0.188 mmol) were heated in a sealed vial at 125° C. in ethanol (0.3 mL) overnight.

Reaction mixture was checked by UPLC-MS, which showed desired product [M+H]⁺⁼⁵⁰⁷·³². The mixture was poured into 15 mL of DCM and 15 mL water and extracted. Organic layer was washed with water and brine, filtered through phase separator and solvent evaporated under reduced pressure. Crude product was then purified on a 5 g silicagel column in the solvent system DCM:MeOH 10:1 (isocratic). After evaporation of the solvent, 13.5 mg of product was isolated. [M+H]⁺=507.04 (yield=20%, purity=93%). ¹H NMR (600 MHz; DMSO) δ/ppm 2.83 (t, J=7.0 Hz, 2H), 3.49 (q, J=6.7 Hz 2H), 3.87 (s, 2H), 6.43 (br.s., 1H), 7.06 (d, J=8.5 Hz, 2H), 7.22 (dd, J=8.9, 3.1 Hz 1H), 7.30 (d, J=8.5 Hz, 2H) 7.40 (d, J=3.0 Hz, 1H), 7.48 (d, J=3.0 Hz, 1H), 7.63 (d, J=3.1 Hz 1H), 7.67-7.69 (m, 2H), 10.93 (br.s., 1H)

E201: 5-Thiazol-2-ylmethyl-2-{2-[4-(3-trifluoromethyl-phenoxy)-phenyl]-ethylamino}-1H-pyrimidin-4-one

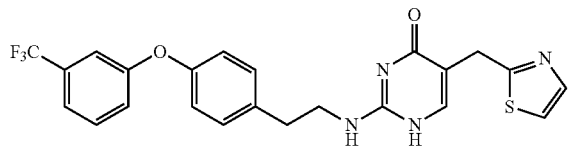 [SMILES: O=c1nc(NCCc2ccc(Oc3cccc(C(F)(F)F)c3)cc2)[nH]cc1Cc1nccs1]

A mixture of 2-Methylsulfanyl-5-thiazol-2-ylmethyl-3H-pyrimidin-4-one (30 mg, 0.125 mmol) and 2-[4-(3-trifluoromethyl-phenoxy)-phenyl]-ethylamine (53 mg, 0.188 mmol) was heated at 125° C. in ethanol (0.3 mL) in a shaker overnight.

The mixture was poured into 15 mL of DCM and 15 mL water and extracted. Organic layer was washed with water and brine, filtered through phase separator and solvent evaporated under reduced pressure. Crude product was then purified on Solid Prep purification system on 5 g silicagel column in the solvent system DCM:MeOH 10:1 (isocratic). After evaporation of the solvent, 12 mg of product was isolated. [M+H]=473.35 (yield=20%, purity=93%). ¹H NMR (600 MHz; DMSO) δ/ppm 2.83 (t, J=7.0 Hz, 2H), 3.50 (q, J=6.7 Hz, 2H), 3.87 (s, 2H), 6.43 (br.s., 1H), 7.03 (d, J=8.4 Hz, 2H), 7.23 (d, J=8.20 Hz, 1H), 7.26 (s, 1H) 7.30 (d, J=8.40 Hz, 2H), 7.45 (d, J=7.50 Hz, 1H), 7.48 (d, J=3.1 Hz, 1H), 7.59 (t, J=8.0 Hz, 1H), 7.63 (d, J=3.1 Hz, 1H), 7.67 (s, 1H), 10.93 (br.s., 1H)

E202: 5-{2-[5-(2-methoxy-pyrimidin-5-ylmethyl)-4-oxo-1.4-dihydro-pyrimidin-2-yl]-amino}-ethyl-2-(5-trifluoromethyl-pyridin-2-yloxy)benzonitrile

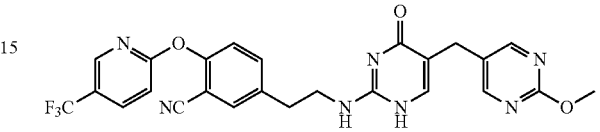

5-(2-amino-ethyl)-2-(5-trifluoromethyl-pyridin-2-yloxy)benzonitrile (0.163 mmol, 1 eq)) and 5-(2-methoxy-pyrimidin-5-ylmethyl)-2-methylsulfanyl-1H-pyrimidin-4-one (0.065 mmol, 0.4 eq) were dissolved in dry ethanol (200 μL) and stirred at 125° C. for 16 hours. Solvent was evaporated and crude product was purified by Waters Mass Direct Autopurification system giving 5-{2-[5-(2-methoxy-pyrimidin-5-ylmethyl)-4-oxo-1.4-dihydro-pyrimidin-2-yl]-amino}-ethyl-2-(5-trifluoromethyl-pyridin-2-yloxy)benzonitrile (9.551 mol, yield: 5%, HPLC-MS/UV: [M+H]⁺=524.09; rt: 10.36 min; purity: 97%). ¹H NMR (300 MHz; CDCl₃) δ/ppm 2.98 (t, J=7.56, 2H), 3.54 (s, 2H), 3.61-3.73 (m, 2H), 3.95 (s, 3H), 5.41 (br.s., 1H), 7.14-7.31 (m, 2H), 7.50-7.71 (m, 2H), 7.89 (d, J=8.77, 1H), 8.32-8.46 (m, 3H), 12.07 (br.s., 1H)

E203: 5-{2-[5-(2-Methyl-pyrimidin-5-ylmethyl)-4-oxo-1,4-dihydro-pyrimidin-2-ylamino]-ethyl}-2-(5-trifluoromethyl-pyridin-2-yloxy)-benzonitrile

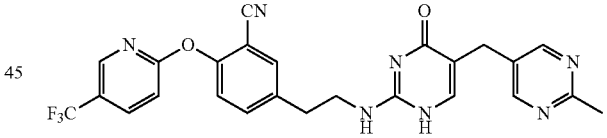

5-(2-Methyl-pyrimidin-5-ylmethyl)-2-methylsulfanyl-1H-pyrimidin-4-one (50 mg, 0.20 mmol, 1 eq) and 5-(2-Amino-ethyl)-2-(5-trifluoromethyl-pyridin-2-yloxy)-benzonitrile (80 mg, 0.26 mmol, 1.3 eq) were heated at 130° C. (sealed bottle) in 500 μl of absolute ethanol for 24 hours. Solvent was then evaporated and the resulting crude was purified by chromatography on BIOTAGE SP1 purification device using 11 g normal phase silica KP—NH column and DCM/10% MEOH in DCM solvent system (gradient 10-80% of 10% MeOH in DCM in 20 column volumes). Solvent from the gathered fractions of appropriate composition was evaporated and the resulting oil was triturated with hexane to obtain 5-{2-[5-(2-methyl-pyrimidin-5-ylmethyl)-4-oxo-1,4-dihydro-pyrimidin-2-ylamino]-ethyl}-2-(5-trifluoromethyl-pyridin-2-yloxy)-benzonitrile (36 mg, yield=32.4%, purity=92%) in form of tain coloured powder. MS: [M+H]⁺=508.40. ¹H NMR (300 MHz; CDCl₃) δ/ppm 2.64 (s, 3H), 2.94 (t, J=7.23 Hz, 2H), 3.53 (s, 2H), 3.57-3.66 (m, 2H), 7.14-7.23

(m, 2H), 7.51 (d, J=8.37 Hz, 2H), 7.55-7.64 (m, 2H), 7.96 (d, J=8.60 Hz, 1H), 8.34 (s, 1H), 8.50 (s, 2H).

E204: 5-pyrimidin-5-ylmethyl-2-{[2-[4-(4-trifluoromethyl-phenoxy)phenyl]-ethylamino}-1H-pyrimidin-4-one

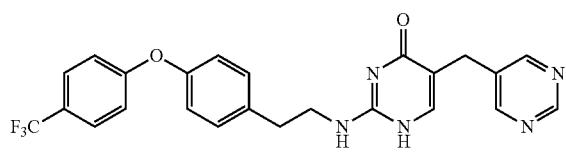 [SMILES: O=c1nc(NCCc2ccc(Oc3ccc(C(F)(F)F)cc3)cc2)[nH]cc1Cc1cncnc1]

2-[4-(4-trifluoromethyl-phenoxy)-phenyl]-ethylamine (50.00 mg, 0.142 mmol) and 2-methylsulfanyl-5-pyrimidin-5-ylmethyl-1H-pyrimidin-4-one (13.33 mg, 0.057 mmol, 0.4 eq) were dissolved in dry ethanol (200 µL) and stirred at 125° C. for 50 hours. Solvent was evaporated and crude product was purified on Biotage SP1 Snap Si 10; 15 ml/min in the gradient of MeOH in DCM: 0-10% in 30CV. The appropriate fractions were combined and evaporated in vacuo to give the required product 5-pyrimidin-5-ylmethyl-2-{[2-[4-(4-trifluoromethyl-phenoxy)phenyl]-ethylamino}-1H-pyriminin-4-one (0.041 mmol, yield: 28%, UPLC-MS/UV: [M+H+= 468.37; rt: 1.05 mins; purity: 98%). $^1$H NMR (300 MHz; CDCl$_3$) δ/ppm 2.91 (t, J=6.72, 2H), 3.53-3.70 (m, 4H), 5.14 (br.s., 1H), 6.95-7.07 (m, 4H), 7.17-7.31 (m, 2H), 7.50-7.59 (m, 2H), 7.71 (s, 1H), 8.62 (s, 2H), 9.04 (s, 1H), 12.01 (br.s., 1H)

E205: 5-[2-(4-oxo-5-pyrimidin-5-ylmethyl-1,4-dihydro-pyrimidin-2-ylamino)-ethyl]-2-(5-trifluoromethyl-pyridin-2-yloxy)benzonitrile

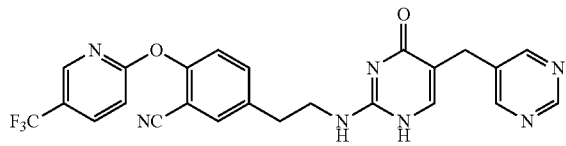 [SMILES: N#Cc1cc(CCNc2nc(=O)c(Cc3cncnc3)c[nH]2)ccc1Oc1ccc(C(F)(F)F)cn1]

5-(2-amino-ethyl)-2-(5-trifluoromethyl-pyridin-2-yloxy)benzonitrile (0.163 mmol, 1 eq) and 2-methylsulfanyl-5-pyrimidin-5-ylmethyl-1H-pyrimidin-4-one (0.065 mmol, 0.4 eq) were dissolved in dry ethanol (200 µL) and stirred at 125° C. overnight. Solvent was evaporated and crude product was purified on Biotage SP1 Snap Si 10; 15 ml/min in the gradient of MeOH in DCM: 0-15% in 20CV. The appropriate fractions were combined and evaporated in vacuo to give the required product 5-[2-(4-oxo-5-pyrimidin-5-ylmethyl-1,4-dihydro-pyrimidin-2-ylamino)-ethyl]-2-(5-trifluoromethyl-pyridin-2-yloxy)benzonitrile (0.028 mmol, yield: 17%, HPLC-MS/UV: [M+H]$^+$=494.17; rt: 9.91 mins; purity: 91%). $^1$H NMR (300 MHz; CDCl$_3$) δ/ppm 2.98 (t, J=6.57, 2H), 3.52-3.75 (m, 4H), 5.31 (br.s., 1H), 7.12-7.30 (m, 3H), 7.48-7.56 (m, 1H), 7.57-7.62 (m, 1H), 7.71 (s, 1H), 7.98 (dd, J=8.40, J=2.55, 1H), 8.57-5.69 (m, 2H), 9.04 (s, 1H), 11.80 (br.s., 1H)

E206: 2-{2-[4-(3-chloro-4-trifluoromethyl-phenoxy)-phenyl]ethylamino}-5-(2-methoxy-pyrimidin-5-ylmethyl)-1H-pyrimidin-4-one

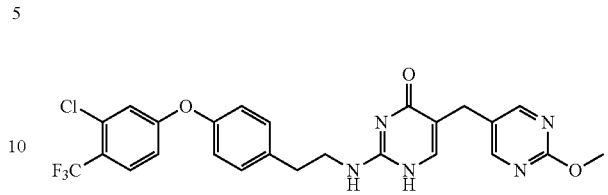

2-[4-(3-chloro-4-trifluoromethyl-phenoxy)-phenyl]-ethylamine (0.317 mmol, 1 eq) and 5-(2-methoxy-pyrimidin-5-ylmethyl)-2-methylsulfanyl-1H-pyrimidin-4-one (0.322 mmol, 0.95 eq) were dissolved in dry ethanol (300 µL) and stirred at 125° C. for 50 hours. Solvent was evaporated and crude product was purified on Biotage SP1 Snap Si 25; 25 ml/min in the gradient of MeOH in DCM: 0-10% in 25CV. The appropriate fractions were combined and evaporated in vacuo to give the required product 2-{2-[4-(3-chloro-4-trifluoromethyl-phenoxy)-phenyl]ethylamino}-5-(2-methoxy-pyrimidin-5-ylmethyl)-1H-pyrimidin-4-one (0.064 mmol, yield: 20%, UPLC-MS/UV: [M+H]$^+$=517.97; rt: 11.53 mins; purity: 90%). $^1$H NMR (300 MHz; CDCl$_3$) δ/ppm 2.92 (t, J=7.76, 2H), 3.51 (s, 2H), 3.59-3.70 (m, 2H), 3.94 (s, 3H), 5.33 (br.s., 1H), 6.86 (dd, J=9.07, J=2.01, 1H), 6.96-7.03 (m, 2H), 7.23-7.31 (m, 3H), 7.58 (d, J=8.82, 1H), 7.67 (s, 1H), 8.39 (s, 2H)

E207: 2-{2-[4-(3-chloro-4-trifluoromethyl-phenoxy)-phenyl]ethylamino}-5-(2-methyl-pyrimidin-5-ylmethyl)-1H-pyrimidin-4-one

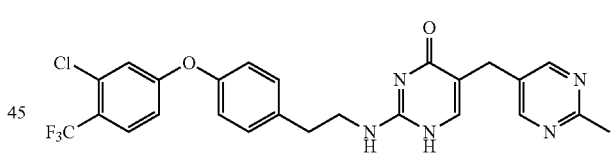

2-[4-(3-chloro-4-trifluoromethyl-phenoxy)-phenyl]-ethylamine (0.317 mmol, 1.01 eq) and 5-(2-methyl-pyrimidin-5-ylmethyl)-2-methylsulfanyl-1H-pyrimidin-4-one (0.322 mmol, 1 eq) were dissolved in dry ethanol (300 µL) and stirred at 125° C. for 50 hours. Solvent was evaporated and crude product was purified on Biotage SP1 Snap Si 10; 15 ml/min in the gradient of MeOH in DCM: 0-10% in 25CV. The appropriate fractions were combined and evaporated in vacuo to give the required product 2-{2-[4-(3-chloro-4-trifluoromethyl-phenoxy)-phenyl]ethylamino}-5-(2-methyl-pyrimidin-5-ylmethyl)-1H-pyrimidin-4-one (0.145 mmol, yield: 44%, HPLC-MS/UV:[M+H]$^+$=517.97; rt: 11.53 mins; purity: 90%). $^1$H NMR (300 MHz; CDCl$_3$) δ/ppm 2.65 (s, 3H), 2.92 (t, J=6.57, 2H), 3.53 (s, 2H), 3.57-3.69 (m, 2H), 5.39 (br.s., 1H), 7.01 (d, J=8.69, 1H), 7.08 (d, J=8.50 2H), 7.27-7.31 (m, 2H), 7.66 (s, 1H), 7.89 (dd, J=9.58, J=2.73, 1H), 8.36-8.42 (m, 1H), 8.51 (s, 2H), 11.21 (br.s., 1H)

E208: 5-(2-methyl-pyrimidin-5-ylmethyl)-2-{2-[4-(5-trifluoromethyl-pyridin-2-yloxy)phenyl]ethylamino}-1H-pyrimidin-4-one

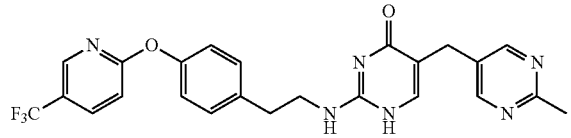 [SMILES: Cc1ncc(Cc2c[nH]c(NCCc3ccc(Oc4ccc(C(F)(F)F)cn4)cc3)nc2=O)cn1]

2-[4-(5-trifluoromethyl-pyridin-2-yloxy)-phenyl]-ethylamine (0.354 mmol, 1 eq) and 5-(2-methyl-pyrimidin-5-ylmethyl)-2-methylsulfanyl-1H-pyrimidin-4-one (0.322 mmol, 0.9 eq) were dissolved in dry ethanol (300 μL) and stirred at 125° C. for 50 hours. Solvent was evaporated and crude product was purified on Biotage SP1 Snap Si 10; 15 ml/min in the gradient of MeOH in DCM: 0-10% in 25CV. The appropriate fractions were combined and evaporated in vacuo to give the required product 5-(2-methyl-pyrimidin-5-ylmethyl)-2-{2-[4-(5-trifluoromethyl-pyridin-2-yloxy)phenyl]ethylamino}-1H-pyrimidin-4-one (0.064 mmol, yield: 18%, HPLC-MS/UV:[M+H]$^+$=483.37; rt: 0.89 mins; purity: 93%). $^1$H NMR (300 MHz; CDCl$_3$) δ/ppm 2.66 (s, 3H), 2.93 (t, J=7.39, 2H), 3.54 (s, 2H), 3.60-3.70 (m, 2H), 5.39 (br.s., 1H), 7.01 (d, J=8.69, 1H), 7.08 (d, J=8.50 2H), 7.27-7.31 (m, 2H), 7.66 (s, 1H), 7.89 (dd, J=9.58, J=2.73, 1H), 8.36-8.42 (m, 1H), 8.51 (s, 2H), 11.21 (br.s., 1H)

E209: 2-{2-[4-(4-chloro-3-trifluoromethyl-phenoxy)-phenyl]ethylamino}-5-(2-oxo-1,2-dihydro-pyrimidin-5-ylmethyl)-1H-pyrimidin-4-one

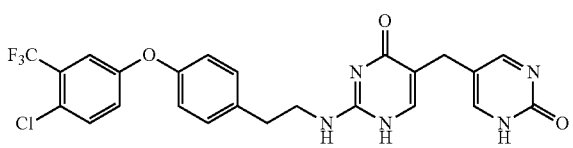 [SMILES: O=c1ncc(Cc2c[nH]c(NCCc3ccc(Oc4ccc(Cl)c(C(F)(F)F)c4)cc3)nc2=O)c[nH]1]

2-[4-(4-chloro-3-trifluoromethyl-phenoxy)-phenyl]-ethylamine (0.380 mmol, 1.00 eq) and 2-methylsulfanyl-5-(2-oxo-1,2-dihydro-pyrimidin-5-ylmethyl)-1H-pyrimidin-4-one (0.240 mmol, 0.63 eq) were dissolved in dry pyridine (300 μL) and stirred at 150° C. overnight. Solvent was evaporated and crude product was purified on Biotage SP1 Snap Si 10; 15 ml/min in the gradient of MeOH in DCM: 0-10% in 25CV. The appropriate fractions were combined and evaporated in vacuo to give the required product 2-{2-[4-(4-chloro-3-trifluoromethyl-phenoxy)-phenyl]ethylamino}-5-(2-oxo-1,2-dihydro-pyrimidin-5-ylmethyl)-1H-pyrimidin-4-one (0.041 mmol, yield: 11%, HPLC-MS/UV:[M+H]$^+$=518.047; rt: 10.97 mins; purity: 85%). $^1$H NMR (300 MHz; CDCl$_3$) δ/ppm 2.80 (t, J=6.50, 2H), 3.19-3.22 (m, 2H), 3.41-3.52 (m, 2H), 5.39 (br.s., 1H), 6.33-6.64 (m, 1H), 6.99-7.10 (m, 2H), 7.22 (dd, J=9.24, J=3.42, 1H), 7.26-7.32 (m, 2H), 7.38-7.43 (m, 1H), 7.58-7.72 (m, 2H), 8.11 (br.s., 1H), 10.93 (br.s., 1H)

E210: 2-{2-[4-(4-Chloro-3-trifluoromethyl-phenoxy)-phenyl]-ethylamino}-5-(6-methyl-pyridin-3-ylmethyl)-1H-pyrimidin-4-one

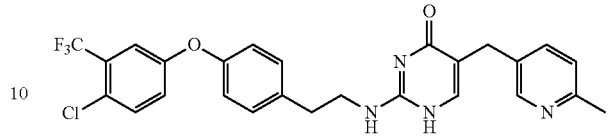

5-(6-methyl-pyridin-3-ylmethyl)-2-methylsulfanyl-1H-pyrimidin-4-one (50 mg, 0.202 mmol, 1 eq) and 2-[4-(4-chloro-3-trifluoromethyl-phenoxy)-phenyl]-ethylamine (100 mg, 0.317 mmol, 1.57 eq) were heated in a sealed vial at 130° C. in 300 μl of absolute ethanol for 20 hours. Solvent was then evaporated and the resulting crude was purified by chromatography on BIOTAGE SP1 purification device using 10 g normal phase silica SNAP column and DCM/20% MEOH in DCM solvent system (gradient 5-40% of 20% MeOH in DCM in 25 column volumes). Solvent from the gathered fractions of appropriate composition was evaporated and the resulting crude was purified once more under the same conditions. Solvent from the gathered fractions of appropriate composition was evaporated the resulting oil was triturated with cyclohexane and diethyl ether to afford 2-{2-[4-(4-chloro-3-trifluoromethyl-phenoxy)-phenyl]-ethylamino}-5-(6-methyl-pyridin-3-ylmethyl)-1H-pyrimidin-4-one (51 mg, yield=46.54%, purity=95%). MS: [M+H]=515.34. $^1$H NMR (300 MHz; CDCl$_3$) δ/ppm 2.48 (s, 3H), 2.87 (t, J=7.23 Hz, 2H), 3.57 (s, 2H), 3.52-3.62 (m, 4H), 5.55 (br.s., 1H), 6.93 (d, J=8.23 Hz, 2H), 6.98-7.06 (m, 2H), 7.21 (d, J=8.23 Hz, 1H), 7.28 (d, J=2.84 Hz, 1H), 7.36-7.43 (m, 2H), 7.60 (br.s., 1H), 8.39 (s, 1H).

E211: 2-(4-Chloro-3-trifluoromethyl-phenoxy)-5-{2-[5-(2-methyl-pyrimidin-5-ylmethyl)-4-oxo-1,4-dihydro-pyrimidin-2-ylamino]-ethyl}-benzonitrile

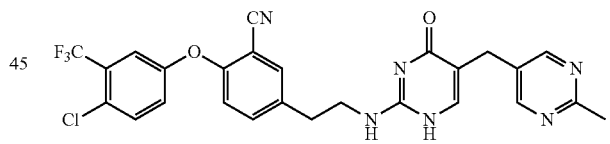

5-(2-Methyl-pyrimidin-5-ylmethyl)-2-methylsulfanyl-1H-pyrimidin-4-one (50 mg, 0.201 mmol, 1 eq) and 5-(2-Amino-ethyl)-2-(4-chloro-3-trifluoromethyl-phenoxy)-benzonitrile (110 mg, 1.6 eq) were heated in a sealed vial at 130° C. for 20 hours. Solvent was then evaporated and the resulting crude was purified by chromatography on BIOTAGE SP1 purification device using 10 g normal phase silica SNAP column and DCM/20% MEOH in DCM solvent system (gradient 5-50% of 20% MeOH in DCM in 25 column volumes). Solvent from the gathered fractions of appropriate composition was evaporated and the resulting oil was triturated with cyclohexane and diethyl ether to obtain 2-(4-chloro-3-trifluoromethyl-phenoxy)-5-{2-[5-(2-methyl-pyrimidin-5-ylmethyl)-4-oxo-1,4-dihydro-pyrimidin-2-ylamino]-ethyl}-benzonitrile (36 mg, yield=29.7%, purity=90%) in form of tain coloured powder. MS: [M+H]$^+$=541.34. $^1$H NMR (300 MHz; CDCl$_3$) δ/ppm 2.65 (s, 3H), 2.94 (t, J=7.02 Hz, 2H), 3.57 (s, 2H), 3.59-3.68 (m, 2H), 5.49 (br.s., 1H), 6.89 (d, J=8.61 Hz, 1H), 7.15 (dd, J=8.30 Hz, J=2.98 Hz, 1H), 7.38 (d, J=2.76 Hz, 1H), 7.44 (dd, J=8.82 Hz, J=1.91 Hz, 1H), 7.51 (d, J=8.51 Hz, 1H), 7.60 (d, J=2.02 Hz, 1H), 7.71 (s, 1H), 8.53 (s, 2H).

E212: 2-{2-[4-(4-Chloro-3-trifluoromethyl-phenoxy)-phenyl]-ethylamino}-5-(6-oxo-1,6-dihydro-pyridin-3-ylmethyl)-1H-pyrimidin-4-one

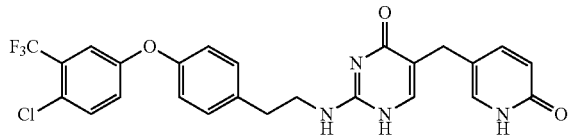 [SMILES: O=c1ccc(Cc2c[nH]c(NCCc3ccc(Oc4ccc(Cl)c(C(F)(F)F)c4)cc3)nc2=O)c[nH]1]

2-methylsulfanyl-5-(6-oxo-1,6-dihydro-pyridin-3-ylmethyl)-1H-pyrimidin-4-one (20 mg, 0.08 mmol, 1 eq) and 2-[4-(4-chloro-3-trifluoromethyl-phenoxy)-phenyl]-ethylamine (40 mg, 0.127 mmol, 1.58 eq) were heated in 300 μl of dry pyridine at 150° C. for 16 hours. Solvent was then evaporated and the resulting crude was purified by chromatography on BIOTAGE SP1 purification device using 10 g normal phase silica SNAP column and DCM/30% MEOH in DCM solvent system (gradient 5-100% of 30% MeOH in DCM in 25 column volumes). Solvent from the gathered fractions of appropriate composition was evaporated and obtained was 2-{2-[4-(4-chloro-3-trifluoromethyl-phenoxy)-phenyl]-ethylamino}-5-(6-oxo-1,6-dihydro-pyridin-3-ylmethyl)-1H-pyrimidin-4-one (5.4 mg, yield=11.7%, purity=90%). MS: [M+H]=517.34. $^1$H NMR (300 MHz; DMSO-$d_6$) δ/ppm 2.81 (t, J=7.032 Hz, 2H), 3.23 (s, 2H), 3.43-3.53 (m, 2H), 6.24 (d, J=9.45 Hz, 1H), 6.36 (br.s., 1H), 7.03-7.14 (m, 3H), 7.20-7.37 (m, 4H), 7.41 (d, J=2.55 Hz, 1H), 7.54 (s, 1H), 7.70 (d, J=8.82 Hz, 1H).

E213: 5-(6-chloro-pyridin-3-ylmethyl)-2-{2-[4-(4-chloro-3-trifluoromethyl-phenoxy)-phenyl]-ethylamino}-1H-pyrimidin-4-one

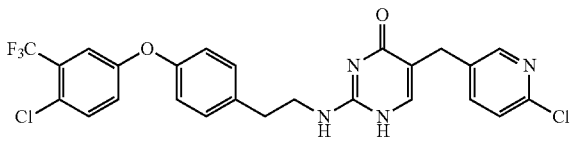 [SMILES: O=c1nc(NCCc2ccc(Oc3ccc(Cl)c(C(F)(F)F)c3)cc2)[nH]cc1Cc1ccc(Cl)nc1]

2-[4-(4-chloro-3-trifluoromethyl-phenoxy)-phenyl]-ethylamine (0.317 mmol, 1.0 eq) and 5-(6-chloro-pyridin-3-ylmethyl)-2-methylsulfanyl-1H-pyrimidin-4-one (0.190 mmol, 0.6 eq) were dissolved in dry ethanol (300 μL) and stirred at 130° C. overnight. Solvent was evaporated and crude product was purified on Biotage SP1 Snap Si 10; 15 ml/min in the gradient of MeOH in DCM: 0-7% in 15 CV. The appropriate fractions were combined and evaporated in vacuo to give the required product 5-(6-chloro-pyridin-3-ylmethyl)-2-{2-[4-(4-chloro-3-trifluoromethyl-phenoxy)-phenyl]-ethylamino}-1H-pyrimidin-4-one (0.084 mmol, yield: 26%, HPLC-MS/UV:[M+H]$^+$=536.33; rt: 1.24 mins; purity: 95%). $^1$H NMR (300 MHz; CDCl$_3$) δ/ppm 2.89 (t, J=7.17, 2H), 3.57 (s, 2H), 3.59-3.66 (m, 2H), 5.23 (br.s., 1H), 6.95 (dd, J=8.51, J=9.86, 2H), 7.03 (dd, J=9.41 J=2.24, 1H), 7.17-7.23 (m, 3H), 7.27-7.30 (m, 2H), 7.39 (dd, J=9.07, J=8.31, 1H), 7.47 (dd, J=8.06, J=2.51, 1H), 7.65 (s, 1H), 8.28 (d, J=2.26, 1H), 12.01 (br.s., 1H)

E214: 2-{2-[4-(4-chloro-3-trifluoromethyl-phenoxy)-phenyl]ethylamino}-5-pyridazin-4-ylmethyl-1H-pyrimidin-4-one

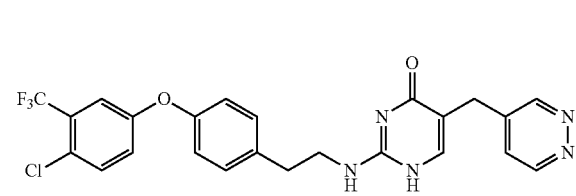 [SMILES: O=c1nc(NCCc2ccc(Oc3ccc(Cl)c(C(F)(F)F)c3)cc2)[nH]cc1Cc1ccnnc1]

2-[4-(4-chloro-3-trifluoromethyl-phenoxy)-phenyl]-ethylamine (0.317 mmol, 1.00 eq) and 2-methylsulfanyl-5-pyridazin-4-ylmethyl-1H-pyrimidin-4-one (0.341 mmol, 1.01 eq) were dissolved in dry ethanol (300 μL) and stirred at 150° C. overnight. Solvent was evaporated and crude product was purified on Biotage SP1 Snap Si 10; 15 ml/min in the gradient of MeOH in DCM: 0-7% in 15 CV. The appropriate fractions were combined and evaporated in vacuo to give the required product 2-{2-[4-(4-chloro-3-trifluoromethyl-phenoxy)-phenyl]ethylamino}-5-pyridazin-4-ylmethyl-1H-pyrimidin-4-one (0.135 mmol, yield: 43%, UPLC-MS/UV:[M+H]$^+$= 502.30; rt: 1.07 mins; purity: 95%). $^1$H NMR (300 MHz; CDCl$_3$) δ/ppm 1.42 (s, 1H), 2.89 (t, J=7.33, 2H), 3.55-3.60 (m, 2H), 3.62 (s, 2H), 6.99 (dd, J=8.40, J=10.08, 2H), 7.01 (dd, J=9.07 J=3.02, 1H), 7.16-7.28 (m, 3H), 7.35-7.42 (m, 2H), 7.62-7.70 (m, 1H), 8.94 (dd, J=5.42, J=0.95, 1H), 9.09-9.12 (m, 1H)

E215: 2-{2-[4-(4-chloro-3-trifluoromethyl-phenoxy)-phenyl]-ethylamino}-5-pyrrolidin-1-ylmethyl-1H-pyrimidin-4-one

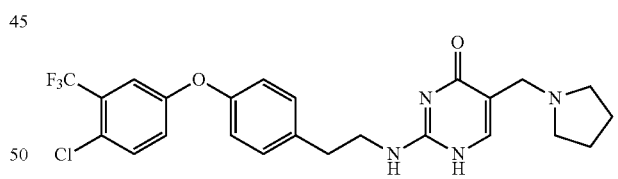

2-{2-[4-(4-chloro-3-trifluoromethyl-phenoxy)-phenyl]-ethylamino}-1H-pyrimidin-4-one (0.122 mmol, 1 eq), paraformaldehyde (3.66 mg, 0.112 mmol, 1 eq) and pyrrolidine (10 μl, 0.112 mmol, 1 eq) were refluxed for 90 mins. Solvent was evaporated in vacuo to give 2-{2-[4-(4-chloro-3-trifluoromethyl-phenoxy)-phenyl]-ethylamino}-5-pyrrolidin-1-ylmethyl-1H-pyrimidin-4-one (0.089 mmol, yield: 73%, UPLC-MS/UV:[M+H]=493.39; rt: 0.98 min; purity: 85%). $^1$H NMR (300 MHz; CDCl$_3$) δ/ppm 1.88-1.91 (m, 4H), 2.68-2.76 (m, 4H), 2.90 (t, J=7.51, 2H), 3.60 (s, 2H), 3.61-3.68 (m, 2H), 6.89-6.96 (m, 2H), 7.02 (dd, J=8.93 J=3.12, 1H), 7.21-7.23 (m, 1H), 7.30 (d, J=2.97, 1H), 7.40 (d, J=9.07, 1H), 7.74 (s, 1H)

E216: 2-{2-[4-(4-Chloro-3-trifluoromethyl-phenoxy)-phenyl]-ethylamino}-5-(2-oxo-1,2-dihydro-pyridin-4-ylmethyl)-1H-pyrimidin-4-one

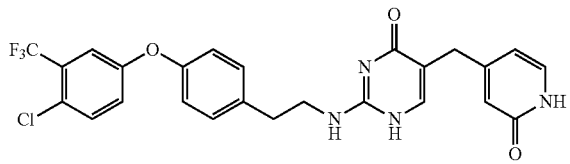 [SMILES: O=c1cc(Cc2c[nH]c(NCCc3ccc(Oc4ccc(Cl)c(C(F)(F)F)c4)cc3)nc2=O)cc[nH]1]

2-Methylsulfanyl-5-(2-oxo-1,2-dihydro-pyridin-4-ylmethyl)-1H-pyrimidin-4-one (100 mg, 0.40 mmol, 1 eq) and 2-[4-(4-Chloro-3-trifluoromethyl-phenoxy)-phenyl]-ethylamine (200 mg, 0.63 mmol, 1.58 eq) were stirred in a sealed vial in 500 µl of dry pyridine at 150° C. for 16 hours. Solvent was then evaporated and the resulting crude was purified by chromatography on BIOTAGE SP1 purification device using 10 g normal phase silica SNAP column and DCM/30% MEOH in DCM solvent system (gradient 5-100% of 30% MeOH in DCM in 20 column volumes). Solvent from the gathered fractions of appropriate composition was evaporated and obtained was 2-{2-[4-(4-Chloro-3-trifluoromethyl-phenoxy)-phenyl]-ethylamino}-5-(2-oxo-1,2-dihydro-pyridin-4-ylmethyl)-1H-pyrimidin-4-one (92 mg, yield=42.15%, purity=95%). MS: [M+H]=517.32. H NMR (300 MHz; DMSO-d6) δ/ppm 2.83 (t, J=7.23 Hz, 2H), 3.31 (s, 2H), 3.45-3.55 (m, 2H), 6.02-6.08 (m, 2H), 6.37 (br.s., 1H), 7.41 (d, J=8.46 Hz, 2H) 7.19-7.26 (m, 2H), 7.32 (d, J=8.46 Hz, 2H), 7.42 (d, J=2.87 Hz, 1H), 7.59 (s, 1H), 7.70 (d, J=8.85 Hz, 1H), 10.39 (br.s., 1H), 11.27 (br.s., 1H).

D. BIOLOGICAL ASSAY AND DATA

The compounds of present invention are Lp-PLA$_2$ inhibitors, and are useful in the treatment of diseases mediated by Lp-PLA$_2$. The biological activities of the compounds of present invention can be determined by using any suitable assay for determining the activity of a compound as a Lp-PLA$_2$ inhibitor, as well as tissue and in vivo models.

The biological activity data for each compound was either reported in at least one experiment or the average of multiple experiments. It is understood that the data described herein may have reasonable variations depending on the specific conditions and procedures used by the person conducting the experiments.

Lipoprotein-Associated Phospholipase A2 (Lp-PLA$_2$) Biochemical Assay (1) Recombinant Human Lp-PLA$_2$ Assay (rhLp-PLA$_2$) (Also Referred to as "PED6" Assay)

N-((6-(2,4-dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labelled phospholipid, which is commercially available from Molecular Probes. There is a quenching para-nitro phenyl (PNP) group in the sn3 position and a Bodipy fluorescein (FL) group in the sn2 position. Upon cleavage with Lp-PLA$_2$, the Bodipy Fl group is liberated and then may result in an increase in fluorescence. Inhibitors of Lp-PLA$_2$ therefore prevent this cleavage and no fluorescent increase is observed.

The PED6 assay was run as an unquenched 10 µL assay. Compounds source plate was prepared by making 1:3 (by volume) serial dilution of the compounds into pure DMSO on 384-well microplate. Then, 0.01 µL of compounds on compound source plate were transferred into 384 well Greiner 784076 (black) plates by ECHO liquid dispenser. 5 µL of recombinant human Lp-PLA$_2$ enzyme (2 nM rhLp-PLA$_2$ in assay buffer of 50 mM HEPES, pH7.4, 150 mM NaCl, 1 mM CHAPS) was added to each well of the plate with compounds. Plates were centrifuged for 10 sec at 500 rpm. After 30 minutes preincubation, 5 µL of substrate (4 µM PED6 [from 5 mM DMSO stock] in assay buffer of 50 mM HEPES, pH7.4, 150 mM NaCl, 1 mM CHAPS) was added to 384 well Greiner 784076 (black) plates. Plates were centrifuged for 10 sec at 500 rpm. Plate was covered to protect from light and incubated for 20 min at room temperature. Plates were read for fluorescence intensity at ex: 480/em: 540 using ViewLux microplate imager. PIC50 data, curve and QC analysis was conducted by using XL fit module in Excel.

All exemplified compounds of the present invention were tested according to the above assays or similar assay as described above and were found to demonstrate inhibition activity to Lp-PLA$_2$. The compounds described below were tested generally according to the PED6 assay described above. The pIC$_{50}$ value for each compound was either reported in at least one experiment or the average of multiple experiments. It is noted that the upper limit for pIC$_{50}$ obtained in the PED6 assay described above is 9.3. If a refined assay is used, compounds that exhibit pIC$_{50}$ equal to 9.3 in the PED6 assay described above may demonstrate pIC$_{50}$ higher than 9.3.

The pIC$_{50}$ values in the PED6 assay for all compounds except examples 37, 46, 147, 180 were at least 5.0.

The pIC$_{50}$ values in the PED6 assay for examples 2-18, 20-32, 34-36, 52, 53, 56-61, 64, 73-80, 83-97, 100, 105-113, 115-120, 123-126, 129-130, 133, 134, 137, 141, 143, 149-157, 161, 162, 164-169, 172-178, 181, 188, 195, 196, 202, 204-206, 210, 212, 214, and 216 were at least 8.0.

The pIC$_{50}$ values in the PED6 assay for examples 11, 20-22, 24, 25, 29, 30, 31, 58, 60, 74, 75, 77-79, 84, 85, 87, 89, 90, 93, 95, 96, 97, 100, 107-113, 116, 118, 119, 141, 150, 151, and 172 were at least 9.0.

Table 1 below provides the pIC50 for some exemplified compounds.

| Example No. | rhLp-PLA$_2$ (PED6 assay) (pIC50) |
|---|---|
| E11 | 9.0 |
| E20 | 9.1 |
| E22 | 9.1 |
| E24 | 9.1 |
| E58 | 9.3 |
| E74 | 9.2 |
| E81 | 7.6 |
| E112 | 9.3 |
| E129 | 8.4 |
| E130 | 8.6 |
| E133 | 8.5 |
| E134 | 8.6 |
| E202 | 8.1 |
| E212 | 8.2 |
| E216 | 8.5 |

(2) PLA2 VIIB Assay

PLA2 VIIB (also known as Novel Serine Dependent Lipase, NSDL) is a serine hydrolase with 40% amino acid identity with human Lp-PLA$_2$. Sequence comparisons indicate that the PLA VIIB active site catalytic triad positions are similar to those of Lp-PLA$_2$. Similar to Lp-PLA$_2$, it is capable of hydrolyzing oxidatively modified phospholipids and may be assayed using known Lp-PLA$_2$ substrates.

Upon cleavage by a phopholipase, it liberates a fluorescent Bodipy group. Recombinant human PLA2 VIIB is used as the phospholipase source in this assay, and compounds are screened to test their degree of inhibition in this assay. The assay is used to determine the degree of selectivity of the testing compounds between PLA2 VIIB and Lp-PLA$_2$.

The PLA2 VIIB assay was applied as an unquenched 10 μL assay. Compounds source plate is prepared by making 1:3 (by volume) serial dilution of the compounds into pure DMSO on 384-well microplate. 0.01 μL of compounds on compound source plate were transferred into 384 well Greiner 784076 (black) plates-by ECHO liquid dispenser. 5 μL of Novel Serine Dependent Lipase (NSDL) enzyme (5 nM NSDL in assay buffer of 50 mM HEPES, pH 7.4, 150 mM NaCl, 1 mM CHAPS) was added to each well with compounds. Plates were centrifuged for 10 sec at 500 rpm. After 30 minutes preincubation, 5 μL of substrate (5 μM PED6 [from 5 mM DMSO stock] in assay buffer of 50 mM HEPES, pH7.4, 150 mM NaCl, 1 mM CHAPS) was added to 384 well Greiner 784076 (black) low-volume plates by BRAVO liquid handling station. Plates were kinetic read by starting read immediately after PED6 addition at ex: 480/em: 540 using ViewLux microplate reader. pIC50 data, curve and QC analysis was conducted using XLfit module in Excel.

All exemplified compounds of the present invention were tested in PLA2 VIIB assay or similar assay as described above. All tested compounds except Examples 37, 39, 41, 42, 43, 44, 45, 46, 47, 50, 67, 69, 71, 102, 103, 131, 140, 144, 147, 158, 160, 171, 180, 189, 190, 192, 194, 201 and 208 had over 100 fold selectivity between human recombinant Lp-PLA$_2$ and PLA2 VIIB.

(3) Lipoprotein-Associated Phospholipase A2 (Lp-PLA$_2$) Human Plasma Assay (Also Referred to as "Thio-PAF Assay")

The human plasma assay utilizes a thioester analog of PAF (phosphatidylcholine), where hydrolysis yields to the formation of a phospholipid containing a free thiol group. The amount of thiol is quantitated continuously by reacting with CPM (7-diethylamino-3-(4'-maleimidylphenyl)-4-methylcoumarin), a maleimide which increases in fluorescence after Michael addition of thiols. This assay may detect the activity of Lp-PLA$_2$ from plasma, as determined by specific inhibition by Lp-PLA$_2$ inhibitors.

The thio-PAF assay was run as a quenched 15 μL assay. Compounds source plate was prepared by making 1:3 (by volume) serial dilution of the compounds into pure DMSO on 384-well microplate. 0.01 μL of compounds on compound source plate were transferred to 384 well Greiner 784076 (black) low-volume plates by ECHO liquid dispenser. 8 μL pooled human plasma, which was previously aliquoted and frozen, was added. Plates were centrifuged for 10 sec at 500 rpm. After 30 minutes preincubation, 2 μL of substrate (2.5 mM thio-PAF, 3.2 mM NEM (N-ethylmaleimide) [made fresh daily in DMSO], and 32 μM CPM [from a DMSO stock] in assay buffer of 50 mM HEPES, pH7.4, 150 mM NaCl, 1 mM CHAPS was added to 384 well Greiner 784076 (black) low-volume plates by BRAVO liquid handling station. Plates were centrifuged for 10 sec at 500 rpm. Plate was covered to protect from light and incubated for 2 min at room temperature. Reaction was quenched with 5 μL of 5% aqueous trifluoroacetic acid (TFA). Plates were covered to protect from light and incubated for 40 min at room temperature. Plates were read at ex: 380/em: 485 using-Envision microplate reader. PIC50 data, curve and QC analysis was conducted by using XLFit module in Excel.

All exemplified compounds of the present invention were tested in thio-PAF assay or similar assay as described above.

The pIC$_{50}$ values in the thio-PAF assay for all compounds except examples 19, 27, 37, 39, 41-48, 50, 52, 62, 63, 66-72, 81, 83, 89, 98, 101-104, 114, 125, 127-129, 131, 140, 142, 144, 145, 147, 158, 160, 163, 170, 171, 173, 179, 180, 183, 184, 192, 198, 215 were at least 5.0.

The pIC$_{50}$ values in the thio-PAF assay for examples 3, 4, 6-17, 20-26, 28-32, 34-36, 56-61, 73-75, 78-80, 84, 85, 87, 88, 90, 92, 93, 95, 97, 105-113, 115-120, 123-124, 126, 130, 133, 134, 137-139, 141, 143, 149-154, 157, 161, 162, 165, 167-169, 172, 174-178, 185-188, 193-195, 196, 202-212, 214, and 216 were at least 6.0.

The pIC$_{50}$ values in the thio-PAF assay for examples 9, 11-16, 20-26, 29-31, 60-61, 73, 75, 79, 85, 88, 90, 92, 93, 95, 97, 105, 107-111, 113, 115-116, 118-120, 134, 141, 150, 151, 162, 165, 167, 168, 169, 172, 174-178, 188, 195, 202-204, 210, 212, and 214 were at least 7.0.

E. METHODS OF USE

The compounds of this invention are inhibitors of Lp-PLA$_2$. Therefore, these compounds may be used in therapy, for example, in the treatment of disorders associated with the activity of Lp-PLA$_2$. Accordingly, another aspect of the invention is directed to methods of treating conditions associated with the activity of Lp-PLA$_2$. As will be appreciated by those skilled in the art, a particular condition or its treatment may involve one or more underlying mechanisms associated with Lp-PLA$_2$ activity, including one or more of the mechanisms described herein.

In some embodiments, an inhibitor of Lp-PLA$_2$ according to the invention may be used in treating any of the disorders disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO002/30904, WO002/30911, WO003/015786, WO003/016287, WO003/041712, WO03/042179, WO003/042206, WO003/042218, WO003/086400, WO003/87088, WO008/048867, US 2008/0103156, US 2008/0090851, US 2008/0090852, WO008/048866, WO05/003118 CA 2530816A1), W06/063811, WO006/063813, WO 2008/141176, JP 200188847, US 2008/0279846 A1, US 2010/0239565 A1, and US 2008/0280829 A1.

In one embodiment, the compounds of this invention may be used to treat any disease that involves endothelial dysfunction, for example, atherosclerosis, (e.g. peripheral vascular atherosclerosis and cerebrovascular atherosclerosis), diabetes, hypertension, angina pectoris and after ischaemia and reperfusion.

In one embodiment, the compounds of the present invention may be used to treat any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In one embodiment, the compounds of the present invention may be used to treat disease that involves activated monocytes, macrophages or lymphocytes, as all of these cell types express Lp-PLA$_2$ including diseases involving activated macrophages such as M1, dendritic and/or other macrophages which generate oxidative stress; exemplary disorder includes, but are not limited to, psoriasis, rheumatoid arthritis, wound healing chronic obstructive pulmonary disease (COPD) liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In one embodiment, the present invention provides methods of treating a disease associated with the activity of Lp-PLA$_2$, which comprises treating a subject in need thereof with a therapeutically effective amount of an inhibitor of Lp-PLA$_2$. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

In other embodiments, the compounds of the invention may be used for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiment, the compounds of the present invention may be used to treat the disease described herein in combination with an anti-hyperlipidaemic, anti-atherosclerotic, anti-diabetic, anti-anginal, anti-inflammatory, or anti-hypertension agent or an agent for lowering Lipoprotein (a) (Lp (a)). Examples of the above include, but are not limited to, cholesterol synthesis inhibitors such as statins, anti-oxidants such as probucol, insulin sensitizers, calcium channel antagonists, and anti-inflammatory drugs such as non-steroidal anti-inflammatory Drugs (NSAIDs). Examples of agents for lowering Lp(a) include the aminophosphonates described in WO 97/02037, WO 98/28310, WO 98/28311 and WO 98/28312.

In one embodiment, the compounds of the present invention may be used with statin. The statins are a well-known class of cholesterol lowering agents and include atorvastatin, simvarstatin, pravastatin, cerivastatin, fluvastatin, lovastatin and rosuvastatin. The two agents may be administered at substantially the same time or at different times, according to the discretion of the physician.

In certain embodiment, the compounds of the present invention may be used with an anti-diabetic agent or an insulin sensitizer. In one embodiment, a compound of the present invention may be used with PPAR gamma activators, for instance GI262570 (GlaxoSmithKline) and the glitazone class of compounds such as rosiglitazone, troglitazone and pioglitazone.

In one embodiment, the compounds of the present invention may be used to treat a neurodegeneration disease in a subject. The methods comprise administering to a subject in need thereof a pharmaceutical composition comprising an agent that inhibits the activity of Lp-PLA$_2$. Exemplary neurodegeneration diseases include, but are not limited to, Alzheimer's disease, vascular dementia, Parkinson's disease and Huntington's disease. In certain embodiment, the neurodegeneration disease described herein is associated with an abnormal blood brain barrier. In one embodiment, the subject administered an agent that inhibits the activity of Lp-PLA$_2$ is a human.

In one embodiment, the present invention provides methods of treating a subject with or at risk of vascular dementia. The methods comprise administering to the subject a pharmaceutical composition comprising a safe and effective amount of a compound of present invention. In certain embodiment, the vascular dementia is associated with Alzheimer's disease.

In one embodiment, the present invention provides methods of treating a neurological disorder associated with an abnormal blood brain barrier (BBB) function, inflammation, and/or microglia activation in a subject in need thereof. The methods comprise administering to the subject a safe and effective amount of a compound of present invention. In certain embodiment, the abnormal blood-brain barrier is a permeable blood brain barrier. In one embodiment, the disease is a neurodegeneration disease. Such neurodegeneration diseases are, for example, but are not limited to, vascular dementia, Alzheimer's disease, Parkinson's disease and Huntington's disease. In certain embodiment, the present invention provides methods of treating disease associated with a subject with blood brain barrier (BBB) leakage. Exemplary disease include, but is not limited to, brain hemorrhage, cerebral amyloid angiopathy. In one embodiment, the neurodegeneration disease is Alzheimer's disease. In certain embodiment, the neurodegeneration disease is vascular dementia. In one embodiment, the neurodegeneration disease is Multiple Sclerosis (MS).

In one embodiment, the present invention provides methods of decreasing beta amyloid, referred to as "Aβ" accumulation in the brain of a subject. The methods comprise administering to a subject in need thereof a pharmaceutical composition comprising a safe and effective amount of a compound of the present invention. In certain embodiment, the beta amyloid is Abeta-42.

In certain embodiment, when a subject is administered a safe and effective amount of a compound of the present invention, the methods may further comprise administering to the subject another therapeutic agent that may be useful in treating the neurodegenerative disease for which the subject is being treated, or that may be a co-morbidity. For example, when the neurodegenerative disease is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation.

In one embodiment, the present invention relates to methods of treating metabolic bone diseases by administering to the subject in need thereof a safe and effective amount of a compound of the present invention. Exemplary metabolic bone diseases include, diseases associated with loss of bone mass and density including, but are not limited to, osteoporosis and osteopenic related diseases. Exemplary osteoporosis and osteopenic related diseases include, but are not limited to, bone marrow abnormalities, dyslipidemia, Paget's diseases, type II diseases, metabolic syndrome, insulin resistance, hyperparathyroidism and related diseases. In certain embodiment, the subject in need thereof is a human.

It is believed that methods of preventing osteoporosis and/or osteopenic diseases described herein may be affected by inhibiting the expression of Lp-PLA$_2$ and/or inhibiting the protein activity of Lp-PLA$_2$. Accordingly, some embodiments of the present invention provide methods for inhibiting Lp-PLA$_2$ by blocking enzyme activity. In one embodiment, methods for inhibiting Lp-PLA$_2$ by reducing and/or down-regulating the expression of Lp-PLA$_2$ RNA are provided. In certain embodiment, preventing and/or reducing loss of bone mass and/or loss of bone density leads to preventing or reducing symptoms associated with metabolic bone diseases such as osteoporosis and/or osteopenic diseases.

In one embodiment, the methods further comprise administering to a subject in need thereof additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene, a selective estrogen modulator (SERM), estrogen therapy, hormone replacement therapy (ET/HRT) and teriparatide) may be used.

One aspect of the present invention provides methods for treating eye diseases by administering a safe and effective amount of a compound of present invention. Eye diseases applicable in the present invention may be associated with the breakdown of the inner blood-retinal barrier (iBRB). Exemplary eye diseases relate to diabetic eye diseases and disorders include macular edema, diabetic retinopathy, and the like. Further, in one embodiment, the present invention relates to methods for treating eye diseases by administering a compound of the present invention to inhibit Lp-PLA$_2$. Exemplary eye diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like.

Further, some embodiments of the present invention provide methods for treating diabetic macular edema in a subject. The method comprises administering to a subject in need thereof a safe and effective amount of a compound of present invention.

In one embodiment, the present invention provides methods of treating a subject with or at risk of macular edema. The methods comprise administering to the subject a safe and effective amount of a compound of the present invention. In certain embodiment, the macular edema is associated with diabetic eye disease, for example, diabetic retinopathy. In one embodiment, the macular edema is associated with posterior uveitis.

In one embodiment, the present invention provides methods of treating glaucoma or macular degeneration. The methods comprise administering to the subject a safe and effective amount of a compound of the present invention.

In one embodiment, the present invention provides methods of treating a disease associated with the breakdown of the inner blood-retinal barrier in a subject in need thereof. The methods comprise administering to the subject a safe and effective amount of a compound of the present invention.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. The present invention relates to methods for treating posterior uveitis or any of these systemic inflammatory diseases by administering a safe and effective amount of a compound of the present invention.

It is believed that Lp-PLA$_2$ inhibitors may have beneficial effects on indications associated with M1/M2 macrophage polarization. The belief is based on the following studies. A study was carried out by GSK to investigate the relationship between M1/M2 macrophage polarization and different diseases. 94 human markers described in Martinez F O et al., distinguishing M1 and M2 phenotypes was used against a GSK subscribed GeneLogic database. (See Martinez F O et al. (2006) J Immunol 177, 7303-7311.) The Connectivity Map methodology described in Lamb J et al. was used to identify the fraction of samples in each disease state having expression characteristics consistent with a M1-favoring or M2-favoring macrophage population. (See Lamb J et al. (2006) Science 313, 1929-1935) (PMID 17008526)). The study showed that liver cirrhosis, skin psoriasis, atopic dermatitis, pulmonary emphysema, chronic pancreatitis, chronic gastritis, aortic aneurysm have M1/M2 imbalance.

A further study was carried out to study the impact of Lp-PLA$_2$ inhibitors on modulating M1/M2 imbalance. In this study, rats were induced to develop experimental autoimmune encephalomyelitis (EAE) by immunization with myelin basic protein (MBP) antigen and treated with a known Lp-PLA$_2$ inhibitor: 5-((9-Methoxy-4-oxo-6,7-dihydro-4H-pyrimido[6,1-a]isoquinolin-2-yl)oxy)-2-(3-(trifluoromethyl)phenoxy)benzonitrile (See PCT application no. PCT/CN2011/001597) For preventive treatment, compound administration started at day 0 whereas it started at 7 day in therapeutic treatment. Rats were subsequently monitored for symptoms of EAE. Rats were immunized with MBP to develop EAE and symptoms were monitored daily. Plasma Lp-PLA$_2$ activity and LysoPC concentration were determined at different time points through the course of EAE.

Ex vivo analysis of proinflammatory (M1) and anti-inflammatory (M2) markers in control and compound treated EAE mice. Splenic macrophages were harvested at day 13 post MBP-immunization and assayed for expression of a variety of markers by realtime PCR. CNS infiltrating cells were harvested and macrophages were analyzed for expression of M1 and M2 markers by realtime PCR. Treatment with compound resulted in the decrease in M1 markers and increase in M2 markers, which potentially indicated the possibility of anti-inflammation and tissue repair.

Therefore, in one embodiment, the present invention provides methods of treating disease associated with macrophage polarization, particularly M1/M2 macrophage polarization. Exemplary diseases associated with macrophage polarization are, but not limited to, liver cirrhosis, skin psoriasis, atopic dermatitis, pulmonary emphysema, chronic pancreatitis, chronic gastritis, aortic aneurysm, atherosclerosis, multiple sclerosis, and other autoimmune diseases that are associated with macrophage polarization.

One aspect of the present invention provides the use of a compound of the present invention for the preparation of a medicament for carrying out a method described herein. Another aspect of the present invention provides a compound of the present invention for use in carrying out methods of treatment described herein.

F. COMPOSITION

The compounds of the present invention may be formulated into pharmaceutical compositions prior to administration to a subject. Accordingly, one aspect of the invention is directed to pharmaceutical compositions comprising a compound of the invention and one or more pharmaceutically-acceptable excipients. In accordance with another aspect of the invention, a process for the preparation of a pharmaceutical composition including admixing a compound of the Formula (I) or Formula (IA) or salts thereof, solvates etc thereof, with one or more pharmaceutically acceptable excipients.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formula (I) or Formula (IA) or salts thereof, solvates etc thereof, depending on the condition being treated, the route of administration and the age, weight and condition of the patient, or pharmaceutical compositions may be presented in unit dose forms containing a predetermined amount of active ingredient per unit dose. In one embodiment, the unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of the Formula (I) or Formula (IA) or salts thereof, solvates etc thereof for the treatment of anemia will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. An effective amount of a salt or solvate, etc., may be determined as a proportion of the effective amount of the compound of formula (I) per se. It is envisaged that similar dosages would be appropriate for treatment of the other conditions referred to above.

The pharmaceutical compositions of the invention may contain one compound of the invention. In one embodiment, the pharmaceutical compositions may contain more than one compound of the invention. For example, in certain embodiment, the pharmaceutical compositions may contain two compounds of the invention. In addition, the pharmaceutical compositions may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any method known in the art of pharmacy, for example by bringing into association a compound of Formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate carrying or transporting of the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

What is claimed is:

1. A compound of Formula (I) or a pharmaceutically acceptable salt thereof

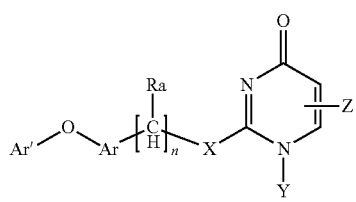

(I)

wherein:
n is 1, 2 or 3;
X is $CH_2$, O, S, NH, or $N(C_1\text{-}C_6\text{alkyl})$;
Y is H, $C_1\text{-}C_6$alkyl or $C_3\text{-}C_6$ cycloalkyl;
Z is H, $C_1\text{-}C_6$alkyl, $C_1\text{-}C_6$-haloalkyl, —$CH_2$-phenyl, —$CH_2$-heteroaryl, —$(CH_2)_2C(=O)$—$OCH_3$, —$CH_2$-heterocycloalkyl, —$CH_2COOH$, —$CH_2C(=O)$-heterocycloalkyl, wherein phenyl, heteroaryl or heterocycloalkyl may be optionally substituted with one or more substituents independently selected from the group consisting of $C_1\text{-}C_6$alkyl, $C_1\text{-}C_6$alkoxyl, $C_1\text{-}C_3$haloalkyl, CN, halo and —OH;
Ra is hydrogen or $C_1\text{-}C_3$alkyl;
Ar is phenyl or heteroaryl which is a monocyclic ring system having 6 members atoms, either of which is optionally substituted with one or more substituents independently selected from the group consisting of CN, halo, $C_1\text{-}C_6$alkyl, $C_1\text{-}C_6$alkoxy, and $C_1\text{-}C_6$haloalkyl; and
Ar' is phenyl or heteroaryl, either of which is optionally substituted with one or more substituents independently selected from the group consisting of CN, halo, $C_1\text{-}C_6$alkyl, $C_1\text{-}C_6$alkoxy, $C_1\text{-}C_6$haloalkyl, and —O—$C_1\text{-}C_6$haloalkyl; and
with the proviso that when X is S and Z is $C_1\text{-}C_6$alkyl, Ar' is not unsubstituted phenyl.

2. A compound according to claim 1, wherein
n is 1 or 2;
X is $CH_2$, O, S, NH, or $NCH_3$;
Y is H or $C_1\text{-}C_3$alkyl;
Z is H, $C_1\text{-}C_3$alkyl, $C_1\text{-}C_3$haloalkyl, —$CH_2$-phenyl, —$CH_2$-heteroaryl, $(CH_2)_2C(=O)$—$OCH_3$, —$CH_2$-heterocycloalkyl, —$CH_2COOH$, —$CH_2C(=O)$-heterocycloalkyl, wherein phenyl, heteroaryl or heterocycloalkyl is optionally substituted with one or more substituents independently selected from the group consisting of $C_1\text{-}C_6$alkyl, $C_1\text{-}C_6$alkoxyl, $C_1\text{-}C_3$haloalkyl, CN, halo and —OH;
$R_a$ is hydrogen or $CH_3$;
Ar is phenyl optionally substituted with one or more substituents independently selected from the group consisting of CN, halo, $C_1\text{-}C_6$alkyl, $C_1\text{-}C_6$alkoxy and $CF_3$; and
Ar' is phenyl or heteroaryl, either of which is optionally substituted with one or more substituents independently selected from the group consisting of CN, halo, $C_1\text{-}C_6$alkyl, $C_1\text{-}C_6$alkoxy, $C_1\text{-}C_6$haloalkyl, and —O—$C_1\text{-}C_6$haloalkyl.

3. A compound according to claim 1, wherein n is 2.
4. A compound according to claim 1, wherein X is O.
5. A compound according to 1, wherein Y is H or $CH_3$.
6. A compound according to claim 1, wherein Z is —$CH_2$-pyrimidinyl, substituted with one substituent selected from $CH_3$ or $OCH_3$.
7. A compound according to claim 1, wherein $R_a$ is hydrogen.
8. A compound according to claim 1, wherein Ar is unsubstituted phenyl.
9. A compound according to claim 1, wherein Ar' is phenyl substituted with Cl and $CF_3$.
10. A compound according to claim wherein the compound has the structure of Formula (IA), or pharmaceutically acceptable salts thereof,

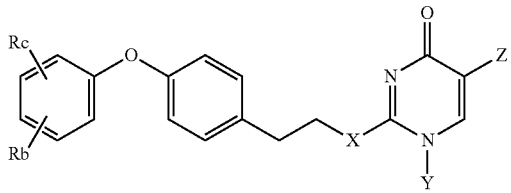

wherein Z is —$CH_2$-pyrimidinyl, wherein pyrimidinyl is optionally substituted with one $OCH_3$;
X is O;
Y is H; and
Rc and Rb are independently halo or $CF_3$.

11. A compound according to claim 1, wherein the compound has the structure of

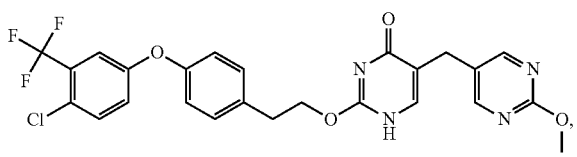 [SMILES: COc1ncc(Cc2c[nH]c(OCCc3ccc(Oc4ccc(Cl)c(C(F)(F)F)c4)cc3)nc2=O)cn1]

or a pharmaceutically acceptable salt thereof.

12. A pharmaceutical composition comprising a compound of Formula (I) according to claim 1 and a pharmaceutically acceptable carrier.

13. A method for treating Alzheimer's disease in a subject comprising administering to a subject in need thereof a safe and effective amount of a compound of Formula (I) or a pharmaceutically acceptable salt thereof according to claim 1.

14. A method for treating atherosclerosis in a subject comprising administering to a subject in need thereof a safe and effective amount of a compound of Formula (I) or a pharmaceutically acceptable salt thereof according to claim 1.

* * * * *